(12) United States Patent
Wu et al.

(10) Patent No.: US 6,492,408 B1
(45) Date of Patent: Dec. 10, 2002

(54) SMALL MOLECULES USEFUL IN THE TREATMENT OF INFLAMMATORY DISEASE

(75) Inventors: Jiang-Ping Wu, Danbury, CT (US); Terence Alfred Kelly, Ridgefield, CT (US); Rene Lemieux, Plantsville, CT (US); Daniel R. Goldberg, New Canaan, CT (US); Jonathan Emilian Emeigh, Danbury, CT (US); Ronald John Sorcek, Bethel, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 13 days.

(21) Appl. No.: 09/604,312

(22) Filed: Jun. 27, 2000

Related U.S. Application Data

(60) Provisional application No. 60/150,939, filed on Aug. 26, 1999, and provisional application No. 60/144,905, filed on Jul. 21, 1999.

(51) Int. Cl.⁷ .................. A61K 31/4188; C07D 239/00; C07D 403/00; C07D 235/00; C07D 403/02

(52) U.S. Cl. ................. 514/387; 514/386; 544/242; 544/333; 548/303.1; 548/302.7

(58) Field of Search ................. 514/387, 386; 544/242, 333; 548/303.1, 302.7

(56) References Cited

FOREIGN PATENT DOCUMENTS

| JP | 04273877 | * | 9/1992 |
| WO | 9839303 | * | 9/1998 |

* cited by examiner

Primary Examiner—Mukund J. Shah
Assistant Examiner—Sudhaker B. Patel
(74) Attorney, Agent, or Firm—Robert P. Raymond; Alan R. Stempel; Mary-Ellen M. Devlin

(57) ABSTRACT

Compounds of the formula I

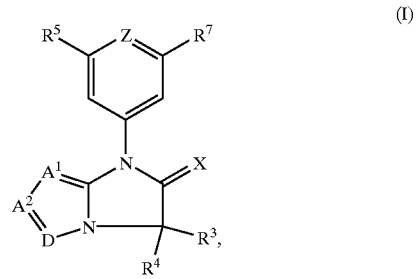

which are useful for treating or preventing inflammatory and immune cell-mediated diseases. Exemplary are:

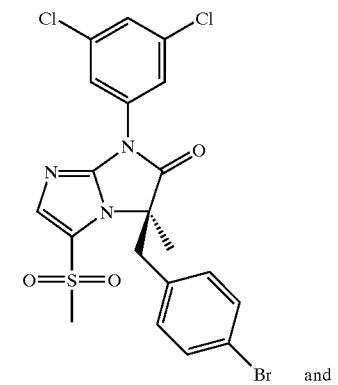

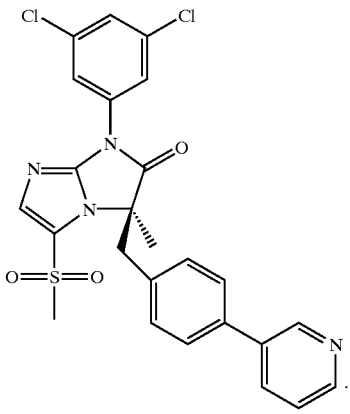

11 Claims, No Drawings

SMALL MOLECULES USEFUL IN THE TREATMENT OF INFLAMMATORY DISEASE

RELATED APPLICATIONS

The benefit of prior provisional application Ser. No. 60/144,905, filed on Jul. 21, 1999 and of prior provisional application Ser. No. 60/150,939, filed on Aug. 26, 1999 are hereby claimed.

FIELD OF THE INVENTION

The present invention relates generally to a series of novel small molecules, their synthesis and their use in the treatment of inflammatory disease.

BACKGROUND OF THE INVENTION

Research spanning the last decade has helped to elucidate the molecular events attending cell-cell interactions in the body, especially those events involved in the movement and activation of cells in the immune system. See generally, Springer, T. *Nature*, 1990, 346, 425–434. Cell surface proteins, and especially the Cellular Adhesion Molecules ("CAMs") and "Leukointegrins", including LFA-1, MAC-1 and gp150.95 (referred to in WHO nomenclature as CD18/CD11a, CD18/CD11b, and CD18/CD11c, respectively) have correspondingly been the subject of pharmaceutical research and development having as its goal the intervention in the processes of leukocyte extravasation to sites of injury and leukocyte movement to distinct targets. For example, it is presently believed that prior to the leukocyte extravasation, which is a mandatory component of the inflammatory response, activation of integrins constitutively expressed on leukocytes occurs and is followed by a tight ligand/receptor interaction between integrins (e.g., LFA-1) and one or several distinct intercellular adhesion molecules (ICAMs) designated ICAM-1, ICAM-2, ICAM-3 or ICAM-4 which are expressed on blood vessel endothelial cell surfaces and on other leukocytes. The interaction of the CAMs with the Leukointegrins is a vital step in the normal functioning of the immune system. Immune processes such as antigen presentation, T-cell mediated cytotoxicity and leukocyte extravasation all require cellular adhesion mediated by ICAMs interacting with the Leukointegrins. See generally Kishimoto, T. K.; Rothlein; R. R. *Adv. Pharmacol.* 1994, 25, 117–138 and Diamond, M.; Springer, T. *Current Biology*, 1994, 4, 506–532.

A group of individuals has been identified which lack the appropriate expression of Leukointegrins, a condition termed "Leukocyte Adhesion Deficiency" (Anderson, D. C.; et al., *Fed Proc.* 1985, 44, 2671–2677 and Anderson, D. C.; et al., *J. Infect. Dis.* 1985, 152, 668–689). These individuals are unable to mount a normal inflammatory and/or immune response(s) due to an inability of their cells to adhere to cellular substrates. These data show that immune reactions are mitigated when lymphocytes are unable to adhere in a normal fashion due to the lack of functional adhesion molecules of the CD18 family. By virtue of the fact that LAD patients who lack CD18 cannot mount an inflammatory response, it is believed that antagonism of CD18, CD11/ICAM interactions will also inhibit an inflammatory response.

It has been demonstrated that the antagonism of the interaction between the CAMs and the Leukointegrins can be realized by agents directed against either component. Specifically, blocking of the CAMs, such as for example ICAM-1, or the Leukointegrins, such as for example LFA-1, by antibodies directed against either or both of these molecules effectively inhibits inflammatory responses. In vitro models of inflammation and immune response inhibited by antibodies to CAMs or Leukointegrins include antigen or mitogen-induced lymphocyte proliferation, homotypic aggregation of lymphocytes, T-cell mediated cytolysis and antigen-specific induced tolerance. The relevance of the in vitro studies are supported by in vivo studies with antibodies directed against ICAM-1 or LFA-1. For example, antibodies directed against LFA-1 can prevent thyroid graft rejection and prolong heart allograft survival in mice (Gorski, A.; *Immunology Today*, 1994, 15, 251–255). Of greater significance, antibodies directed against ICAM-1 have shown efficacy in vivo as anti-inflammatory agents in human diseases such as renal allograft rejection and rheumatoid arthritis (Rothlein, R. R.; Scharschmidt, L., in: *Adhesion Molecules*; Wegner, C. D., Ed.; 1994, 1–38, Cosimi, C. B.; et al., *J. Immunol.* 1990, 144, 4604–4612 and Kavanaugh, A.; et al., *Arthritis Rheum.* 1994, 37, 992–1004) and antibodies directed against LFA-1 have demonstrated immunosuppressive effects in bone marrow transplantation and in the prevention of early rejection of renal allografis (Fischer, A.; et al., *Lancet*, 1989, 2, 1058–1060 and Le Mauff, B.; et al., *Transplantation*, 1991, 52, 291–295).

It has also been demonstrated that a recombinant soluble form of ICAM-1 can act as an inhibitor of the ICAM-1 interaction with LFA-1. Soluble ICAM-1 acts as a direct antagonist of CD18,CD11/ICAM-1 interactions on cells and shows inhibitory activity in in vitro models of immune response such as the human mixed lymphocyte response, cytotoxic T cell responses and T cell proliferation from diabetic patients in response to islet cells (Becker, J. C.; et al., *J. Immunol.* 1993, 151, 7224 and Roep, B. O.; et al., *Lancet*, 1994, 343, 1590). Thus, the prior art has demonstrated that large protein molecules which antagonize the binding of the CAMs to the Leukointegrins have therapeutic potential in mitigating inflammatory and immunological responses often associated with the pathogenesis of many autoimmune or inflammatory diseases. However proteins have significant deficiencies as therapeutic agents, including the inability to be delivered orally and potential immunoreactivity which limits the utility of theses molecules for chronic administration. Furthermore, protein-based therapeutics are generally expensive to produce.

Several small molecules have been described in the literature which affect the interaction of CAMs and Leukointegrins. A natural product isolated from the root of *Trichilia rubra* was found to be inhibitory in an in vitro cell binding assay (Musza, L. L.; et al., *Tetrahedron*, 1994, 50, 11369–11378). One series of molecules (Boschelli, D. H.; et al., *J. Med Chem.* 1994, 37, 717 and Boschelli, D. H.; et al., *J. Med Chem.* 1995, 38, 4597–4614) was found to be orally active in a reverse passive Arthus reaction, an induced model of inflammation that is characterized by neutrophil accumulation (Chang, Y. H.; et al, *Eur. J Pharmacol.* 1992, 69, 155–164). Another series of molecules was also found to be orally active in a delayed type hypersensitivity reaction in rats (Sanfilippo, P. J.; et al., *J. Med. Chem.* 1995, 38, 1057–1059). All of these molecules appear to act nonspecifically, either by inhibiting the transcription of ICAM-1 along with other proteins or act intracellularly to inhibit the activation of the Leukointegrins by an unknown mechanism. None of the molecules directly antagonize the interaction of the CAMs with the Leukointegrins. Due to lack of potency, lack of selectivity and lack of a specific mechanism of action, the described small molecules are not likely to be satisfactory for therapeutic use.

It follows that small molecules having the similar ability as large protein molecules to directly and selectively antagonize the binding of the CAMs to the Leukointegrins would make preferable therapeutic agents. WO9839303 discloses a class of small molecule inhibitors of the interaction of LFA-1 and ICAM-1. WO9911258 discloses that the fungal metabolite mevinolin and derivatives bind to LFA-1 and disrupt the interaction of LFA-1 and ICAM-1. WO9949856 discloses a class of peptidomimetic inhibitors of ICAM binding to LFA-1 and Mac-1.

SUMMARY OF THE INVENTION

A first aspect of the invention comprises a method for treating or preventing inflammatory and immune cell-mediated diseases by the administration of certain novel small molecules. These compounds act by inhibiting the interaction of cellular adhesion molecules, specifically by antagonizing the binding of human intercellular adhesion molecules (including ICAM-1, ICAM-2 and ICAM-3) to the Leukointegrins (especially CD18/CD11a). A second aspect of the invention comprises novel small molecules having the above-noted therapeutic activities. A third aspect of the invention comprises methods for making these novel compounds. A final aspect of the invention comprises pharmaceutical compositions comprising the above-mentioned compounds suitable for the prevention or treatment of inflammatory and immune cell-mediated conditions.

DETAILED DESCRIPTION OF THE INVENTION

In its first and broadest aspect, the invention comprises compounds of the formula I

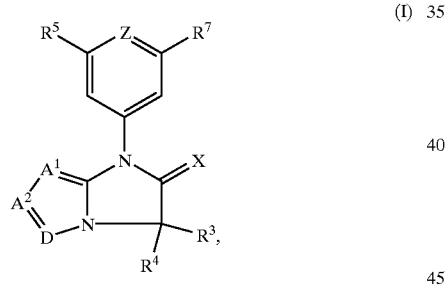

wherein:
$A^1$ is =N— or =C(H)—;
$A^2$ is =N—, =C(H)—, or =C(R')— wherein R' is halogen, —CN, —Oalkyl, —$CO_2$alkyl or —$SO_2$alkyl, wherein the foregoing alkyl moieties are of 1 to 3 carbon atoms;
D is =N—, =C($R^1$)—, =C(H)—, =C($SO_2R^1$)—, =C(S(O)$R^1$)—, =C(C(O)$R^1$)—, =C(C(O)H)—, =C($SR^{1a}$)—, =C($OR^{1a}$)— or =C($NHR^{1a}$)—,
wherein $R^1$ is selected from the class consisting of:
(A) —$R^{100}$, which is:
branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
  (i) halogen,
  (ii) oxo,
  (iii) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:
(a) alkyl of 1 to 3 carbon atoms,
(b) —COOH,
(c) —$SO_2$OH,
(d) —PO(OH)$_2$,
(e) a group of the formula —COO$R^8$, wherein $R^8$ is straight or branched alkyl of 1 to 5 carbon atoms or cycloalkyl of 3 to 5 carbon atoms,
(f) a group of the formula —N$R^9R^{10}$, wherein $R^9$ and $R^{10}$ are each independently a hydrogen atom, alkyl of 1 to 6 carbon atoms, cycloalkyl of 3 to 6 carbon atoms or acyl of 1 to 7 carbon atoms, or wherein $R^9$ and $R^{10}$ constitute a saturated hydrocarbon bridge of 3 to 5 carbon atoms which together with the nitrogen atom between them form a heterocyclic ring,
(g) a group of the formula —CON$R^{11}R^{12}$, wherein $R^{11}$ and $R^{12}$ are each independently a hydrogen atom, alkyl of 1 to 6 carbon atoms or cycloalkyl of 3 to 6 carbon atoms, or wherein $R^{11}$ and $R^{12}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, $SO_2$—, —NH—, or —NMe—,
(h) a group of the formula —O$R^{13}$, wherein $R^{13}$ is a hydrogen atom, or an alkyl or acyl group of 1 to 7 carbon atoms,
(i) a group of the formula —S$R^{14}$, wherein $R^{14}$ is a hydrogen atom, or an alkyl or acyl group of 1 to 7 carbon atoms,
(j) —CN, or
(k) an amidino group of the formula

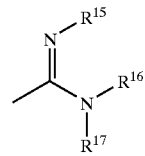

wherein $R^{15}$, $R^{16}$ and $R^{17}$ are each, independently, a hydrogen atom or alkyl of 1 to 3 carbon atoms and wherein two of $R^{15}$, $R^{16}$ and $R^{17}$ may additionally constitute a saturated hydrocarbon bridge of 3 to 5 carbon atoms which together with the nitrogen atom(s) between them form a heterocyclic ring,
(l) halogen,
(m) a group of the formula —NHCONHalkyl, wherein the alkyl moiety contains 1 to 3 carbon atoms,
(n) a group of the formula —NHCOOalkyl, wherein the alkyl moiety contains 1 to 3 carbon atoms, (iv) a group of the formula —COOR$^{18}$, wherein R$^{18}$ is straight or branched alkyl of 1 to 7 carbon atoms or cycloalkyl of 3 to 6 carbon atoms,
(v) —CN,
(vi) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—,
(vii) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH2, —NHMe and —NMe$_2$,
(viii) a group of the formula —SR$^{22}$, wherein R$^{22}$ is a hydrogen atom, or an alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
(ix) a group of the formula —NR$^{23}$R$^{24}$, wherein R$^{23}$ and R$^{24}$ are each, independently,
 (a) a hydrogen atom,
 (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
 (c) a group of the formula —(CH$_2$)$_m$COOH, wherein m is 0, 1 or 2,
 (d) a group of the formula —(CH$_2$)$_n$COOR$^{25}$, wherein n is 0, 1 or 2, and wherein R$^{25}$ is straight or branched alkyl of 1 to 6 carbon atoms, or
 (e) a group of the formula —CH$_2$)$_n$CONHR$^{25}$, wherein n is 0, 1 or 2, and wherein R$^{25}$ is straight or branched alkyl of 1 to 6 carbon atoms,
(x) a quaternary group of the formula

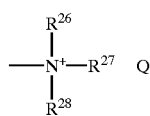

wherein R$^{26}$, R$^{27}$ and R$^{28}$ are each, independently, a branched or unbranched alkyl group of 1 to 7 carbon atoms and Q— is a pharmaceutically acceptable counter ion,
(xi) a saturated, or partially unsaturated heterocyclic group consisting of 3 to 7 ring atoms selected from N, O, C and S, including but not limited to imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or polysubstituted with oxo, and
(xii) a cycloalkyl group of 3 to 7 carbon atoms,
(B) branched or unbranched carboxylic acid groups of 3 to 6 carbon atoms,
(C) branched or unbranched phosphonic acid groups of 2 to 6 carbon atoms,
(D) branched or unbranched sulfonic acid groups of 2 to 6 carbon atoms,
(E) amidino groups of the formula

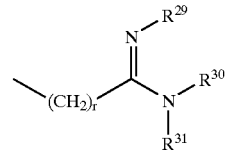

wherein r is 2, 3, 4, 5 or 6, and R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring,
(F) guanidino groups of the formula

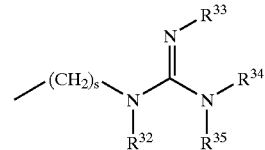

wherein s is 2, 3, 4, 5 or 6, and R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring,
(G) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:
 (i) alkyl of 1 to 3 carbon atoms,
 (ii) —COOH,
 (iii) —SO$_2$OH,
 (iv) —PO(OH)$_2$,
 (v) a group of the formula —COOR$^{36}$, wherein R$^{36}$ is straight or branched alkyl of 1 to 5 carbon atoms or cycloalkyl of 3 to 5 carbon atoms, (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring, (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, (viii) a group of the formula —OR$^{41}$, wherein R$^{41}$ is a hydrogen atom, or an alkyl or acyl group of 1 to 7 carbon atoms, (ix) a group of the formula —SR$^{42}$, wherein R$^{42}$ is a hydrogen atom, or an alkyl or acyl group of 1 to 7 carbon atoms, (x) —CN, or (xi) an amidino group of the formula

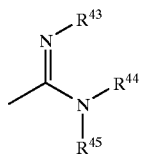

wherein R$^{43}$, R$^{44}$ and R$^{45}$ are each, independently, a hydrogen atom or alkyl of 1 to 3 carbon atoms, and wherein two of R$^{43}$, R$^{44}$ and R$^{45}$ may additionally constitute a saturated hydrocarbon bridge of 3 to 5 carbon atoms which together with the nitrogen atom(s) between them form a heterocyclic ring, (H) groups of the formula —NR$^{46}$R$^{47}$, wherein R$^{46}$ and R$^{47}$ are each independently a hydrogen atom, phenyl which is optionally mono-or polysubstituted with halogen, or R$^{100}$, wherein R$^{100}$ is as hereinbefore defined, (I) saturated or unsaturated heterocyclic groups consisting of 3 to 7 ring atoms selected from N, O, C and S, or bicyclic heterocyclic groups consisting of 8 to 11 atoms selected from N, O, C and S, including but not limited to imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or poly-substituted with moieties selected from the class consisting of:

(i) oxo, (ii) —OR$^{101}$, wherein R$^{101}$ is:
 (a) a hydrogen atom,
 (b) alkyl of 1 to 7 carbons, wherein any hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
 (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
 (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, or
 (e) —COOR$^{104}$, wherein R$^{104}$ is alkyl of 1 to 7 atoms, (iii) —CONR$^{105}$R$^{106}$, wherein R$^{105}$ and R$^{106}$ are each independently:
 (a) a hydrogen atom,
 (b) straight or branched alkyl of 1 to 7 atoms or cycloalkyl of 3 to 7 atoms,
 (c) benzoyl,
 (d) benzyl or
 (e) phenyl, wherein said phenyl ring is optionally mono- or polysubstituted with —OR$^{112}$, wherein R$^{112}$ is alkyl of 1 to 6 carbon atoms,
 or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, (iv) —COOR$^{107}$, wherein R$^{107}$ is a hydrogen atom, or straight or branched alkyl of 1 to 7 carbon atoms, (v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of:
 (a) oxo,
 (b) —OH,
 (c) —OR$^{113}$, wherein R$^{113}$ is alkyl of 1 to 6 carbon atoms,
 (d) —OCOCH$_3$,
 (e) —NH$_2$,
 (f) —NHMe,
 (g) —NMe$_2$,
 (h) —CO$_2$H, and
 (i) —CO$_2$R$^{114}$ wherein R$^{114}$ is alkyl of 1 to 3 carbon atoms, or cycloalkyl of 3 to 7 carbons, (vi) acyl of 1 to 7 carbon atoms, which may be straight, branched or cyclic, and wherein one or more hydrogen atoms of said acyl group is optionally replaced with a moiety independently selected from the class consisting of:
 (a) —OH,
 (b) —OR$^{115}$, wherein R$^{115}$ is alkyl of 1 to 6 carbon atoms,
 (c) —NH$_2$,
 (d) —NHMe,
 (e) —NMe$_2$,
 (f) —NHCOMe,
 (g) oxo,
 (h) —CO$_2$R$^{116}$, wherein R$^{116}$ is alkyl of 1 to 3 carbon atoms, (i) —CN,
(j) the halogen atoms,
(k) heterocycles selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, and
(l) aryl or heteroaryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, (vii) —$SO_2R^{108}$, wherein $R^{108}$ is:
(a) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —$OR^{117}$ (wherein $R^{117}$ is hydrogen or alkyl of 1 to 6 carbon atoms),
(b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally substituted with one or more moieties selected from the class consisting of the halogen atoms, straight or branched alkyl of 1 to 6 carbons, and —$OR^{118}$ (wherein $R^{118}$ is hydrogen or alkyl of 1 to 6 carbon atoms), or
(c) straight or branched alkyl of 1 to 7 atoms, wherein said alkyl moiety is optionally substituted with one or more moieties selected from the class consisting of the halogen atoms, straight or branched alkyl of 1 to 6 carbons, and —$OR^{119}$ (wherein $R^{119}$ is hydrogen or alkyl of 1 to 6 carbon atoms), (viii) —$COR^{109}$, wherein $R^{109}$ is:
(a) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —$OR^{120}$ (wherein $R^{120}$ is hydrogen or alkyl of 1 to 6 carbon atoms),
(b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclyl is optionally substituted with one or more halogen, straight or branched alkyl of 1 to 6 carbons, or —$OR^{121}$ (wherein $R^{121}$ is hydrogen or alkyl of 1 to 6 carbon atoms), or
(c) straight or branched alkyl of 1 to 7 atoms, wherein said alkyl moiety is optionally substituted with one or more moieties selected from the class consisting of the halogen atoms, straight or branched alkyl of 1 to 6 carbons, and —$OR^{122}$ (wherein $R^{122}$ is hydrogen or alkyl of 1 to 6 carbon atoms), (ix) —CHO,
(x) the halogen atoms, and
(xi) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, (J) the halogen atoms, and
(K) —CN, and
wherein $R^{1a}$ is $R^{100}$;

X is an oxygen or sulfur atom;
$R^3$ is:
(A) a hydrogen atom, or
(B) branched or unbranched alkyl of 1 to 3 carbon atoms or cycloalkyl of 3 to 5 carbon atoms wherein said alkyl or cycloalkyl group is optionally substituted with:
(i) a group of the formula —$OR^{48}$, wherein $R^{48}$ is a hydrogen atom, or an alkyl or acyl group of 1 to 7 carbon atoms, or
(ii) a group of the formula —$NR^{49}R^{50}$, wherein $R^{49}$ and $R^{50}$ are each, independently, a hydrogen atom, alkyl of 1 to 2 carbon atoms, or acyl of 1 to 2 carbon atoms;

$R^4$ is a group of the formula —$(CR^{51}R^{52})_x(CR^{53}R^{54})_yR^{55}$, wherein,
x is 0 or 1,
y is 0 or 1, $R^{51}$, $R^{52}$ and $R^{53}$ are each, independently:
- (A) a hydrogen atom,
- (B) a group of the formula —$OR^{56}$, wherein $R^{56}$ is a hydrogen atom, or an alkyl or acyl group of 1 to 7 carbon atoms, or
- (C) branched or unbranched alkyl of 1 to 3 carbon atoms or cycloalkyl of 3 to 5 carbon atoms, $R^{54}$ is:
- (A) a group of the formula $R^{57}$, wherein $R^{57}$ is independently selected from the same class as is $R^1$, or
- (B) a group of the formula —$OR^{58}$, wherein $R^{58}$ is independently selected from the same class as is $R^1$;

$R^{55}$ is:
aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
- (A) $R^{59}$, which is aryl or heteroaryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
    - (i) branched or unbranched alkyl of 1 to 6 carbon atoms or cycloalkyl of 3 to 6 carbon atoms, which alkyl or cycloakyl group is optionally mono- or polysubstituted with halogen or oxo,
    - (ii) a group of the formula —$COOR^{60}$, wherein $R^{60}$ is straight or branched alkyl of 1 to 5 carbon atoms or cycloalkyl of 3 to 5 carbon atoms,
    - (iii) a group of the formula —$NR^{61}R^{62}$, wherein $R^{61}$ and $R^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{61}$ and $R^{62}$ constitute a saturated hydrocarbon bridge of 3 to 5 carbon atoms which together with the nitrogen atom between them form a heterocyclic ring,
    - (iv) a group of the formula —$CONR^{63}R^{64}$, wherein $R^{63}$ and $R^{64}$ are each, independently, a hydrogen atom, alkyl or fluoroalkyl of 1 to 6 carbon atoms or cycloalkyl of 3 to 6 carbon atoms, or wherein $R^{63}$ and $R^{64}$ constitute a saturated hydrocarbon bridge of 3 to 5 carbon atoms which together with the nitrogen atom between them form a heterocyclic ring,
    - (v) a group of the formula —$OR^{65}$, wherein $R^{65}$ is a hydrogen atom, or an alkyl, fluoroalkyl or acyl group of 1 to 7 carbon atoms,
    - (vi) a group of the formula —$SR^{66}$, wherein $R^{66}$ is a hydrogen atom, or an alkyl, fluoroalkyl or acyl group of 1 to 7 carbon atoms,
    - (vii) —CN,
    - (viii) nitro, or
    - (ix) halogen,
- (B) methyl, which is optionally mono- or polysubstituted with fluorine atoms and additionally is optionally monosubstituted with $R^{59}$,
- (C) branched or unbranched alkyl of 2 to 6 carbon atoms or cycloalkyl of 3 to 6 carbon atoms, which alkyl or cycloakyl group is optionally mono- or polysubstituted with halogen or oxo,
- (D) a group of the formula —$COOR^{67}$, wherein $R^{67}$ is straight or branched alkyl of 1 to 5 carbon atoms or cycloalkyl of 3 to 5 carbon atoms,
- (E) a group of the formula —$NR^{68}R^{69}$, wherein $R^{68}$ and $R^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{68}$ and $R^{69}$ constitute a saturated hydrocarbon bridge of 3 to 5 carbon atoms which together with the nitrogen atom between them form a heterocyclic ring, and wherein one of $R^{68}$ and $R^{69}$ may additionally be the group $R^{59}$,
- (F) a group of the formula —$CONR^{70}R^{71}$, wherein $R^{70}$ and $R^{71}$ are each, independently, a hydrogen atom, alkyl or fluoroalkyl of 1 to 6 carbon atoms or cycloalkyl of 3 to 6 carbon atoms, or wherein $R^{70}$ and $R^{71}$ constitute a saturated hydrocarbon bridge of 3 to 5 carbon atoms which together with the nitrogen atom between them form a heterocyclic ring, and wherein one of $R^{70}$ and $R^{71}$ may additionally be the group $R^{59}$,
- (G) a group of the formula —$COR^{72}$, wherein $R^{72}$ is a hydrogen atom, straight or branched alkyl of 1 to 5 carbon atoms, cycloalkyl of 3 to 5 carbon atoms or $R^{59}$,
- (H) a group of the formula —$OR^{73}$, wherein $R^{73}$ is a hydrogen atom, an alkyl, fluoroalkyl or acyl group of 1 to 7 carbon atoms, or $R^{59}$,
- (I) a group of the formula —$SR^{74}$, wherein $R^{74}$ is a hydrogen atom, an alkyl, fluoroalkyl or acyl group of 1 to 7 carbon atoms, or $R^{59}$,
- (J) —CN,
- (K) nitro, or
- (L) halogen;

$R^5$ is Cl or trifluoromethyl;

Z is =N— or =$C(R^6)$— wherein $R^6$ is a hydrogen, fluorine, chlorine, bromine or iodine atom, methyl or trifluoromethyl; and, $R^7$ is a hydrogen, fluorine, chlorine, bromine or iodine atom, methyl, —CN, nitro or trifluoromethyl, with the condition that when Z is =N— or =C(H)—, $R^7$ is chlorine, trifluoromethyl, —CN or nitro;

and pharmaceutically acceptable salts thereof.

As the term is used herein, a "pharmaceutically acceptable counter ion" is any counter ion generally regarded by those skilled in the pharmaceutical art as being pharmaceutically acceptable. For a discussion of what are pharmaceutically acceptable counter ions, reference may be had to Stephen M. Bergle, Lyle D. Bighley and Donald C. Monkhouse, "Pharmaceutical Salts", *Journal of Pharmaceutical Sciences*, 66 (1977), 1–19. By way of non-limiting example, the chloride, bromide, acetate, and sulphate ions are pharmaceutically acceptable counter ions.

Preferred are compounds of the formula I wherein:
A$^1$ is =N— or =C(H)—;
A$^2$ is =N—, =C(H)—, or =C(R')— wherein R' is halogen, —CN, —Oalkyl, —CO$_2$alkyl or —SO$_2$alkyl, wherein the foregoing alkyl moieties are of 1 to 3 carbon atoms;
D is =N—, =C(R$^1$)—, =C(H)—, =C(SO$_2$R$^1$)—, =C(S(O)R$^1$)—, =C(C(O)R$^1$)—, =C(C(O)H)—, =C(SR$^{1a}$)—, =C(OR$^{1a}$)— or =C(NHR$^{1a}$)—,
wherein R$^1$ is selected from the class consisting of:
(A) —R$^{100a}$, which is:
branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
(i) halogen,
(ii) oxo,
(iii) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:
(a) alkyl of 1 to 3 carbon atoms,
(b) —COOH,
(c) —SO$_2$OH,
(d) —PO(OH)$_2$,
(e) a group of the formula —COOR$^8$, wherein R$^8$ is straight or branched alkyl of 1 to 5 carbon atoms or cycloalkyl of 3 to 5 carbon atoms,
(f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ constitute a saturated hydrocarbon bridge of 3 to 5 carbon atoms which together with the nitrogen atom between them form a heterocyclic ring,
(g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—,
(h) a group of the formula —OR$^{13}$, wherein R$^{13}$ is a hydrogen atom, or an alkyl or acyl group of 1 to 7 carbon atoms,
(i) a group of the formula —SR$^{14}$, wherein R$^{14}$ is a hydrogen atom, or an alkyl or acyl group of 1 to 7 carbon atoms,
(j) —CN, or (k) an amidino group of the formula

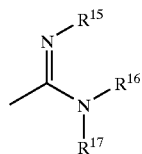

wherein R$^{15}$, R$^{16}$ and R$^{17}$ are each, independently, a hydrogen atom or alkyl of 1 to 3 carbon atoms and wherein two of R$^{15}$, R$^{16}$ and R$^{17}$ may additionally constitute a saturated hydrocarbon bridge of 3 to 5 carbon atoms which together with the nitrogen atom(s) between them form a heterocyclic ring,
(l) halogen,
(m) a group of the formula —NHCONHalkyl, wherein the alkyl moiety contains 1 to 3 carbon atoms,
(n) a group of the formula —NHCOOalkyl, wherein the alkyl moiety contains 1 to 3 carbon atoms,
(iv) a group of the formula —COOR$^{18}$, wherein R$^{18}$ is straight or branched alkyl of 1 to 7 carbon atoms or cycloalkyl of 3 to 6 carbon atoms,
(v) —CN,
(vi) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—,
(vii) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH$_2$, —NHMe and —NMe$_2$,
(viii) a group of the formula —SR$^{22}$, wherein R$^{22}$ is a hydrogen atom, or an alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
(ix) a group of the formula —NR$^{23}$R$^{24}$, wherein R$^{23}$ and R$^{24}$ are each, independently,
(a) a hydrogen atom,
(b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$, —(c) a group of the formula —(CH$_2$)$_m$COOH, wherein m is 0, 1 or 2, (d) a group of the formula —CH$_2$)$_n$COOR$^{25}$, wherein n is 0, 1 or 2, and wherein R$^{25}$ is straight or branched alkyl of 1 to 6 carbon atoms, or (e) a group of the formula —CH$_2$)$_n$CONHR$^{25}$, wherein n is 0, 1 or 2, and wherein R$^{25}$ is straight or branched alkyl of 1 to 6 carbon atoms, (x) a quaternary group of the formula

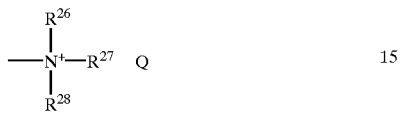

wherein R$^{26}$, R$^{27}$ and R$^{28}$ are each, independently, a branched or unbranched alkyl group of 1 to 7 carbon atoms and Q— is pharmaceutically acceptable counter ion, (xi) a saturated, or partially unsaturated heterocyclic group consisting of 3 to 7 ring atoms selected from N, O, C and S, including but not limited to imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or polysubstituted with oxo, and (xii) a cycloalkyl group of 3 to 7 carbon atoms, (B) branched or unbranched carboxylic acid groups of 3 to 6 carbon atoms, (C) branched or unbranched phosphonic acid groups of 2 to 6 carbon atoms, (D) branched or unbranched sulfonic acid groups of 2 to 6 carbon atoms, (E) amidino groups of the formula

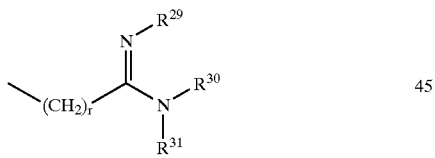

wherein r is 2, 3, 4, 5 or 6, and R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring, (F) guanidino groups of the formula

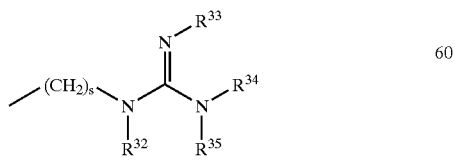

wherein s is 2, 3, 4, 5 or 6, and R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring, (G) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more hydrogen atoms of said aryl or heteroaryl group are optionally and independently replaced with:

(i) alkyl of 1 to 3 carbon atoms, (ii) —COOH, (iii) —SO$_2$OH, (iv) —PO(OH)$_2$, (v) a group of the formula —COOR$^{36}$, wherein R$^{36}$ is straight or branched alkyl of 1 to 5 carbon atoms or cycloalkyl of 3 to 5 carbon atoms, (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring, (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, SO$_2$—, —NH—, or —NMe—, (viii) a group of the formula —OR$^{41}$, wherein R$^{41}$ is a hydrogen atom, or an alkyl or acyl group of 1 to 7 carbon atoms, (ix) a group of the formula —SR$^{42}$, wherein R$^{42}$ is a hydrogen atom, or an alkyl or acyl group of 1 to 7 carbon atoms, (x) —CN, or (xi) an amidino group of the formula

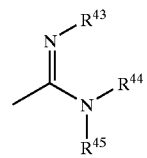

wherein R$^{43}$, R$^{44}$ and R$^{45}$ are each, independently, a hydrogen atom or alkyl of 1 to 3 carbon atoms, and wherein two of R$^{43}$, R$^{44}$ and R$^{45}$ may additionally constitute a saturated hydrocarbon bridge of 3 to 5 carbon atoms which together with the nitrogen atom(s) between them form a heterocyclic ring, (H) groups of the formula —NR$^{46}$R$^{47}$, wherein R$^{46}$ and R$^{47}$ are each independently a hydrogen atom, phenyl which is optionally mono- or polysubstituted with halogen, or $R^{100a}$, wherein $R^{100a}$ is as hereinbefore defined, (I) saturated or unsaturated heterocyclic groups consisting of 3 to 7 ring atoms selected from N, O, C and S, or bicyclic heterocyclic groups consisting of 8 to 11 atoms selected from N, O, C and S, including but not limited to imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or poly-substituted with moieties independently selected from the class consisting of:

(i) oxo,
(ii) —$OR^{101}$, wherein $R^{101}$ is:
  (a) a hydrogen atom,
  (b) alkyl of 1 to 7 carbons, wherein any hydrogen atom of said alkyl group is optionally replaced with —OH, —$OR^{110}$ (wherein $R^{110}$ is an alkyl moiety of 1 to 6 carbon atoms), —$NH_2$, —NHMe or —$NMe_2$,
  (c) acyl of 1 to 7 carbons, wherein any hydrogen atom of said acyl group is optionally replaced with —OH, —$OR^{111}$ (wherein $R^{111}$ is an alkyl moiety of 1 to 6 carbon atoms), —$NH_2$, —NHMe or —$NMe_2$,
  (d) —$CONR^{102}R^{103}$, wherein $R^{102}$ and $R^{103}$ are each independently a hydrogen atom or alkyl of 1 to 7 atoms, or wherein $R^{102}$ and $R^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, $SO_2$—, —NH—, or —NMe—, or
  (e) —$COOR^{104}$, wherein $R^{104}$ is alkyl of 1 to 7 atoms,
(iii) —$CONR^{105}R^{106}$, wherein $R^{105}$ and $R^{106}$ are each independently:
  (a) a hydrogen atom,
  (b) straight or branched alkyl of 1 to 7 atoms or cycloalkyl of 3 to 7 atoms,
  (c) benzoyl,
  (d) benzyl or
  (e) phenyl, wherein said phenyl ring is optionally mono- or polysubstituted with —$OR^{112}$, wherein $R^{112}$ is alkyl of 1 to 6 carbon atoms, or, wherein $R^{105}$ and $R^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —S—, S(O)—, $SO_2$—, —NH—, or —NMe—,
(iv) —$COOR^{107}$, wherein $R^{107}$ is a hydrogen atom, or straight or branched alkyl of 1 to 7 carbon atoms,
(v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of:
  (a) oxo,
  (b) —OH,
  (c) —$OR^{113}$, wherein $R^{113}$ is alkyl of 1 to 6 carbon atoms,
  (d) —$OCOCH_3$,
  (e) —$NH_2$,
  (f) —NHMe,
  (g) —$NMe_2$,
  (h) —$CO_2H$, and
  (i) —$CO_2R^{114}$ wherein $R^{114}$ is alkyl of 1 to 3 carbon atoms, or cycloalkyl of 3 to 7 carbons,
(vi) acyl of 1 to 7 carbon atoms, which may be straight, branched or cyclic, and wherein one or more hydrogen atoms of said acyl group is optionally replaced with a moiety independently selected from the class consisting of
  (a) —OH,
  (b) —$OR^{115}$, wherein $R^{115}$ is alkyl of 1 to 6 carbon atoms,
  (c) —$NH_2$,
  (d) —NHMe,
  (e) —$NMe_2$,
  (f) —NHCOMe,
  (g) oxo,
  (h) —$CO_2R^{116}$, wherein $R^{116}$ is alkyl of 1 to 3 carbon atoms,
  (i) —CN,
  (j) the halogen atoms,
  (k) heterocycles selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, and
  (l) aryl or heteroaryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
(vii) —$SO_2R^{108}$, wherein $R^{108}$ is:
  (a) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —$OR^{117}$ (wherein $R^{117}$ is hydrogen or alkyl of 1 to 6 carbon atoms), (b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally substituted with one or more moieties selected from the class consisting of the halogen atoms, straight or branched alkyl of 1 to 6 carbons, and —$OR^{118}$ (wherein $R^{118}$ is hydrogen or alkyl of 1 to 6 carbon atoms), or (c) straight or branched alkyl of 1 to 7 atoms, wherein said alkyl moiety is optionally substituted with one or more moieties selected from the class consisting of the halogen atoms, straight or branched alkyl of 1 to 6 carbons, and —$OR^{119}$ (wherein $R^{119}$ is hydrogen or alkyl of 1 to 6 carbon atoms), (viii) —$COR^{109}$, wherein $R^{109}$ is:
(a) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —$OR^{120}$ (wherein $R^{120}$ is hydrogen or alkyl of 1 to 6 carbon atoms), (b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclyl is optionally substituted with one or more halogen, straight or branched alkyl of 1 to 6 carbons, or —$OR^{121}$ (wherein $R^{121}$ is hydrogen or alkyl of 1 to 6 carbon atoms), or (c) straight or branched alkyl of 1 to 7 atoms, wherein said alkyl moiety is optionally substituted with one or more moieties selected from the class consisting of the halogen atoms, straight or branched alkyl of 1 to 6 carbons, and —$OR^{122}$ (wherein $R^{122}$ is hydrogen or alkyl of 1 to 6 carbon atoms), (ix) —CHO,
(x) the halogen atoms, and
(xi) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, (J) the halogen atoms, and
(K) —CN and,
wherein $R^{1a}$ is $R^{100a}$;
X is an oxygen or sulfur atom;
$R^3$ is:
(A) a hydrogen atom, or
(B) branched or unbranched alkyl of 1 to 3 carbon atoms or cycloalkyl of 3 to 5 carbon atoms wherein said alkyl or cycloalkyl group is optionally substituted with:
(i) a group of the formula —$OR^{48}$, wherein $R^{48}$ is a hydrogen atom, or an alkyl or acyl group of 1 to 7 carbon atoms, or
(ii) a group of the formula —$NR^{49}R^{50}$, wherein $R^{49}$ and $R^{50}$ are each, independently, a hydrogen atom, alkyl of 1 to 2 carbon atoms, or acyl of 1 to 2 carbon atoms;

$R^4$ is a group of the formula —$CH_2R^{55}$, wherein,
$R^{55}$ is:
aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
(A) $R^{59a}$, which is aryl or heteroaryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein one or more of the hydrogen atoms of said aryl or heteroaryl group is optionally and independently replaced with:
(i) branched or unbranched alkyl of 1 to 6 carbon atoms or cycloalkyl of 3 to 6 carbon atoms, which alkyl or cycloakyl group is optionally mono- or polysubstituted with halogen or oxo,
(ii) a group of the formula —$COOR^{60}$, wherein $R^{60}$ is straight or branched alkyl of 1 to 5 carbon atoms or cycloalkyl of 3 to 5 carbon atoms,
(iii) a group of the formula —$NR^{61}R^{62}$, wherein $R^{61}$ and $R^{62}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein $R^{61}$ and $R^{62}$ constitute a saturated hydrocarbon bridge of 3 to 5 carbon atoms which together with the nitrogen atom between them form a heterocyclic ring, (iv) a group of the formula —CONR$^{63}$R$^{64}$, wherein R$^{63}$ and R$^{64}$ are each, independently, a hydrogen atom, alkyl or fluoroalkyl of 1 to 6 carbon atoms or cycloalkyl of 3 to 6 carbon atoms, or wherein R$^{63}$ and R$^{64}$ constitute a saturated hydrocarbon bridge of 3 to 5 carbon atoms which together with the nitrogen atom between them form a heterocyclic ring, (v) a group of the formula —OR$^{65}$, wherein R$^{65}$ is a hydrogen atom, or an alkyl, fluoroalkyl or acyl group of 1 to 7 carbon atoms, (vi) a group of the formula —SR$^{66}$, wherein R$^{66}$ is a hydrogen atom, or an alkyl, fluoroalkyl or acyl group of 1 to 7 carbon atoms, (vii) —CN, (viii) nitro, or (ix) halogen, (B) methyl, which is optionally mono- or polysubstituted with fluorine atoms and additionally is optionally monosubstituted with R$^{59a}$, (C) branched or unbranched alkyl of 2 to 6 carbon atoms or cycloalkyl of 3 to 6 carbon atoms, which alkyl or cycloakyl group is optionally mono- or polysubstituted with halogen or oxo, (D) a group of the formula —COOR$^{67}$, wherein R$^{67}$ is straight or branched alkyl of 1 to 5 carbon atoms or cycloalkyl of 3 to 5 carbon atoms, (E) a group of the formula —NR$^{68}$R$^{69}$, wherein R$^{68}$ and R$^{69}$ are each, independently, a hydrogen atom, alkyl or fluoroalkyl of 1 to 6 carbon atoms, cycloalkyl of 3 to 6 carbon atoms or acyl of 1 to 7 carbon atoms, or wherein R$^{68}$ and R$^{69}$ constitute a saturated hydrocarbon bridge of 3 to 5 carbon atoms which together with the nitrogen atom between them form a heterocyclic ring, and wherein one of R$^{68}$ and R$^{69}$ may additionally be the group R$^{59a}$, (F) a group of the formula —CONR$^{70}$R$^{71}$, wherein R$^{70}$ and R$^{71}$ are each, independently, a hydrogen atom, alkyl or fluoroalkyl of 1 to 6 carbon atoms or cycloalkyl of 3 to 6 carbon atoms, or wherein R$^{70}$ and R$^{71}$, constitute a saturated hydrocarbon bridge of 3 to 5 carbon atoms which together with the nitrogen atom between them form a heterocyclic ring, and wherein one of R$^{70}$ and R$^{71}$ may additionally be the group R$^{59a}$, (G) a group of the formula —COR$^{72}$, wherein R$^{72}$ is a hydrogen atom, straight or branched alkyl of 1 to 5 carbon atoms, cycloalkyl of 3 to 5 carbon atoms or R$^{59a}$, (H) a group of the formula —OR$^{73}$, wherein R$^{73}$ is a hydrogen atom, an alkyl, fluoroalkyl or acyl group of 1 to 7 carbon atoms, or R$^{59a}$, (I) a group of the formula —SR$^{74}$, wherein R$^{74}$ is a hydrogen atom, an alkyl, fluoroalkyl or acyl group of 1 to 7 carbon atoms, or R$^{59a}$, (J) —CN, (K) nitro, or (L) halogen;

R$^5$ is Cl or trifluoromethyl;

Z is =N— or =C(R$^6$)— wherein R$^6$ is a hydrogen, fluorine, chlorine, bromine or iodine atom, methyl or trifluoromethyl; and, R$^7$ is a hydrogen, fluorine, chlorine, bromine or iodine atom, methyl, —CN, nitro or trifluoromethyl, with the condition that when Z is =N— or =C(H)—, R$^7$ is chlorine, trifluoromethyl, —CN or nitro;

and pharmaceutically acceptable salts thereof.

More preferred are compounds of the formula I wherein:

A$^1$ is =N— or =C(H)—;

A$^2$ is =N—, or =C(H)—;

D is =N—, =C(R$^1$)—, =C(H)—, =C(SO$_2$R$^1$)—, =C(C(O)H)— or =C(C(O)R$^1$)—, wherein R$^1$ is selected from the class consisting of:

(A) —R$^{100b}$, which is:

branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:

(i) oxo, (ii) phenyl, wherein one hydrogen atom of said phenyl group is optionally replaced with:

(a) alkyl of 1 to 3 carbon atoms, (b) —COOH, (c) —SO$_2$OH, (d) —PO(OH)$_2$, (e) a group of the formula —COOR$^8$, wherein R$^8$ is straight or branched alkyl of 1 to 5 carbon atoms or cycloalkyl of 3 to 5 carbon atoms, (f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ constitute a saturated hydrocarbon bridge of 3 to 5 carbon atoms which together with the nitrogen atom between them form a heterocyclic ring, (g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, (h) a group of the formula —OR$^{13}$, wherein R$^{13}$ is a hydrogen atom, or an alkyl or acyl group of 1 to 7 carbon atoms, (i) a group of the formula —SR$^{14}$, wherein R$^{14}$ is a hydrogen atom, or an alkyl or acyl group of 1 to 7 carbon atoms, (j) —CN, or (k) an amidino group of the formula wherein R$^{15}$, R$^{16}$ and R$^{17}$ are each, independently, a hydrogen atom or alkyl of 1 to 3 carbon atoms and wherein two of R$^{15}$, R$^{16}$ and R$^{17}$ may additionally constitute a saturated hydrocarbon bridge of 3 to 5 carbon atoms which together with the nitrogen atom(s) between them form a heterocyclic ring, (l) a group of the formula —NHCONHalkyl, wherein the alkyl moiety contains 1 to 3 carbon atoms, (m) a group of the formula —NHCOOalkyl, wherein the alkyl moiety contains 1 to 3 carbon atoms,
(iii) a group of the formula —COOR$^{18}$, wherein R$^{18}$ is straight or branched alkyl of 1 to 7 carbon atoms or cycloalkyl of 3 to 6 carbon atoms,
(iv) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(v) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH$_2$, —NHMe and —NMe$_2$,
(vi) a group of the formula —NR$^{23}$R$^{24}$, wherein R$^{23}$ and R$^{24}$ are each, independently,
  (a) a hydrogen atom,
  (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
  (c) a group of the formula —(CH$_2$)$_m$COOH, wherein m is 0, 1 or 2,
  (d) a group of the formula —(CH$_2$)$_n$COOR$^{25}$, wherein n is 0, 1 or 2, and wherein R$^{25}$ is straight or branched alkyl of 1 to 6 carbon atoms, or
  (e) a group of the formula —(CH$_2$)$_n$CONHR$^{25}$, wherein n is 0, 1 or 2, and wherein R$^{25}$ is straight or branched alkyl of 1 to 6 carbon atoms,
(vii) a quaternary group of the formula

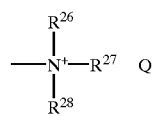

wherein R$^{26}$, R$^{27}$ and R$^{28}$ are each, independently, a branched or unbranched alkyl group of 1 to 7 carbon atoms and Q— is a pharmaceutically acceptable counter ion, or
(viii) a cycloalkyl group of 3 to 7 carbon atoms,
(B) branched or unbranched carboxylic acid groups of 3 to 6 carbon atoms,
(C) branched or unbranched phosphonic acid groups of 2 to 6 carbon atoms,
(D) branched or unbranched sulfonic acid groups of 2 to 6 carbon atoms, (E) amidino groups of the formula

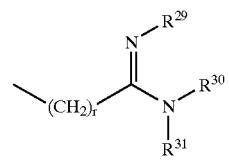

wherein r is 2, 3, 4, 5 or 6, and R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring,
(F) guanidino groups of the formula

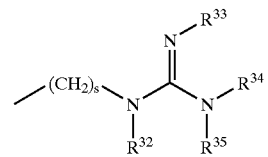

wherein s is 2, 3, 4, 5 or 6, and R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring,
(G) phenyl, wherein one or more hydrogen atoms of said phenyl group are optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein R$^{36}$ is straight or branched alkyl of 1 to 5 carbon atoms or cycloalkyl of 3 to 5 carbon atoms,
  (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
  (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (viii) a group of the formula —OR$^{41}$, wherein R$^{41}$ is a hydrogen atom, or an alkyl or acyl group of 1 to 7 carbon atoms,
  (ix) a group of the formula —SR$^{42}$, wherein R$^{42}$ is a hydrogen atom, or an alkyl or acyl group of 1 to 7 carbon atoms, (x) —CN, or
(xi) an amidino group of the formula

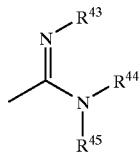

wherein $R^{43}$, $R^{44}$ and $R^{45}$ are each, independently, a hydrogen atom or alkyl of 1 to 3 carbon atoms, and wherein two of $R^{43}$, $R^{44}$ and $R^{45}$ may additionally constitute a saturated hydrocarbon bridge of 3 to 5 carbon atoms which together with the nitrogen atom(s) between them form a heterocyclic ring, (H) groups of the formula —$NR^{46}R^{47}$, wherein $R^{46}$ and $R^{47}$ are each independently a hydrogen atom, phenyl which is optionally mono-or polysubstituted with halogen, or $R^{100b}$, wherein $R^{100b}$ is as hereinbefore defined, (I) saturated or unsaturated heterocyclic groups selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally mono- or poly-substituted with moieties independently selected from the class consisting of:
  (i) oxo,
  (ii) —$OR^{101}$, wherein $R^{101}$ is:
    (a) a hydrogen atom,
    (b) alkyl of 1 to 7 carbons, wherein any hydrogen atom of said alkyl group is optionally replaced with —OH, —$OR^{110}$ (wherein $R^{110}$ is an alkyl moiety of 1 to 6 carbon atoms), —$NH_2$, —NHMe or —$NMe_2$,
    (c) acyl of 1 to 7 carbons, wherein any hydrogen atom of said acyl group is optionally replaced with —OH, —$OR^{111}$ (wherein $R^{111}$ is an alkyl moiety of 1 to 6 carbon atoms), —$NH_2$, —NHMe or —$NMe_2$,
    (d) —$CONR^{102}R^{103}$, wherein $R^{102}$ and $R^{103}$ are each independently a hydrogen atom or alkyl of 1 to 7 atoms, or wherein $R^{102}$ and $R^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
    (e) —$COOR^{104}$, wherein $R^{104}$ is alkyl of 1 to 7 atoms,
  (iii) —$CONR^{105}R^{106}$, wherein $R^{105}$ and $R^{106}$ are each independently:
    (a) a hydrogen atom,
    (b) straight or branched alkyl of 1 to 7 atoms or cycloalkyl of 3 to 7 atoms,
    (c) benzoyl,
    (d) benzyl or
    (e) phenyl, wherein said phenyl ring is optionally mono- or polysubstituted with —$OR^{112}$, wherein $R^{112}$ is alkyl of 1 to 6 carbon atoms,
  or, wherein $R^{105}$ and $R^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (iv) —$COOR^{107}$, wherein $R^{107}$ is a hydrogen atom, or straight or branched alkyl of 1 to 7 carbon atoms,
  (v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of
    (a) oxo,
    (b) —OH,
    (c) $OR^{113}$, wherein $R^{113}$ is alkyl of 1 to 6 carbon atoms,
    (d) —$OCOCH_3$,
    (e) —$NH_2$,
    (f) —NHMe,
    (g) —$NMe_2$,
    (h) —$CO_2H$, and
    (i) —$CO_2R^{114}$ wherein $R^{114}$ is alkyl of 1 to 3 carbon atoms, or cycloalkyl of 3 to 7 carbons,
  (vi) acyl of 1 to 7 carbon atoms, which may be straight, branched or cyclic, and wherein one or more hydrogen atoms of said acyl group is optionally replaced with a moiety independently selected from the class consisting of:
    (a) —OH,
    (b) —$OR^{115}$, wherein $R^{115}$ is alkyl of 1 to 6 carbon atoms,
    (c) —$NH_2$,
    (d) —NHMe,
    (e) —$NMe_2$,
    (f) —NHCOMe,
    (g) oxo,
    (h) —$CO_2R^{116}$, wherein $R^{116}$ is alkyl of 1 to 3 carbon atoms,
    (i) —CN,
    (j) the halogen atoms,
    (k) heterocycles selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, and
    (l) aryl or heteroaryl selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl,
  (vii) —$SO_2R^{108}$, wherein $R^{108}$ is:
    (a) aryl or heteroaryl which is selected from the group consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b] thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —OR$^{117}$ (wherein R$^{117}$ is hydrogen or alkyl of 1 to 6 carbon atoms),
- (b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclic group is optionally substituted with one or more moieties selected from the class consisting of the halogen atoms, straight or branched alkyl of 1 to 6 carbons, and —OR$^{118}$ (wherein R$^{118}$ is hydrogen or alkyl of 1 to 6 carbon atoms), or
- (c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{119}$ (wherein R$^{119}$ is hydrogen or alkyl of 1 to 6 carbon atoms), (viii) —COR$^{109}$, wherein R$^{109}$ is:
- (a) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, wherein said aryl or heteroaryl moiety is optionally substituted with one or more moieties selected from the class consisting of the halogen atoms, straight or branched alkyl of 1 to 6 carbons, and —OR$^{120}$ (wherein R$^{120}$ is hydrogen or alkyl of 1 to 6 carbon atoms),
- (b) a heterocyclic group selected from the class consisting of imidazolinyl, imidazolidinyl, pyrrolinyl, pyrrolidinyl, piperidinyl, piperazinyl, morpholinyl, thiomorpholinyl, thiazolidinyl, azepinyl, tetrahydropyranyl, tetrahydrofuranyl, benzodioxolyl, tetrahydrothiophenyl and sulfolanyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or
- (c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{122}$ (wherein R$^{122}$ is hydrogen or alkyl of 1 to 6 carbon atoms), (ix) —CHO,
(x) the halogen atoms, and
(xi) aryl or heteroaryl which is selected from the class consisting of phenyl, naphthyl, indolyl, thiophenyl, pyridyl, pyrimidinyl, furyl, pyrrolyl, oxazolyl, thiazolyl, pyrazolyl, isoxazolyl, imidazolyl, isothiazolyl, oxadiazolyl, triazolyl, thiadiazolyl, pyridazinyl, pyrazinyl, triazinyl, indolyzinyl, isoindolyl, benzo[b]furanyl, benzo[b]thiophenyl, indazolyl, benzthiazolyl, benzimidazolyl, quinolinyl, isoquinolinyl, purinyl, quinolizinyl, cinnolinyl, pthalaninyl, quinoxalinyl, napthyridinyl, pteridinyl and quinazolinyl, (J) the halogen atoms, and
(K) —CN;

X is an oxygen atom;
R$^3$ is branched or unbranched alkyl of 1 to 3 carbon atoms;
R$^4$ is a group of the formula —CH$_2$R$^{55}$, wherein,
  R$^{55}$ is:
    aryl or heteroaryl which is selected from the class consisting of phenyl, pyridyl, and pyrimidinyl, wherein one or more of the hydrogen atoms of said aryl or heteroaryl group is optionally and independently replaced with:
    - (A) R$^{59b}$, which is aryl or heteroaryl selected from the class consisting of phenyl, thiophenyl, pyridyl, pyrimidinyl, furyl, pyrrolyl, oxazolyl, and thiazolyl, wherein one of the hydrogen atoms of said aryl or heteroaryl group is optionally replaced with:
      - (i) branched or unbranched alkyl of 1 to 6 carbon atoms or cycloalkyl of 3 to 6 carbon atoms, which alkyl or cycloakyl group is optionally mono- or polysubstituted with halogen or oxo,
      - (ii) —CN,
      - (iii) nitro, or
      - (iv) halogen,
    - (B) methyl, which is optionally trisubstituted with fluorine atoms or is optionally monosubstituted with R$^{59b}$,
    - (C) branched or unbranched alkyl of 2 to 6 carbon atoms or cycloalkyl of 3 to 6 carbon atoms, which alkyl or cycloakyl group is optionally monosubstituted with halogen or oxo,
    - (D) a group of the formula —COOR$^{67}$, wherein R$^{67}$ is straight or branched alkyl of 1 to 5 carbon atoms or cycloalkyl of 3 to 5 carbon atoms,
    - (E) a group of the formula —COR$^{72}$, wherein R$^{72}$ is a hydrogen atom, straight or branched alkyl of 1 to 5 carbon atoms, cycloalkyl of 3 to 5 carbon atoms or R$^{59b}$,
    - (F) a group of the formula —OR$^{73}$, wherein R$^{73}$ is a hydrogen atom, an alkyl, fluoroalkyl or acyl group of 1 to 7 carbon atoms, or R$^{59b}$,
    - (G) —CN,
    - (H) nitro, or
    - (I) halogen;

R$^5$ is Cl;
Z is =C(H)—; and,
R$^7$ is Cl;
and pharmaceutically acceptable salts thereof Even more preferred are compounds of the formula I, wherein:
A$^1$ is =N—;
A$^2$ is =C(H)—;
D is =C(R$^1$)—, =C(H)—, =C(SO$_2$R$^1$)—, =C(C(O)H)— or =C(C(O)R$^1$)—, wherein R$^1$ is selected from the class consisting of:
- (A) —R$^{100c}$, which is:
    branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
(i) oxo,
(ii) phenyl, wherein one hydrogen atom of said phenyl group is optionally replaced with:
   (a) alkyl of 1 to 3 carbon atoms,
   (b) —COOH,
   (c) —SO$_2$OH,
   (d) —PO(OH)$_2$,
   (e) a group of the formula —COOR$^8$, wherein R$^8$ is straight or branched alkyl of 1 to 5 carbon atoms or cycloalkyl of 3 to 5 carbon atoms,
   (f) a group of the formula —NR$^9$R$^{10}$, wherein R$^9$ and R$^{10}$ are each independently a hydrogen atom, alkyl of 1 to 6 carbon atoms, cycloalkyl of 3 to 6 carbon atoms or acyl of 1 to 7 carbon atoms, or wherein R$^9$ and R$^{10}$ constitute a saturated hydrocarbon bridge of 3 to 5 carbon atoms which together with the nitrogen atom between them form a heterocyclic ring,
   (g) a group of the formula —CONR$^{11}$R$^{12}$, wherein R$^{11}$ and R$^{12}$ are each independently a hydrogen atom, alkyl of 1 to 6 carbon atoms or cycloalkyl of 3 to 6 carbon atoms, or wherein R$^{11}$ and R$^{12}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
   (h) a group of the formula —OR$^{13}$, wherein R$^{13}$ is a hydrogen atom, or an alkyl or acyl group of 1 to 7 carbon atoms,
   (i) a group of the formula —SR$^{14}$, wherein R$^{14}$ is a hydrogen atom, or an alkyl or acyl group of 1 to 7 carbon atoms,
   (j) —CN, or
   (k) an amidino group of the formula

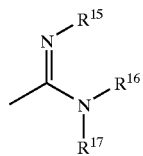

wherein R$^{15}$, R$^{16}$ and R$^{17}$ are each, independently, a hydrogen atom or alkyl of 1 to 3 carbon atoms and wherein two of R$^{15}$, R$^{16}$ and R$^{17}$ may additionally constitute a saturated hydrocarbon bridge of 3 to 5 carbon atoms which together with the nitrogen atom(s) between them form a heterocyclic ring,
   (l) a group of the formula —NHCONHalkyl, wherein the alkyl moiety contains 1 to 3 carbon atoms,
   (m) a group of the formula —NHCOOalkyl, wherein the alkyl moiety contains 1 to 3 carbon atoms,
(iii) a group of the formula —COOR$^{18}$, wherein R$^{18}$ is straight or branched alkyl of 1 to 7 carbon atoms or cycloalkyl of 3 to 6 carbon atoms,
(iv) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(v) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH$_2$, —NHMe and —NMe$_2$,
(vi) a group of the formula —NR$^{23}$R$^{24}$, wherein R$^{23}$ and R$^{24}$ are each, independently,
   (a) a hydrogen atom,
   (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
   (c) a group of the formula —(CH$_2$)$_m$COOH, wherein m is 0, 1 or 2,
   (d) a group of the formula —(CH$_2$)$_n$COOR$^{25}$, wherein n is 0, 1 or 2, and wherein R$^{25}$ is straight or branched alkyl of 1 to 6 carbon atoms, or
   (e) a group of the formula —(CH$_2$)$_n$CONHR$^{25}$, wherein n is 0, 1 or 2, and wherein R$^{25}$ is straight or branched alkyl of 1 to 6 carbon atoms,
(vii) a quaternary group of the formula

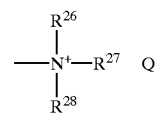

wherein R$^{26}$, R$^{27}$ and R$^{28}$ are each, independently, a branched or unbranched alkyl group of 1 to 7 carbon atoms and Q— is a pharmaceutically acceptable counter ion, or
(viii) a cycloalkyl group of 3 to 7 carbon atoms,
(B) branched or unbranched carboxylic acid groups of 3 to 6 carbon atoms,
(C) branched or unbranched phosphonic acid groups of 2 to 6 carbon atoms,
(D) branched or unbranched sulfonic acid groups of 2 to 6 carbon atoms,
(E) amidino groups of the formula

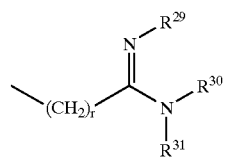

wherein r is 2, 3, 4, 5 or 6, and R$^{29}$, R$^{30}$ and R$^{31}$ are each, independently, a hydrogen atom or alkyl of 1 to 3 carbon atoms, and wherein two of $R^{29}$, $R^{30}$ and $R^{31}$ may additionally constitute a saturated hydrocarbon bridge of 3 to 5 carbon atoms which together with the nitrogen atom(s) between them form a heterocyclic ring, (F) guanidino groups of the formula

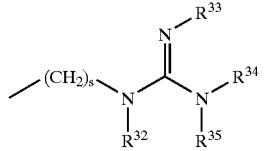

wherein s is 2, 3, 4, 5 or 6, and $R^{32}$, $R^{33}$, $R^{34}$ and $R^{35}$ are each, independently, a hydrogen atom or alkyl of 1 to 3 carbon atoms, and wherein two of $R^{32}$, $R^{33}$, $R^{34}$ and $R^{35}$ may additionally constitute a saturated hydrocarbon bridge of 3 to 5 carbon atoms which together with the nitrogen atom(s) between them form a heterocyclic ring, (G) phenyl, wherein one or more hydrogen atoms of said phenyl group are optionally and independently replaced with:
  (i) alkyl of 1 to 3 carbon atoms,
  (ii) —COOH,
  (iii) —SO$_2$OH,
  (iv) —PO(OH)$_2$,
  (v) a group of the formula —COOR$^{36}$, wherein R$^{36}$ is straight or branched alkyl of 1 to 5 carbon atoms or cycloalkyl of 3 to 5 carbon atoms,
  (vi) a group of the formula —NR$^{37}$R$^{38}$, wherein R$^{37}$ and R$^{38}$ are each, independently, a hydrogen atom, alkyl of 1 to 6 carbon atoms, cycloalkyl of 3 to 6 carbon atoms or acyl of 1 to 7 carbon atoms, or wherein R$^{37}$ and R$^{38}$ constitute a saturated hydrocarbon bridge of 3 to 5 carbon atoms which together with the nitrogen atom between them form a heterocyclic ring,
  (vii) a group of the formula —CONR$^{39}$R$^{40}$, wherein R$^{39}$ and R$^{40}$ are each, independently, a hydrogen atom, alkyl of 1 to 6 carbon atoms or cycloalkyl of 3 to 6 carbon atoms, or wherein R$^{39}$ and R$^{40}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (viii) a group of the formula —OR$^{41}$, wherein R$^{41}$ is a hydrogen atom, or an alkyl or acyl group of 1 to 7 carbon atoms,
  (ix) a group of the formula —SR$^{42}$, wherein R$^{42}$ is a hydrogen atom, or an alkyl or acyl group of 1 to 7 carbon atoms,
  (x) —CN, or
  (xi) an amidino group of the formula

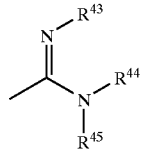

wherein $R^{43}$, $R^{44}$ and $R^{45}$ are each, independently, a hydrogen atom or alkyl of 1 to 3 carbon atoms, and wherein two of $R^{43}$, $R^{44}$ and $R^{45}$ may additionally constitute a saturated hydrocarbon bridge of 3 to 5 carbon atoms which together with the nitrogen atom(s) between them form a heterocyclic ring, (H) groups of the formula —NR$^{46}$R$^{47}$, wherein R$^{46}$ and R$^{47}$ are each independently a hydrogen atom, phenyl which is optionally monosubstituted with halogen, or R$^{100c}$, wherein R$^{100c}$ is as hereinbefore defined, (I) saturated or unsaturated heterocyclic groups selected from the class consisting of pyrrolinyl, pyrrolidinyl, piperidinyl, piperazinyl, morpholinyl and thiomorpholinyl, wherein said heterocyclic groups are optionally mono- or poly-substituted with moieties independently selected from the class consisting of:
  (i) oxo,
  (ii) —OR$^{101}$, wherein R$^{101}$ is:
    (a) a hydrogen atom,
    (b) alkyl of 1 to 7 carbons, wherein any hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
    (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
    (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
    (e) —COOR$^{104}$, wherein R$^{104}$ is alkyl of 1 to 7 atoms,
  (iii) —CONR$^{105}$R$^{106}$, wherein R$^{105}$ and R$^{106}$ are each independently:
    (a) a hydrogen atom,
    (b) straight or branched alkyl of 1 to 7 atoms or cycloalkyl of 3 to 7 atoms,
    (c) benzoyl,
    (d) benzyl or
    (e) phenyl, wherein said phenyl ring is optionally mono- or polysubstituted with —OR$^{112}$, wherein R$^{112}$ is alkyl of 1 to 6 carbon atoms,
    or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (iv) —COOR$^{107}$, wherein R$^{107}$ is a hydrogen atom, or straight or branched alkyl of 1 to 7 carbon atoms,
  (v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of:
    (a) oxo,
    (b) —OH,
    (c) —OR$^{113}$, wherein R$^{113}$ is alkyl of 1 to 6 carbon atoms,
    (d) —OCOCH$_3$, (e) —NH$_2$,
(f) —NHMe,
(g) —NMe$_2$,
(h) —CO$_2$H, and
(i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which may be straight, branched or cyclic, and wherein one or more hydrogen atoms of said acyl group is optionally replaced with a moiety independently selected from the class consisting of:
(a) —OH,
(b) —OR$^{115}$, wherein R$^{115}$ is alkyl of 1 to 6 carbon atoms,
(c) —NH$_2$,
(d) —NHMe,
(e) —NMe$_2$,
(f) —NHCOMe,
(g) oxo,
(h) —CO$_2$R$^{116}$, wherein R$^{116}$ is alkyl of 1 to 3 carbon atoms,
(i) —CN,
(j) the halogen atoms,
(k) heterocycles selected from the class consisting of pyrrolidinyl, piperidinyl, piperazinyl, morpholinyl and thiomorpholinyl, and
(l) aryl or heteroaryl selected from the class consisting of phenyl, thiophenyl, pyridyl, pyrimidinyl, furyl, pyrrolyl and oxazolyl,
(vii) —SO$_2$R$^{108}$, wherein R$^{108}$ is:
(a) aryl or heteroaryl which is selected from the group consisting of phenyl, thiophenyl, pyridyl, pyrimidinyl, furyl, pyrrolyl, oxazolyl thiazolyl and pyrazolyl, wherein said aryl or heteroaryl moiety is optionally substituted with one or more moieties selected from the class consisting of the halogen atoms, straight or branched alkyl of 1 to 6 carbons, and —OR$^{117}$ (wherein R$^{117}$ is hydrogen or alkyl of 1 to 6 carbon atoms),
(b) a heterocyclic group selected from the class consisting of pyrrolidinyl, piperidinyl, piperazinyl, morpholinyl and thiomorpholinyl, wherein said heterocyclic group is optionally substituted with one or more moieties selected from the class consisting of the halogen atoms, straight or branched alkyl of 1 to 6 carbons, and —OR$^{118}$ (wherein R$^{118}$ is hydrogen or alkyl of 1 to 6 carbon atoms), or
(c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{119}$ (wherein R$^{119}$ is hydrogen or alkyl of 1 to 6 carbon atoms),
(viii) —COR$^{109}$, wherein R$^{109}$ is:
(a) aryl or heteroaryl which is selected from the class consisting of phenyl, thiophenyl, pyridyl, pyrimidinyl, furyl, pyrrolyl, oxazolyl, thiazolyl and pyrazolyl, wherein said aryl or heteroaryl moiety is optionally substituted with one or more moieties selected from the class consisting of the halogen atoms, straight or branched alkyl of 1 to 6 carbons, and —OR$^{120}$ (wherein R$^{120}$ is hydrogen or alkyl of 1 to 6 carbon atoms),
(b) a heterocyclic group selected from the class consisting of pyrrolidinyl, piperidinyl, piperazinyl, morpholinyl and thiomorpholinyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or (c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{122}$ (wherein R$^{122}$ is hydrogen or alkyl of 1 to 6 carbon atoms),
(ix) —CHO,
(x) the halogen atoms, and
(xi) aryl or heteroaryl which is selected from the class consisting of phenyl, thiophenyl, pyridyl, pyrimidinyl, furyl, pyrrolyl, oxazolyl, thiazolyl, pyrazolyl, isoxazolyl and imidazolyl,
(J) the halogen atoms, and
(K) —CN;
X is an oxygen atom;
R$^3$ is branched or unbranched alkyl of 1 to 3 carbon atoms;
R$^4$ is a group of the formula —CH$_2$R$^{55}$, wherein,
R$^{55}$ is:
phenyl, which is optionally substituted at the 4-position with:
(A) R$^{59c}$, which is aryl or heteroaryl selected from the class consisting of phenyl, thiophenyl, pyridyl, pyrimidinyl and furyl, wherein one of the hydrogen atoms of said aryl or heteroaryl group is optionally replaced with:
(i) branched or unbranched alkyl of 1 to 6 carbon atoms or cycloalkyl of 3 to 6 carbon atoms, which alkyl or cycloakyl group is optionally mono- or polysubstituted with halogen or oxo,
(ii) —CN,
(iii) nitro, or
(iv) halogen,
(B) methyl,
(C) branched or unbranched alkyl of 2 to 6 carbon atoms or cycloalkyl of 3 to 6 carbon atoms, which alkyl or cycloakyl group is optionally monosubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —COR$^{72}$, wherein R$^{72}$ is a hydrogen atom, straight or branched alkyl of 1 to 5 carbon atoms, or cycloalkyl of 3 to 5 carbon atoms,
(F) a group of the formula —OR$^{73}$, wherein R$^{73}$ is a hydrogen atom, an alkyl, or fluoroalkyl or acyl group of 1 to 7 carbon atoms,
(G) —CN,
(H) nitro, or
(I) halogen;
R$^5$ is Cl;
Z is =C(H)—; and,
R$^7$ is Cl;
and pharmaceutically acceptable salts thereof.
Further preferred are compounds of the formula I wherein:
A$^1$ is =N—;
A$^2$ is =C(H)—;
D is =C(H)—, =C(SO$_2$R$^1$)— or =C(C(O)R$^1$)—, wherein R$^1$ is selected from the class consisting of:
(A) —R$^{100d}$, which is:
branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
(i) oxo,
(ii) a group of the formula —COOR$^{18}$, wherein R$^{18}$ is straight or branched alkyl of 1 to 7 carbon atoms or cycloalkyl of 3 to 6 carbon atoms,
(iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH$_2$, —NHMe and —NMe$_2$,
(v) a group of the formula —NR$^{23}$R$^{24}$, wherein R$^{23}$ and R$^{24}$ are each, independently,
  (a) a hydrogen atom,
  (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
  (c) a group of the formula —(CH$_2$)$_m$COOH, wherein m is 0, 1 or 2,
  (d) a group of the formula —(CH$_2$)$_n$COOR$^{25}$, wherein n is 0, 1 or 2, and wherein R$^{25}$ is straight or branched alkyl of 1 to 6 carbon atoms, or
  (e) a group of the formula —(CH$_2$)$_n$CONHR$^{25}$, wherein n is 0, 1 or 2, and wherein R$^{25}$ is straight or branched alkyl of 1 to 6 carbon atoms,
(vi) a quaternary group of the formula

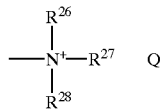

wherein R$^{26}$, R$^{27}$ and R$^{28}$ are each, independently, a branched or unbranched alkyl group of 1 to 7 carbon atoms and Q— is a pharmaceutically acceptable counter ion, or
(vii) a cycloalkyl group of 3 to 7 carbon atoms,
(B) branched or unbranched carboxylic acid groups of 3 to 6 carbon atoms,
(C) branched or unbranched phosphonic acid groups of 2 to 6 carbon atoms,
(D) branched or unbranched sulfonic acid groups of 2 to 6 carbon atoms, (E) amidino groups of the formula

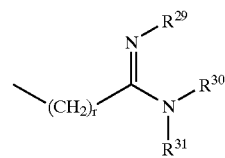

wherein r is 2, 3, 4, 5 or 6, and R$^{29}$, R$^{30}$ and R$^{31}$ are each, independently, a hydrogen atom or alkyl of 1 to 3 carbon atoms, and wherein two of R$^{29}$, R$^{30}$ and R$^{31}$ may additionally constitute a saturated hydrocarbon bridge of 3 to 5 carbon atoms which together with the nitrogen atom(s) between them form a heterocyclic ring, (F) guanidino groups of the formula

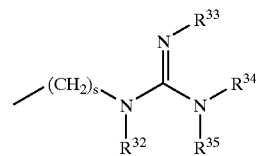

wherein s is 2, 3, 4, 5 or 6, and R$^{32}$, R$^{33}$, R$^{34}$ and R$^{35}$ are each, independently, a hydrogen atom or alkyl of 1 to 3 carbon atoms, and wherein two of R$^{32}$, R$^{33}$, R$^{34}$ and R$^{35}$ may additionally constitute a saturated hydrocarbon bridge of 3 to 5 carbon atoms which together with the nitrogen atom(s) between them form a heterocyclic ring, (G) groups of the formula —NR$^{46}$R$^{47}$, wherein R$^{46}$ and R$^{47}$ are each independently a hydrogen atom, phenyl which is optionally monosubstituted with halogen, or R$^{100d}$, wherein R$^{100d}$ is as hereinbefore defined, (H) saturated or unsaturated heterocyclic groups selected from the class consisting of pyrrolinyl, pyrrolidinyl, piperidinyl, piperazinyl, morpholinyl and thiomorpholinyl, wherein said heterocyclic groups are optionally mono- or poly-substituted with moieties independently selected from the class consisting of:
  (i) oxo,
  (ii) —OR$^{101}$, wherein R$^{101}$ is:
    (a) a hydrogen atom,
    (b) alkyl of 1 to 7 carbons, wherein any hydrogen atom of said alkyl group is optionally replaced with —OH, —OR$^{110}$ (wherein R$^{101}$ is an alkyl moiety of 1 to 6 carbon atoms), —NH$_2$, —NHMe or —NMe$_2$,
    (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
    (d) —CONR$^{102}$R$^{103}$, wherein R$^{102}$ and R$^{103}$ are each independently a hydrogen atom or alkyl of 1 to 7 atoms , or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
    (e) —COOR$^{104}$, wherein R$^{104}$ is alkyl of 1 to 7 atoms, (iii) —CONR$^{105}$R$^{106}$, wherein R$^{105}$ and R$^{106}$ are each independently:
  (a) a hydrogen atom,
  (b) straight or branched alkyl of 1 to 7 atoms or cycloalkyl of 3 to 7 atoms,
  (c) benzoyl,
  (d) benzyl or
  (e) phenyl, wherein said phenyl ring is optionally mono- or polysubstituted with —OR$^{112}$, wherein R$^{112}$ is alkyl of 1 to 6 carbon atoms,
  or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) —COOR$^{107}$, wherein R$^{107}$ is a hydrogen atom, or straight or branched alkyl of 1 to 7 carbon atoms,
(v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of:
  (a) oxo,
  (b) —OH,
  (c) —ORI 13, wherein R$^{113}$ is alkyl of 1 to 6 carbon atoms,
  (d) —OCOCH$_3$,
  (e) —NH$_2$,
  (f) —NHMe,
  (g) —NMe$_2$,
  (h) —CO$_2$H, and
  (i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which may be straight, branched or cyclic, and wherein one or more hydrogen atoms of said acyl group is optionally replaced with a moiety independently selected from the class consisting of:
  (a) —OH,
  (b) —OR$^{115}$, wherein R$^{115}$ is alkyl of 1 to 6 carbon atoms,
  (c) —NH$_2$,
  (d) —NHMe,
  (e) —NMe$_2$,
  (f) —NHCOMe,
  (g) oxo,
  (h) —CO$_2$ R$^{116}$, wherein R$^{116}$ is alkyl of 1 to 3 carbon atoms,
  (i) —CN,
  (j) the halogen atoms,
  (k) heterocycles selected from the class consisting of pyrrolidinyl, piperidinyl, piperazinyl, morpholinyl and thiomorpholinyl, and
  (l) aryl or heteroaryl selected from the class consisting of phenyl, thiophenyl, pyridyl, pyrimidinyl, furyl, pyrrolyl and oxazolyl,
(vii) —SO$_2$R$^{108}$, wherein R$^{108}$ is:
  (a) aryl or heteroaryl which is selected from the group consisting of phenyl, thiophenyl, pyridyl, pyrimidinyl, furyl, pyrrolyl, oxazolyl thiazolyl and pyrazolyl, wherein said aryl or heteroaryl moiety is optionally substituted with one or more moieties selected from the class consisting of the halogen atoms, straight or branched alkyl of 1 to 6 carbons, and —OR$^{117}$ (wherein R$^{117}$ is hydrogen or alkyl of 1 to 6 carbon atoms),
  (b) a heterocyclic group selected from the class consisting of pyrrolidinyl, piperidinyl, piperazinyl, morpholinyl and thiomorpholinyl, wherein said heterocyclic group is optionally substituted with one or more moieties selected from the class consisting of the halogen atoms, straight or branched alkyl of 1 to 6 carbons, and —OR$^{118}$ (wherein R$^{118}$ is hydrogen or alkyl of 1 to 6 carbon atoms), or
  (c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{119}$ (wherein R$^{119}$ is hydrogen or alkyl of 1 to 6 carbon atoms),
(viii) —COR$^{109}$, wherein R$^{109}$ is:
  (a) aryl or heteroaryl which is selected from the class consisting of phenyl, thiophenyl, pyridyl, pyrimidinyl, furyl, pyrrolyl, oxazolyl, thiazolyl and pyrazolyl, wherein said aryl or heteroaryl moiety is optionally substituted with one or more moieties selected from the class consisting of the halogen atoms, straight or branched alkyl of 1 to 6 carbons, and —OR$^{120}$ (wherein R$^{120}$ is hydrogen or alkyl of 1 to 6 carbon atoms),
  (b) a heterocyclic group selected from the class consisting of pyrrolidinyl, piperidinyl, piperazinyl, morpholinyl and thiomorpholinyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or
  (c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{122}$ (wherein R$^{122}$ is hydrogen or alkyl of 1 to 6 carbon atoms),
(ix) —CHO,
(x) the halogen atoms, and
(xi) aryl or heteroaryl which is selected from the class consisting of phenyl, thiophenyl, pyridyl, pyrimidinyl, furyl, pyrrolyl, oxazolyl, thiazolyl, pyrazolyl, isoxazolyl and imidazolyl, and
(I) the halogen atoms,
X is an oxygen atom;
R$^3$ is branched or unbranched alkyl of 1 to 3 carbon atoms;
R$^4$ is a group of the formula —CH$_2$R$^{55}$, wherein,
R$^{55}$ is:
  phenyl, which is optionally substituted at the 4-position with:
    (A) R$^{59d}$, which is aryl or heteroaryl selected from the class consisting of phenyl, thiophenyl, pyridyl, pyrimidinyl and furyl, wherein one of the hydrogen atoms of said aryl or heteroaryl group is optionally replaced with:
      (i) branched or unbranched alkyl of 1 to 6 carbon atoms or cycloalkyl of 3 to 6 carbon atoms, which alkyl or cycloakyl group is optionally mono- or polysubstituted with halogen or oxo,
      (ii) —CN,
      (iii) nitro, or
      (iv) halogen, (B) methyl,
(C) branched or unbranched alkyl of 2 to 6 carbon atoms or cycloalkyl of 3 to 6 carbon atoms, which alkyl or cycloakyl group is optionally monosubstituted with halogen or oxo,
(D) a group of the formula —COOR$^{67}$, wherein R$^{67}$ is straight or branched alkyl of 1 to 5 carbon atoms or cycloalkyl of 3 to 5 carbon atoms,
(E) a group of the formula —COR$^{72}$, wherein R$^{72}$ is a hydrogen atom, straight or branched alkyl of 1 to 5 carbon atoms, or cycloalkyl of 3 to 5 carbon atoms,
(F) a group of the formula —OR$^{73}$, wherein R$^{73}$ is a hydrogen atom, an alkyl, or fluoroalkyl or acyl group of 1 to 7 carbon atoms,
(G) —CN,
(H) nitro, or
(I) halogen;

R$^5$ is Cl;
Z is =C(H)—; and,
R$^7$ is Cl;
and pharmaceutically acceptable salts thereof Especially preferred are compounds of the formula I wherein:
A$^1$ is=N—,
A$^2$ is =C(H)—;
D is =C(SO$_2$R$^1$)— or =C(C(O)R$^1$)—, wherein R$^1$ is selected from the class consisting of
(A) —R$^{100e}$, which is:
  branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
  (i) oxo,
  (ii) a group of the formula —COOR$^{18}$, wherein R$^{18}$ is straight or branched alkyl of 1 to 7 carbon atoms or cycloalkyl of 3 to 6 carbon atoms,
  (iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (iv) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the class consisting of —OH, —Oalkyl (wherein the alkyl moiety contains 1 to 6 carbon atoms), —NH$_2$, —NHMe and —NMe$_2$, or
  (v) a group of the formula —NR$^{23}$R$^{24}$, wherein R$^{23}$ and R$^{24}$ are each, independently,
    (a) a hydrogen atom,
    (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the class consisting of —OH, —Oalkyl (wherein the alkyl moiety is 1 to 6 carbon atoms), —NH$_2$, —NHMe and —NMe$_2$,
    (c) a group of the formula —(CH$_2$)$_m$COOH, wherein m is 0, 1 or 2,
    (d) a group of the formula —(CH$_2$)$_n$COOR$^{25}$, wherein n is 0, 1 or 2, and wherein R$^{25}$ is straight or branched alkyl of 1 to 6 carbon atoms, or
    (e) a group of the formula —(CH$_2$)$_n$CONHR$^{25}$, wherein n is 0, 1 or 2, and wherein R$^{25}$ is straight or branched alkyl of 1 to 6 carbon atoms,
(B) groups of the formula —NR$^{46}$R$^{47}$, wherein R$^{46}$ and R$^{47}$ are each independently a hydrogen atom, phenyl which is optionally monosubstituted with halogen, or R$^{100e}$, wherein R$^{100e}$ is as hereinbefore defined, and
(C) saturated or unsaturated heterocyclic groups selected from the class consisting of pyrrolinyl, pyrrolidinyl, piperidinyl, piperazinyl, morpholinyl and thiomorpholinyl, wherein said heterocyclic groups are optionally mono- or poly-substituted with moieties independently selected from the class consisting of:
  (i) oxo,
  (ii) —OR$^{101}$, wherein R$^{101}$ is:
    (a) a hydrogen atom,
    (b) alkyl of 1 to 7 carbons, wherein any hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
    (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
    (d) —CONR$^{102}$R$^{103}$, wherein R$^{102}$ and R$^{103}$ are each independently a hydrogen atom or alkyl of 1 to 7 atoms , or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
    (e) —COOR$^{104}$, wherein R$^{104}$ is alkyl of 1 to 7 atoms ,
  (iii) —CONR$^{105}$R$^{106}$, wherein R$^{105}$ and R$^{106}$ are each independently:
    (a) a hydrogen atom, or
    (b) straight or branched alkyl of 1 to 7 atoms or cycloalkyl of 3 to 7 atoms,
      or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (iv) —COOR$^{107}$, wherein R$^{107}$ is a hydrogen atom, or straight or branched alkyl of 1 to 7 carbon atoms,
  (v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the class consisting of:
    (a) oxo, (b) —OH,
(c) —OR$^{113}$, wherein R$^{113}$ is alkyl of 1 to 6 carbon atoms,
(d) —OCOCH$_3$,
(e) —NH$_2$,
(f) —NHMe,
(g) —NMe$_2$,
(h) —CO$_2$H, and
(i) —CO$_2$R$^{114}$ wherein R$^{114}$ is alkyl of 1 to 3 carbon atoms, or cycloalkyl of 3 to 7 carbons, (vi) acyl of 1 to 7 carbon atoms, which may be straight, branched or cyclic, and wherein one or more hydrogen atoms of said acyl group is optionally replaced with a moiety independently selected from the class consisting of:
(a) —OH,
(b) —OR$^{115}$, wherein R$^{115}$ is alkyl of 1 to 6 carbon atoms,
(c) —NH$_2$,
(d) —NHMe,
(e) —NMe$_2$,
(f) —NHCOMe,
(g) oxo,
(h) —CO$_2$R$^{116}$, wherein R$^{116}$ is alkyl of 1 to 3 carbon atoms,
(i) —CN,
(j) the halogen atoms,
(k) heterocycles selected from the class consisting of pyrrolidinyl, piperidinyl, piperazinyl, morpholinyl and thiomorpholinyl, and
(l) aryl or heteroaryl selected from the class consisting of phenyl, thiophenyl, pyridyl, pyrimidinyl, furyl, pyrrolyl and oxazolyl, (vii) —SO$_2$R$^{108}$, wherein R$^{108}$ is:
(a) phenyl, wherein said phenyl moiety is optionally substituted with one or more moieties selected from the class consisting of the halogen atoms, straight or branched alkyl of 1 to 6 carbons, and —OR$^{117}$ (wherein R$^{117}$ is hydrogen or alkyl of 1 to 6 carbon atoms),
(b) a heterocyclic group selected from the class consisting of pyrrolidinyl, piperidinyl, piperazinyl, morpholinyl and thiomorpholinyl, wherein said heterocyclic group is optionally substituted with one or more moieties selected from the class consisting of the halogen atoms, straight or branched alkyl of 1 to 6 carbons, and —OR$^{118}$ (wherein R$^{118}$ is hydrogen or alkyl of 1 to 6 carbon atoms), or
(c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{119}$ (wherein R$^{119}$ is hydrogen or alkyl of 1 to 6 carbon atoms), (viii) —COR$^{109}$, wherein R$^{109}$ is:
(a) phenyl, wherein said phenyl moiety is optionally substituted with one or more moieties selected from the class consisting of the halogen atoms, straight or branched alkyl of 1 to 6 carbons, and —OR$^{120}$ (wherein R$^{120}$ is hydrogen or alkyl of 1 to 6 carbon atoms),
(b) a heterocyclic group selected from the class consisting of pyrrolidinyl, piperidinyl, piperazinyl, morpholinyl and thiomorpholinyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or
(c) straight or branched alkyl of 1 to 7 atoms, wherein said alkyl moiety is optionally substituted with one or more moieties selected from the class consisting of the halogen atoms, straight or branched alkyl of 1 to 6 carbons, and —OR$^{122}$ (wherein R$^{122}$ is hydrogen or alkyl of 1 to 6 carbon atoms), and (ix) —CHO,
X is an oxygen atom;
R$^3$ is branched or unbranched alkyl of 1 to 3 carbon atoms;
R$^4$ is a group of the formula —CH$_2$R$^{55}$, wherein,
  R$^{55}$ is:
    phenyl, which is optionally substituted at the 4-position with:
      (A) R$^{59e}$, which is aryl or heteroaryl selected from the class consisting of phenyl, thiophenyl, pyridyl, pyrimidinyl and furyl, wherein one of the hydrogen atoms of said aryl or heteroaryl group is optionally replaced with:
        (i) methyl,
        (ii) —CN,
        (iii) nitro, or
        (iv) halogen,
      (B) methyl,
      (C) —CN,
      (D) nitro, or
      (E) halogen;
R$^5$ is Cl;
Z is =C(H)—; and,
R$^7$ is Cl;
and pharmaceutically acceptable salts thereof More especially preferred are compounds of the formula I wherein:
A$^1$ is =N—;
A$^2$ is =C(H)—;
D is =C(SO$_2$R$^1$)— or =C(C(O)R$^1$)—, wherein R$^1$ is selected from the class consisting of
  (A) —R$^{100e}$, which is:
    branched or unbranched alkyl of 1 to 6 carbon atoms or cycloalkyl of 3 to 6 carbon atoms, in which alkyl, or cycloalkyl group one to three hydrogen atoms are optionally and independently replaced with:
      (i) oxo,
      (ii) a group of the formula —COOR$^{18}$, wherein R$^{18}$ is straight or branched alkyl of 1 to 7 carbon atoms or cycloalkyl of 3 to 6 carbon atoms,
      (iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
      (iv) a group of the formula —OR$^{21}$, wherein R$^{21}$ is a hydrogen atom, or a straight or branched alkyl or acyl group of 1 to 7 carbon atoms, or
      (v) a group of the formula —NR$^{23}$R$^{24}$, wherein R$^{23}$ and R$^{24}$ are each, independently,
        (a) a hydrogen atom,
        (b) straight or branched alkyl or acyl of 1 to 7 carbon atoms or cycloalkyl of 3 to 7 carbon atoms, (c) a group of the formula —(CH$_2$)$_m$COOH, wherein m is 0, 1 or 2, (d) a group of the formula —(CH$_2$)$_n$COOR$^{25}$, wherein n is 0, 1 or 2, and wherein R$^{25}$ is straight or branched alkyl of 1 to 6 carbon atoms, or (e) a group of the formula —(CH$_2$)$_n$CONHR$^{25}$, wherein n is 0, 1 or 2, and wherein R$^{25}$ is straight or branched alkyl of 1 to 6 carbon atoms, and (B) saturated heterocyclic groups selected from the class consisting of pyrrolidinyl, piperidinyl, piperazinyl, morpholinyl and thiomorpholinyl, wherein said heterocyclic groups are optionally mono- or di-substituted with moieties independently selected from the class consisting of (i) oxo, (ii) —OR$^{101}$, wherein R$^{101}$ is:
  (a) a hydrogen atom,
  (b) alkyl of 1 to 7 carbons, wherein one hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
  (c) acyl of 1 to 7 carbons, wherein one hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
  (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
  (e) —COOR$^{104}$, wherein R$^{104}$ is alkyl of 1 to 7 atoms, (iii) —CONR$^{105}$R$^{106}$, wherein R$^{105}$ and R$^{106}$ are each independently:
  (a) a hydrogen atom, or
  (b) straight or branched alkyl of 1 to 7 atoms or cycloalkyl of 3 to 7 atoms, wherein said alkyl or cycloalkyl group is optionally monosubstituted with —OH, —OR$^{123}$ (wherein R$^{123}$ is an alkyl moiety of 1 to 6 carbon atoms), —NH$_2$, —NHMe, —NMe$_2$, pyrrolidinyl, piperidinyl, piperazinyl or morpholinyl, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, (iv) —COOR$^{107}$, wherein R$^{107}$ is a hydrogen atom, or straight or branched alkyl of 1 to 7 carbon atoms, (v) straight or branched alkyl of 1 to 7 carbon atoms or cycloalkyl of 3 to 7 carbons, wherein one to three hydrogen atoms of said alkyl or cycloalkyl group is optionally replaced with a moiety independently selected from the class consisting of:
  (a) oxo,
  (b) —OH,
  (c) —OR$^{113}$, wherein R$^{113}$ is alkyl of 1 to 6 carbon atoms,
  (d) —OCOCH$_3$,
  (e) —NH$_2$,
  (f) —NHMe,
  (g) —NMe$_2$,
  (h) —CO$_2$H, and
  (i) —CO$_2$R$^{114}$ wherein R$^{114}$ is alkyl of 1 to 3 carbon atoms, or cycloalkyl of 3 to 7 carbons, (vi) acyl of 1 to 7 carbon atoms, which may be straight, branched or cyclic, and wherein one or two hydrogen atoms of said acyl group is optionally replaced with a moiety selected from the class consisting of:
  (a) —OH,
  (b) —OR$^{115}$, wherein R$^{115}$ is alkyl of 1 to 6 carbon atoms,
  (c) —NH$_2$,
  (d) —NHMe,
  (e) —NMe$_2$,
  (f) —NHCOMe,
  (g) oxo,
  (h) —CO$_2$R$^{116}$, wherein R$^{116}$ is alkyl of 1 to 3 carbon atoms,
  (i) —CN,
  (j) the halogen atoms,
  (k) heterocycles selected from the class consisting of pyrrolidinyl, piperidinyl, piperazinyl, morpholinyl and thiomorpholinyl, and
  (l) aryl or heteroaryl selected from the class consisting of phenyl, thiophenyl, pyridyl, pyrimidinyl, furyl, pyrrolyl and oxazolyl, (vii) —SO$_2$R$^{108}$, wherein R$^{108}$ is:
  (a) phenyl, wherein said phenyl moiety is optionally substituted with one moiety selected from the class consisting of the halogen atoms, straight or branched alkyl of 1 to 6 carbons, and —OR$^{117}$ (wherein R$^{117}$ is hydrogen or alkyl of 1 to 6 carbon atoms),
  (b) a heterocyclic group selected from the class consisting of pyrrolidinyl, piperidinyl, piperazinyl, morpholinyl and thiomorpholinyl, wherein said heterocyclic group is optionally substituted with one moiety selected from the class consisting of the halogen atoms, straight or branched alkyl of 1 to 6 carbons, and —OR$^{118}$ (wherein R$^{118}$ is hydrogen or alkyl of 1 to 6 carbon atoms), or
  (c) straight or branched alkyl of 1 to 7 atoms, wherein said alkyl moiety is optionally substituted with one moiety selected from the class consisting of the halogen atoms, straight or branched alkyl of 1 to 6 carbons, and —OR$^{119}$ (wherein R$^{119}$ is hydrogen or alkyl of 1 to 6 carbon atoms), (viii) —COR$^{109}$, wherein R$^{109}$ is:
  (a) phenyl, wherein said phenyl moiety is optionally substituted with one moiety selected from the class consisting of the halogen atoms, straight or branched alkyl of 1 to 6 carbons, and —OR$^{120}$ (wherein R$^{120}$ is hydrogen or alkyl of 1 to 6 carbon atoms),
  (b) a heterocyclic group selected from the class consisting of pyrrolidinyl, piperidinyl, piperazinyl, morpholinyl and thiomorpholinyl, wherein said heterocyclyl is optionally substituted with one halogen, straight or branched alkyl of 1 to 6 carbons, or —OR$^{121}$ (wherein R$^{121}$ is hydrogen or alkyl of 1 to 6 carbon atoms), or
  (c) straight or branched alkyl of 1 to 7 atoms, wherein said alkyl moiety is optionally substituted with one moeity selected from the class consisting of the halogen atoms, straight or branched alkyl of 1 to 6 carbons, and —OR$^{122}$ (wherein R$^{122}$ is hydrogen or alkyl of 1 to 6 carbon atoms), and
(ix) —CHO;

X is an oxygen atom;

R$^3$ is branched or unbranched alkyl of 1 to 3 carbon atoms;

R$^4$ is a group of the formula —CH$_2$R$^{55}$, wherein,

R$^{55}$ is:

phenyl, which is optionally substituted at the 4-position with:
(A) R$^{59e}$, which is aryl or heteroaryl selected from the class consisting of phenyl, thiophenyl, pyridyl, pyrimidinyl and furyl, wherein one of the hydrogen atoms of said aryl or heteroaryl group is optionally replaced with:
(i) methyl,
(ii) —CN,
(iii) nitro, or
(iv) halogen,
(B) methyl,
(C) —CN,
(D) nitro, or
(E) halogen;

R$^5$ is Cl;

Z is =C(H)—; and,

R$^7$ is Cl;

and pharmaceutically acceptable salts thereof.

Penultimately preferred are compounds of formula I wherein:

A$^1$ is =N—;

A$^2$ is =C(H)—;

D is =C(SO$_2$R$^1$)—, wherein R$^1$ is selected from the class consisting of:
(A) methyl, and
(B) saturated heterocyclic groups selected from the class consisting of pyrrolidinyl, piperidinyl, piperazinyl and morpholinyl wherein said heterocyclic groups are optionally mono- or di-substituted with moieties independently selected from the class consisting of:
(i) oxo,
(ii) —OR$^{101}$, wherein R$^{101}$ is:
(a) a hydrogen atom,
(b) alkyl of 1 to 7 carbons, wherein one hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$, or
(c) acyl of 1 to 7 carbons, wherein one hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
(iii) —CONR$^{105}$R$^{106}$, wherein R$^{105}$ and R$^{106}$ are each independently:
(a) a hydrogen atom, or
(b) straight or branched alkyl of 1 to 7 atoms or cycloalkyl of 3 to 7 atoms, wherein said alkyl or cycloalkyl group is optionally monosubstituted with —OH, —OR$^{123}$ (wherein R$^{123}$ is an alkyl moiety of 1 to 6 carbon atoms), —NH$_2$, —NHMe, —NMe$_2$, pyrrolidinyl, piperidinyl, piperazinyl or morpholinyl, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) —COOR$^{107}$, wherein R$^{107}$ is a hydrogen atom, or straight or branched alkyl of 1 to 7 carbon atoms,
(v) straight or branched alkyl of 1 to 7 carbon atoms wherein one or two hydrogen atoms of said alkyl group are optionally replaced with moieties independently selected from the class consisting of:
(a) oxo,
(b) —OH,
(c) —OR$^{113}$, wherein R$^{113}$ is alkyl of 1 to 6 carbon atoms,
(d) —OCOCH$_3$,
(e) —NH$_2$,
(f) —NHMe,
(g) —NMe$_2$,
(h) —CO$_2$H, and
(i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which may be straight, branched or cyclic, and wherein one or two hydrogen atoms of said acyl group is optionally replaced with a moiety selected from the class consisting of:
(a) —OH,
(b) —OR$^{115}$, wherein R$^{115}$ is alkyl of 1 to 6 carbon atoms,
(c) —NH$_2$,
(d) —NMe,
(e) —NMe$_2$,
(f) —NHCOMe,
(g) oxo,
(h) —CO$_2$R$^{116}$, wherein R$^{116}$ is alkyl of 1 to 3 carbon atoms,
(i) —CN,
(j) the halogen atoms,
(k) heterocycles selected from the class consisting of pyrrolidinyl, piperidinyl, piperazinyl, morpholinyl and thiomorpholinyl, and
(l) aryl or heteroaryl selected from the class consisting of phenyl, thiophenyl, pyridyl, pyrimidinyl, furyl, pyrrolyl and oxazolyl,
(vii) —SO$_2$R$^{108}$, wherein R$^{108}$ is:
(a) a heterocyclic group selected from the class consisting of pyrrolidinyl, piperidinyl, piperazinyl and morpholinyl wherein said heterocyclic group is optionally substituted with one moiety selected from the class consisting of straight or branched alkyl of 1 to 6 carbons, and —OR$^{118}$ (wherein R$^{118}$ is hydrogen or alkyl of 1 to 6 carbon atoms),
(viii) —COR$^{109}$, wherein R$^{109}$ is:
(a) a heterocyclic group selected from the class consisting of pyrrolidinyl, piperidinyl, piperazinyl and morpholinyl wherein said heterocyclyl is optionally substituted with one halogen, straight or branched alkyl of 1 to 6 carbons, or —OR$^{121}$ (wherein R$^{121}$ is hydrogen or alkyl of 1 to 6 carbon atoms), and
(ix) —CHO;

X is an oxygen atom;

R$^3$ is methyl;

R$^4$ is a group of the formula —CH$_2$R$^{55}$, wherein,

R$^{55}$ is:

phenyl, which is optionally substituted at the 4-position with:
(A) R$^{59e}$, which is aryl or heteroaryl selected from the class consisting of phenyl, pyridyl, and pyrimidinyl (B) —CN,
(B) nitro, or
(C) halogen;
$R^{55}$ is Cl;
Z is =C(H)—; and,
$R^7$ is Cl;
and pharmaceutically acceptable salts thereof It will be appreciated that the compounds of the formula I have at least one chiral center. Ultimately preferred are those compounds of formula I with the absolute stereochemistry depicted below in formula II.

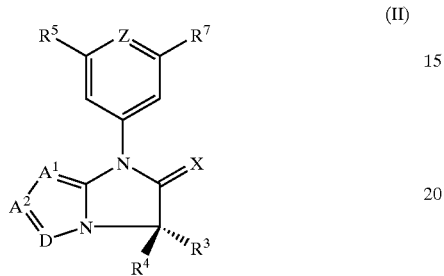

Also preferred are the following specific compounds:

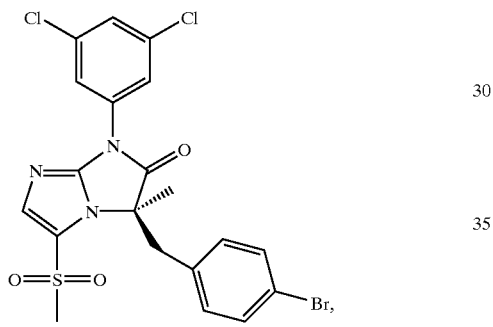

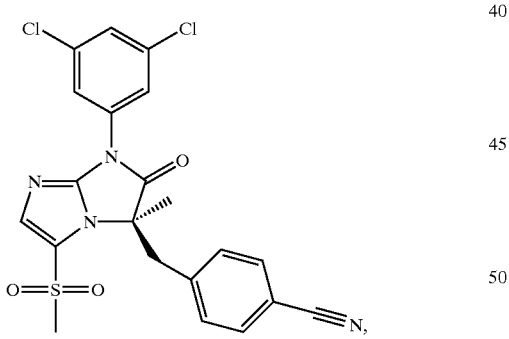

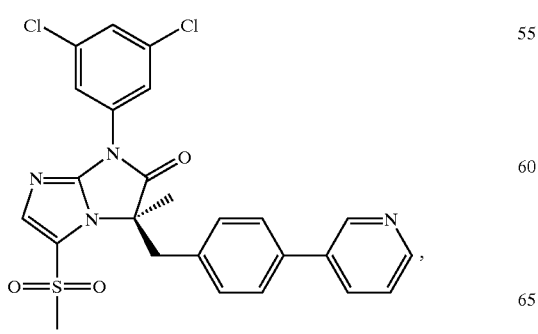

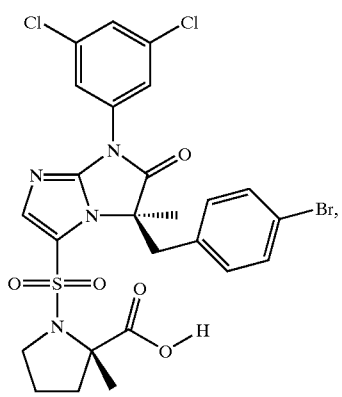

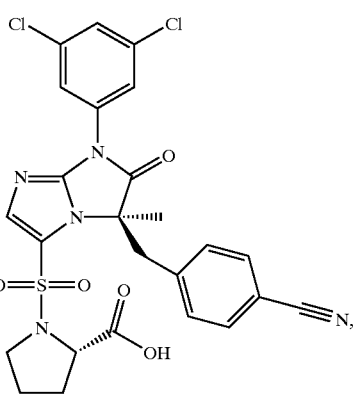

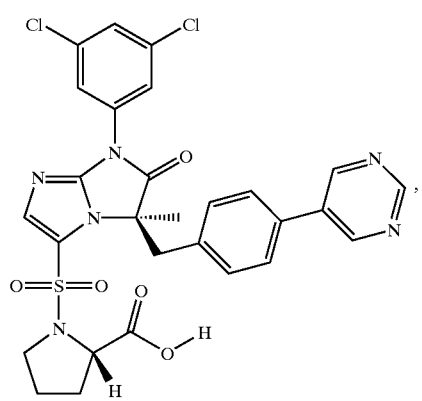

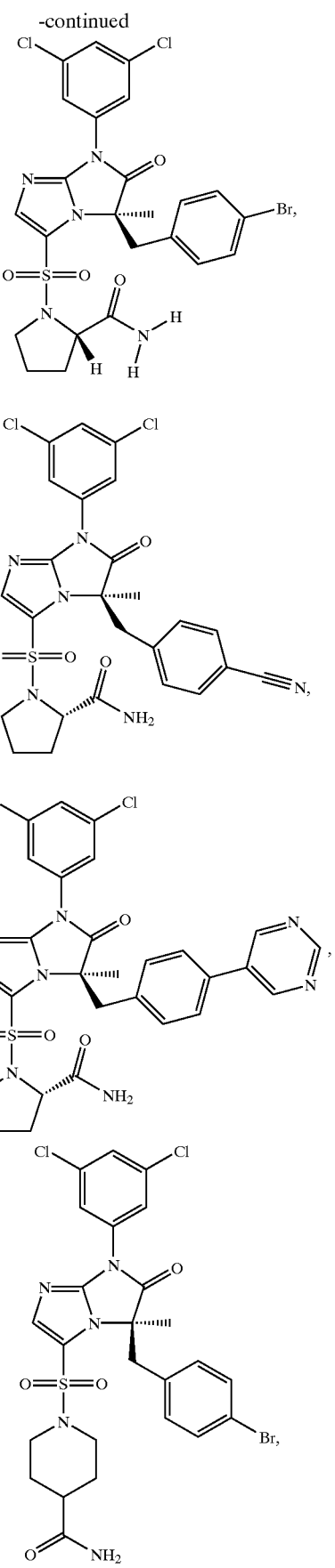
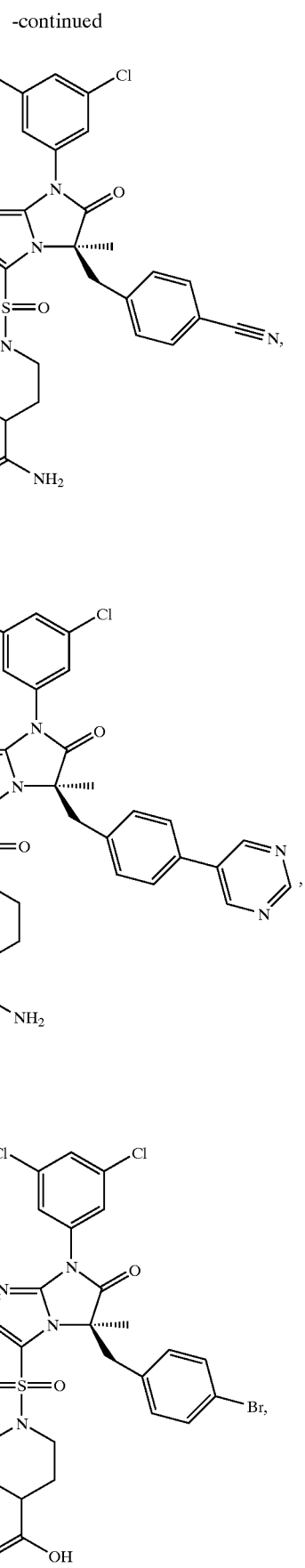

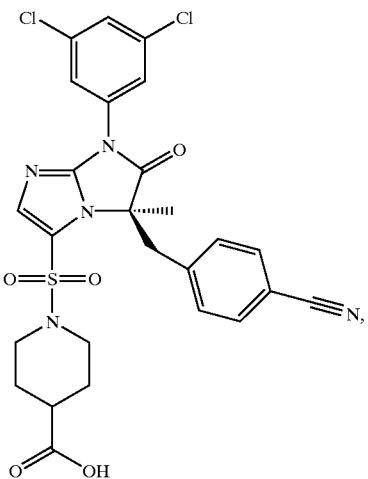
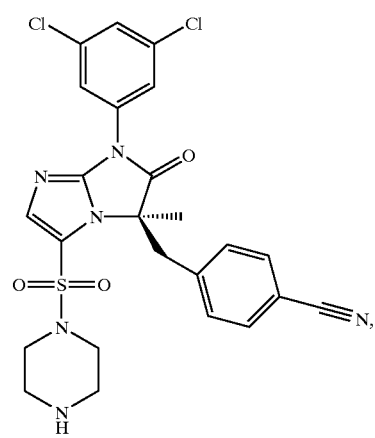
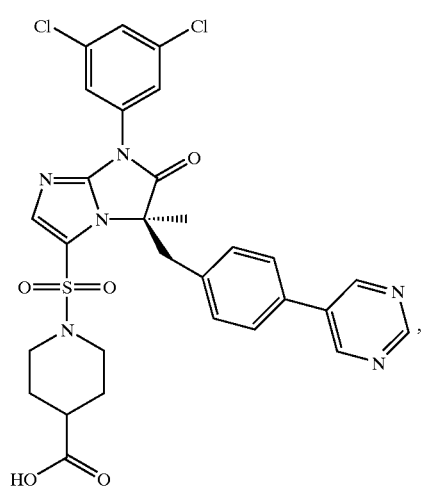
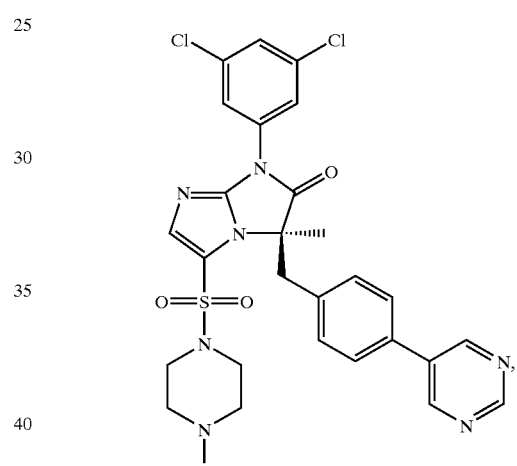
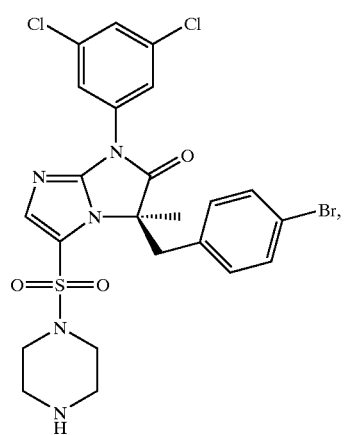
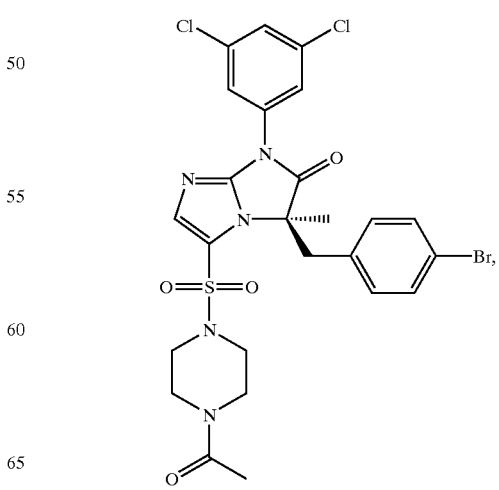

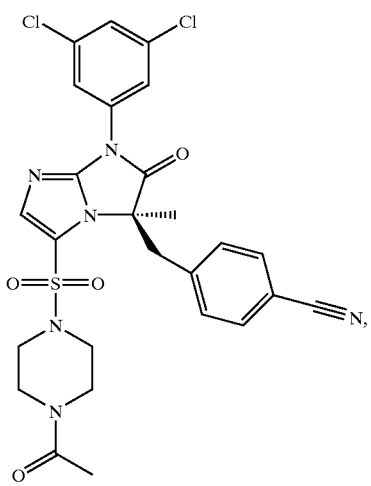
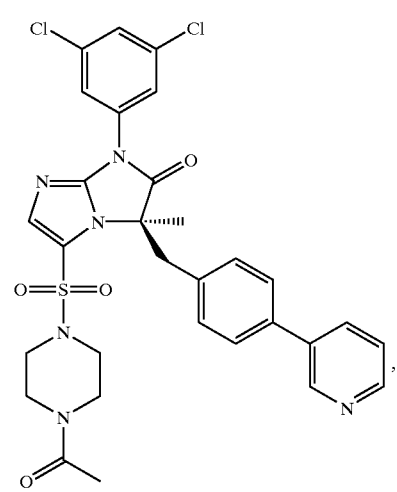
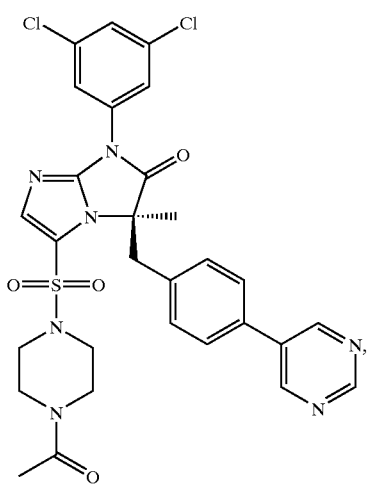
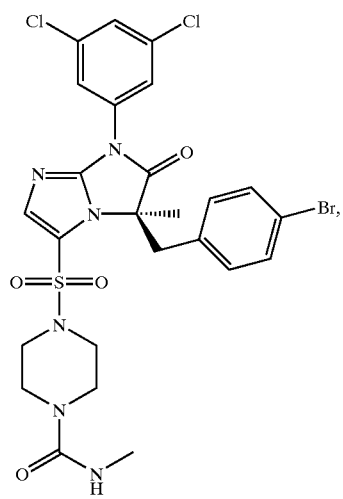
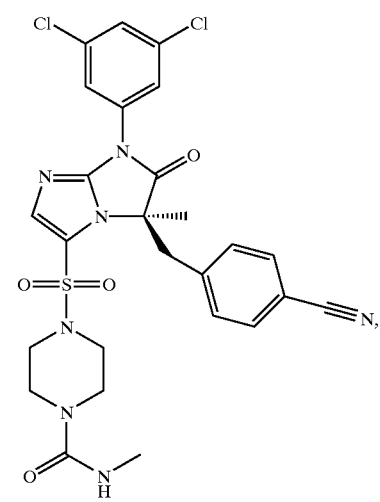
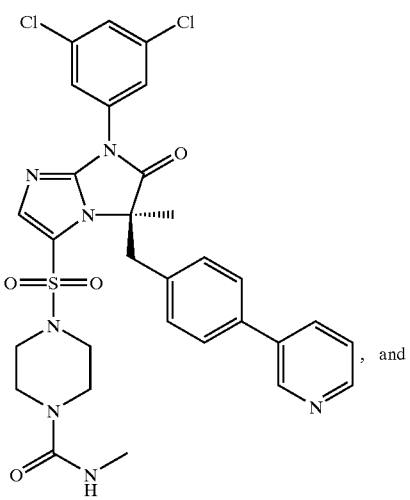

-continued

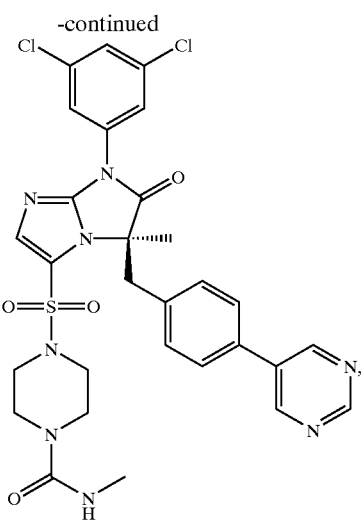

and their pharmaceutically acceptable salts.

Additionally it will be noted that certain compounds are usedul as intermediates in the synthesis of the above compounds of the invention. In particular, compounds of the formula

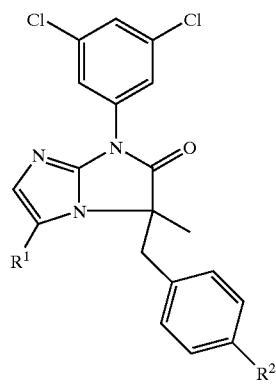

wherein,
R$^1$ is selected from the class consisting of:
(A) hydrogen,
(B) the halogen atoms, and
(C) SO$_2^-$M$^+$, wherein M$^+$ is
(i) Li$^+$,
(ii) Na$^+$,
(iii) K$^+$, or
(iv) MgX$^+$, wherein X is a halogen; and
R$^2$ is selected from the class consisting of:
(A) the halogen atoms,
(B) aryl, selected from the class of
(i) phenyl,
(ii) pyridyl, and
(iii) pyrimidyl, and
(C) CN.

Synthesis of the Compounds of the Invention

Compounds of the invention may be prepared by the general methods described below. Typically, reaction progress may be monitored by thin layer chromatography (TLC) if desired. If desired, intermediates and products may be purified by chromatography on silica gel and/or recrystallization, and characterized by one or more of the following techniques: NMR, mass spectroscopy and melting point. Starting materials and reagents are either commercially available or may be prepared by one skilled in the art using methods described in the chemical literature.

Intermediates used in the preparation of the compounds of formula I may be prepared by the method described below and outlined in Scheme I.

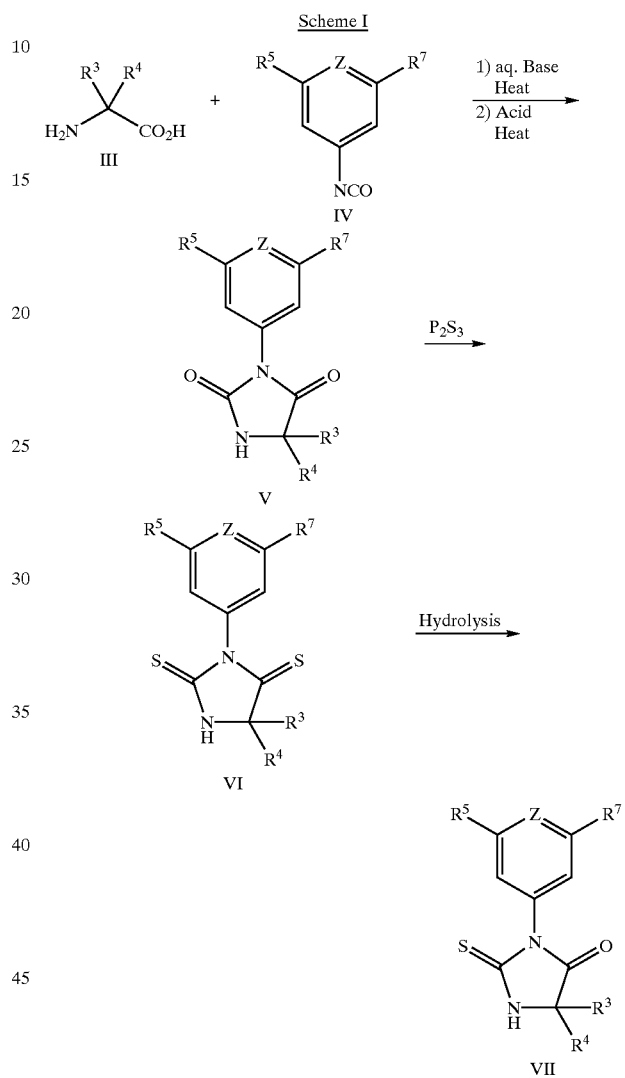

An appropriate amino acid (III) is dissolved in aqueous base (such as, for example, NaOH, KOH, Na$_2$CO$_3$, NaHCO$_3$, K$_2$CO$_3$ or KHCO$_3$) and warmed to between about 20 and 90° C. An appropriate isocyanate (IV) is added to this mixture and the resulting solution is stirred until the reaction essentially reaches completion. Upon cooling, the mixture is acidified and the resulting ureidoacetic acid is isolated by filtration or by extraction into organic solvent. Removal of solvent produces the intermediate ureidoacetic acid. In the manner reported by Sauli (U.S. Pat. No. 4,099,008), the intermediate ureidoacetic acid is cyclized by heating in the presence of a catalytic amount of acid (such as, for example, sulfuric acid, methanesulfonic acid, benzenesulfonic acid or hydrochloric acid) in an organic or aqueous solvent, to produce the desired hydantoin (V). Workup consists of collection of the hydantoin by filtration and purification by, for example, silica gel chromatography or recrystallization.

If the thiocarbonyl VII is desired, several reagents are known in the literature which will convert carbonyls to thiocarbonyls. A typical sequence involves heating the substrate with a reagent such as $P_2S_3$ in a high boiling solvent such as tetralin for between 1 and 48 h. Isolation of the product follows relatively standard conditions such as the dilution of the mixture into an organic solvent such as EtOAc and washing this mixture with water and saturated aqueous NaCl followed by drying and concentration. Purification is accomplished by silica gel chromatography or recrystallization, to afford VI.

Intermediate VI can be selectively hydrolyzed to the desired monothiocarbonyl compound depending on the choice of conditions. In general the thiocarbonyl at the 4-position of the ring is more susceptible to nucleophilic conditions. It can be converted to the 4-oxo-species (VII) by treatment with aqueous ethanolamine followed by acid hydrolysis. Purification is easily performed by silica gel chromatography or recrystallization.

Alternatively, the methyl or ethyl ester of III may be reacted with an aryl thioisocyanate (IV: —NCS instead of —NCO) in a suitable solvent, such as 1,4-dioxane, under an inert atmosphere at about 50–100° C. for about 1–24 h to provide VII.

If one uses the racemic III or ester of III, the product (V or VII) is racemic at the asymmetric carbon. By starting with a single enantiomer of III or ester of III, one obtains the single enantiomer of V or VII. Compounds of formula I where $A^1$=N, $A^2$=CH and D=CH may be synthesized as illustrated in Scheme II and described below.

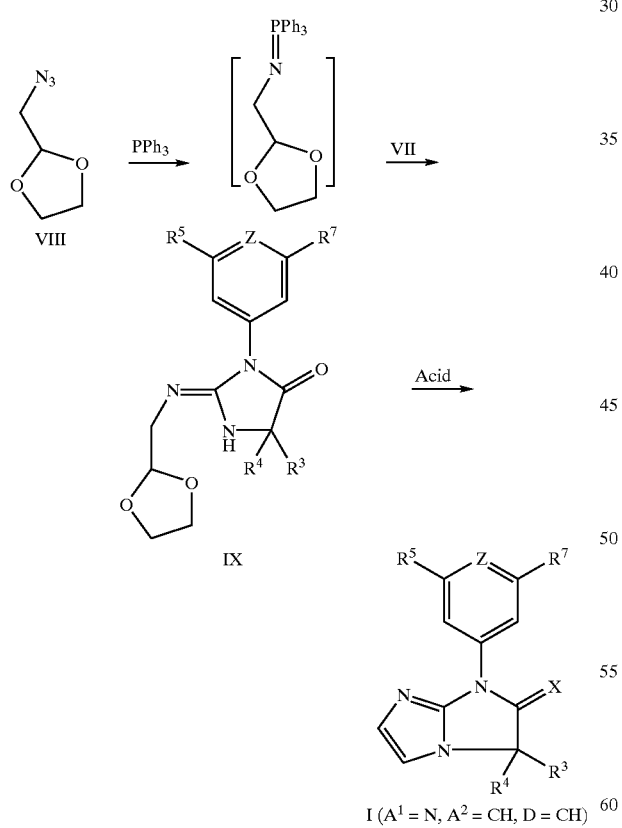

Azide VIII is added to a solution of $PPh_3$ in a suitable solvent such as toluene, under inert atmosphere and allowed to stir at ambient temperature for about 12–24 h. The appropriate thiohydantoin VII is then added and the reaction heated under inert atmosphere, preferably in a sealed tube at about 130–140° C. for about 1–4 days to provide IX after concentration and purification by silica gel chromatography. An acid, such as trifluoroacetic acid, is added to a solution of IX in a solvent such as dichloroethane and heated under inert atmosphere at about 50–100° C. for about 12–24 h to provide I ($A^1$=N, $A^2$=CH, D=CH) after standard workup and purification.

Analogs of I ($A^1$=N, $A^2$=CH) where D is a carbon substituted with various groups, such as halogen, CN, CHO, an alkyl group, an alkyl or aryl sulfide, sulfoxide or sulfone, may be prepared as described below and outlined in Scheme III.

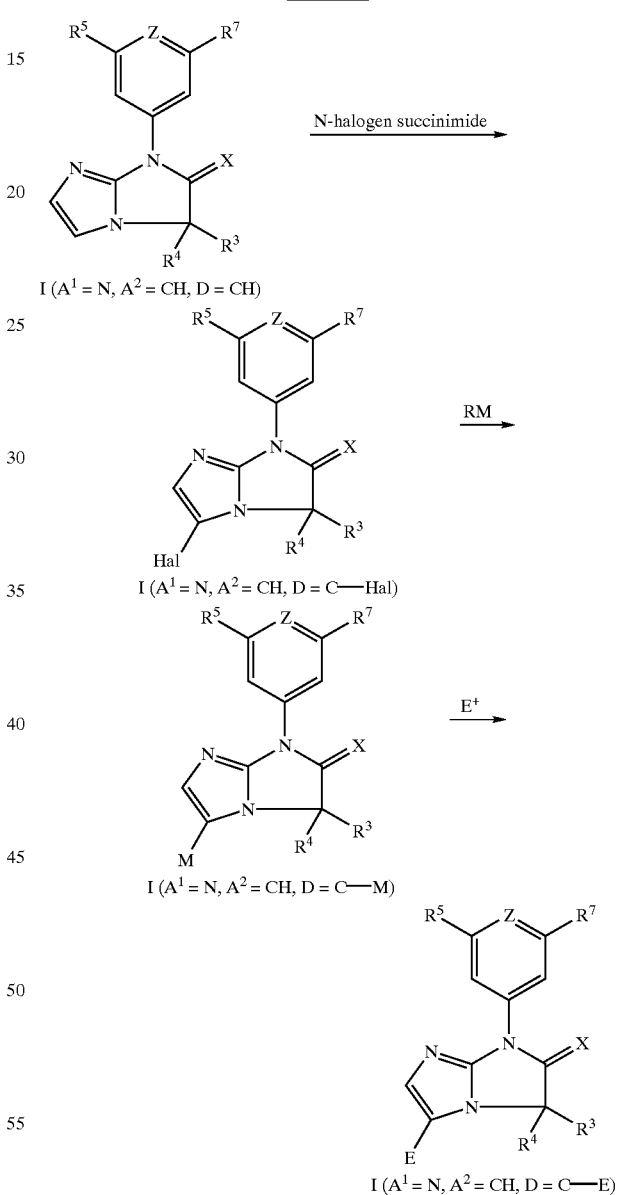

In Scheme III, M is a metal atom such as Li or Mg, Hal is Cl, Br or I and E is a functional group transferable by an electrophilic reagent and can be, but is not restricted to, Cl, Br, I, CN, alkyl, CHO, $SO_2M$, $SO_2R$ or $CO_2R$, where R is alkyl or aryl.

The desired N-halosuccinimide (about 1 mole equivalent) is added in portions to a solution of I ($A^1$=N, $A^2$=CH, D=CH), in a suitable solvent such as methylene chloride at about −10° C. to ambient temperature, preferably at about 0° C., and stirred for about 2 to 15 h. Following workup and purification, I (A¹=N, A²=CH, D=C—Cl, C—Br, C—I) is obtained.

The halogen substituted compound I (A¹=N, A²=CH, D=C—Cl, C—Br, C—I) may be transformed to an organometallic intermediate I (A¹=N, A²=CH, D=C—M, where M is a metal atom, such as Li or Mg) by treatment with an organometallic reagent, such as an alkyl or aryl lithium or a Grignard reagent. This organometallic intermediate may be reacted with an electrophile, such as an N-chloro-, bromo- or iodo- succinimide, tosyl cyanide, an alkyl or aryl sulfonyl chloride, an alkyl or aryl disulfide, an alkyl- or arylthiosulfonate, an alkyl or aryl chloroformate, an alkyl halide, N,N-dimethylformamide or sulfur dioxide, to produce the anolog of I (A¹=N, A²=CH) where D is a carbon substituted with various groups, such as Cl, Br, I, CN, an alkyl group, an alkyl or aryl sulfone, an alkyl or aryl sulfide, CHO, or a sulfinate salt. The sulfides may be further oxidized with a reagent, such as potassium peroxymonosulfate, or m-chlorobenzoic acid, to provide sulfoxides or sulfones. The sulfinate salts may be further transformed to produce sulfones and sulfonamides as described below.

More specifically, compounds I (A¹=N, A²=CH) with D=CN may be obtained by treating a solution of the corresponding halide, preferably iodide I (A¹=N, A²=CH, D=C—I), in a solvent such as THF with an alkyl magnesium reagent, such as cyclopentyl magnesium bromide, at about −78 to 0° C., preferably about −30 to 40° C., under an inert atmosphere, for about 1 to 5 h to generate an organomagnesium species I (A¹=N, A²=CH, D=C—Mg). Tosyl cyanide is then added and the reaction allowed to gradually warm to ambient temperature and to proceed for about 1 to 24 h. Following workup and purification, I (A¹=N, A²=CH, D=C—CN) is obtained.

Compounds I (A¹=N, A²=CH, D=C—SO₂R where R=alkyl or aryl) may be obtained by treating the organomagnesium species I (A¹=N, A²=CH, D=C—Mg) as generated above with an alkyl or aryl sulfonyl chloride. Alternatively, one may add an alkyl- or aryldisulfide, or an alkyl- or arylthiosulfonate (prepared by oxidizing the corresponding alkyl or aryl disulfide, for example with m-chloroperoxybenzoic acid in a suitable solvent such as methylene chloride) and then heating the reaction at about the reflux temperature of the solvent for about 1 to 3 h to obtain I (A¹=N, A²=CH, D=C—SR, where R=alkyl or aryl) after workup and purification. The resulting product may be oxidized to the corresponding sulfoxide or sulfone with a suitable oxidizing agent such as potassium peroxymonosulfate or m-chloroperoxybenzoic acid.

Compounds I (A¹=N, A²=CH) with D=C—CO₂R, where R is an alkyl or an aryl group, may be obtained by treating the organomagnesium species as generated above with an appropriate alkyl or aryl chloroformate, in a solvent such as THF, at about −20 to −78° C., preferably about −40° C., under an inert atmosphere for about 15 min to 1 h before allowing the reaction to warm to room temperature over about 30 min to 1 h. Following quenching, for example with aqueous sodium bicarbonate, workup and purification, I (A¹=N, A² =CH, D=C—CO₂R) is obtained.

Compounds I (A¹=N, A²=CH) with D=C—CHO may be obtained by treating a solution of the corresponding halide, preferably iodide (I: A¹=N, A²=CH, D=C—I), in a solvent such as THF with an alkyl lithium, such as n-BuLi at about −50 to −120° C., preferably about −100° C., under an inert atmosphere for about 15 min to 1 h. N,N-Dimethylformamide is added and the reaction gradually allowed to warm to about 0° C. and stirred for about 1 h. Following quenching, for example with aqueous ammonium chloride, workup and purification, I (A¹=N, A²=CH, D=C—CHO) is obtained.

One may also synthesize certain compounds of the invention by treating the organomagnesium intermediate as generated above with sulfur dioxide to generate an intermediate magnesium sulfinate salt. This intermediate may be treated with alkylating reagents, such as alkyl halides to produce additional compounds of the formula I (A¹=N, A²=CH ) with D=C—SO₂R (R=alkyl). The intermediate magnesium sulfinate salt may also be treated with N-chlorosuccinimide to generate the sulfonyl chloride I (A¹=N, A²=CH, D=C—SO₂Cl). The sulfonyl chloride can in turn be treated with amines to produce desired sulfonamides I (A¹=N, A²=CH, D=C—SO₂NRR' where R and R'=a hydrogen atom, an alkyl or aryl group, or together comprise part of a heterocyclic ring).

Analogs of I (A¹=N, A²=CH) with D=C—SO₂NRR' where R and R' together comprise part of a heterocyclic ring and where R and/or R' contains a second nitrogen, for example piperazine, can be further substituted on the second nitrogen, for example with acyl, alkyl, aryl, carbamyl or sulfonyl as described below and outlined in Scheme IV.

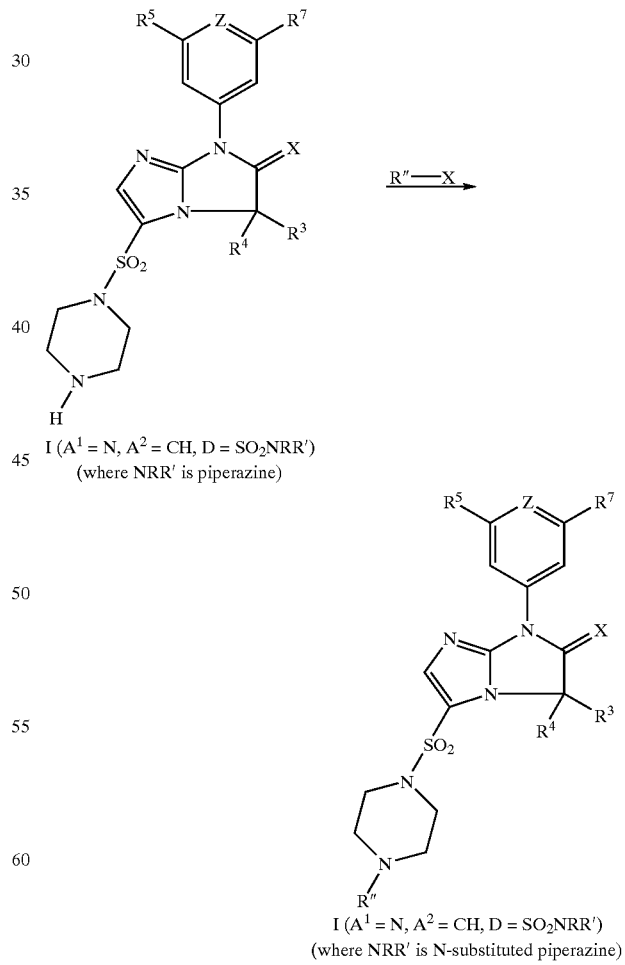

Scheme IV

I (A¹ = N, A² = CH, D = SO₂NRR')
(where NRR' is piperazine)

I (A¹ = N, A² = CH, D = SO₂NRR')
(where NRR' is N-substituted piperazine)

In Scheme IV, R" is a functional group transferable by an electrophilic reagent and can be, but is not restricted to, an alkyl group, COR, CONRR', CO$_2$R, or SO$_2$R, where R or R' is alkyl or aryl.

The compound bearing the heteroatom can be treated with reagents such as an alkanoyl or aroyl chloride, alkanoyl or aroyl anhydride, alkyl halide, alkyl or aryl sulfonyl chloride or alkyl or aryl isocyanate to produce compounds where I (A$^1$=N, A$^2$=CH) and D is a carbon substituted with a sulfonamide which itself is further substituted with various groups such as alkyl or aryl amides, alkyl amines, alkyl or aryl sulfonamides, and alkyl or aryl ureas.

More specifically, compounds I (A$^1$=N, A$^2$=CH) and where D is a carbon substituted with a piperazinesulfonamide which itself is further N-acylated may be obtained by treating a solution of the corresponding piperazinesulfonamide, in a solvent such as N,N-dimethylformamide with an appropriate carboxylic acid, in the presence of a coupling agent, such as polystyrene resin-bound carbodiimide, at about 20° C. for about 2 to 24 h.

Following workup and purification, compounds I (A$^1$=N, A$^2$=CH) and where D=is a carbon substituted with an acylated piperazinesulfonamide are obtained.

Alternatively, these compounds may be obtained by treating a solution of the corresponding piperazinesulfonamide, in a solvent such as dichloromethane with an appropriate alkanoyl or aroyl chloride, in the presence of a base, such as triethylamine, at about −20 to 20° C., preferably about 0° C. for about 15 min to 2 h. Following quenching, for example with aqueous sodium bicarbonate, workup and purification, the desired acylated piperazinesulfonamides are obtained.

Compounds I (A$^1$=N, A$^2$=CH) and where D is a carbon substituted with a piperazinesulfonamide which itself participates additionally in an urea linkage may be obtained by treating a solution of the corresponding piperazinesulfonamide in a solvent such as dichloromethane with an appropriate isocyanate, at about 0 to 40° C., preferably about 20° C. for about 2 to 24 h. Following workup and purification, compounds I (A$^1$=N, A$^2$=CH) and where D=is a carbon substituted with an urea functionalized piperazinesulfonamide are obtained.

Alternatively, compounds I (A$^1$=N, A$^2$=CH) and where D is a carbon substituted with a piperazinesulfonamide which itself is further N-sulfonylated may be obtained by treating a solution of the corresponding piperazinesulfonamide, in a solvent such as dichloromethane with an appropriate sulfonyl chloride, in the presence of a base, such as triethylamine, at about −20 to 20° C., preferably about 0° C. for about 15 min to 2 h. Following quenching, for example with aqueous sodium bicarbonate, workup and purification, compounds I (A$^1$=N, A$^2$=CH) and where D=is a carbon substituted with a sulfonylated piperazinesulfonamide are obtained.

Functional group transformations well known in the art may be employed to modify the substituents on D illustrated above to obtain additional compounds of the invention.

Analogs of I (A$^1$=N, D=CH) where A$^2$ is a carbon substituted with various groups, such as halogen, CN, CHO, an alkyl group, an alkyl or aryl sulfide, sulfoxide or sulfone, may be prepared as described below and outlined in Scheme V. In Scheme V, M is a metal atom, such as Li or Mg, Hal is Cl, Br or I, and E is an functional group transferable by an electrophilic reagent and can be, but is not restricted to, Cl, Br, I, CN, alkyl, CHO, SO$_2$M, SO$_2$R or CO$_2$R, where R is alkyl or aryl.

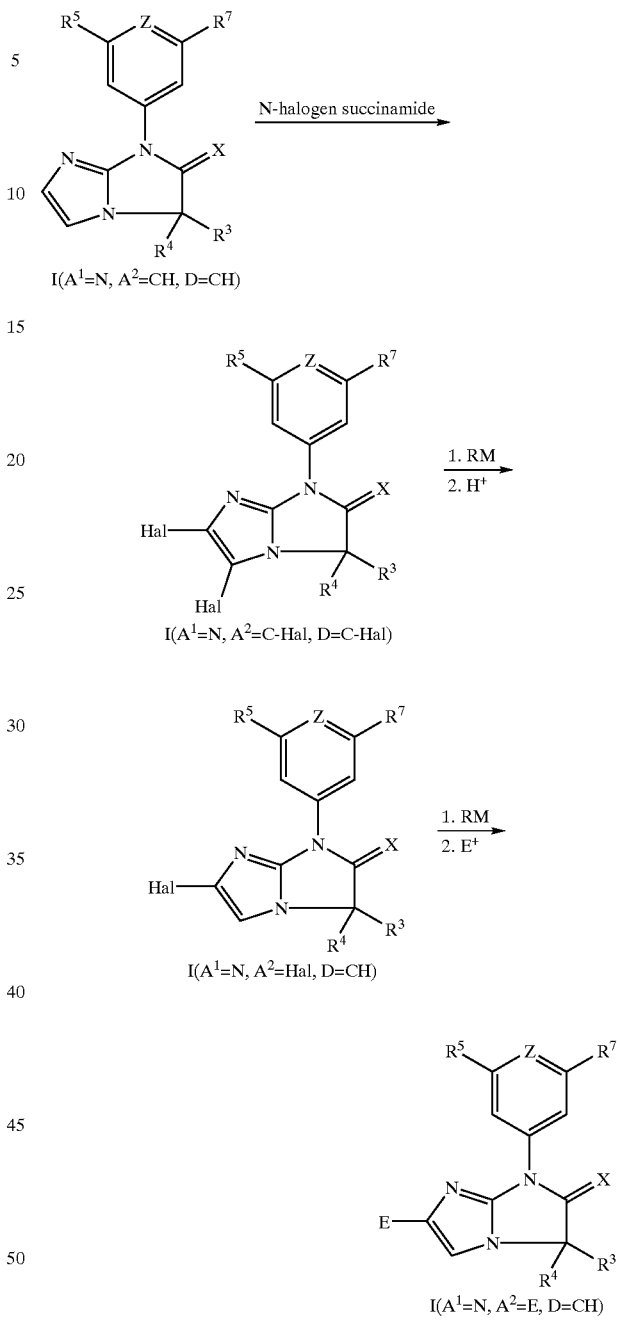

Scheme V

The desired N-halosuccinimide (about 2 mole equivalent relative to I) is added in portions to a solution of I (A$^1$=N, A$^2$=CH, D=CH), in a suitable solvent such as methylene chloride at about −10° C. to ambient temperature, preferably at about 0° C., and stirred for about 2 to 15 h. Following workup and purification, I (A$^1$=N, A$^2$=D=C—Cl, C—Br or C—I) is obtained.

The compound I (A$^1$=N, A$^2$=D=C—Cl, C—Br or C—I) may be treated in a solvent such as THF with an alkyl magnesium bromide, such as cyclopentyl magnesium bromide, at about −78 to 0° C., preferably about −30 to −40° C., under an inert atmosphere, for about 1 to 5 h. An aqueous acid, such as 1N hydrogen chloride or saturated NH$_4$Cl solution, is then added. Following workup and purification, I ($A^1$=N, $A^2$=C—Cl, C—Br or C—I, and D=CH) is obtained.

The halogen substituted compound I ($A^1$=N, $A^2$=C—Cl, C—Br or C—I, and D=CH) may be transformed to an organometallic intermediate I ($A^1$=N, $A^2$=C—M, D=CH, where M is an metal atom, such as Li or Mg) by treatment with an organometallic reagent, such as an alkyl or aryl lithium or magnesium reagent. This organometallic intermediate may be reacted with an electrophile, such as an N-chloro-, bromo- or iodo- succinimide, tosyl cyanide, an alkyl halide, an alkyl or aryl sulfonyl chloride, an alkyl or aryl disulfide, an alkyl- or arylthiosulfonate, an alkyl or aryl chloroformate, N,N-dimethylformamide or sulfur dioxide, to produce the analog of I ($A^1$=N, D=CH) where $A^2$ is a carbon substituted with various groups, such as Cl, Br, I, CN, an alkyl group, an alkyl or aryl sulfone, an alkyl or aryl sulfide, CHO, or a sulfinate salt. The sulfides may be further oxidized with a reagent, such as potassium peroxymonosulfate, or m-chlorobenzoic acid, to sulfoxides or sulfones. The sulfinate salts may also be reacted with an alkylating reagent, such as an alkyl bromide or iodide to produce sulfones. Alternatively, the sulfinate salts may be transformed into the sulfonyl chlorides with a chlorinating reagent, such as NCS. The sulfonyl chlorides may be reacted with an amine to produce sulfonamides I ($A^1$=N, $A^2$=C—$SO_2NR^1R^2$, D=CH).

More specifically, compounds I ($A^1$=N, D=CH) with $A^2$=C—CN, C—$SO_2$R or $CO_2$R, where R is alkyl or aryl, C—CHO, C—$SO_2$Cl and C—$SO_2$NRR' may be prepared from the corresponding halide or organomagnesium species as described above (Scheme III) for D.

Functional group transformations well known in the art may be employed to modify the substituents on $A^2$ illustrated above to obtain additional compounds of the invention.

Functional group transformations also allow the derivatization of $R^4$. In particular, when $R^4$ is a brominated or iodonated benzyl group, these halogens can often be replaced with aryl groups by techniques known in the art, for example by treating a solution of the halogenated benzyl group, with an organometallic reagent such as an aryl boronate, boronic acid or stannane, in a solvent such as a mixture of toluene and ethanol, in the presence of a base, such as aqueous sodium carbonate, with a metal catalyst, such as Pd(PPh$_3$)$_4$, at about 75 to 110° C., preferably about 85° C. for about 2 to 24 h. Following workup and purification, I ($R^4$=CH$_2$C$_4$H$_6$Ar) is obtained, where Ar can be, but is not limited to, furyl, phenyl, pyridyl, pyrimidyl and thiophenyl.

Compounds of formula I with $A^1$=$A^2$=D N may be prepared as illustrated in Scheme VI and described below.

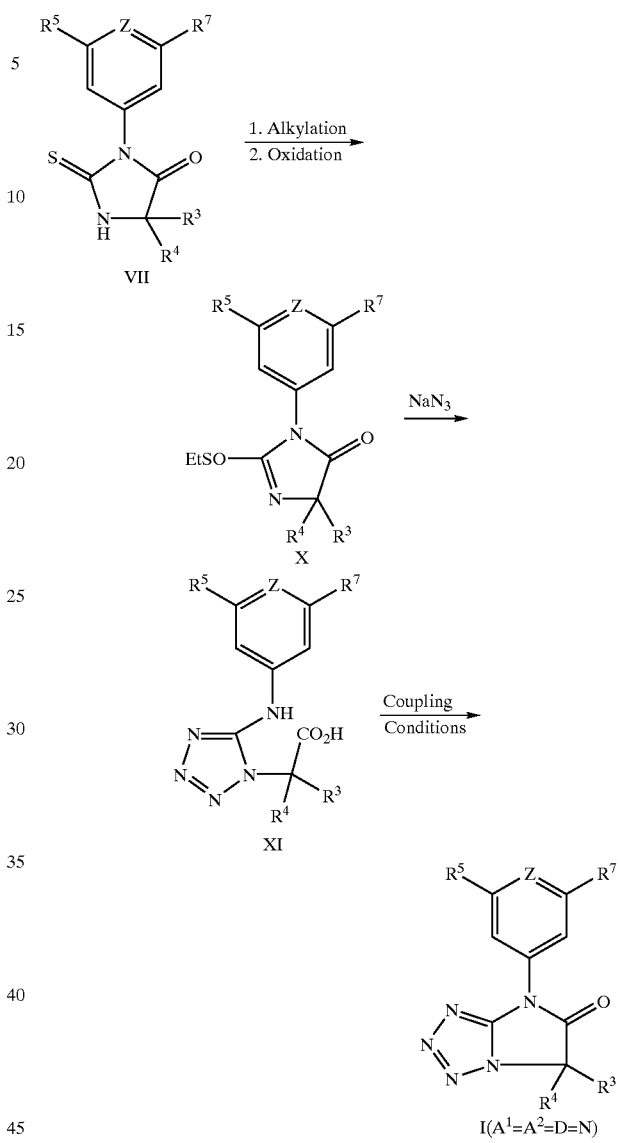

Scheme VI

Intermediate VII is treated with an alkylating agent such as diethyl sulfate, in a suitable solvent such as aqueous base and THF. After workup and purification, the intermediate is treated with a suitable oxidizing agent such as potassium peroxymonosulfate to give sulfoxide X. A solution of X is then treated with NaN$_3$ at ambient temperature for about 12–24 h. Upon workup and purification, carboxylic acid XI is obtained. Intermediate XI is then reacted under standard peptide coupling conditions, for example treatment with 1-(3-dimethylaminopropyl)-3-ethylcarbodiimide hydrochloride (EDC) and 1-hydroxybenzotriazole (HOBT) and a base, such as diisopropylethylamine, in a suitable solvent such as DMF for about 5 to 24 h at ambient temperature. Following workup and purification, I ($A^1$=$A^2$=D=N ) is obtained.

Compounds of formula I where $A^1$=N, $A^2$=N, and D=CH may be prepared as illustrated in Scheme VII and described below.

Scheme VII

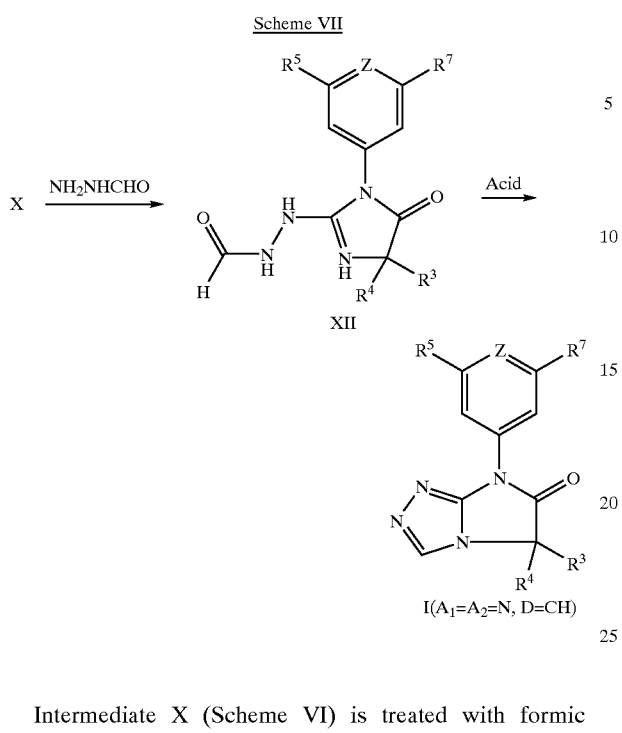

Intermediate X (Scheme VI) is treated with formic hydrazide in a suitable solvent such as DMSO, under an inert atmosphere at about 50 to 100° C. for about 5 to 24 h to provide XII after workup and purification. Intermediate XII is treated with a catalytic amount of an acid, such as p-toluenesulfonic acid in a suitable solvent, such as toluene. Molecular sieves or a trap to collect water formed in the reaction may be employed. The reaction is heated at reflux temperature for about 3 to 12 h. The desired compound of formula I ($A^1$=N, $A^2$=N, and D=CH) is obtained following purification.

Analogs of I ($A^1$=N, $A^2$=N) where D=C substituted with various groups may be prepared as described above for analogs of I ($A^1$=N, $A^2$=CH).

The invention is further described by the following synthetic examples.

SYNTHETIC EXAMPLES

Example 1

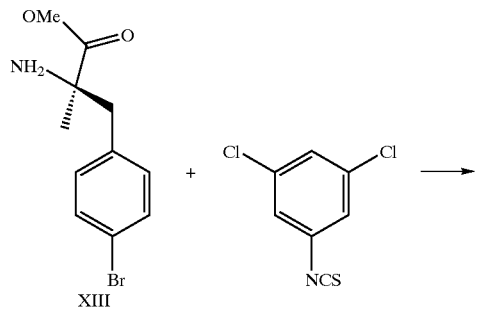

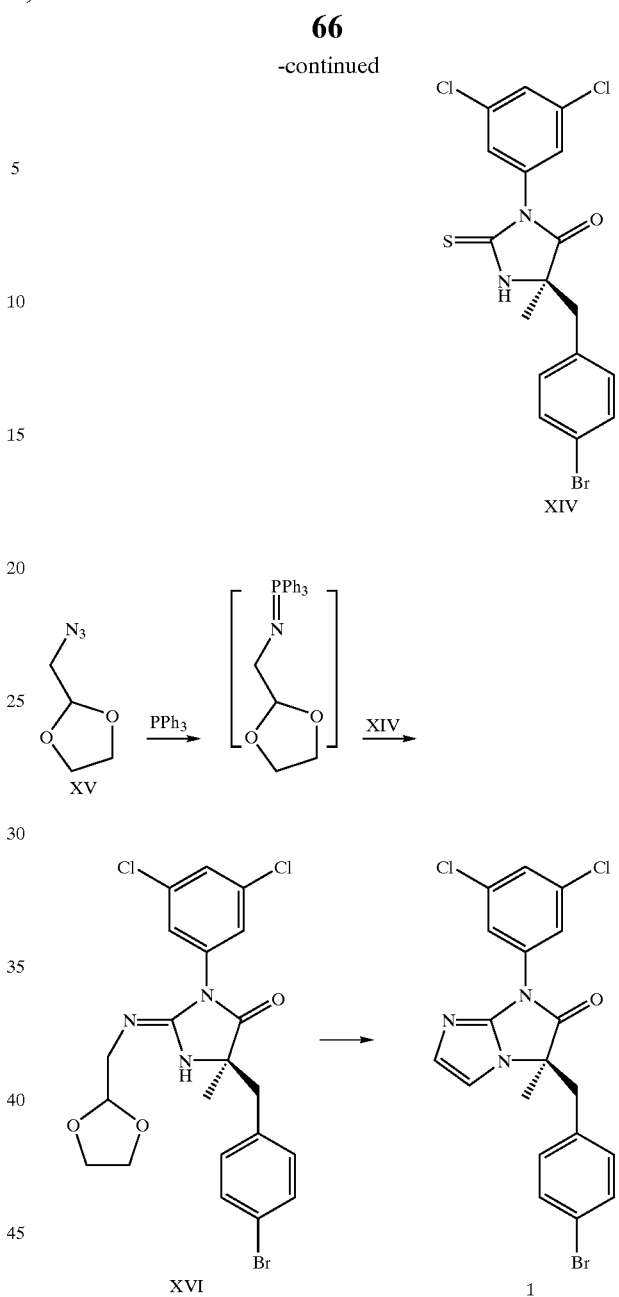

A solution of amino-ester XIII and 3,5-dichlorophenylisothiocyanate (1:1 molar ratio) in 1,4-dioxane was heated at 90° C. under $N_2$ for 10 h. The mixture was concentrated to give the thiohydantoin derivative XIV. The product was characterized by $^1$H NMR and mass spectroscopy.

To a solution of $PPh_3$ (9.0 mmol) in toluene (20 mL) under $N_2$ was added azide XV (9.0 mmol). After stirring at room temperature overnight, thiohydantoin XIV (4.5 mmol) was added. The mixture was sealed under $N_2$ in a pressure tube and heated at 130–140° C. for 3–4 days, concentrated and purified by silica gel chromatography to gave the product XVI. The product was characterized by $^1$H NMR and mass spectroscopy.

To a solution of XVI in dichloroethane was added trifluoroacetic acid (TFA, 5–6 eq). The mixture was heated under $N_2$ at 90° C. overnight. The residue was taken up in EtOAc, washed with saturated NaHCO$_3$, dried (Na$_2$SO$_4$) and concentrated. The residue was purified by silica gel chromatography to give the title compound 1, m.p. 36–37.5° C. The product was characterized by $^1$H NMR and mass spectroscopy.

Example 2

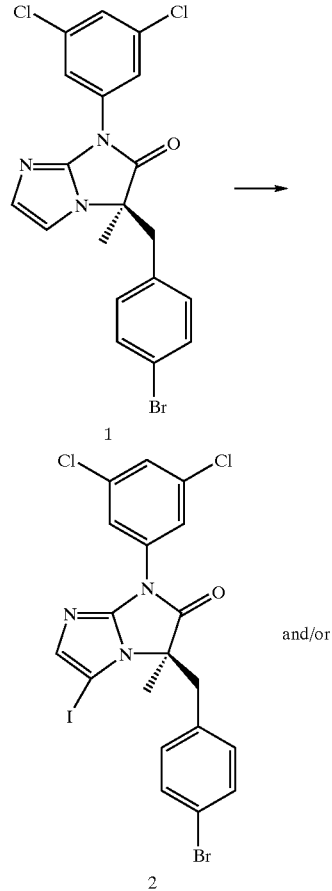

To a solution of compound 1 (1.82 g, 4.04 mmol), in CH$_2$Cl$_2$ (20 mL), cooled to 0° C. was added in small portions N-iodosuccinimide (1.43 g, 6.04 mmol). Pyridinium p-toluenesulfonate (100 mg, 0.40 mmol) was added and the mixture was stirred at 0° C. for 3 h, during which, additional N-iodosuccinimide (400 mg, 1.68 mmol) was added to complete the reaction. The mixture was diluted with CH$_2$Cl$_2$, washed with 10% Na$_2$SO$_3$ solution, dried and concentrated. The residue was purified by silica gel chromatography to give a mixture of the title compounds 2 (1.86 g) and 2a (0.53 g). The products were characterized by $^1$H NMR and mass spectroscopy.

Diiodide 2a may also be produced from 1 as the only product by using more than 2 mole equivalents of N-iodosuccinimide in the same procedure as described above.

Example 3

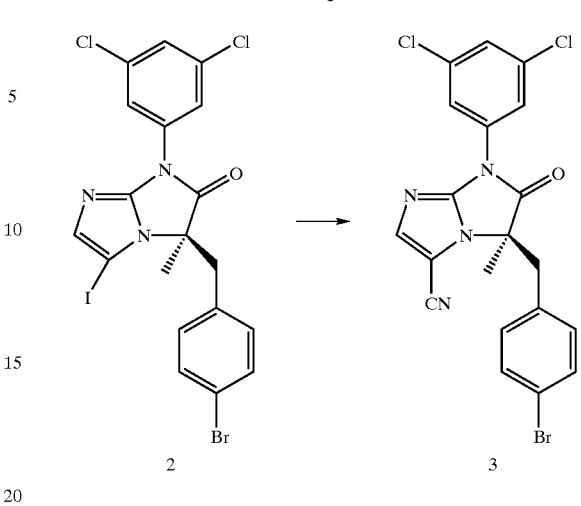

A solution of compound 2 (33 mg, 0.0572 mmol) in THF was treated with a 2.0 M solution of cyclopentylmagnesium bromide (57 μL, 0.114 mmol) at –30° C. under nitrogen. The mixture was stirred at –30° C. for 2 h before a solution of tosylcyanide (70 mg, 0.367 mmol) in THF (0.5 mL) was added. The mixture was stirred at –30° C. for 1 h then at room temperature overnight. The reaction was quenched with a saturated NH$_4$Cl solution at 0° C. Extraction with EtOAc followed by silica gel chromatography gave compound 3 as a foam (9.5 mg, 35%). The product was characterized by $^1$H NMR and mass spectroscopy.

Example 4

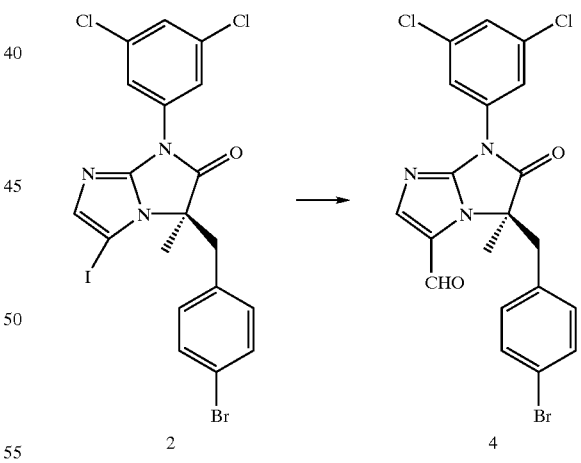

A solution of compound 2 (32 mg, 0.055 mmol) in THF was treated with n-BuLi (44 uL, 1.5 M, 0.067 mmol) at –100° C. under nitrogen. The mixture was stirred at –100° C. for 15 min before DMF (50 uL) was added. The mixture was stirred at –100° C. for 15 min then 0° C. for 1 h before a saturated NH$_4$Cl solution (1 mL) was added. Extraction with EtOAc followed by silica gel chromatography gave compound 4 as an oil (3.0 mg, 11%). The product was characterized by $^1$H NMR and mass spectroscopy.

Example 5

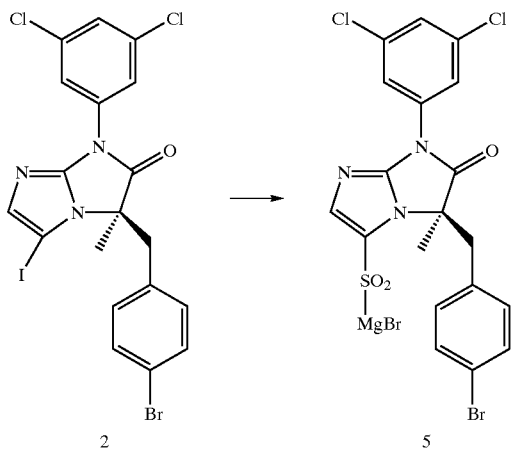

A solution of compound 2 (2.5 g, 4.33 mmol) in 25 mL of THF was treated with cyclopentylmagnesium bromide (2.6 mL, 2 M, 5.2 mmol) at −40° C. under argon. The mixture was stirred at −40° C. for 40 min and then $SO_2$ was bubbled in over 1 min. The mixture was stirred at −40° C. for 15 min then at room temperature for 1 h before being concentrated twice under vacuum from dry THF to produce the solid magnesium salt 5.

Example 6

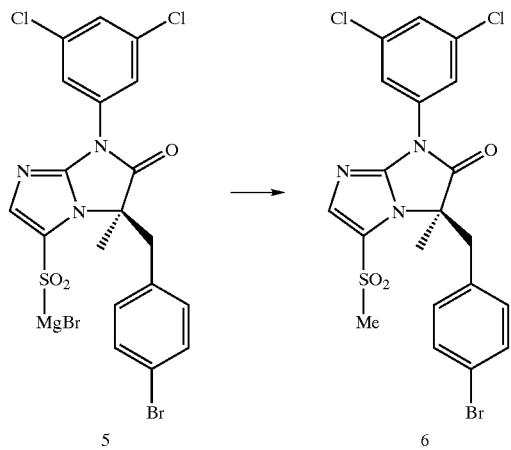

The magnesium salt 5 (1.00 g, 1.62 mmol) was dissolved in 5 mL of dry DMF and treated with MeI (0.5 mL, 8 mmol) at room temperature for 1.5 h. It was then heated to between 40 and 50° C. for 1 h to complete the reaction. The reaction mixture was diluted with water to stop the reaction. Extraction with EtOAc followed by silica gel chromatography gave 6 (3.66 g, 66%). Mp=92–93° C. The product was characterized by $^1$H NMR and mass spectroscopy.

Example 7

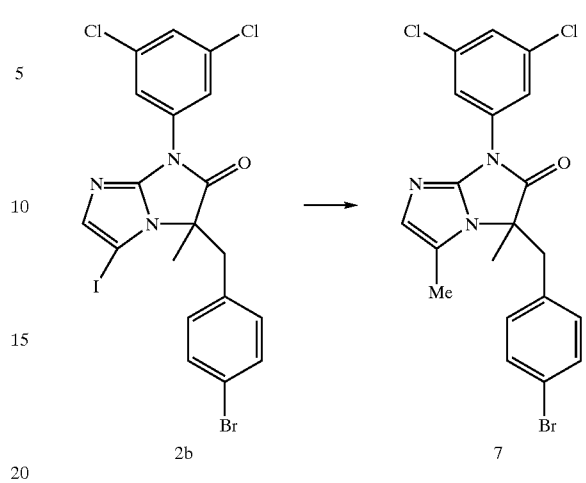

For this example, the racemic iodide 2b was used as the starting material. Compound 2b was prepared by the same procedure as compound 2, using racemic 1.

To a solution of anhydrous LiCl (10.0 mg, 0.236 mmol) and CuCN (10.5 mg, 0.117 mmol) in THF (0.2 mL), cooled at −20° C. was added $CH_3MgBr$ (1.4 M in THF, 0.21 mL, 0.294 mmol) under $N_2$. The solution was stirred at −20° C. for 15 min. A solution of compound 2b (34 mg, 0.059 mmol) in THF (0.5 mL) was added. The reaction mixture was stirred at −20° C. for 2 h and then at room temperature overnight before being quenched with saturated aqueous $NH_4Cl$ at 0° C. The mixture was extracted with EtOAc, dried with $Na_2SO_4$ and concentrated. The residue was purified via preparative thin layer chromatography (prep-TLC) to give 2 mg (yield: 6%) of 7. The product was characterized by $^1$H NMR and mass spectroscopy.

Example 8

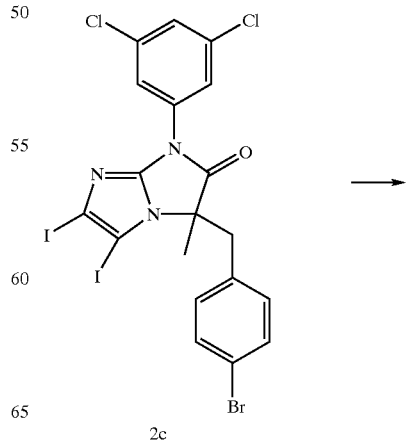

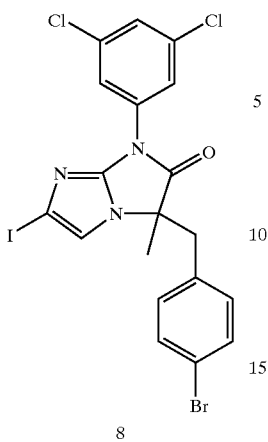

8

For this example, the racemic diiodide 2c was used as the starting material. Compound 2c was prepared by the same procedure as compound 2a, using racemic 1.

To a solution of compound 2c (766 mg, 1.09 mmol) in THF (10 mL) at −30° C. was added cyclopentylmagnesium bromide (2.0 M in ether, 1.36 mL, 2.72 mmol) under nitrogen. The solution was stirred at −30° C. for 1.5 h before a saturated aqueous NH$_4$Cl solution was added. The mixture was warmed to room temperature and extracted with EtOAc. The organic layer was dried with Na$_2$SO$_4$ and concentrated. The residue was purified by silica gel chromatography to give the iodide 8. The product was characterized by $^1$H NMR and mass spectroscopy.

Example 9(9. BIRT0938XX)

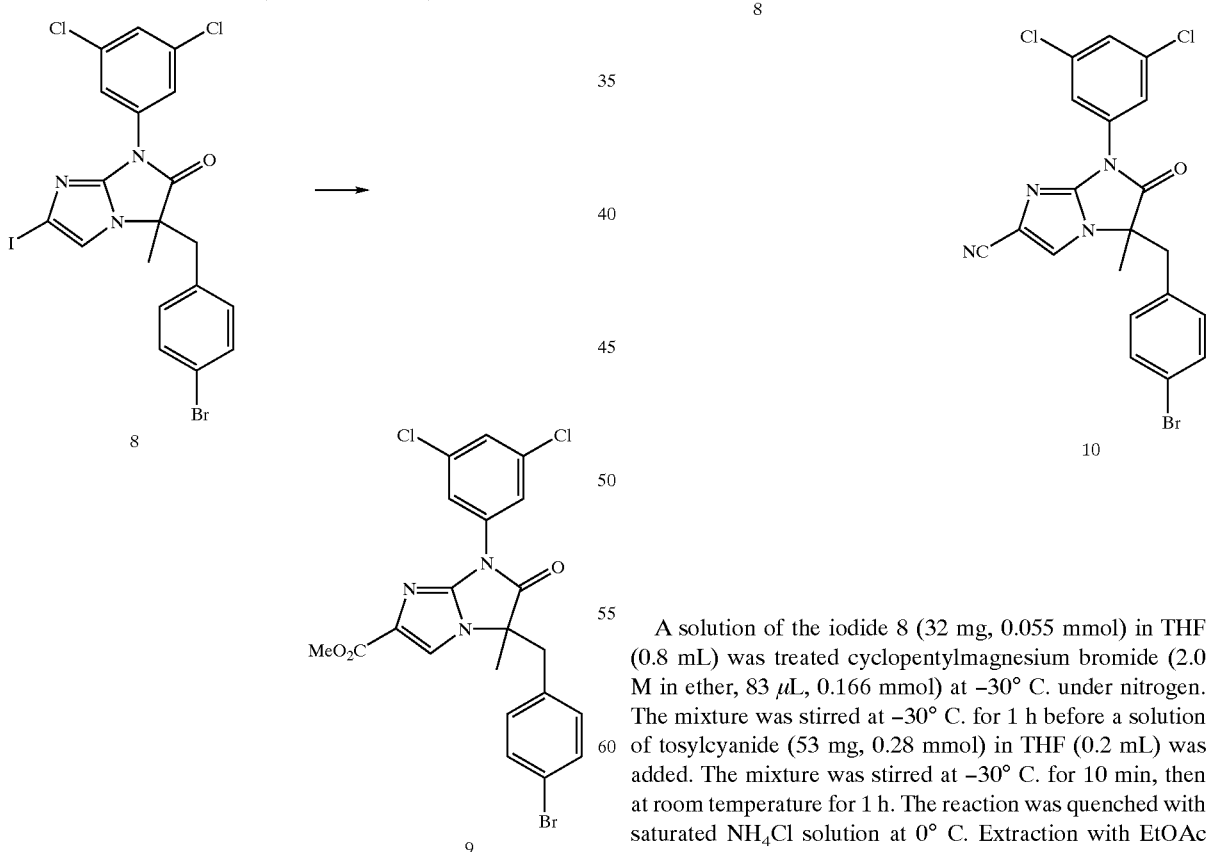

To a solution of the iodide 8 (113 mg, 0.196 mmol) in THF (1 mL) at −40° C. was added cyclopentylmagnesium bromide (2.0 M in ether, 0.293 mL, 0.586 mmol) under nitrogen. The solution was stirred at −35° C. for 90 min before methyl chloroformate (0.1 mL, 1.47 mmol) was added. The mixture was stirred at −35° C. for 30 min and then at room temperature for 1 h before a saturated aqueous solution of NH$_4$Cl was added. The mixture was extracted with EtOAc and the organic layer was dried with Na$_2$SO$_4$ and concentrated. The residue was purified by silica gel chromatography to give the product 9 (16 mg). The product was characterized by $^1$H NMR and mass spectroscopy.

Example 10(10. BIRT0937XX)

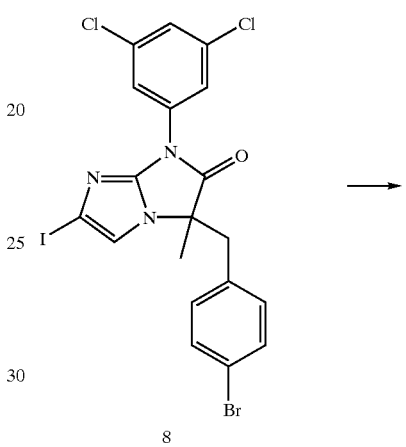

A solution of the iodide 8 (32 mg, 0.055 mmol) in THF (0.8 mL) was treated cyclopentylmagnesium bromide (2.0 M in ether, 83 μL, 0.166 mmol) at −30° C. under nitrogen. The mixture was stirred at −30° C. for 1 h before a solution of tosylcyanide (53 mg, 0.28 mmol) in THF (0.2 mL) was added. The mixture was stirred at −30° C. for 10 min, then at room temperature for 1 h. The reaction was quenched with saturated NH$_4$Cl solution at 0° C. Extraction with EtOAc followed by silica gel chromatography gave compound 10 as a foam (10 mg). The product was characterized by $^1$H NMR and mass spectroscopy.

Example 11

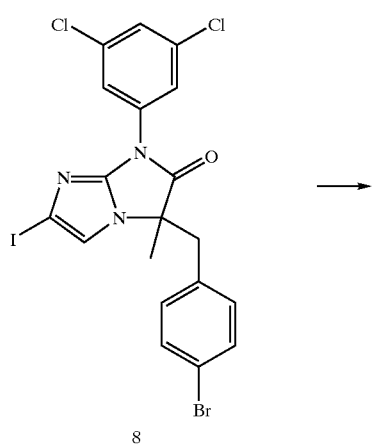

8

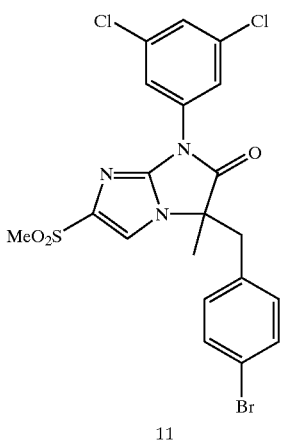

11

A solution of the iodide 8 (88 mg, 0.152 mmol) in THF (1 mL) was treated with cyclopentylmagnesium bromide (2.0 M in ether, 230 μL, 0.46 mmol) at −30° C. under nitrogen. The mixture was stirred at −30° C. for 1 h before methanesulfonyl chloride (60 μL, 0.775 mmol) was added. The mixture was stirred at −30° C. for 1 h then at room temperature for 1 h. The reaction was quenched with saturated NaHCO$_3$ solution at 0° C. Extraction with EtOAc followed by silica gel chromatography gave compound 11 (18 mg, 35%). The product was characterized by $^1$H NMR and mass spectroscopy.

Example 12

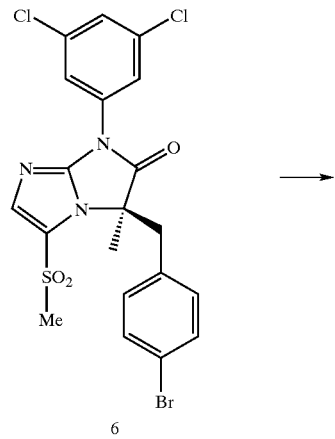

6

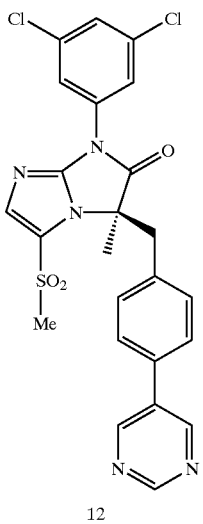

12

A solution of compound 6 (0.1 g, 0.19 mmol) in 2 mL of toluene was treated with 5-trimethylstannylpyrimidine (0.07 g, 0.28 mmol) and Pd (PPh$_3$)$_4$(22 mg, 0.02 mmol) and the mixture was heated to reflux overnight. Upon cooling, the solvent was removed by rotary evaporation and the residue was purified by preparative TLC. This produced 50.4 mg of compound 12. Mp=139–141° C. The product was characterized by $^1$H NMR and mass spectroscopy.

Example 13

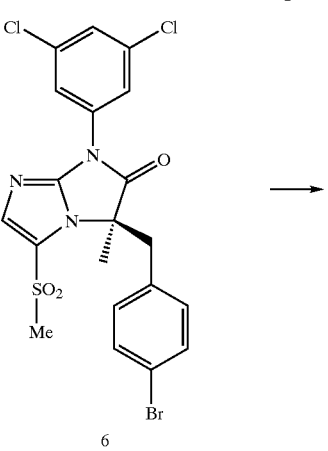

6

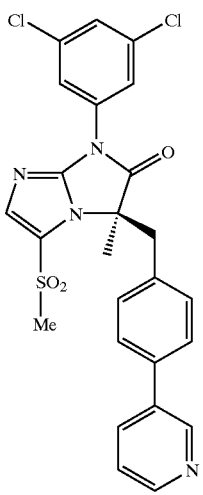

13

A solution of compound 6 (90 mg, 0.17 mmol) in 2 mL of toluene, 1 mL of EtOH and 0.8 mL of 2 M NaHCO$_3$ was treated with pyridine-3-boronic acid (37 mg, 0.22 mmol) and Pd(PPh$_3$)$_4$(20 mg, 0,02 mmol). The mixture was heated to reflux 1.5 h. Upon cooling, the solvent was removed by rotary evaporation and the residue was purified by silica gel chromatography. This produced 50.4 mg of compound 13. Mp 80–82° C. The product was characterized by $^1$H NMR and mass spectroscopy.

Example 14

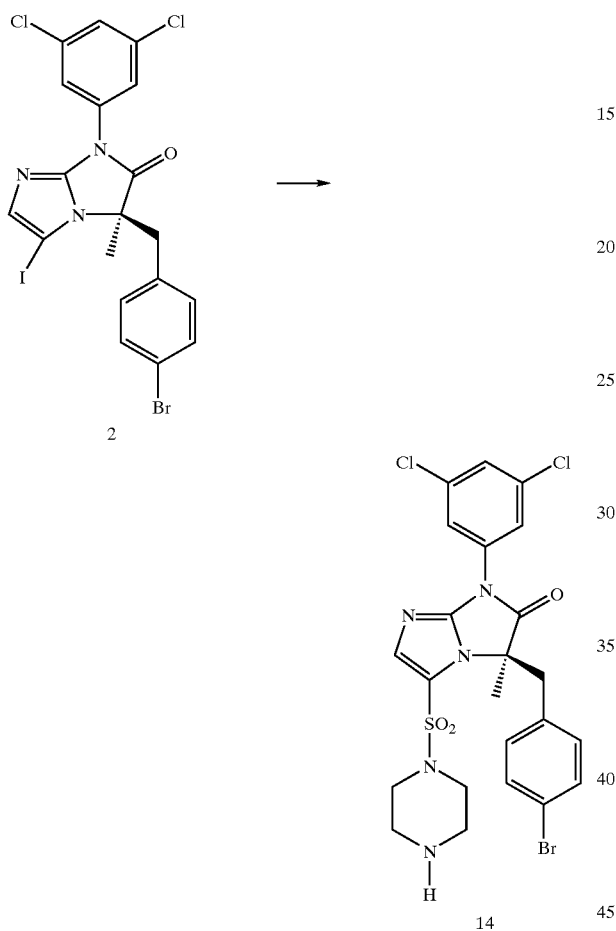

A solution of compound 2 (100 mg, 0.17 mmol) in 2.5 mL of THF was treated with cyclopentylmagnesium bromide (0.14 mL, 2 M in ether, 0.28 mmol) at −40° C. under argon. The mixture was stirred at −40° C. for 40 min and then SO$_2$ was bubbled in over 1 min. The mixture was stirred at −40° C. for 15 min then at room temperature for 1 h and finally at 45° C. before being concentrated twice under vacuum from dry THF to produce the solid magnesium salt. The magnesium salt was treated with a mixture of triethylamine (0.035 mL, 0.36 mmol) and N-chlorosuccinimide (71 mg, 0.53 mmol). After 15 min, an excess of piperazine (119 mg, 1.38 mmol) was added and the reaction stirred at room temperature for 3 h. The mixture was then quenched by the addition of a solution of saturated NH$_4$Cl and extracted into EtOAc. Upon concentration, the crude product was purified using preparative TLC to yield compound 14 (26 mg) as an oil. The product was characterized by $^1$H NMR and mass spectroscopy.

Example 15

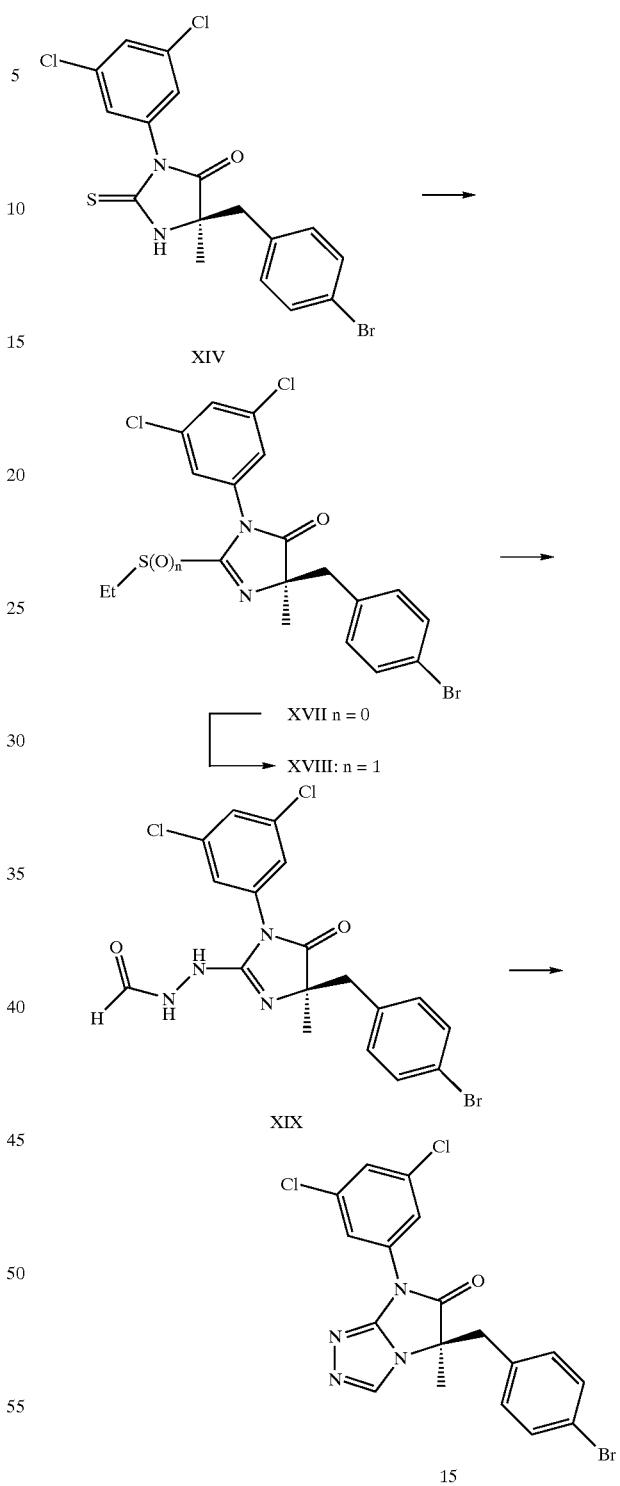

2.00 mL of 1 N NaOH was added to a solution of 0.85 g (1.91 mmol) of XIV and 0.30 mL (0.35 g, 2.30 mmol) of diethyl sulfate in 8.5 mL of THF stirring in an ice-bath. After 10 min in the cold, the reaction was warmed to room temperature and stirred 3.5 h. Aqueous ammonium chloride was added and the reaction extracted with EtOAc, dried over MgSO$_4$, and concentrated in vacuo to give an oil (0.98 g). Flash chromatography on silica gel afforded 0.77 g (85%) of XVII as clear oil. The product was characterized by $^1$H NMR and mass spectroscopy.

A solution of 0.69 g (1.13 mmol) of potassium peroxymonosulfate in 2.5 mL of $4 \times 10^{-4}$ M EDTA was added to a stirred suspension of 0.76 g (1.61 mmol) of XVII and 0.68 g (8.05 mmol) of NaHCO$_3$ in 7.5 mL acetone and 2.5 mL H$_2$O. After stirring 5 h, the reaction was diluted with EtOAc and washed with saturated aqueous Na$_2$SO$_3$ and brine. The combined aqueous phases were extracted with EtOAc and the combined organic phases were dried over MgSO$_4$ and concentrated in vacuo to give 0.82 g of XVIII as a clear oil. The product was characterized by $^1$H NMR and mass spectroscopy.

To this oil was added 0.48 g (8.05 mmol) of formic hydrazide and 3.8 mL of dry DMSO and the reaction was heated at 60° C. under Ar for 10 h. Water was added giving a white precipitate which was extracted into EtOAc, washed with H$_2$O, dried over MgSO$_4$, and concentrated in vacuo to 0.72 g of solid product. This was flash chromatographed on silica gel to give 0.31 g (41%) of XIX as a white solid.

A mixture of 0.15 g (0.319 mmol) of XIX and 15 mg of p-toluenesulfonic acid and 0.30 g of 4 Å molecular sieves in 3 mL of toluene was refluxed 5.5 h. The reaction was applied directly to a silica gel column and was purified via flash chromatography, to afford 0.12 g (82%) of 15 as a yellow foamy resin. The product was characterized by $^1$H NMR and mass spectroscopy.

Example 16

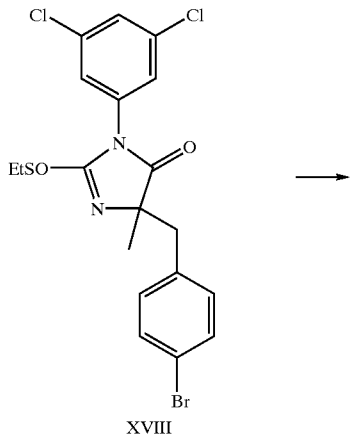

XVIII

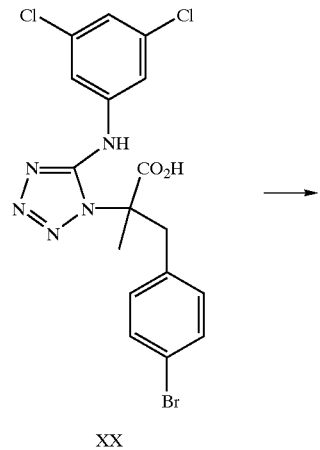

XX

-continued

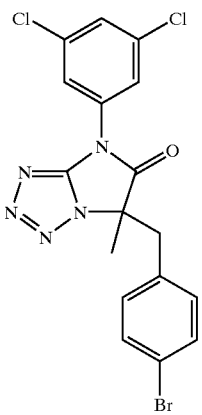

16

A solution of XVIII (Example 15) (130 mg, 0.266 mmol) in DMF (1 mL) was treated with NaN$_3$ (140 mg, 2.15 mmol) at room temperature for 20 h. The mixture was diluted with H$_2$O and extracted with EtOAc. The organic layer was dried (Na$_2$SO$_4$) and concentrated. The residue was purified by silica gel chromatography to give compound XX (80 mg, 64%). The product was characterized by $^1$H NMR and mass spectroscopy.

To a solution of XX (28 mg, 0.060 mmol) in DMF (0.5 mL) was added HOBT(16 mg, 0.118 mmol) and EDC (23 mg, 0.120 mmol). The mixture was stirred at room temperature for 2 h before diisopropylethylamine (31 □L, 0.18 mmol) was added. The mixture was stirred at room temperature for 10 h, diluted with water, and extracted with methylene chloride. The organic layer was dried, concentrated and purified by silica gel chromatography to give 16 (15 mg, 56%). The product was characterized by $^1$H NMR and mass spectroscopy.

Example 17

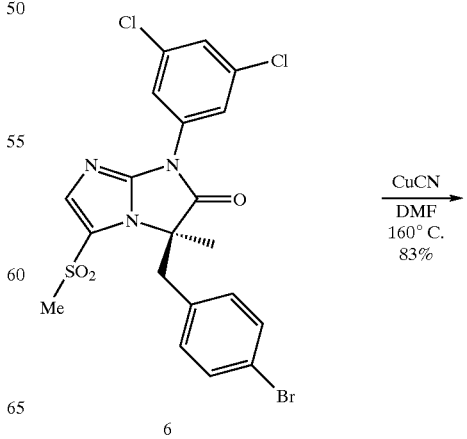

6

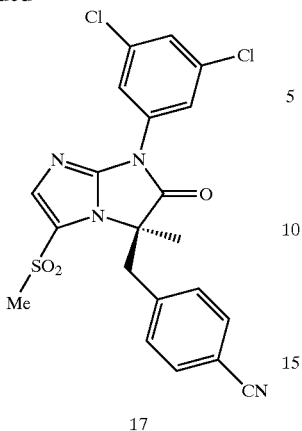

17

A mixture of 375 mg (0.709 mmol) of compound 6 and 70 mg (0.779 mmol) copper (I) cyanide in 1.5 mL was stirred in dry DMF and heated for 4 h at 160° C. under Ar. After cooling, water and EtOAc were added and the reaction was filtered, the solids were washed with EtOAc, to afford 90 mg of a green solid. The filtrate was extracted with EtOAc, washed with water, dried, and concentrated under reduced pressure to 335 mg of resin. The solids were suspended in 2 mL EtOAc and stirred overnight with 16 □L $SOCl_2$. $H_2O$ and EtOAc were added, the reaction was filtered and the filtrate extracted with EtOAc, washed with $H_2O$ and dried, and then was concentrated under reduced pressure. The combined crude products were purified via flash chromatography to afford 234 mg (69%) of compound 17 as a white resin, after drying under vacuum at 60° C. The product was characterized by $^1H$ NMR and mass spectroscopy.

Example 18

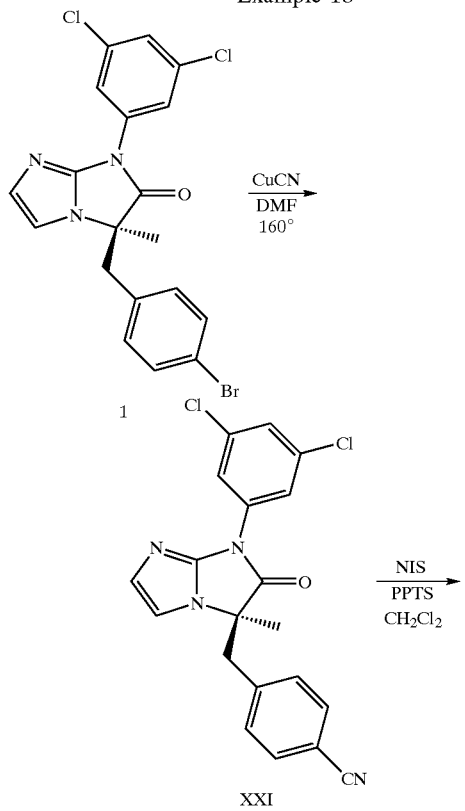

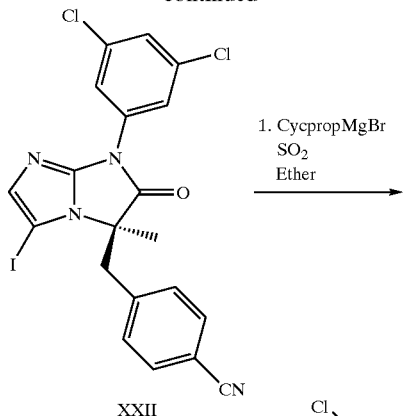

XXII

18

A mixture of 2.50 g (5.54 mmol) of compound 1 and 650 mg (7.20 mmol) of copper (I) cyanide in 8 mL of dry DMF was stirred and heated 5 h at 160° under Ar. After cooling, the mixture was poured into water and EtOAc was added and the reaction was filtered, and the solids were washed with EtOAc, to afford 1.82 g of grey solid. The filtrate was separated and the organic phase washed with $H_2O$ and concentrated under reduced pressure to give 1.35 g of an oil. The grey solids (1.4 g) were refluxed with 0.27 mL $SOCl_2$ in 15 mL EtOAc for 0.5 h. After cooling, $H_2O$ and EtOAc were added, the reaction was filtered and the solids were washed with EtOAc. The filtrate was extracted with EtOAc, the organic layer was dried, and concentrated under reduced pressure. The crude products were combined and purified via flash chromatography to 890 mg (36%) of unreacted 1, 960 mg (46%) of XXI, as well as 310 of mixed fractions.

N-iodosuccinimide (580 mg, 0.256 mmol) was added to a solution of 960 mg (2.44 mmol) of XXI and 61 mg (0.244 mmol) of pyridinium p-toluenesulfonate in 10 mL methylene chloride at 0 C. The reaction was allowed to warm to room temperature and was stirred overnight. The reaction mixture was concentrated under reduced pressure, the residue diluted with EtOAc, washed with saturated aqueous $Na_2S_2O_3$, dried and concentrated under reduced pressure. The 310 mg of mixed fraction were treated similarly as described above. After isolation, the two residues were combined and purified via flash chromatography to afford 1.08 g (64%) of compound XXII as a resin. The product was characterized by $^1H$ NMR and mass spectroscopy.

A solution of 2 M cyclopentylmagnesium bromide (1.24 mL, 2.48 mmol) in $Et_2O$ was added to a solution of 1.08 g (2.06 mmol) of XXII in 20 mL dry $Et_2O$ at −50° C., resulting in a white suspension. The reaction was stirred for 15 min at −50 C and then SO₂ was bubbled in for 2 min. The reaction mixture was stirred for an additional 15 min at that temperature, and then was stirred at room temp for 1 h. The reaction was filtered, the solids washed with Et₂O, and dried under vacuum for 0.5 h at room temperature to give 1.44 g of compound 18 as a beige solid.

Example 19

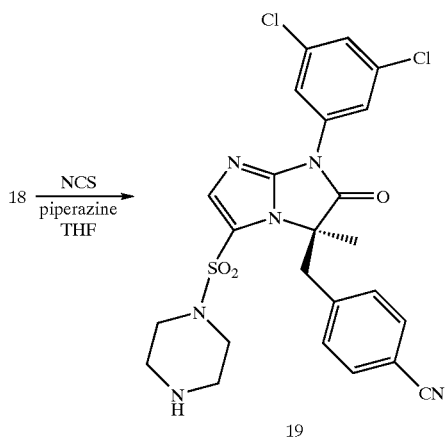

To a stirred solution of 177 mg (1.33 mmol) N-chlorosuccinimide in 10 mL dry THF, was added 500 mg (0.709 mmol) of 18 giving a yellow solution that was stirred 10 min. Piperazine (760 mg, 8.86 mmol) was added giving a pale suspension that was stirred 0.5 h. The reaction was filtered, the filtrate washed successively with water and 2N NaOH was dried, and concentrated under reduced pressure. Purification of the residue via flash chromatography afforded 225 mg (58%) of 19. The product was characterized by ¹H NMR and mass spectroscopy.

Examples 20–22

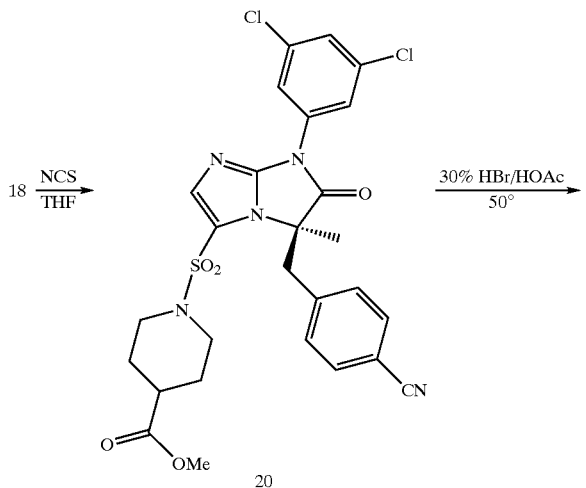

To a stirred solution of 71 mg (0.532 mmol) N-chlorosuccinimide in 4 mL dry THF, was added 200 mg (0.283) of 18 giving a yellow solution that was stirred 10 min. Methyl isonipecotate (479 mL, 3.54 mmol) was added giving a beige suspension that was stirred 0.5 h. The reaction was filtered, the filtrate washed successively with water then 2N NaOH, was dried and then was concentrated under reduced pressure. This residue was purified via preparative TLC to give 87 mg (51%) of 20. The product was characterized by ¹H NMR and mass spectroscopy.

Example 21

A stirred solution of 70 mg of 20 in 0.35 mL 30% HBr in acetic acid was stirred 3.5 h at 50° C. Water was added, the reaction was filtered and the solids were washed with H₂O. The solids were dissolved in alcohol, precipitated with water and filtered, and then were dried under vacuum at 50° C. to give 43 mg of a beige powder. The aqueous filtrates were extracted with EtOAc to afford another 17 mg, to yield a total of 60 mg (88%) of 21. The product was characterized by ¹H NMR and mass spectroscopy

Example 22

A solution of 13 mg (0.069 mmol) of 1-[3-(dimethylamino)propyl]-3-ethylcarbodiimide hydrochloride (EDC) and 34 mg (0.058 mmol) of 21 in 1 mL CH₂Cl₂ was stirred for 0.5 h in at 0° C. Ammonia gas was bubbled in over 1 min and stirred for 15 min at 0° C. and then at room temperature for 7.5 h. An additional 13 mg of EDC was added to the reaction, which was then saturated with NH₃, sealed and the was allowed to stir overnight. The reaction mixture was concentrated to dryness under reduced pressure, and the residue was purified via preparative TLC to afford 13 mg (38%) of 22 as a resin. The product was characterized by ¹H NMR and mass spectroscopy.

Example 23

A stirred solution of 27 mg (0.201 mmol) of N-chlorosuccinimide and 76 mg (0.107 mmol assuming 80% purity) of 18 in 2 mL dry THF was stirred for 5 min at room temperature. N-Acetylpiperazine (86 mg, 0.67 mmol) was added, and the resulting white suspension was stirred for 1 h. The reaction mixture was diluted with EtOAc, filtered and the filtrate was successively washed with 2N HCl, 2N NaOH and H₂O, was dried and concentrated under reduced pressure. The residue was purified via preparative TLC to give 33.5 mg (53%) of 23. The product was characterized by ¹H NMR and mass spectroscopy.

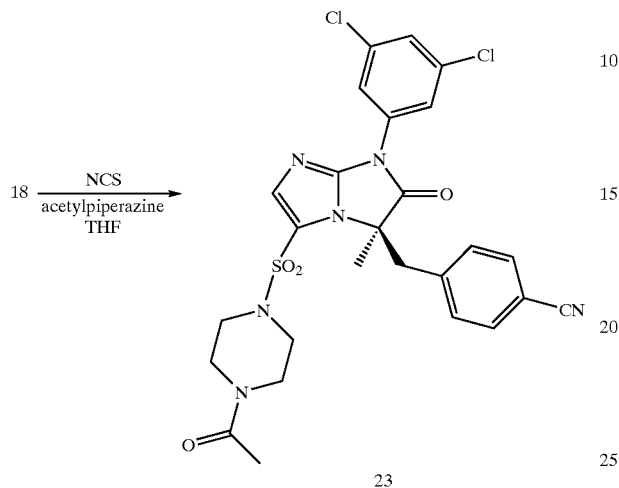

Example 24

This Example describes an alternate synthesis of intermediate XXI of Example 18

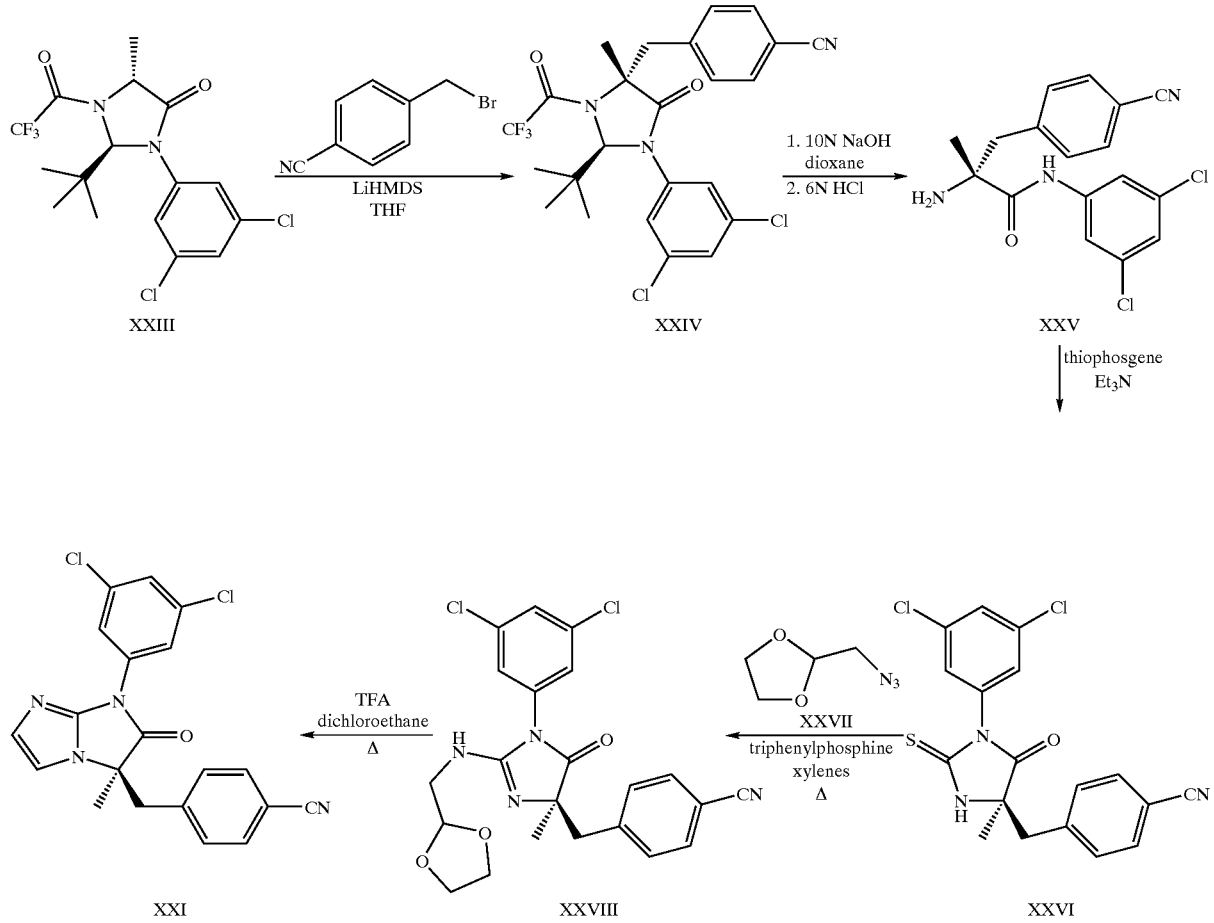

A solution of 15.1 mL (0.0151 mol) of 1 M lithium bis(trimethylsilyl)amide in THF was added to 5.00 g (0.0126 mol) of XXIII in 50 mL dry tetrahydrofuran at −10° C., and the orange solution was stirred for 0.5 h. A mixture of 2.96 g (0.151 mol) □-bromo-4-toluonitrile in 15 mL THF was added dropwise and the resulting suspension was stirred for 5 h between −10 and 0° C. Aqueous ammonium chloride was added, and the aqueous layer was extracted with ether. The organic layer was dried and concentrated under reduced pressure. The residue was purified via flash chromatography and subsequently recrystallized from $CH_2Cl_2$-pet ether to afford 5.04 g (78%) of a white solid. The product was characterized by $^1H$ NMR and mass spectroscopy.

A mixture of 5.00 g (9.67 mmol) of XXIV and 5.78 mL (14.6 mmol) of 40% benzyltrimethylammonium hydroxide in $H_2O$ and 1.95 mL 10 N sodium hydroxide in 25 mL of 1,4-dioxane was stirred at room temperature for 15 h, then was heated at 40° C. for 1 h. The mixture was cooled to room temperature, then 16.3 mL (96.7 mmol) of 6 N HCl was added, and the mixture was allowed to stir overnight. A solution of saturated aqueous $Na_2CO_3$ and the aqueous layer was extracted with EtOAc. The organic layer was dried and concentrated under reduced pressure and the residue was purified via flash chromatography to afford 2.78 g (82%) of XXV as an oil. The product was characterized by $^1H$ NMR and mass spectroscopy.

Thiophosgene (0.723 mL, 9.48 mmol) was added to a solution of 2.75 g (7.90 mmol) XXV in 28 mL $CH_2Cl_2$ at 0° C., resulting in an orange solution. Triethylamine (4.40 mL, 31.6 mmol) was added and the dark solution was allowed to warm to room temperature and was stirred overnight. The reaction was diluted with EtOAc, washed with saturated aqueous $NH_4Cl$, re-extracted 2X EtOAc, then was dried and concentrated under reduced pressure. The residue was purified via flash chromatography to afford 1.35 g recovered impure XXV as well as 1.08 g impure XXVI. The recovered XXV was subjected to reaction conditions similar to that above, and after isolation and purification yielded an additional 0.28 g of impure XXVI. The two samples were combined and purified again via flash chromatography, to afford 0.92 g of pure compound XXVI. The product was characterized by $^1H$ NMR and mass spectroscopy.

Triphenylphosphine (1.18 g, 4.51 mmol) was added portionwise to a solution of 580 mg (4.51 mmol) of XXVII in 10 mL of xylenes and was stirred for 2 h at room temperature. A solution of 880 mg (2.25 mmol) of XXVI in 2 mL of xylenes was added and the reaction was heated to reflux for 3 days and then was concentrated under reduced pressure. The residue was purified via flash chromatography to afford 420 mg of impure XXVI, and 290 mg of impure XXVIII contaminated with triphenylphosphine oxide The sample of XXVIII was treated with 0.49 mL (6.3 mmol) trifluoroacetic acid in 4 mL of 1,2-dichloroethane in a pressure tube, purged with Ar, and heated at 110° C. overnight. The reaction was then treated with saturated aqueous $Na_2CO_3$, extracted with ether, then dried and concentrated under reduced pressure. The 420 mg of impure XXVI was treated under conditions similar to that described above. After isolation, both residues were combined and were purified via flash chromatography to afford 120 mg (13%) of XXI as an oil. The product was characterized by $^1H$ NMR and mass spectroscopy.

Example 25

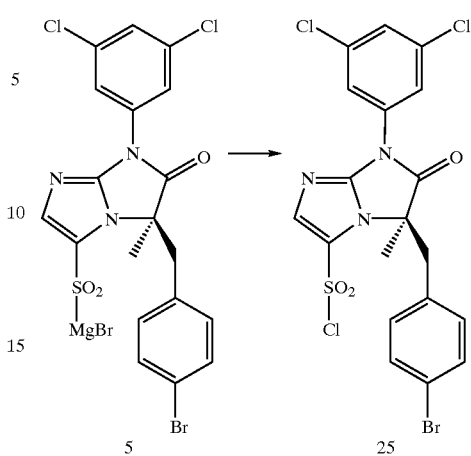

To a stirred solution of magnesium salt 5 (2.61 g, 4.22 mmol) in THF (50 mL) was added N-chlorosuccinimide (0.79 g, 5.94 mmol). The resulting mixture was stirred at room temperature for 1 h, then was poured into brine and extracted with EtOAc. The combined extracts were washed with brine, dried over $MgSO_4$ and filtered and the solvent was removed under reduced pressure. The residue was purified via silica gel chromatography to afford 1.77 g (76%) of 25 as a foam which was characterized via $^1H$ NMR and MS.

Example 26

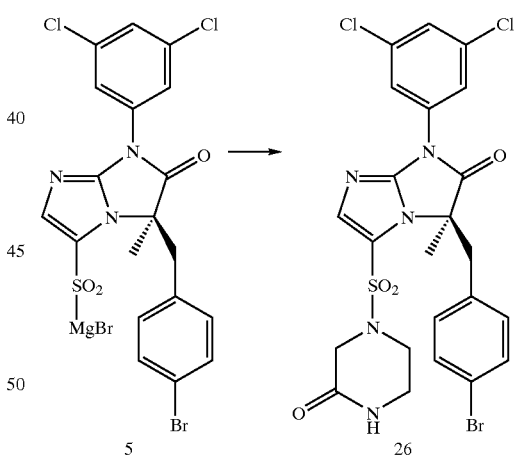

To a stirred solution of N-chlorosuccinimide (155 mg, 1.2 mmol) in THF (18 mL) at room temperature was added 5 (600 mg, 0.97 mmol). The resulting yellow reaction mixture was stirred for 30 min, then piperazinone (214 mg, 2.1 mmol) was added in one portion, followed by a few drops of DMSO. The reaction mixture was stirred overnight, then was diluted with EtOAc, washed with brine, dried over $MgSO_4$ and filtered and the solvent was removed under reduce pressure. The residue was purified via silica gel chromatography to afford 240 mg (40%) of compound 26 as a foam which was characterized via $^1H$ NMR and MS.

Example 27

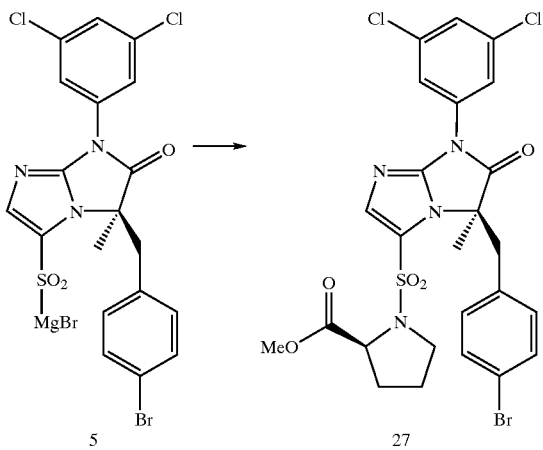

To a stirred solution of 5 (308 mg; 0.50 mmol) in THF (12 mL) at −20° C. was added N-chlorosuccinimide (77.6 mg, 0.58 mmol). The resulting mixture was stirred for 10 min, warmed to 0° C. and then cooled back to −30° C. L-proline methyl ester hydrochloride (50 mg, 0.81 mmol) was added followed by triethylamine (0.12 mL) and the reaction mixture was stirred for 2 h. The mixture was treated with saturated aqueous ammonium chloride, and then was extracted with diethyl ether. The organic layer was dried over MgSO$_4$ and filtered and the residue purified via preparative TLC to afford 127 mg (65%) of compound 27 as a foam which was characterized via $^1$H NMR and MS.

Example 28

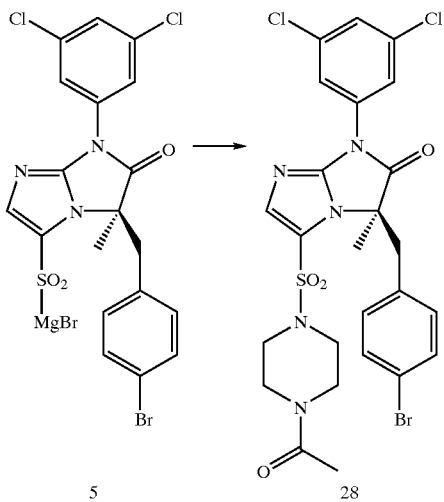

To a stirred solution of N-chlorosuccinimide (325 mg, 2.4 mmol) in THF (10 mL) was added 5 (1.0 g, 1.6 mmol) in portions, at room temperature. The resulting yellow mixture was stirred for 5 min, then 4-acetylpiperazine (830 mg, 6.5 mmol) was added. The reaction mixture was allowed to stir for 1 h, then was treated with brine, and the aqueous layer was extracted with EtOAc. The organic layer was washed successively with 1 M HCl, saturated aqueous sodium bicarbonate and brine, then was dried over MgSO$_4$ and filtered and the solvent was removed under reduced pressure. The residue was purified via silica gel chromatography to afford 650 mg (63%) of compound 28 as a solid (m.p. 153–155° C.) which was characterized via $^1$H NMR and MS. Alternatively, compound 28 can also be prepared by the following method using compound 14 (Example 14): to a stirred solution of 14 (200 mg, 0.33 mmol) in THF (20 mL) at 0° C. was added acetyl chloride (0.23 mL, 3.3 mmol) and triethylamine (0.23 mL, 1.65 mmol). The reaction mixture was allowed to warm to room temperature over 1 h and was stirred an additional 1 h at that temperature. The mixture was poured into saturated aqueous sodium bicarbonate and the aqueous layer was extracted with EtOAc. The organic layer was dried over MgSO$_4$ and filtered and the solvent was removed under reduced pressure. The residue was purified via preparative TLC to afford 193 mg (90%) of compound 28 as a solid which exhibited identical spectral characteristics with those of the title compound prepared via the former method.

Example 29

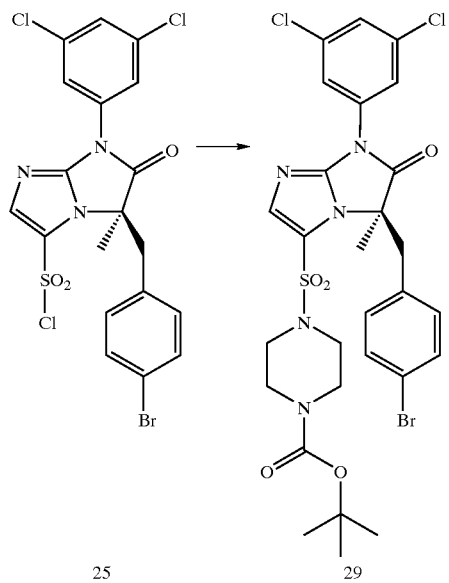

To a stirred solution of 25 (900 mg, 1.6 mmol) in dichloromethane (10 mL) was added a solution of 1-Boc-piperazine (670 mg, 3.6 mmol) in dichloromethane dropwise at 0° C. The reaction mixture was warmed to room temperature and allowed to stir for 2 h. The mixture was diluted with EtOAc, washed successively with 0.1 M HCl, water and brine, dried over MgSO$_4$ and filtered and the solvent was removed under reduced pressure. The residue was purified via silica gel chromatography to afford 931 mg (82%) of compound 29 as a foam which was characterized via $^1$H NMR and MS.

Example 30

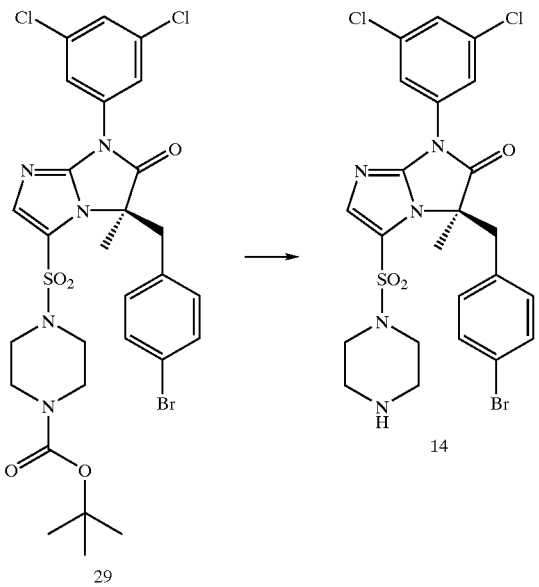

This example describes an alternate synthesis of compound 14 (Example 14) To a stirred solution of 29 (3.43 g, 4.9 mmol) in dichloromethane (30 mL) was added trifluoroacetic acid (5 mL, 65 mmol). The reaction mixture was allowed to stir at room temperature for 2 h, then was poured into 1 M NaOH and was extracted with dichloromethane. The organic layer was dried over MgSO$_4$ and filtered and the solvent was removed under reduced pressure. The residue was purified via silica gel chromatography to afford 2.20 g (75%) of 14 as a foam which was characterized via $^1$H NMR and MS.

Example 31

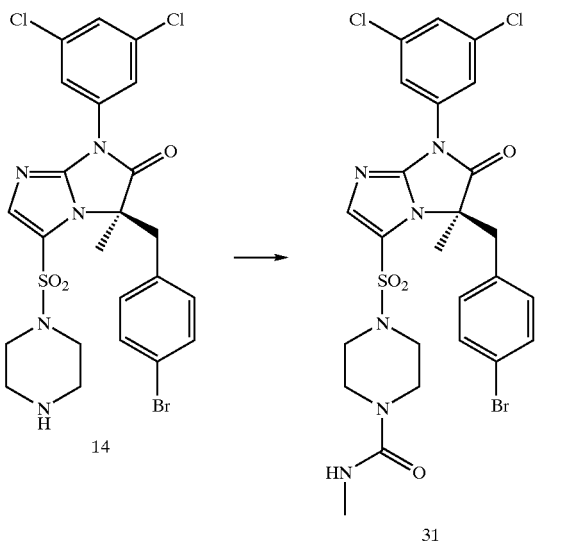

To a stirred solution of 14 (154 mg, 0.26 mmol) in dichloromethane (1.5 mL) was added methyl isocyanate (0.024 mL, 0.39 mmol). The reaction mixture was stirred for 0.5 h, then an additional amount (0.024 mL, 0.39 mmol) of methyl isocyanate was added. The reaction mixture was stirred for an additional 0.5 h, then the solvent was removed under reduced pressure to afford a quantitative yield of 31 which was characterized via $^1$H NMR and MS.

Example 32

To a stirred solution of 3-hydroxypicolinic acid (138 mg, 0.99 mmol) in N,N-dimethylformamide (10 mL) was added the PS-CDI resin (1.86 g, 1.65 mmol). After 1 h, 14 (200 mg, 0.33 mmol) was added and the reaction mixture was allowed to stir overnight. The resin was filtered and then washed with dichloromethane and the combined organic layers were poured into water. The aqueous layer was extracted with dichloromethane, then the organic layer was washed with brine, dried over MgSO$_4$ and filtered and the solvent was removed under reduced pressure. The residue was purified via preparative TLC to afford 89 mg (37%) of compound 32 as a foam which was characterized via $^1$H NMR and MS.

Example 33

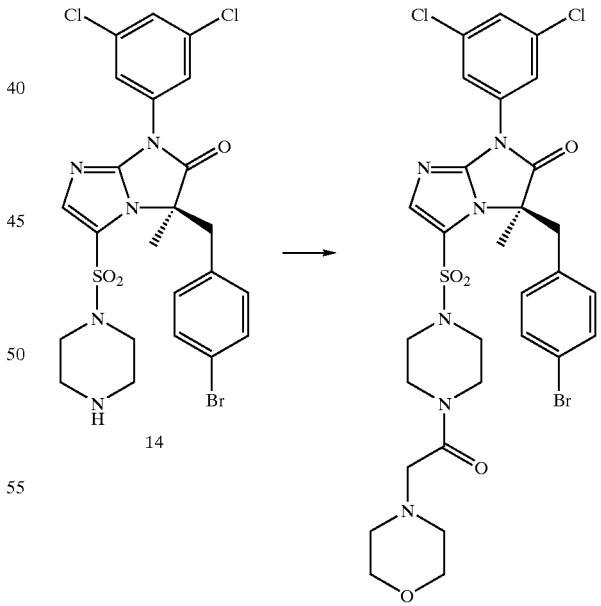

To a stirred solution of morpholinoacetic acid (35 mg, 0.24 mmol) in N,N-dimethylformamide (8 mL) was added the PS-CDI resin (425 mg, 0.48 mmol). After 1 h, 14 (50 mg, 0.08 mmol) was added and the reaction mixture was allowed to stir overnight. The resin was filtered and then washed with dichloromethane and the combined organic layers were poured into water. The aqueous layer was extracted with dichloromethane, then the organic layer was washed with brine, dried over MgSO₄ and filtered and the solvent was removed under reduced pressure. The residue was purified via preparative TLC to afford 59 mg (98%) of compound 33 as a foam which was characterized via ¹H NMR and MS.

Example 34

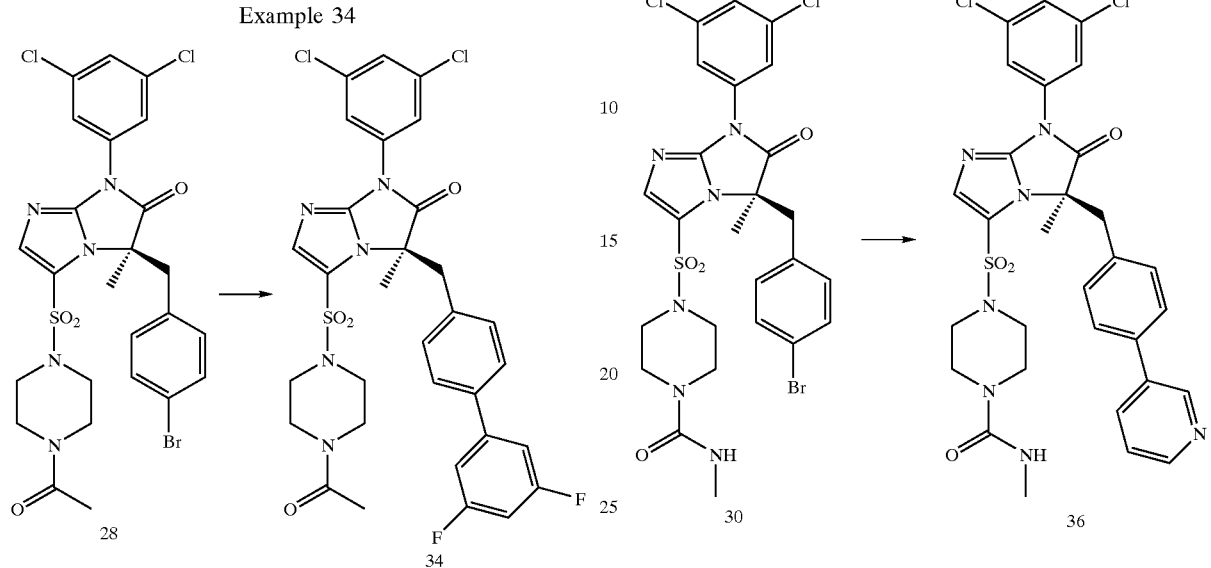

To a solution of 28 (29 mg, 0.045 mmol), 3,5-difluorophenylboronic acid (0.026 mL, 50% wt/wt in THF/H₂O; 0.09 mmol) and PdCl₂(dppf).CH₂Cl₂ (1.8 mg, 0.0022 mmol) in a mixture of toluene (2 mL) and EtOH (1 mL) was added a solution of K₂CO₃ (25 mg, 0.18 mmol) in water (0.5 mL). The reaction mixture was heated to reflux for 4 h, then was diluted with toluene, and washed with brine, was dried over MgSO₄ and filtered and the solvent was removed under reduced pressure. The residue was purified via preparative TLC to afford 18.3 mg (60%) of compound 34 as a foam which was characterized via ¹H NMR and MS.

Example 35

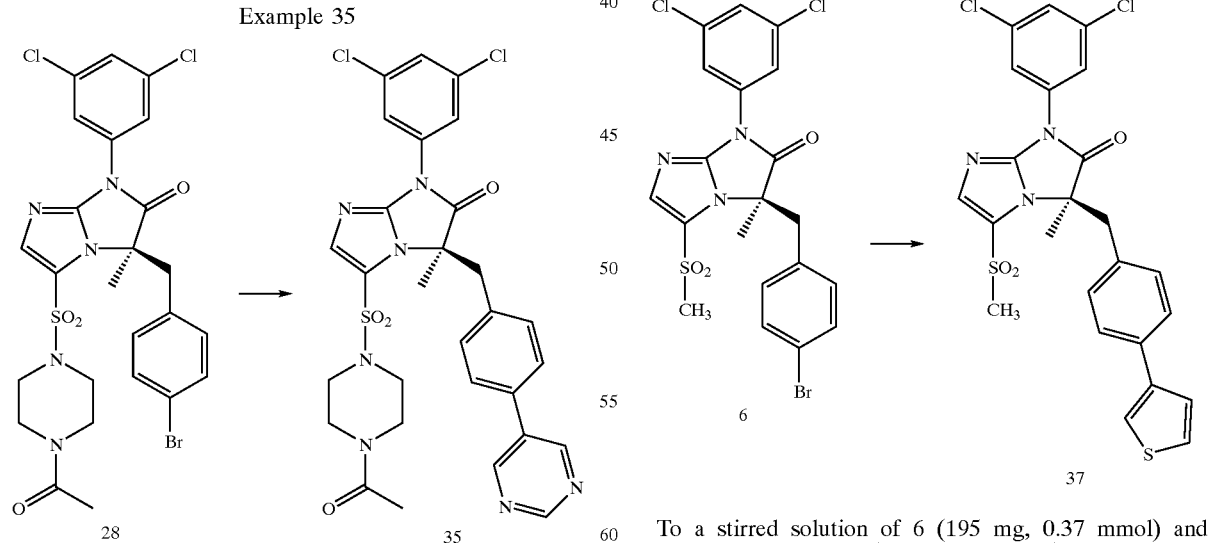

To a stirred solution of 28 (300 mg, 0.47 mmol) and 5-(trimethylstannyl)pyrimidine (180 mg, 0.74 mmol) in toluene (10 mL) was added Pd(PPh₃)₄(120 mg, 0.11 mmol) and the reaction mixture was heated to reflux for 15 h. Decolorizing charcoal was added to the mixture, which was stirred and then filtered and the solvent was removed under reduced pressure. The residue was purified via preparative TLC to afford 78 mg (26%) of compound 35 as a foam which was characterized via ¹H NMR and MS.

Example 36

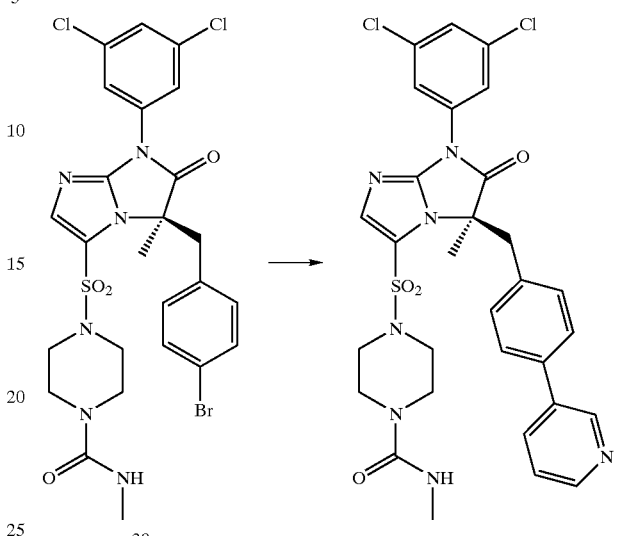

To a stirred solution of 31 (168 mg, 0.26 mmol) and pyridine-3-boronic acid propanediol ester (59 mg, 0.36 mmol) in a mixture of toluene (3 mL), ethanol (1.5 mL) and 2 M aqueous sodium carbonate (1.25 mL) was added Pd(PPh₃)₄(59 mg, 0.05 mmol). The reaction mixture was heated to reflux for 1 h. The mixture was then filtered and the organic layer was diluted with EtOAc, washed with water then dried over MgSO₄ and filtered and the solvent was removed under reduced pressure. The residue was purified via preparative TLC to afford 90 mg (32%) of compound 36 as a solid which was characterized via ¹H NMR and MS.

Example 37

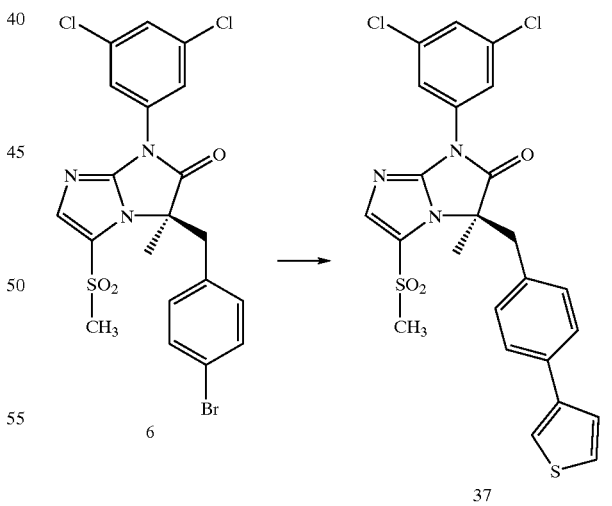

To a stirred solution of 6 (195 mg, 0.37 mmol) and 3-thiopheneboronic acid (94 mg, 0.74 mmol) in a mixture of toluene (4.4 mL), ethanol (2.2 mL) and 2 M aqueous sodium carbonate (0.55 mL) was added Pd(PPh₃)₄(43 mg, 0.037 mmol). The reaction mixture was heated to reflux for 3 h, then was diluted with EtOAc and washed successively with water and brine, dried over MgSO₄ and filtered and the solvent was removed under reduced pressure. The residue was purified via preparative TLC to afford 123 mg (63%) of compound 37 as a foam which was characterized via ¹H NMR and MS.

Example 38

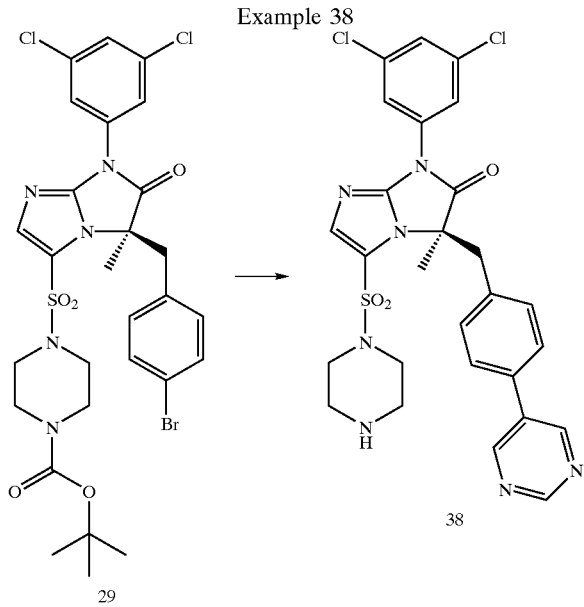

To a stirred solution of 29 (860 mg, 1.23 mmol) and pyrimidine-5-boronic acid pinacol ester (506 mg, 2.46 mmol) in a mixture of toluene (7 mL), ethanol (3.5 mL) and 2 M sodium carbonate (1.7 mL) was added Pd(PPh$_3$)$_4$ (142 mg, 0.12 mmol) and the reaction mixture was heated to reflux for 2 h. The mixture was diluted with EtOAc and washed successively with water and brine, then was dried and filtered and the solvent was removed under reduced pressure. The residue was purified via silica gel chromatography to afford 790 mg (92%) of Boc-protected 38 as a foam. To a stirred solution of Boc-protected 38 (704 mg, 1.0 mmol) in dichloromethane (15 mL) at room temperature was added trifluoroacetic acid (3 mL). The reaction mixture was stirred for 2 h, then was poured into 1 M sodium hydroxide and the aqueous layer was extracted with dichloromethane. The organic layer was washed with brine and dried over MgSO$_4$, was filtered and the solvent was removed under reduced pressure. The residue was purified via silica gel chromatography to afford 447 mg (64%) of compound 38 as a foam which was characterized via ¹H NMR and MS.

The following additional compounds of the invention were prepared by methods analogous to those described above. Each of the compounds below was characterized by NMR and MS.

| Example No. | Structure | Melting Point (° C.) |
|---|---|---|
| 39 | (structure shown) | >190 (decomp.) |
| 40 | (structure shown) | resin |

-continued
| Example No. | Structure | Melting Point (° C.) |
|---|---|---|
| 41 | 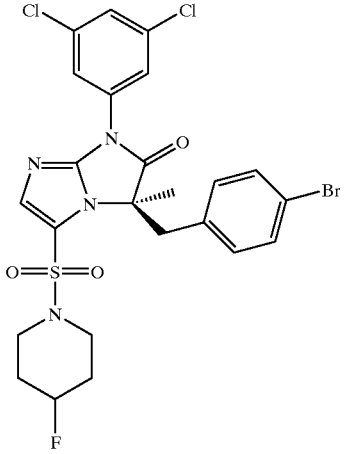 | foam |
| 42 | 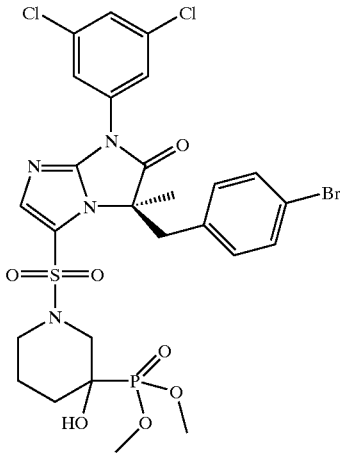 | foam |
| 43 | 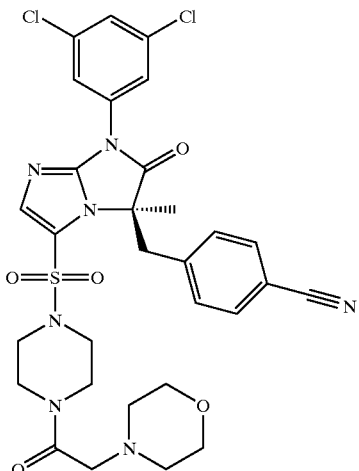 | resin |

-continued
| Example No. | Structure | Melting Point (° C.) |
|---|---|---|
| 44 | 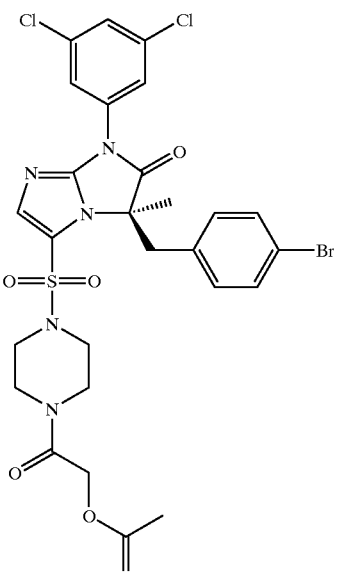 | resin |
| 45 | 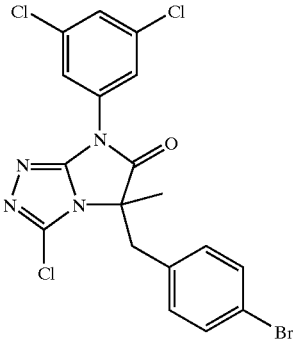 | 185–189 |
| 46 | 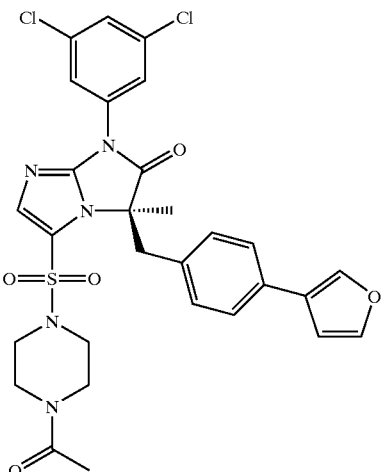 | resin |

-continued
| Example No. | Structure | Melting Point (° C.) |
|---|---|---|
| 47 | 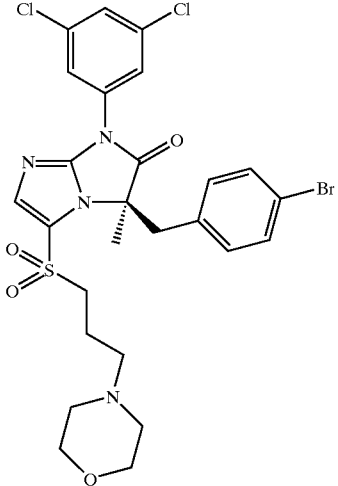 | resin |
| 48 | 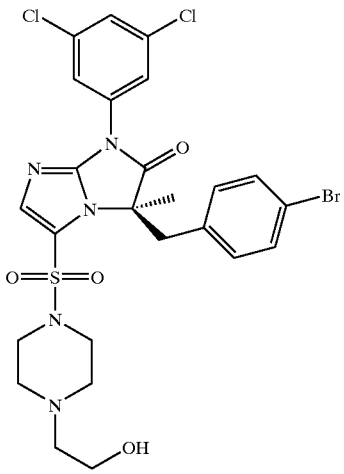 | foam |
| 49 | 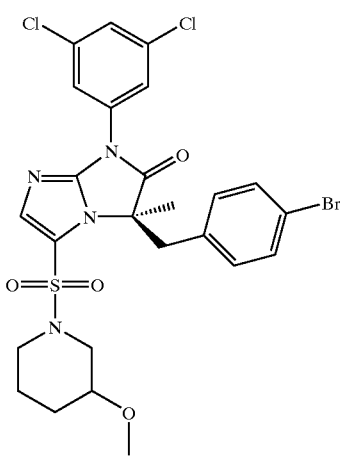 | not determined |

-continued

| Example No. | Structure | Melting Point (° C.) |
|---|---|---|
| 50 | 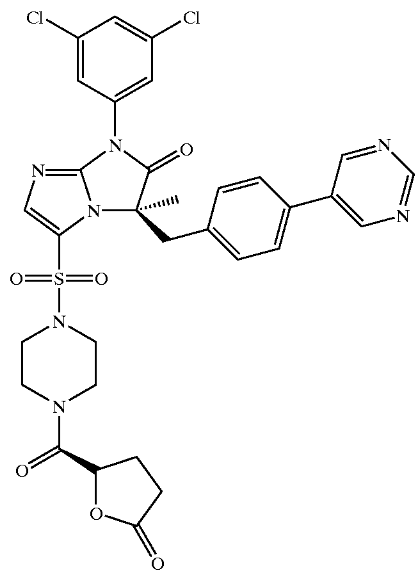 | not determined |
| 51 | 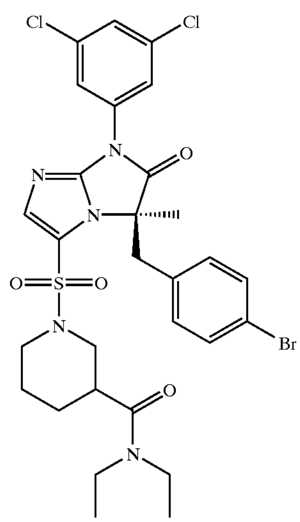 | 75–82 |
| 52 | 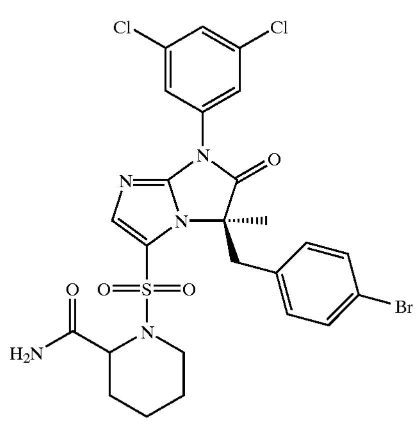 | not determined |

-continued

| Example No. | Structure | Melting Point (° C.) |
|---|---|---|
| 53 | 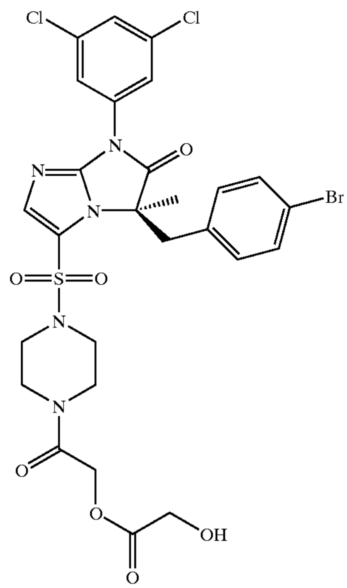 | not determined |
| 54 | 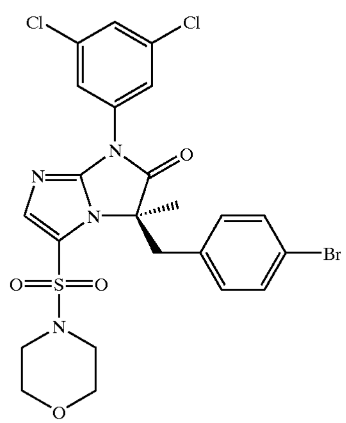 | 79.1–80.9 |
| 55 | 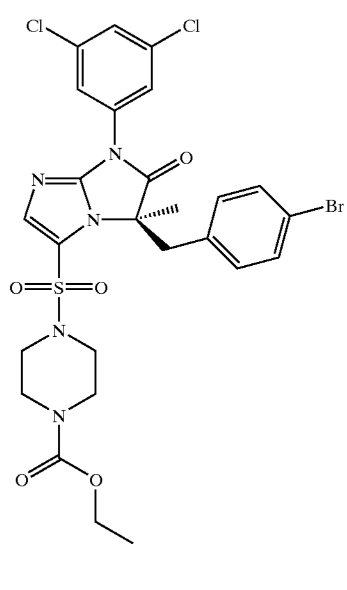 | foam |

-continued
| Example No. | Structure | Melting Point (° C.) |
|---|---|---|
| 56 | 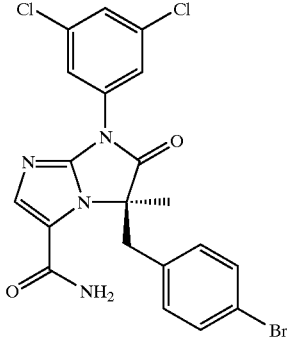 | foam |
| 57 | 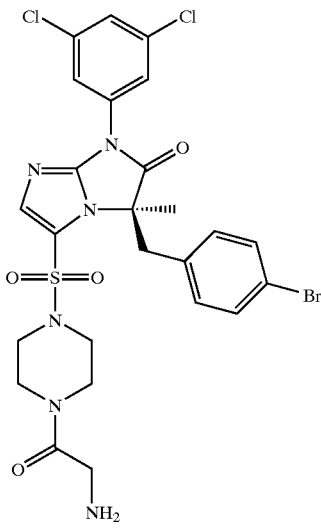 | not determined |
| 58 | 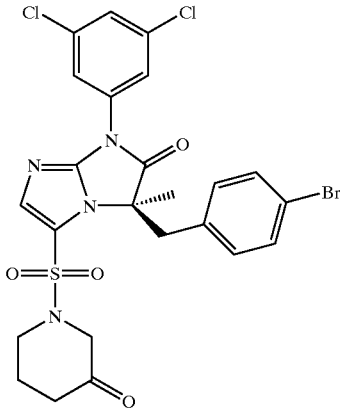 | not determined |

-continued

| Example No. | Structure | Melting Point (° C.) |
|---|---|---|
| 59 | 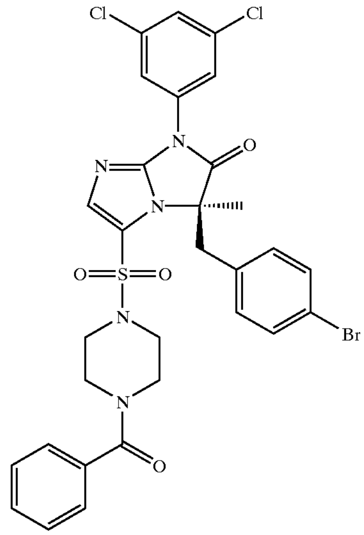 | 195–197 |
| 60 | 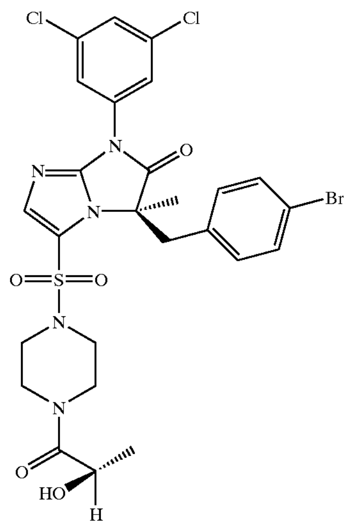 | not determined |
| 61 | 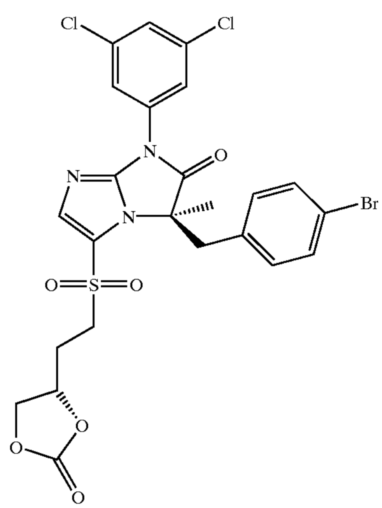 | not determined |

-continued

| Example No. | Structure | Melting Point (° C.) |
|---|---|---|
| 62 | 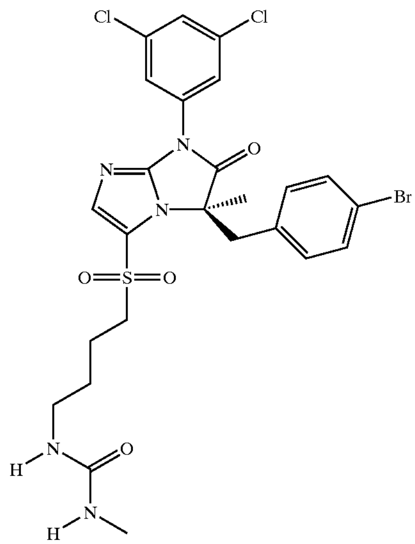 | not determined |
| 63 | 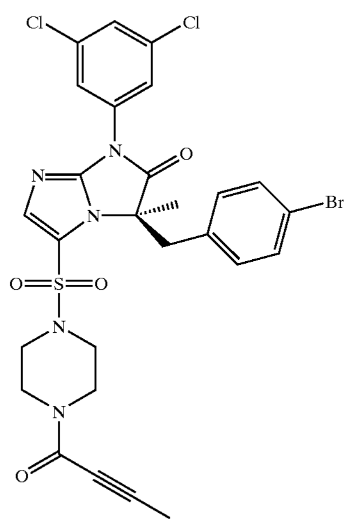 | not determined |
| 64 | 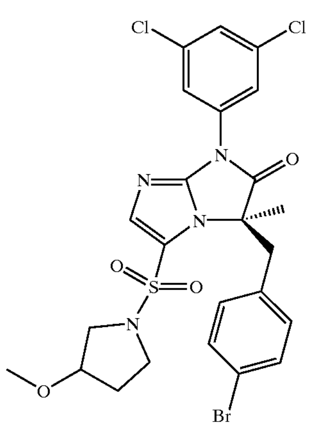 | foam |

-continued
| Example No. | Structure | Melting Point (° C.) |
|---|---|---|
| 65 | 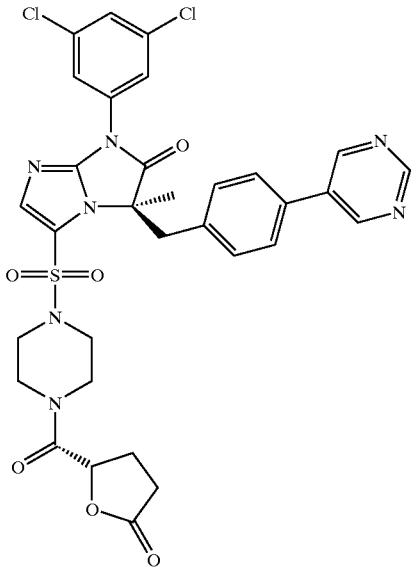 | not determined |
| 66 | 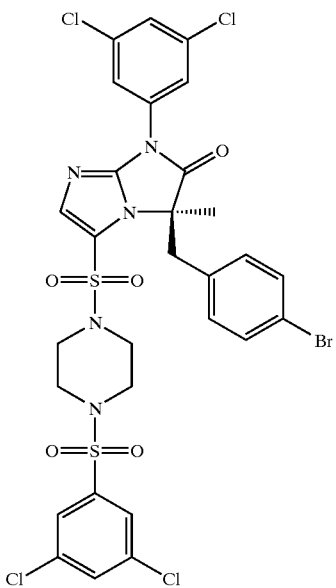 | 146–148 |

-continued

| Example No. | Structure | Melting Point (° C.) |
|---|---|---|
| 67 | 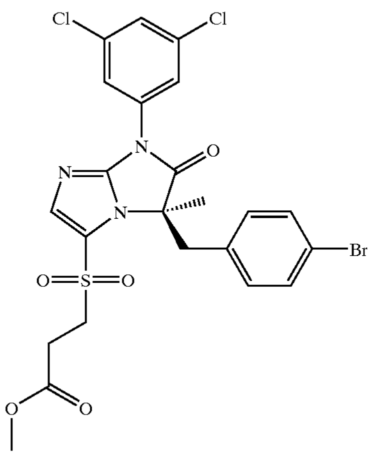 | foam |
| 68 | 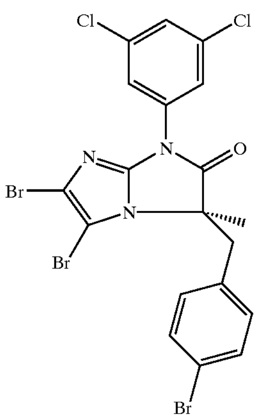 | not determined |
| 69 | 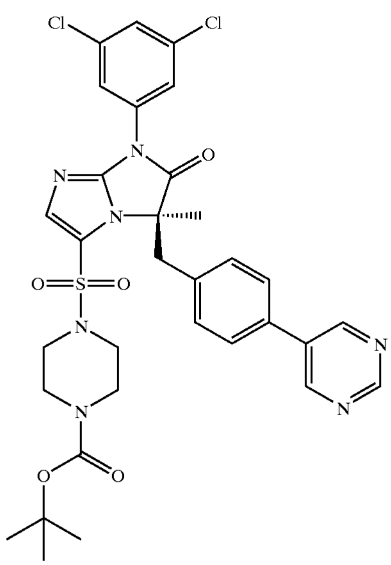 | foam |

-continued
| Example No. | Structure | Melting Point (° C.) |
|---|---|---|
| 70 | 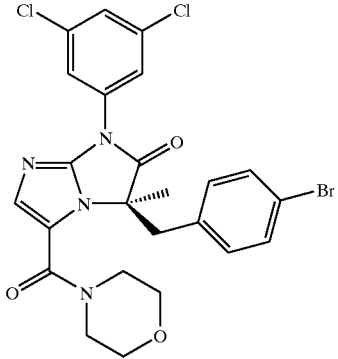 | foam |
| 71 | 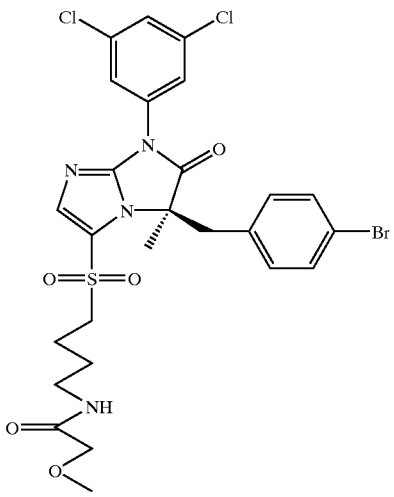 | not determined |
| 72 | 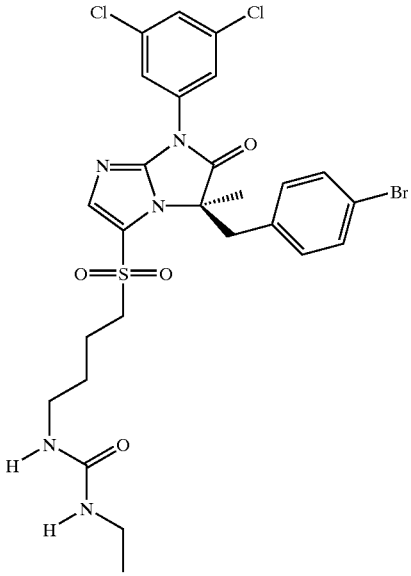 | not determined |

-continued

| Example No. | Structure | Melting Point (° C.) |
|---|---|---|
| 73 | 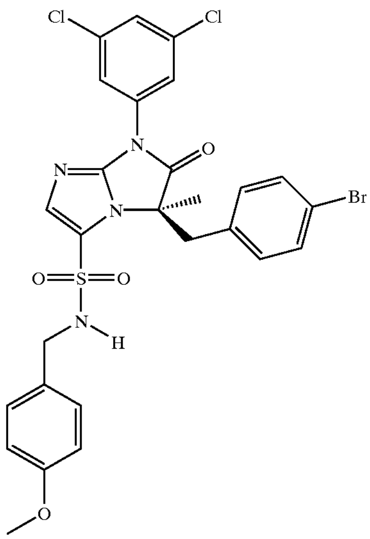 | not determined |
| 74 | 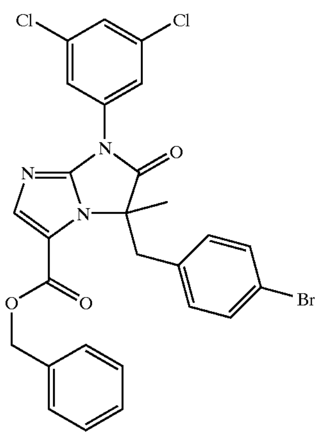 | 145–147 |
| 75 | 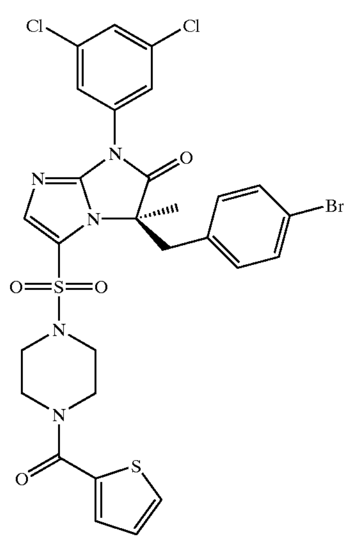 | not determined |

-continued

| Example No. | Structure | Melting Point (° C.) |
|---|---|---|
| 76 | 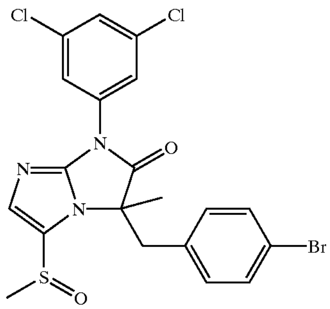 | not determined |
| 77 | 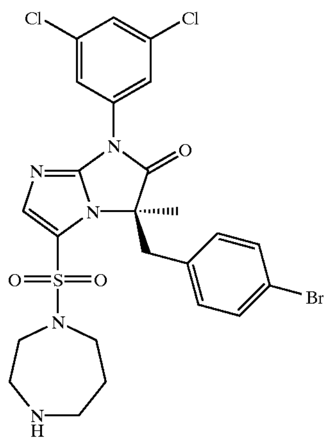 | hard oil |
| 78 | 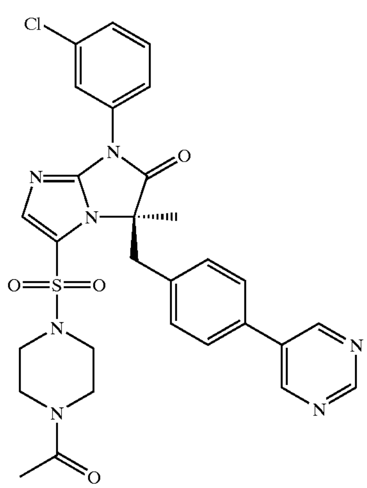 | foam |

-continued

| Example No. | Structure | Melting Point (° C.) |
|---|---|---|
| 79 | 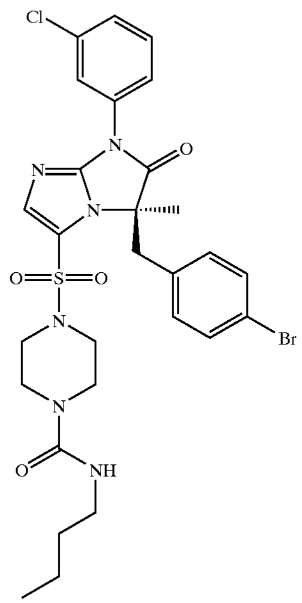 | 83.5–87 |
| 80 | 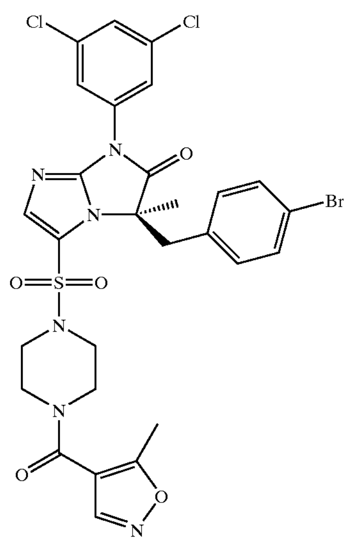 | not determined |
| 81 | 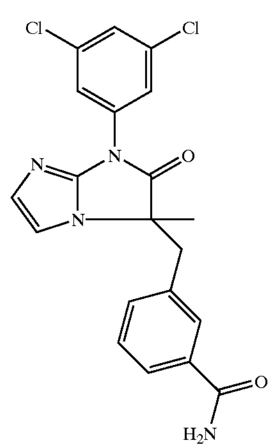 | 158.0–159.3 |

| Example No. | Structure | Melting Point (° C.) |
|---|---|---|
| 82 | 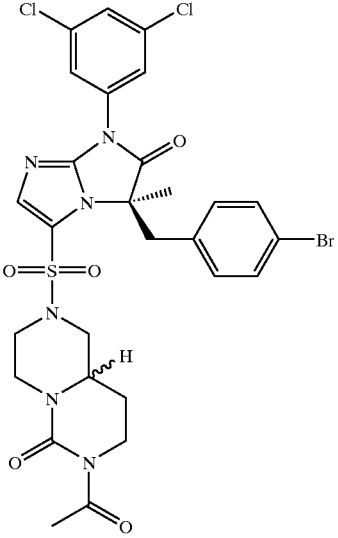 | foam |
| 83 | 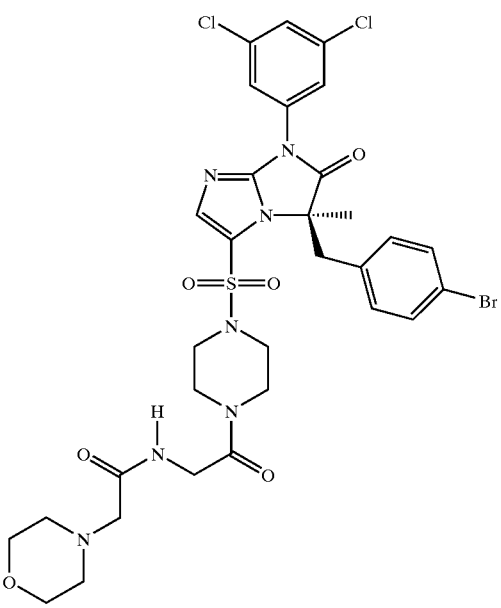 | 114.0–115.5 |

-continued

| Example No. | Structure | Melting Point (° C.) |
|---|---|---|
| 84 | 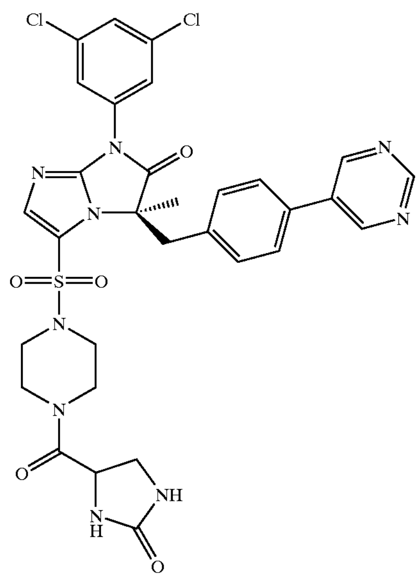 | not determined |
| 85 | 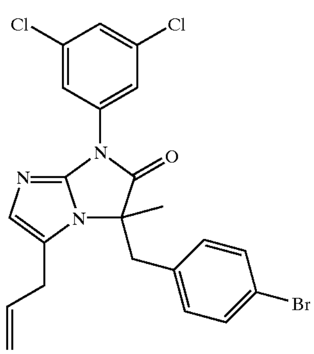 | thick oil |
| 86 | 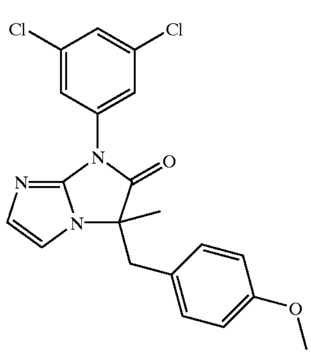 | 65.6–67.0 |

-continued

| Example No. | Structure | Melting Point (° C.) |
|---|---|---|
| 87 | 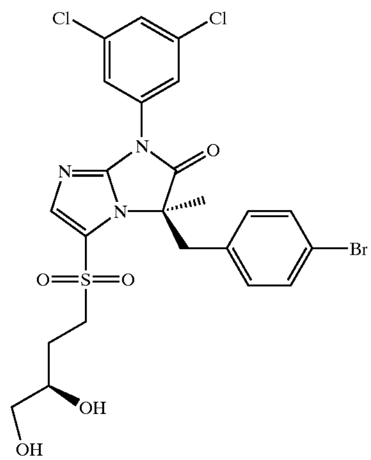 | oil |
| 88 | 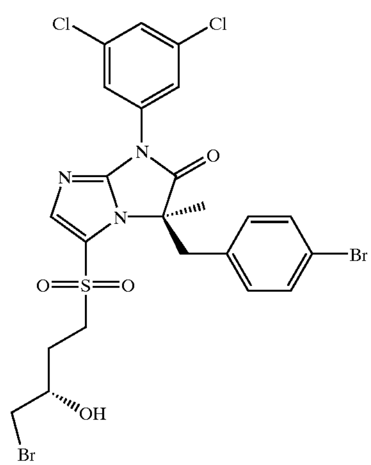 | foam |
| 89 | 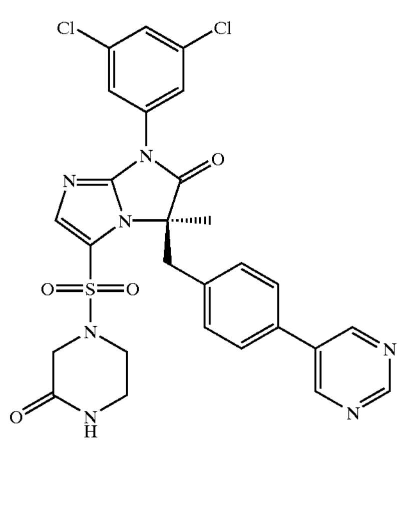 | 163.7–165.2 |

-continued

| Example No. | Structure | Melting Point (° C.) |
|---|---|---|
| 90 | 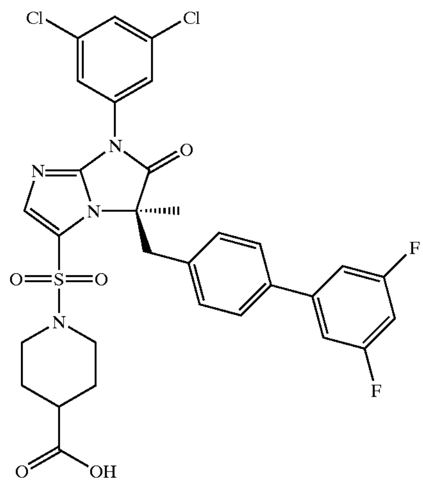 | not determined |
| 91 | 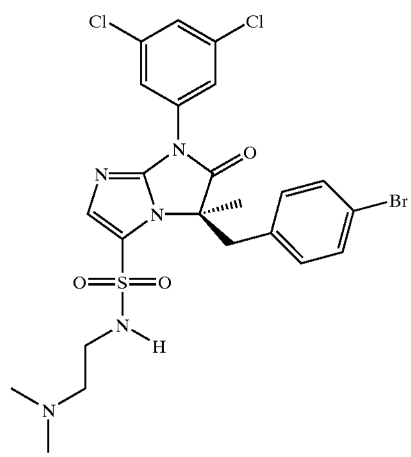 | not determined |
| 92 | 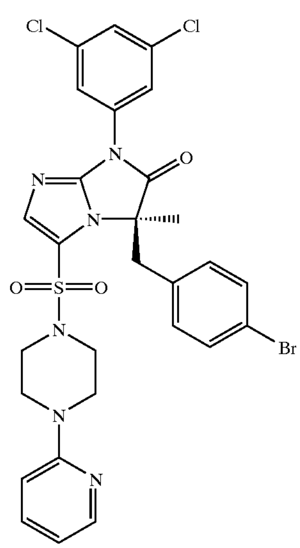 | 90–95 |

US 6,492,408 B1
-continued
| Example No. | Structure | Melting Point (° C.) |
|---|---|---|
| 93 | 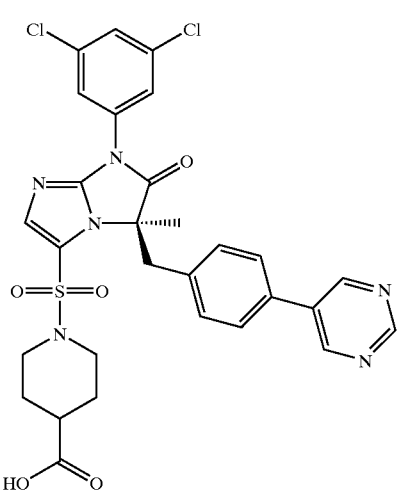 | not determined |
| 94 | 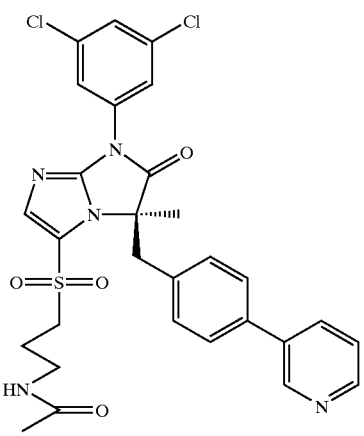 | not determined |
| 95 | 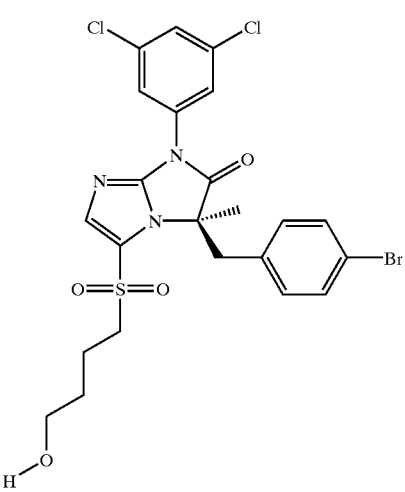 | foam |

-continued
| Example No. | Structure | Melting Point (° C.) |
|---|---|---|
| 96 | 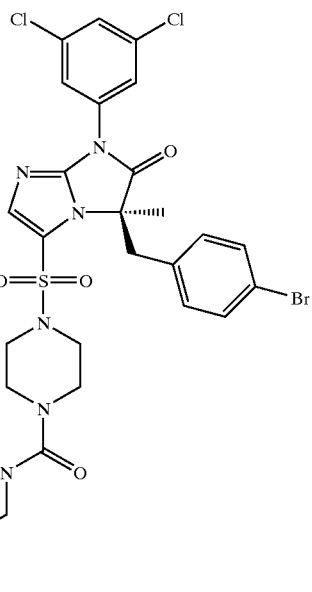 | foam |
| 97 | 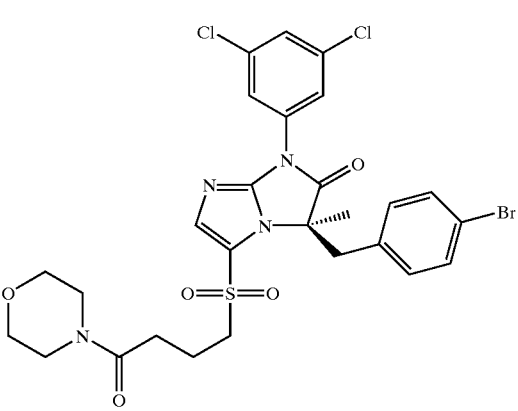 | oil |
| 98 | 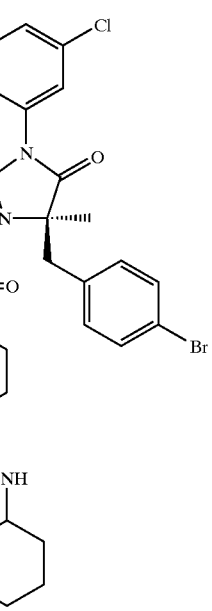 | 108–110 |

-continued
| Example No. | Structure | Melting Point (° C.) |
|---|---|---|
| 99 | 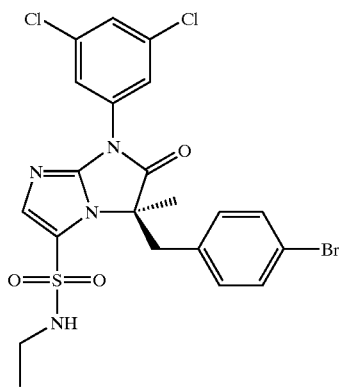 | not determined |
| 100 | 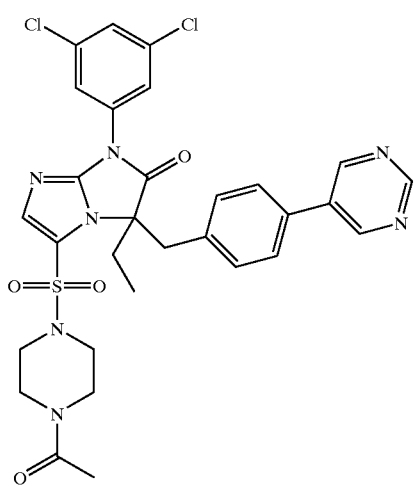 | resin |
| 101 | 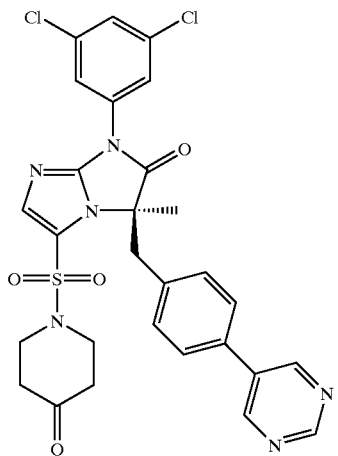 | not determined |

-continued

| Example No. | Structure | Melting Point (° C.) |
|---|---|---|
| 102 | 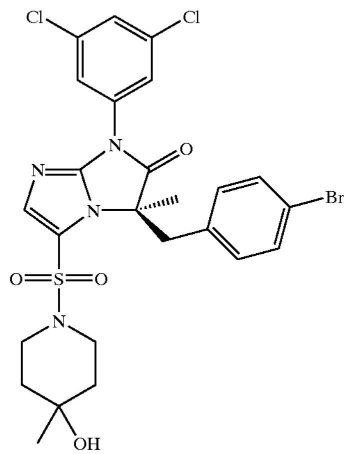 | foam |
| 103 | 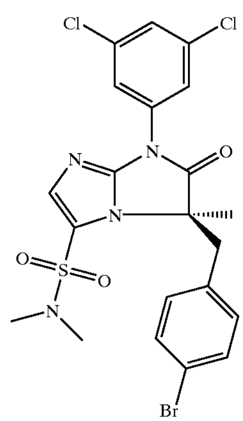 | not determined |
| 104 | 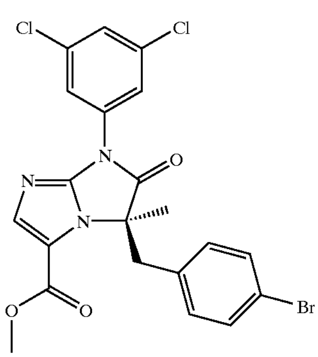 | 72.5–73.6 |

-continued

| Example No. | Structure | Melting Point (° C.) |
|---|---|---|
| 105 | 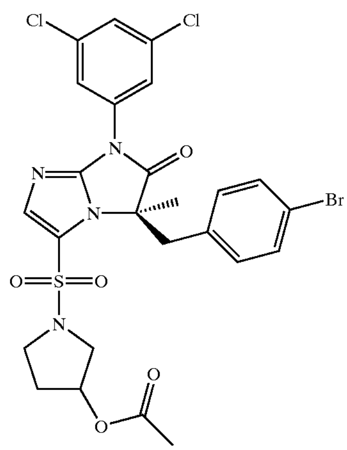 | foam |
| 106 | 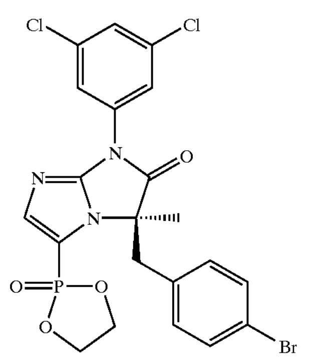 | oil |
| 107 | 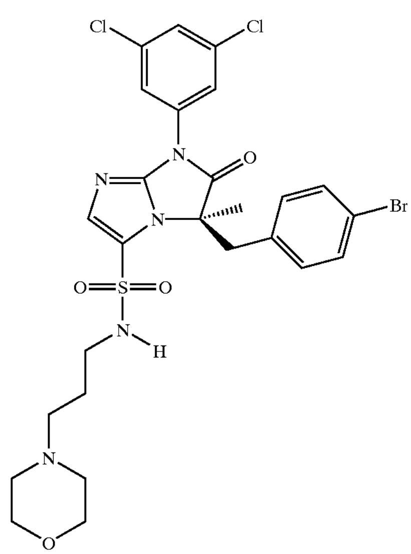 | not determined |

-continued
| Example No. | Structure | Melting Point (° C.) |
|---|---|---|
| 108 | 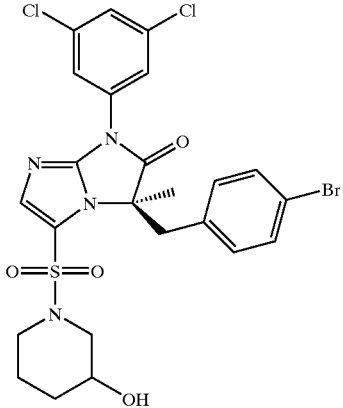 | gummy foam |
| 109 | 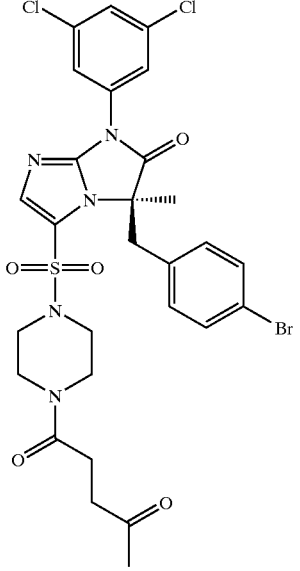 | foam |
| 110 | 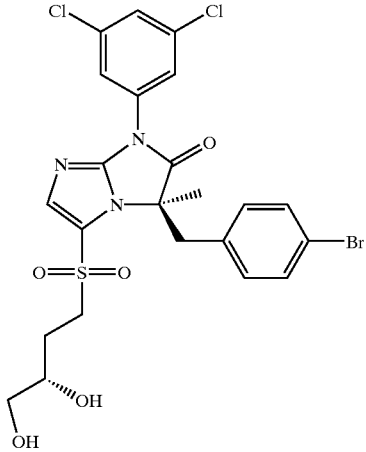 | foam |

-continued
| Example No. | Structure | Melting Point (° C.) |
|---|---|---|
| 111 | 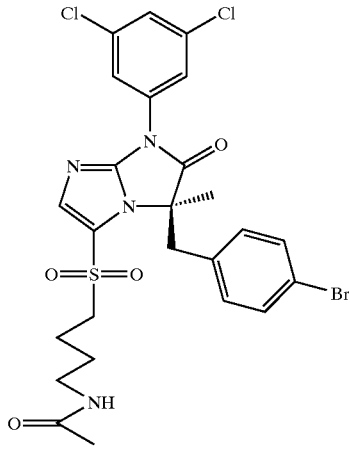 | not determined |
| 112 | 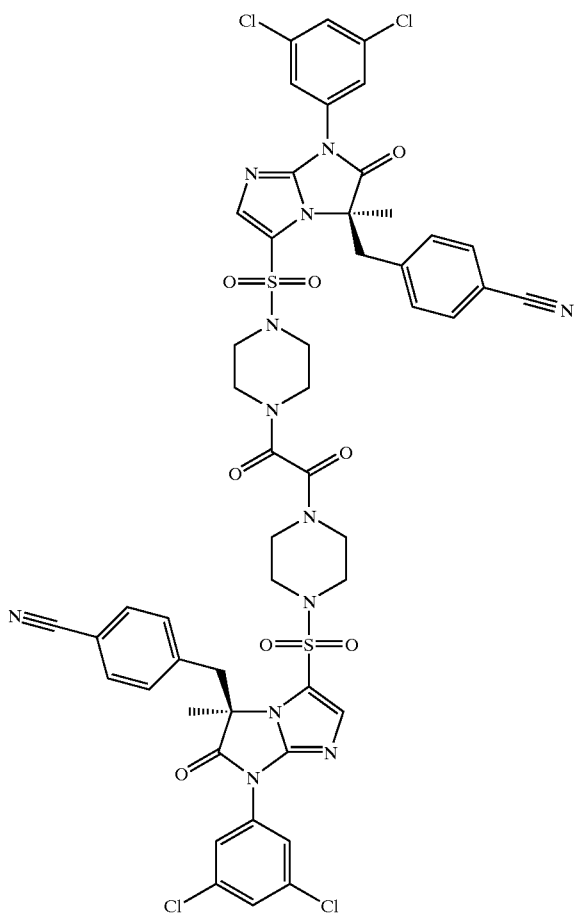 | resin |

-continued
| Example No. | Structure | Melting Point (° C.) |
|---|---|---|
| 113 | 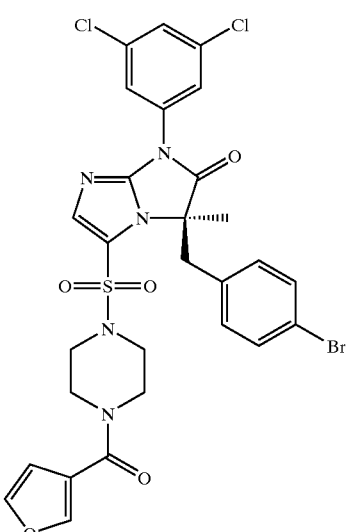 | resin |
| 114 | 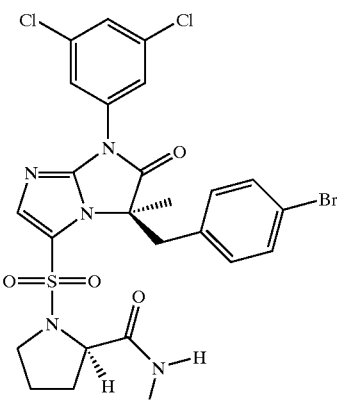 | not determined |
| 115 | 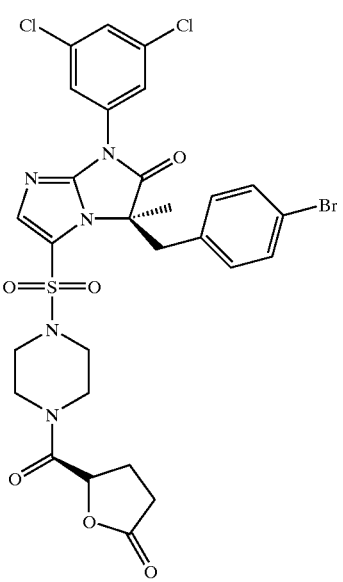 | not determined |

-continued

| Example No. | Structure | Melting Point (° C.) |
|---|---|---|
| 116 | 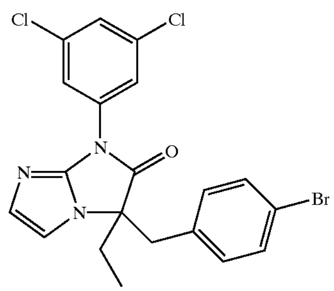 | oil |
| 117 | 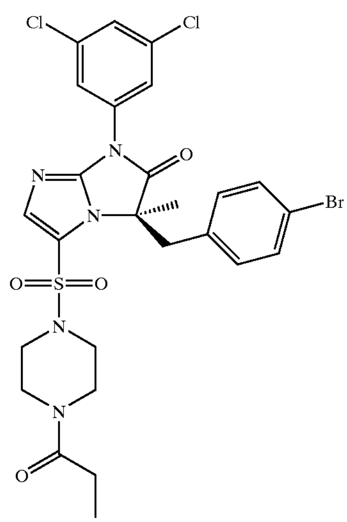 | foam |
| 118 | 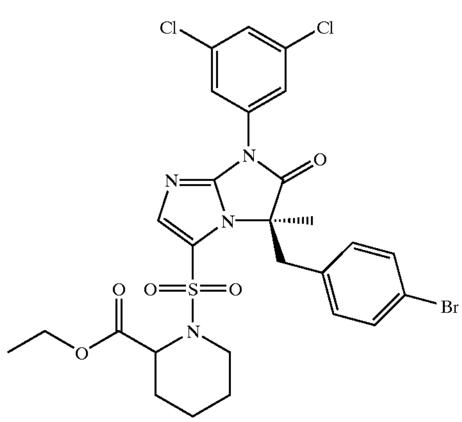 | 71.2–72.5 |

-continued

| Example No. | Structure | Melting Point (° C.) |
|---|---|---|
| 119 | 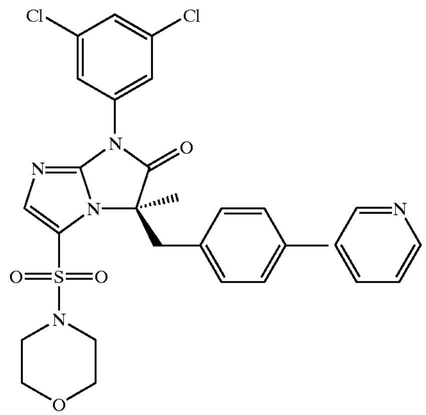 | 164.8–166.3 |
| 120 | 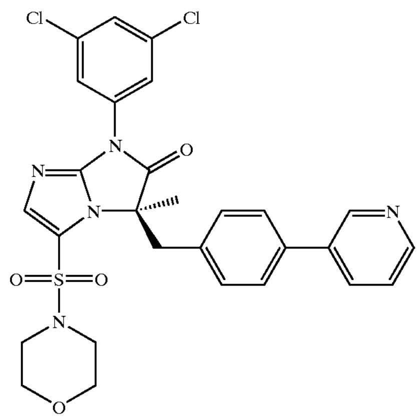 | foam |
| 121 | 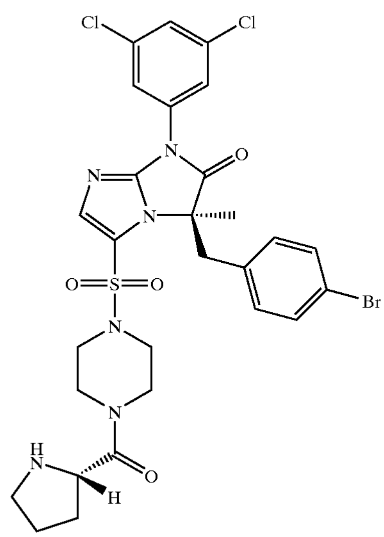 | 125.5–127.8 |

-continued

| Example No. | Structure | Melting Point (° C.) |
|---|---|---|
| 122 | 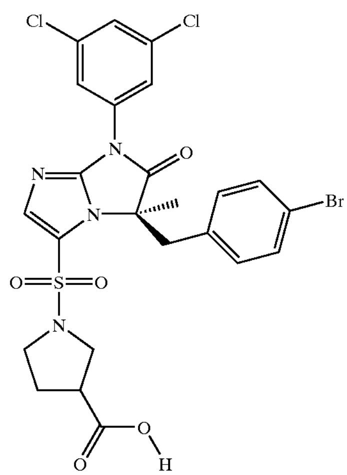 | not determined |
| 123 | 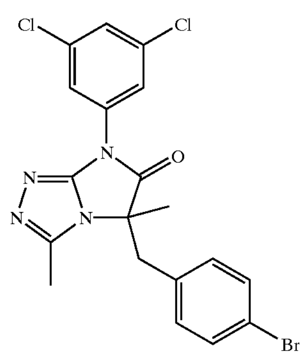 | 201–203 |
| 124 | 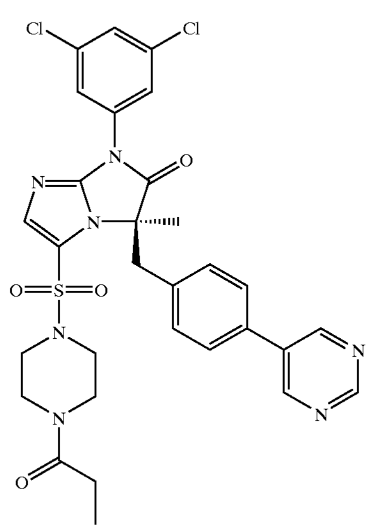 | 101.8–103.6 |

-continued

| Example No. | Structure | Melting Point (° C.) |
|---|---|---|
| 125 | 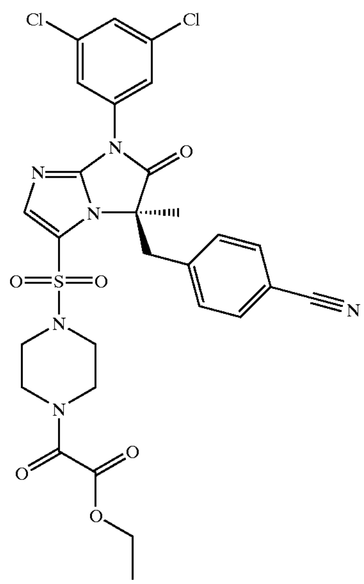 | resin |
| 126 | 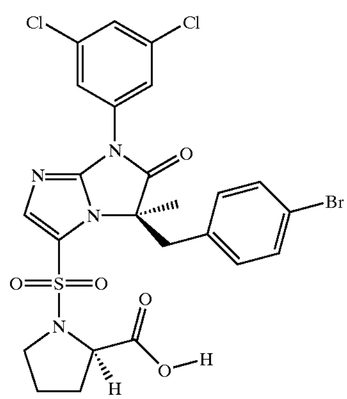 | not determined |
| 127 | 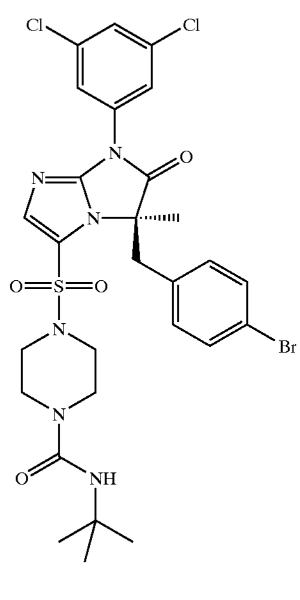 | 101–105 |

-continued

| Example No. | Structure | Melting Point (° C.) |
|---|---|---|
| 128 | 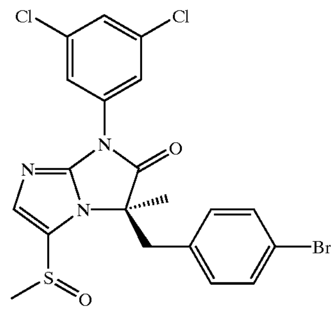 | 120.2–122.2 |
| 129 | 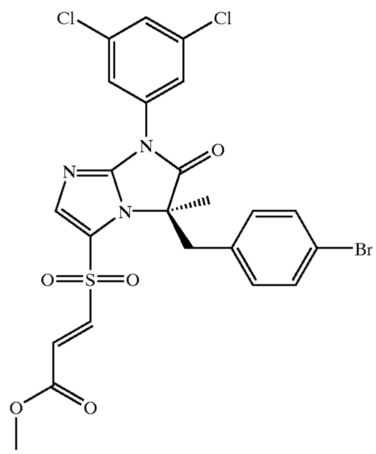 | foam |
| 130 | 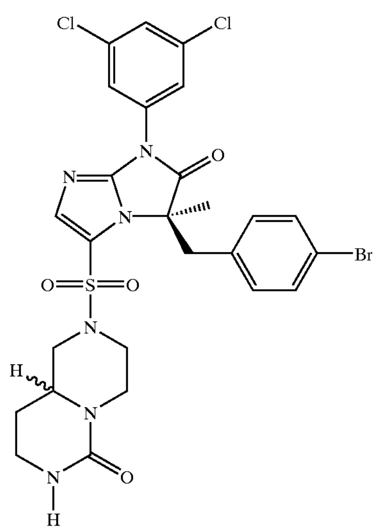 | foam |

-continued

| Example No. | Structure | Melting Point (° C.) |
|---|---|---|
| 131 | 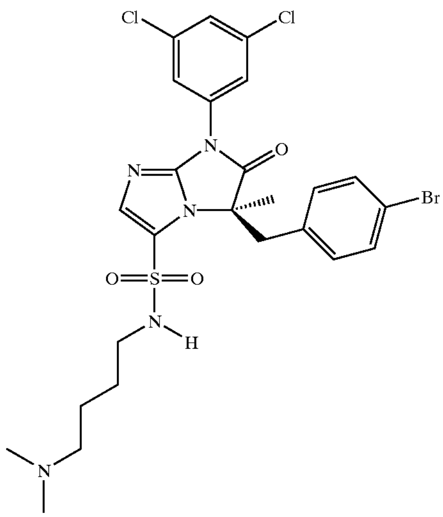 | resin |
| 132 | 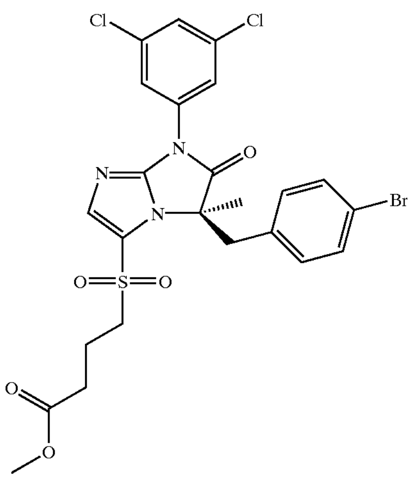 | oil |
| 133 | 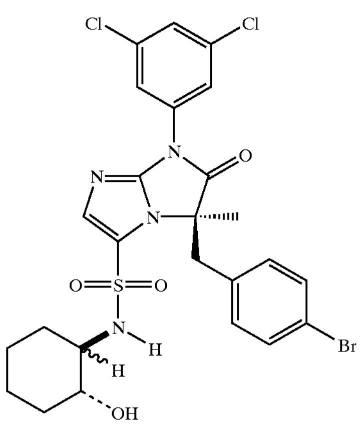 | foam |

-continued

| Example No. | Structure | Melting Point (° C.) |
|---|---|---|
| 134 | 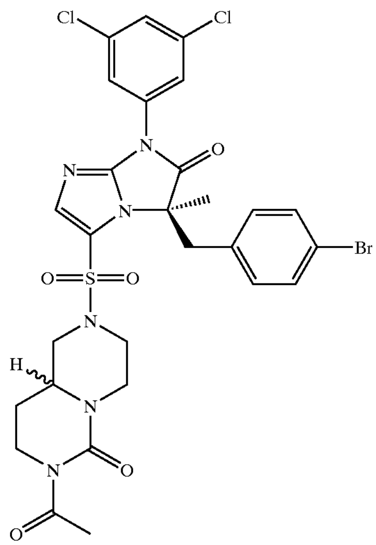 | foam |
| 135 | 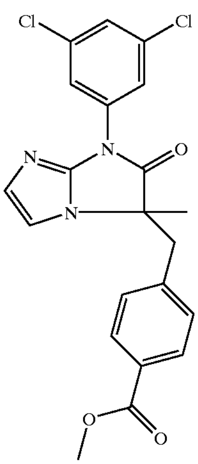 | 34.0–35.5 |
| 136 | 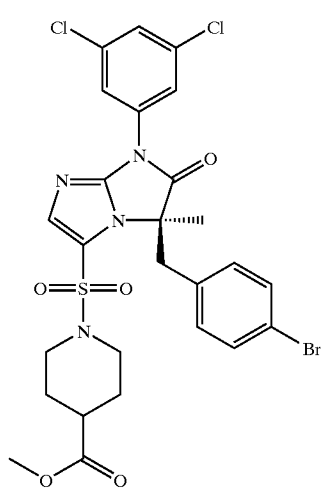 | not determined |

-continued

| Example No. | Structure | Melting Point (° C.) |
|---|---|---|
| 137 | 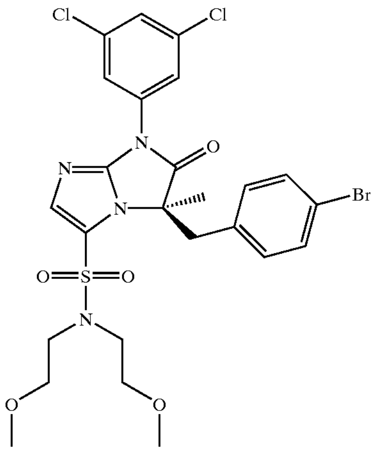 | not determined |
| 138 | 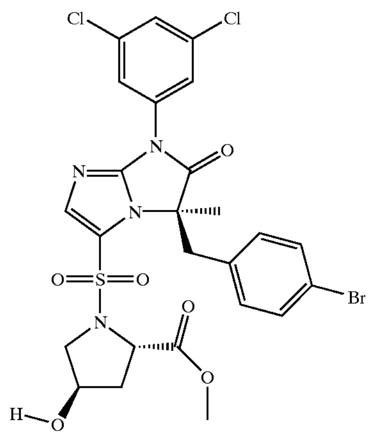 | foam |
| 139 | 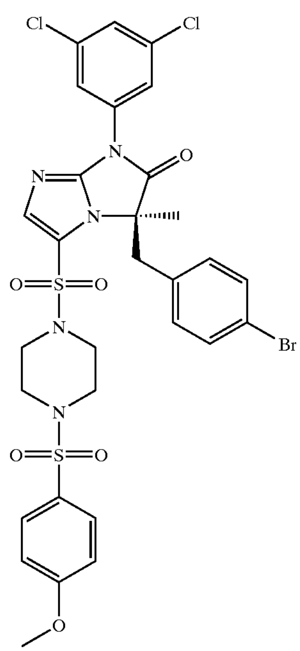 | 166–169 |

-continued
| Example No. | Structure | Melting Point (° C.) |
|---|---|---|
| 140 | 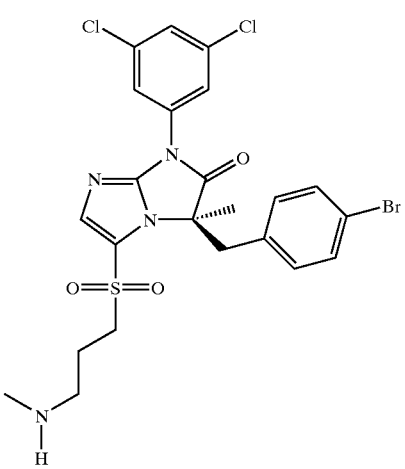 | not determined |
| 141 | 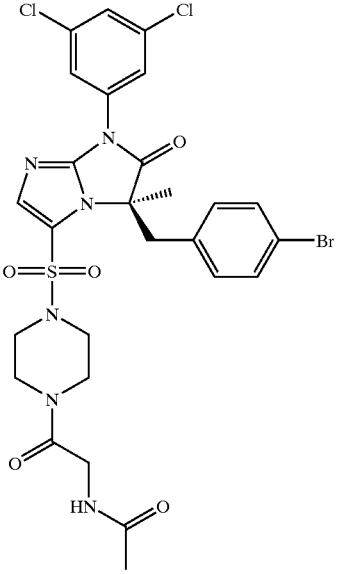 | resin |
| 142 | 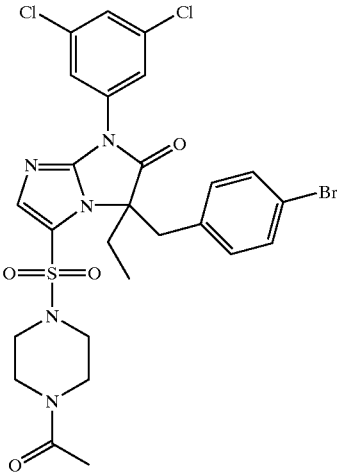 | resin |

-continued

| Example No. | Structure | Melting Point (° C.) |
|---|---|---|
| 143 | 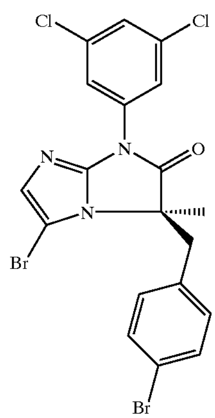 | foam |
| 144 | 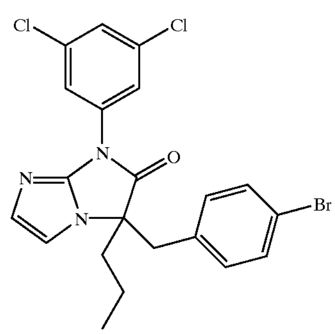 | oil |
| 145 | 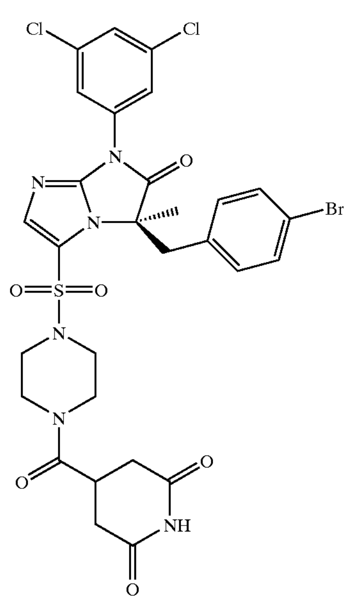 | not determined |

-continued

| Example No. | Structure | Melting Point (° C.) |
|---|---|---|
| 146 | 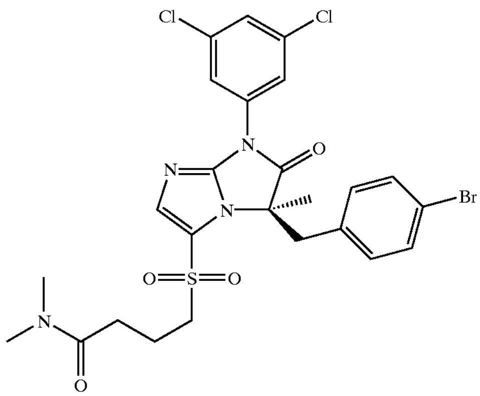 | foam |
| 147 | 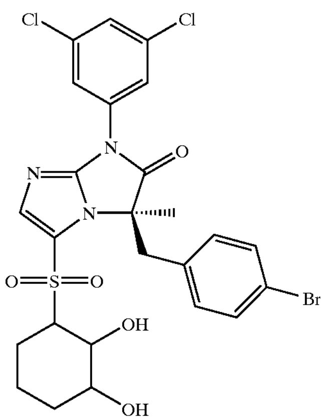 | 123.6–125.1 |
| 148 | 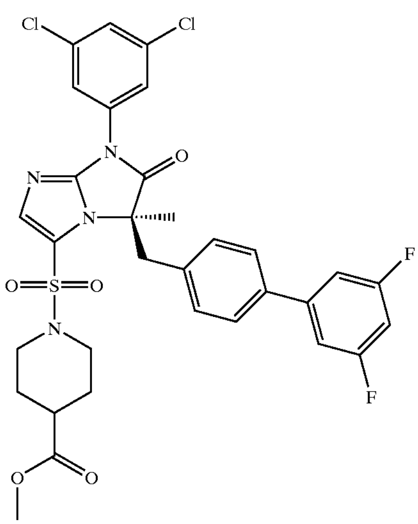 | 51.6–53.0 |

-continued

| Example No. | Structure | Melting Point (° C.) |
|---|---|---|
| 149 | 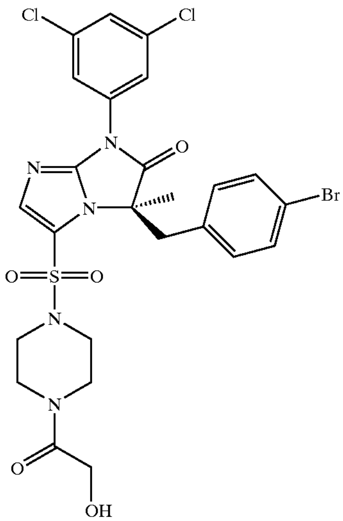 | not determined |
| 150 | 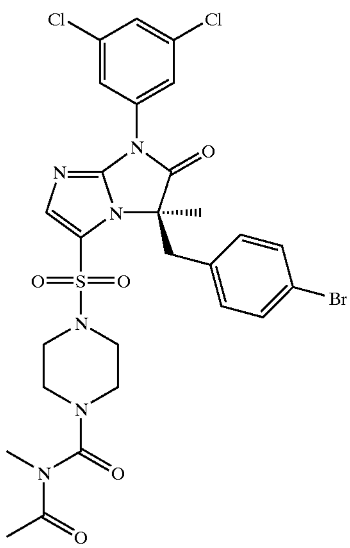 | foam |
| 151 | 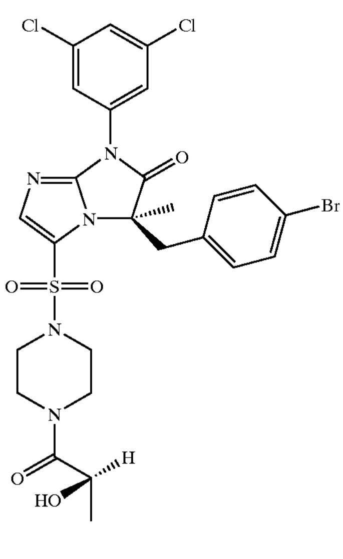 | not determined |

-continued

| Example No. | Structure | Melting Point (° C.) |
|---|---|---|
| 152 | 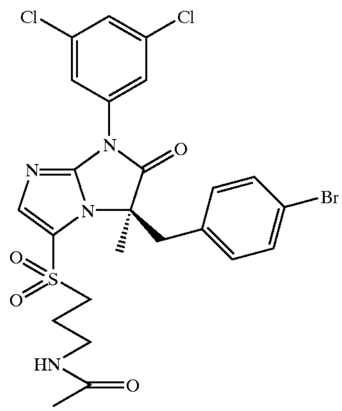 | amorphous |
| 153 | 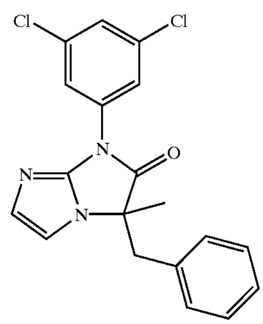 | 83.7–85.3 |
| 154 | 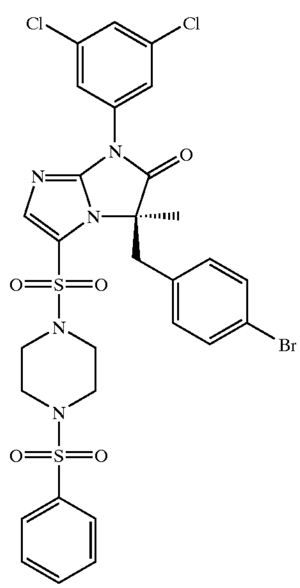 | 167–169 |

-continued
| Example No. | Structure | Melting Point (° C.) |
|---|---|---|
| 155 | 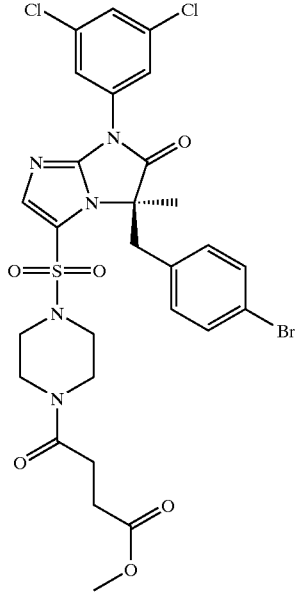 | foam |
| 156 | 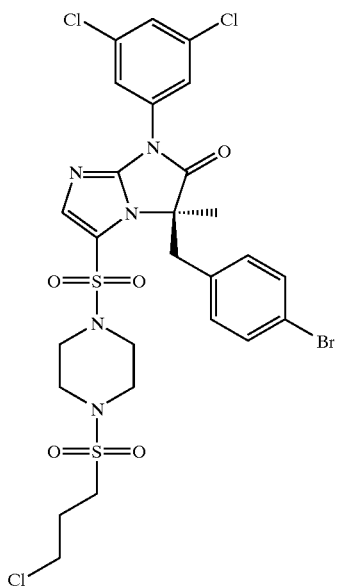 | 170–174 |

-continued

| Example No. | Structure | Melting Point (° C.) |
|---|---|---|
| 157 | 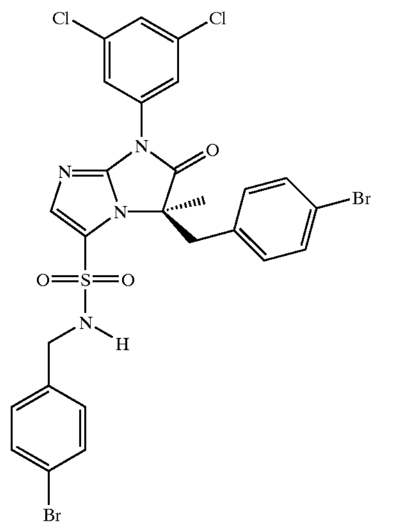 | not determined |
| 158 | 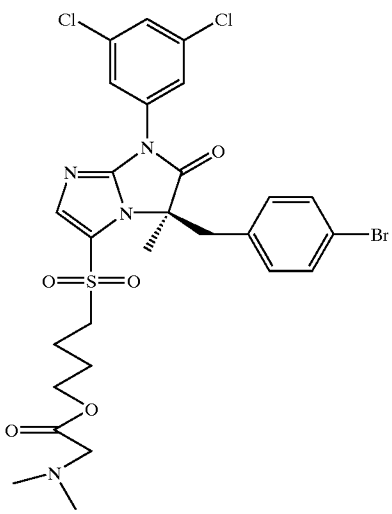 | foam |
| 159 | 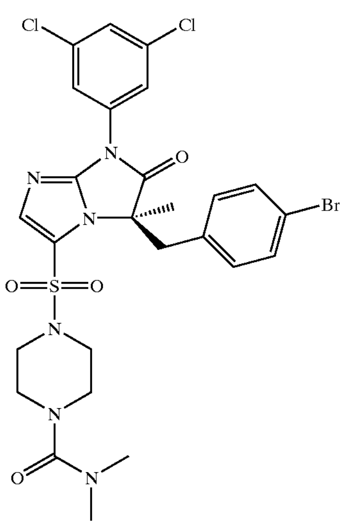 | resin |

-continued

| Example No. | Structure | Melting Point (° C.) |
|---|---|---|
| 160 | 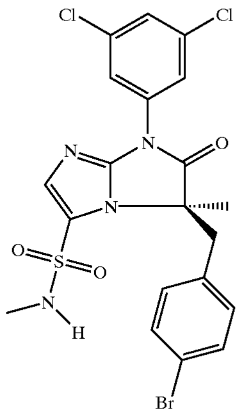 | foam |
| 161 | 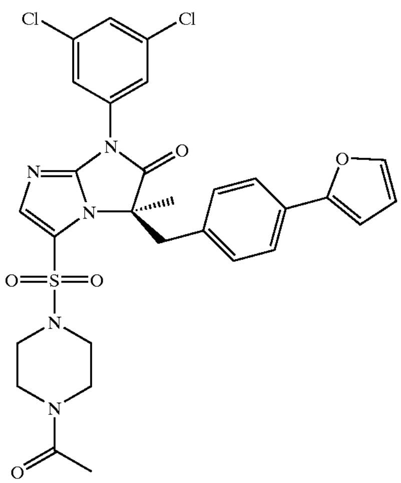 | not determined |
| 162 | 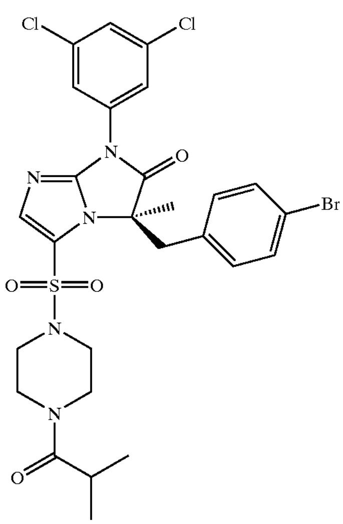 | foam |

-continued
| Example No. | Structure | Melting Point (° C.) |
|---|---|---|
| 163 | 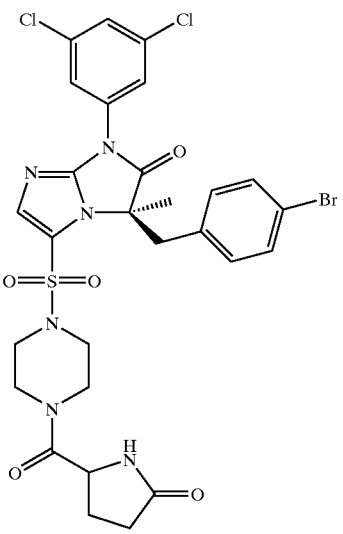 | not determined |
| 164 | 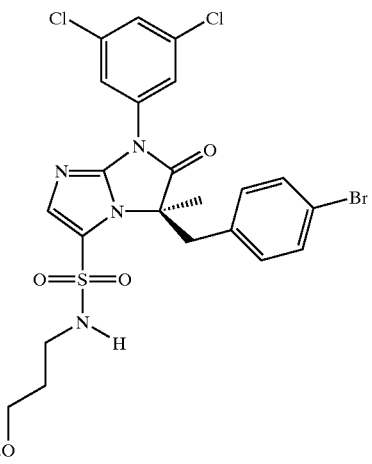 | not determined |
| 165 | 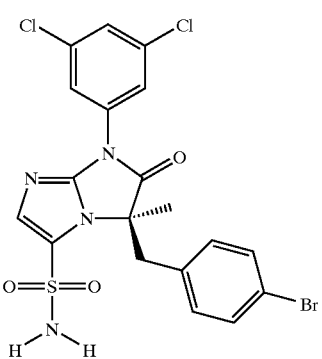 | not determined |

-continued

| Example No. | Structure | Melting Point (° C.) |
|---|---|---|
| 166 | 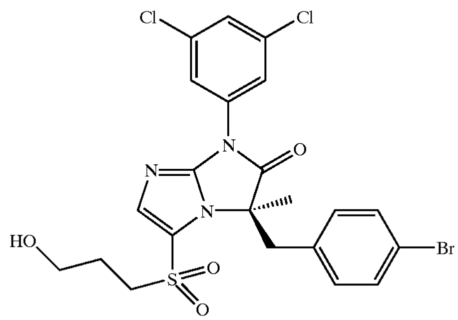 | 112.6–113.6 |
| 167 | 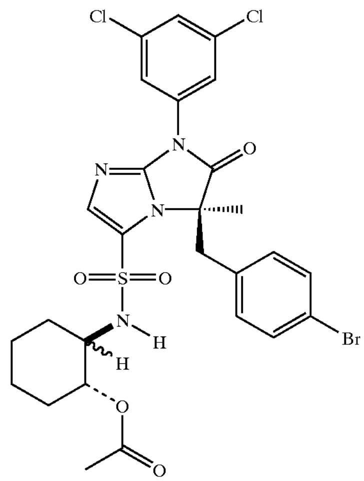 | foam |
| 168 | 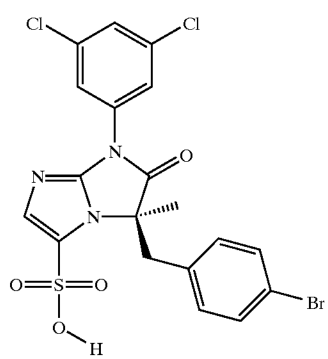 | not determined |
| 169 | 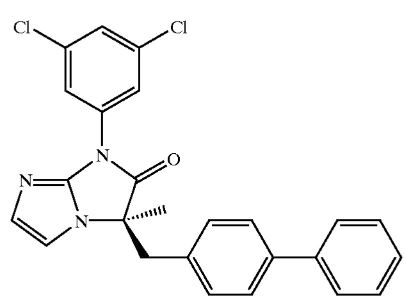 | 51.8—53.1 |

-continued

| Example No. | Structure | Melting Point (° C.) |
|---|---|---|
| 170 | 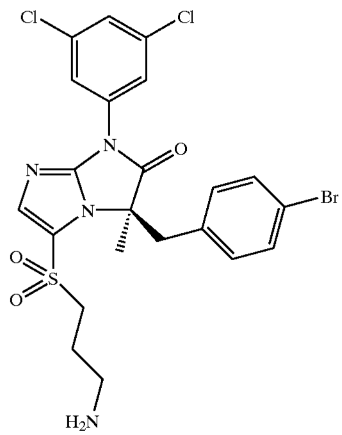 | 75 |
| 171 | 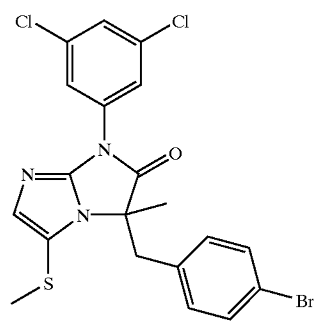 | not determined |
| 172 | 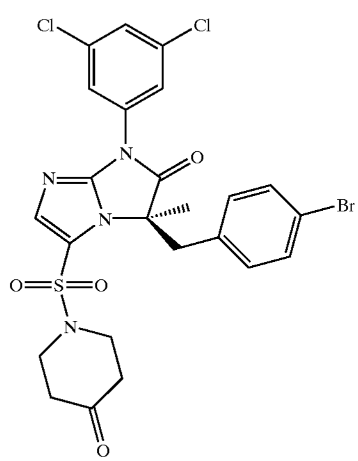 | not determined |

-continued

| Example No. | Structure | Melting Point (° C.) |
|---|---|---|
| 173 | 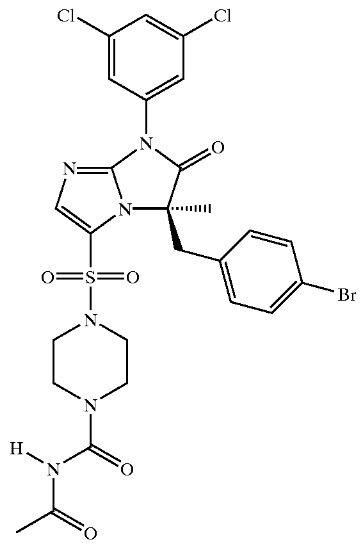 | 51–52 |
| 174 | 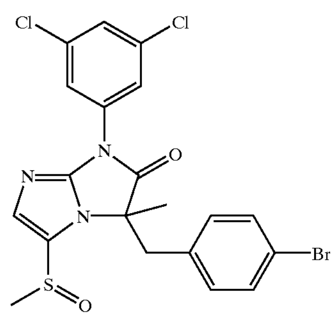 | not determined |
| 175 | 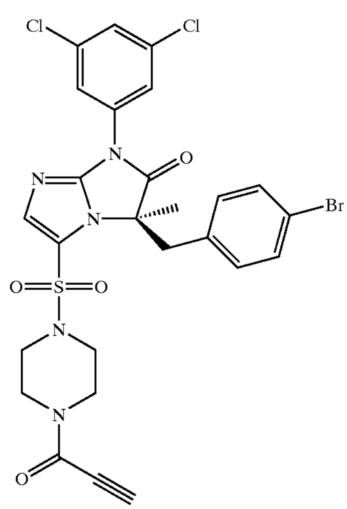 | not determined |

-continued
| Example No. | Structure | Melting Point (° C.) |
|---|---|---|
| 176 | 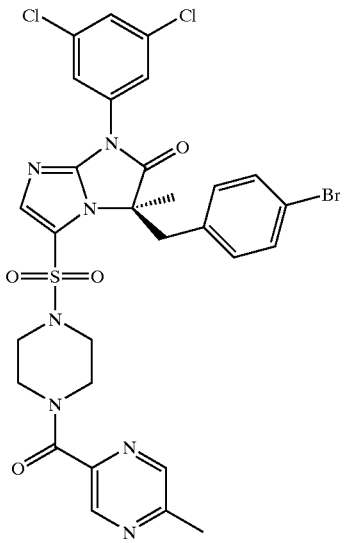 | not determined |
| 177 | 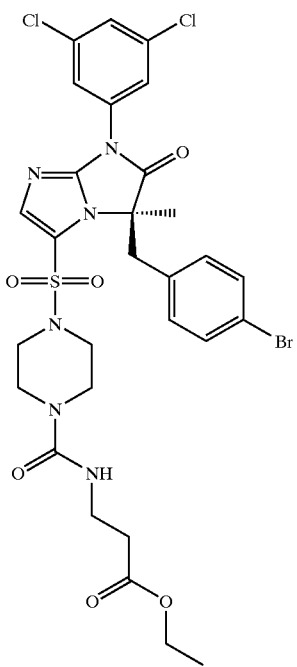 | resin |

-continued

| Example No. | Structure | Melting Point (° C.) |
|---|---|---|
| 178 | 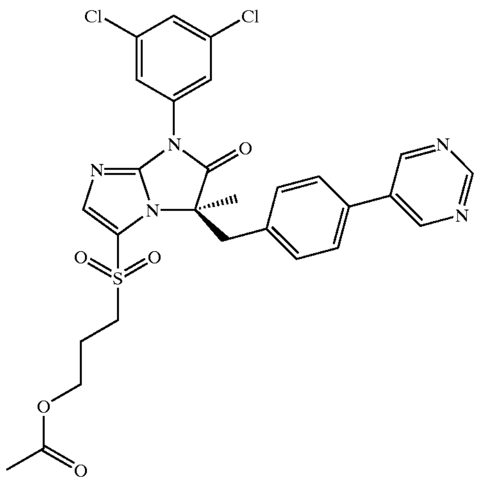 | not determined |
| 179 | 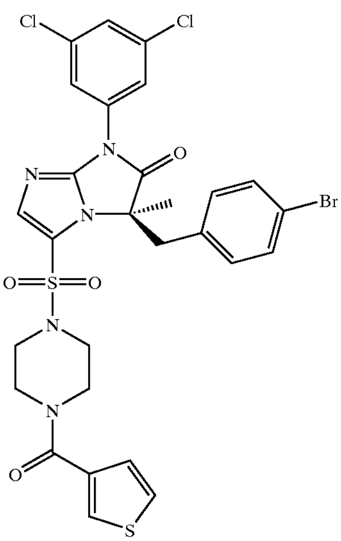 | not determined |
| 180 | 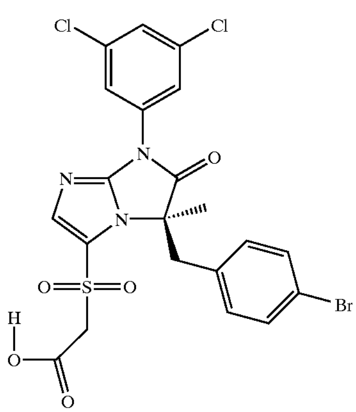 | resin |

| Example No. | Structure | Melting Point (° C.) |
|---|---|---|
| 181 | 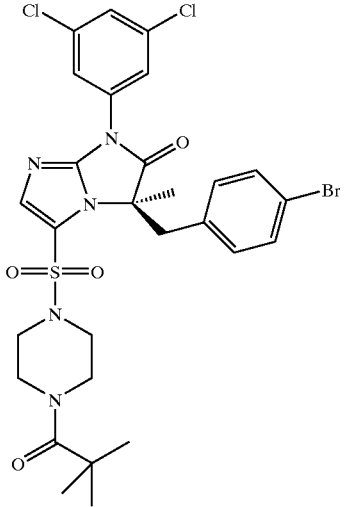 | foam |
| 182 | 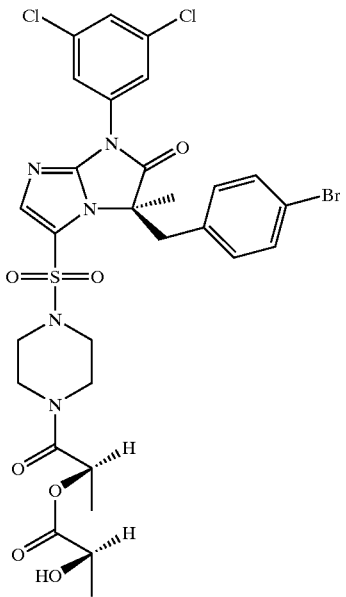 | not determined |

-continued

| Example No. | Structure | Melting Point (° C.) |
|---|---|---|
| 183 | 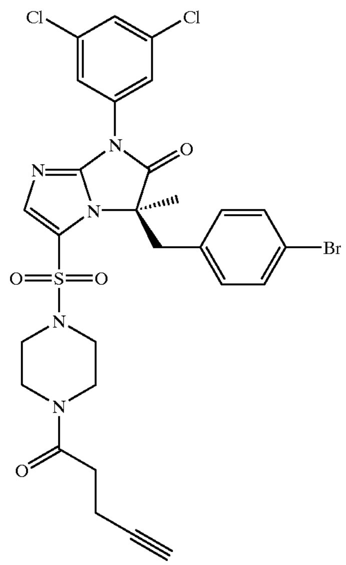 | 80.5–85.5 |
| 184 | 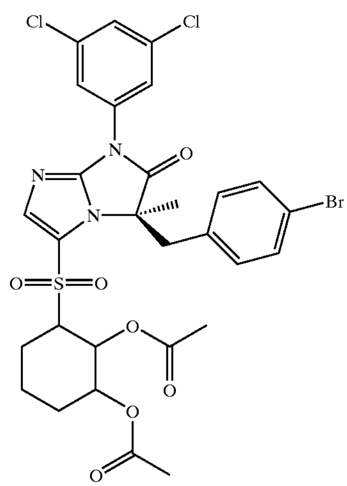 | not determined |
| 185 | 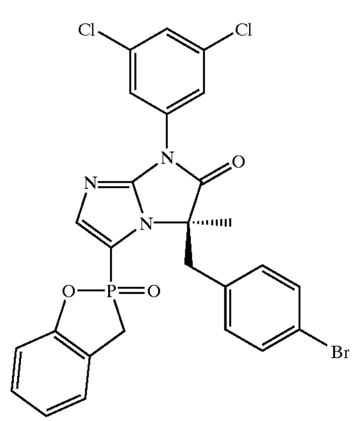 | foam |

-continued

| Example No. | Structure | Melting Point (° C.) |
|---|---|---|
| 186 | 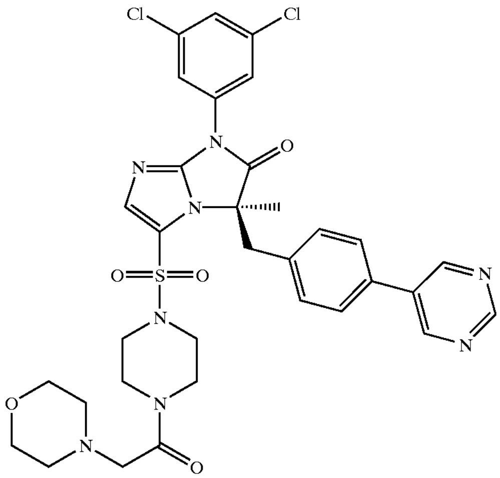 | resin |
| 187 | 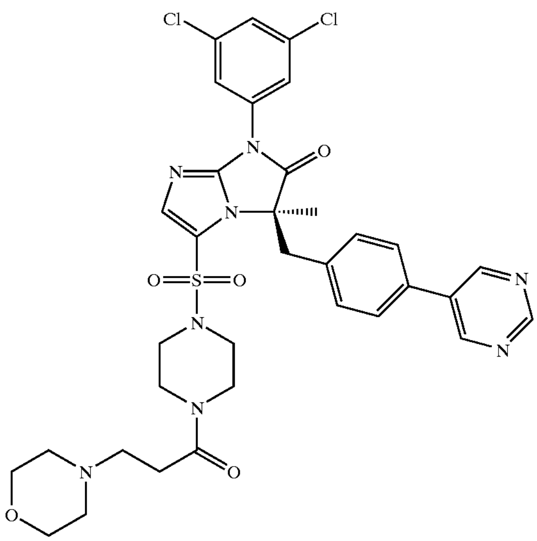 | resin |
| 188 | 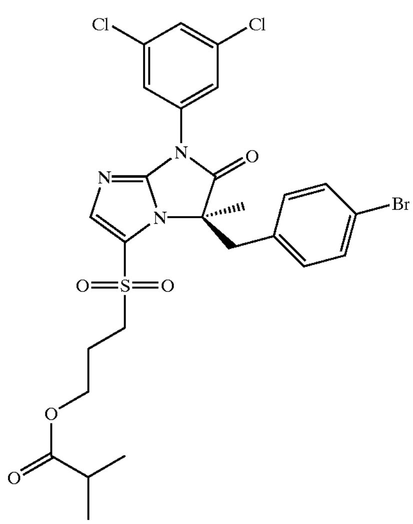 | not determined |

-continued
| Example No. | Structure | Melting Point (° C.) |
|---|---|---|
| 189 | 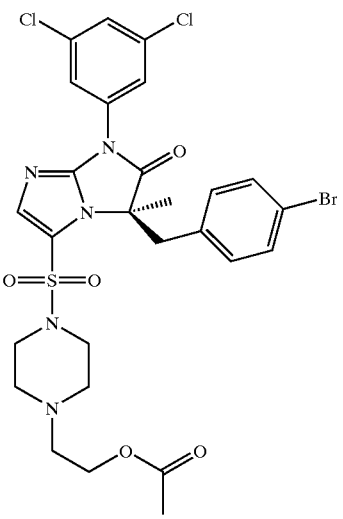 | foam |
| 190 | 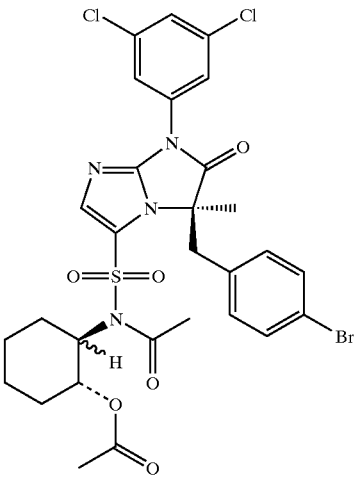 | foam |
| 191 | 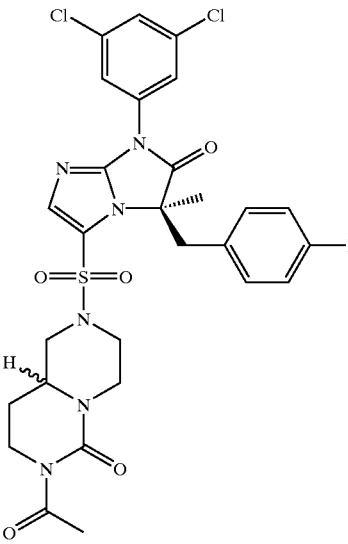 | foam |

-continued

| Example No. | Structure | Melting Point (° C.) |
|---|---|---|
| 192 | 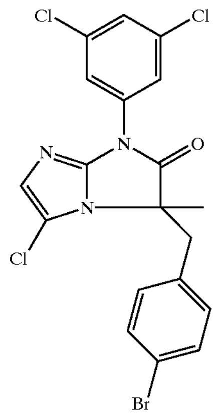 | not determined |
| 193 | 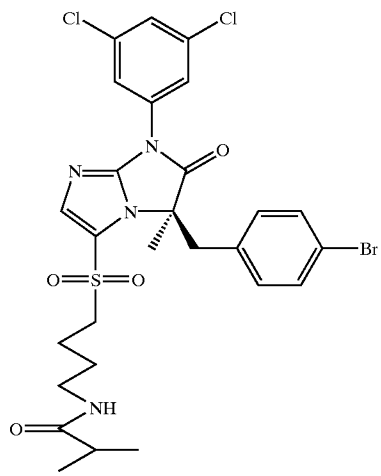 | not determined |
| 194 | 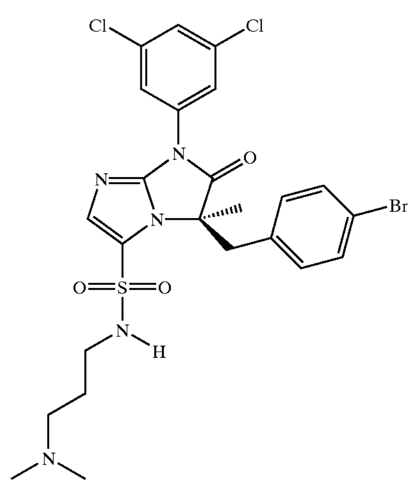 | not determined |

-continued

| Example No. | Structure | Melting Point (° C.) |
|---|---|---|
| 195 | 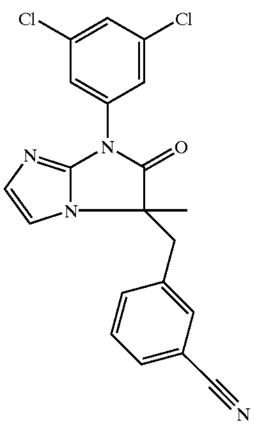 | 66.5–68.1 |
| 196 | 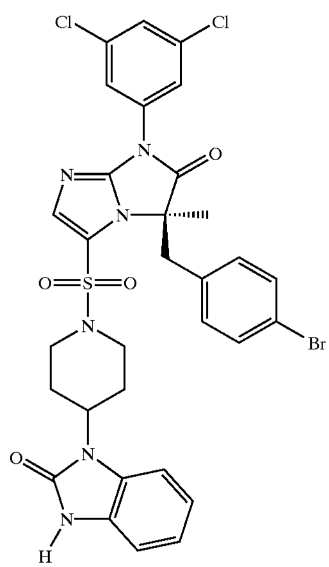 | 150–160 |
| 197 | 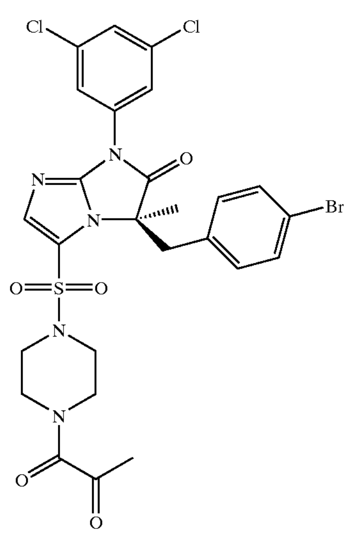 | not determined |

-continued

| Example No. | Structure | Melting Point (° C.) |
|---|---|---|
| 198 | 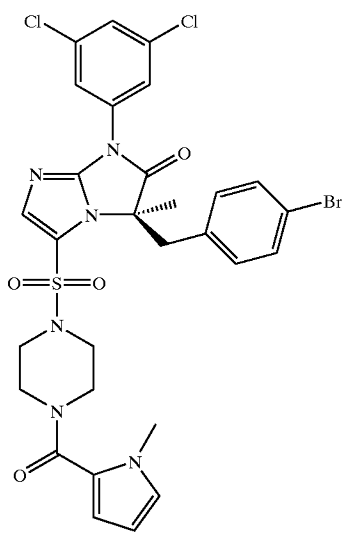 | not determined |
| 199 | 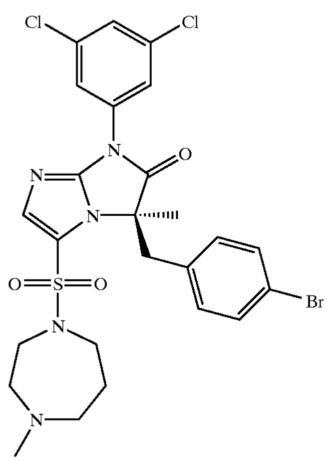 | resin |
| 200 | 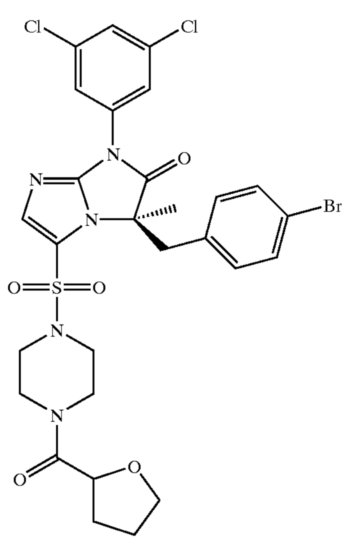 | not determined |

-continued

| Example No. | Structure | Melting Point (° C.) |
|---|---|---|
| 201 | 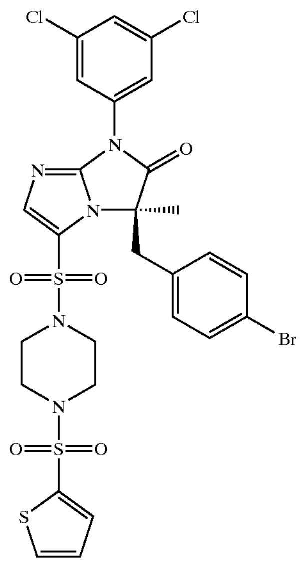 | 191–192 |
| 202 | 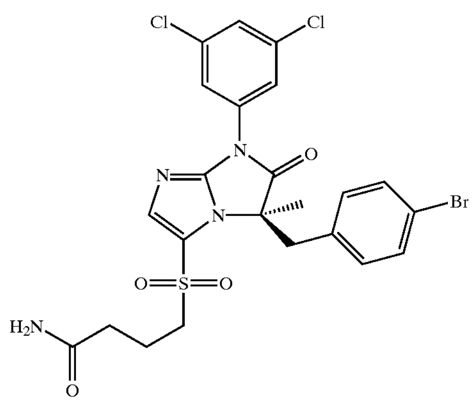 | foam |
| 203 | 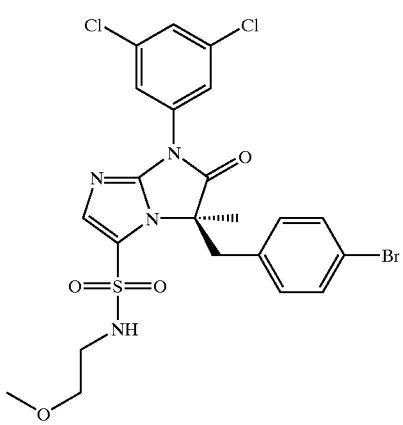 | foam |

-continued

| Example No. | Structure | Melting Point (° C.) |
|---|---|---|
| 204 | 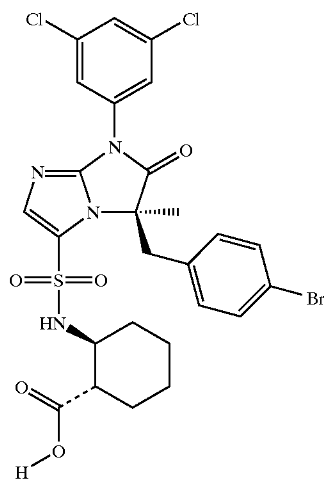 | resin |
| 205 | 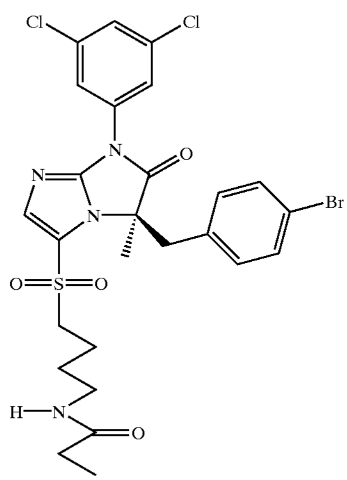 | not determined |
| 206 | 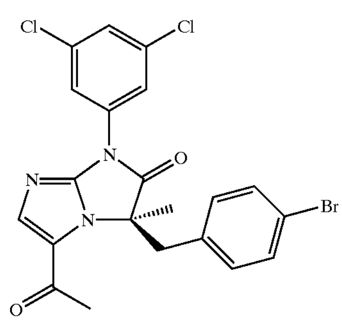 | oil |

-continued

| Example No. | Structure | Melting Point (° C.) |
|---|---|---|
| 207 | 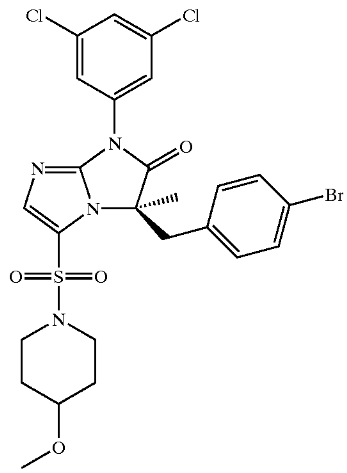 | not determined |
| 208 | 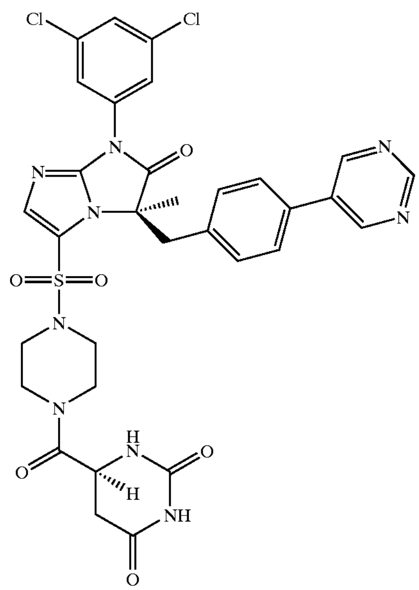 | not determined |
| 209 | 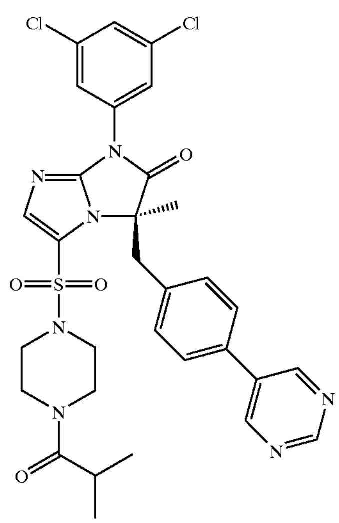 | 103–105 |

-continued
| Example No. | Structure | Melting Point (° C.) |
|---|---|---|
| 210 | 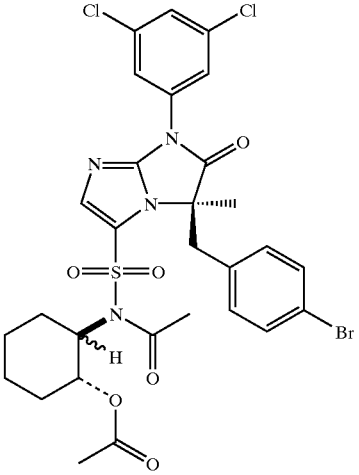 | foam |
| 211 | 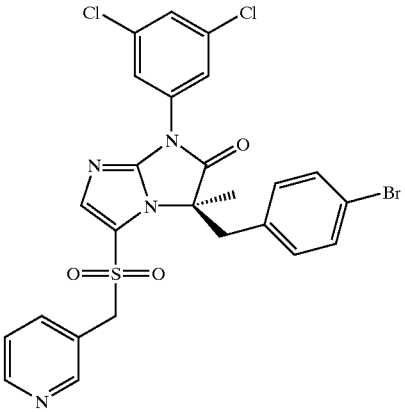 | not determined |
| 212 | 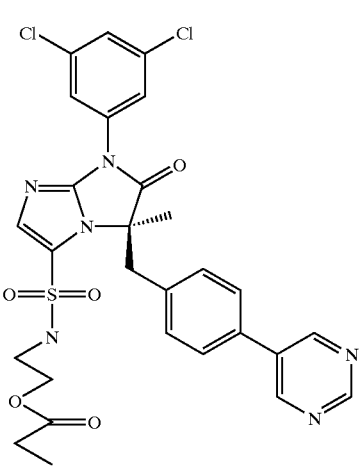 | not determined |

-continued

| Example No. | Structure | Melting Point (° C.) |
|---|---|---|
| 213 | 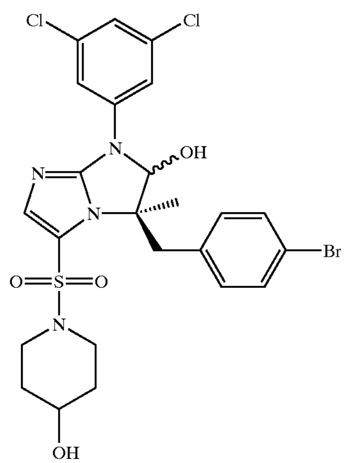 | not determined |
| 214 | 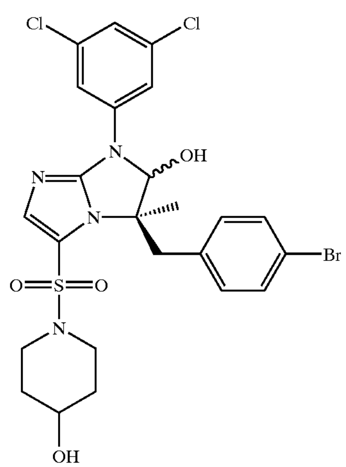 | 187–189 |
| 215 | 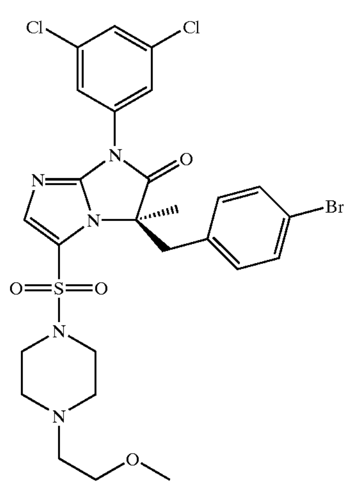 | film |

-continued
| Example No. | Structure | Melting Point (° C.) |
|---|---|---|
| 216 | 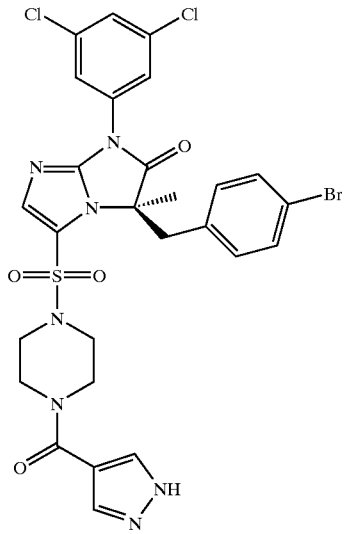 | not determined |
| 217 | 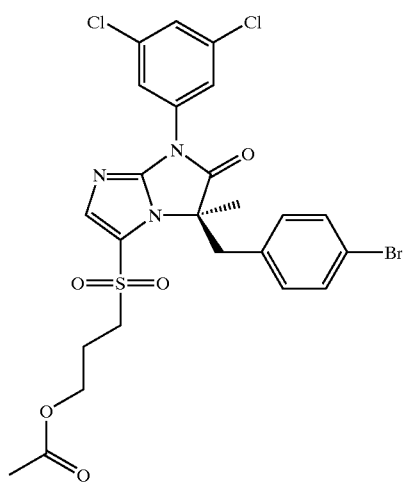 | foam |

-continued

| Example No. | Structure | Melting Point (° C.) |
|---|---|---|
| 218 | 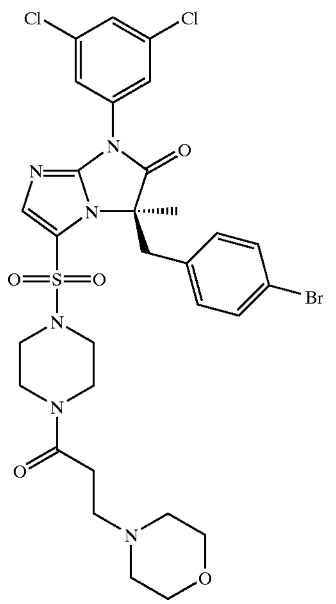 | not determined |
| 219 | 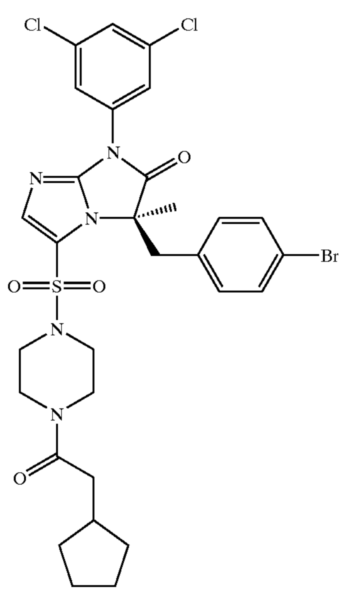 | resin |

-continued

| Example No. | Structure | Melting Point (° C.) |
|---|---|---|
| 220 | 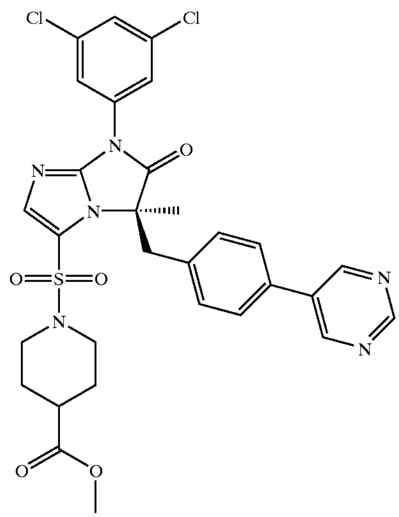 | 79.1–81.0 |
| 221 | 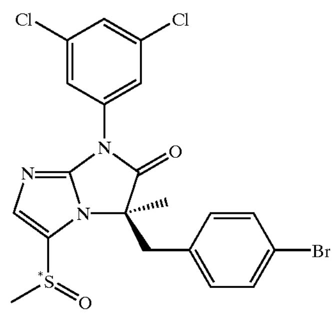 | 100.9–102.2 |
| 222 | 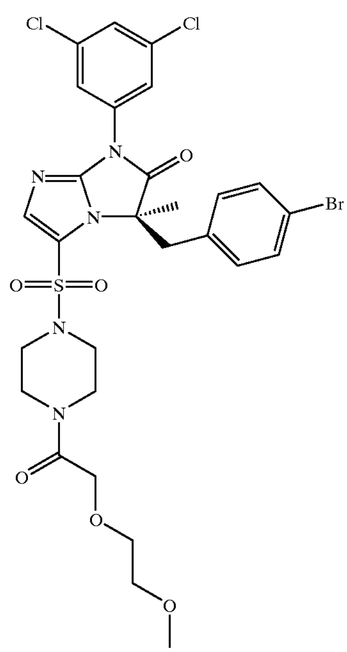 | not determined |

-continued

| Example No. | Structure | Melting Point (° C.) |
|---|---|---|
| 223 | 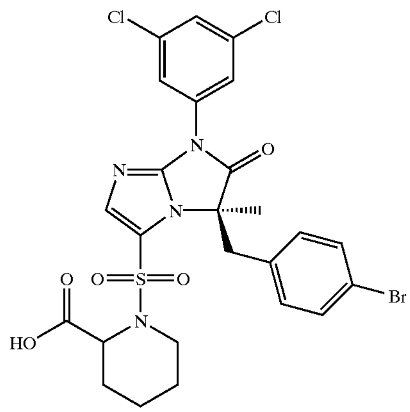 | not determined |
| 224 | 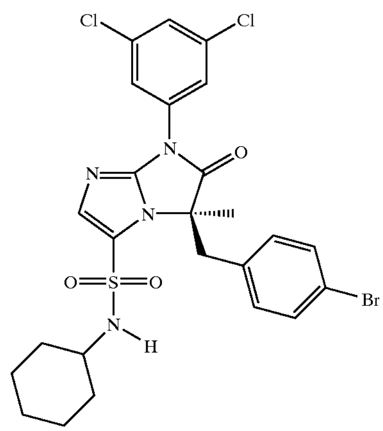 | foam |
| 225 | 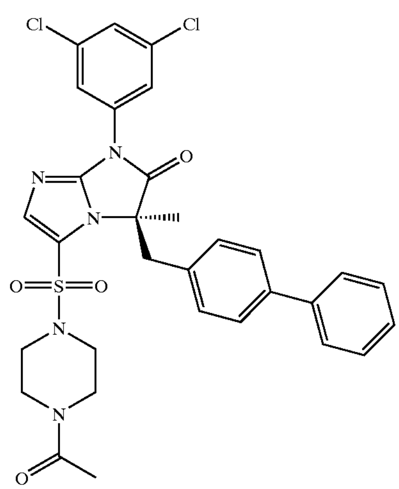 | resin |

-continued

| Example No. | Structure | Melting Point (° C.) |
|---|---|---|
| 226 | 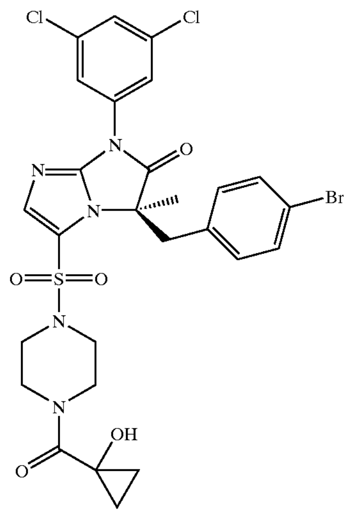 | not determined |
| 227 | 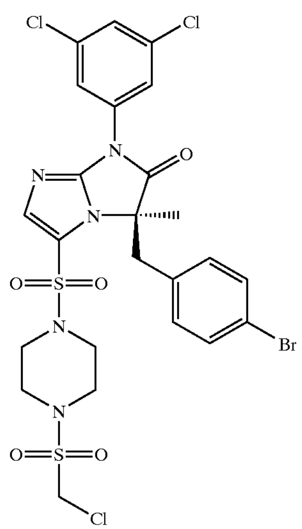 | 170–172 |
| 228 | 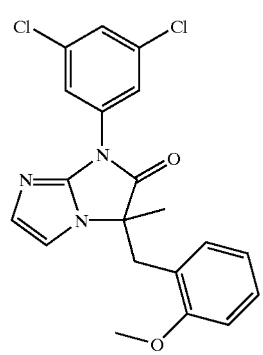 | 114.9–116.0 |

-continued
| Example No. | Structure | Melting Point (° C.) |
|---|---|---|
| 229 | 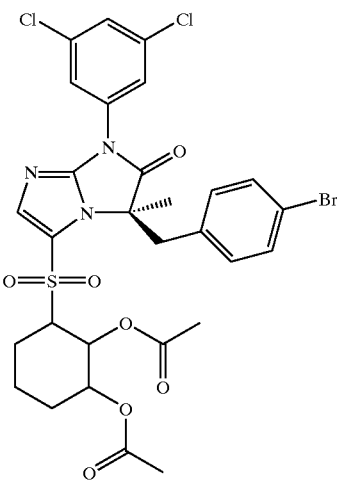 | not determined |
| 230 | 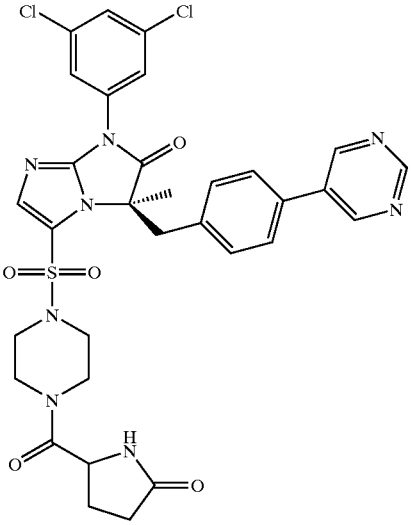 | not determined |
| 231 | 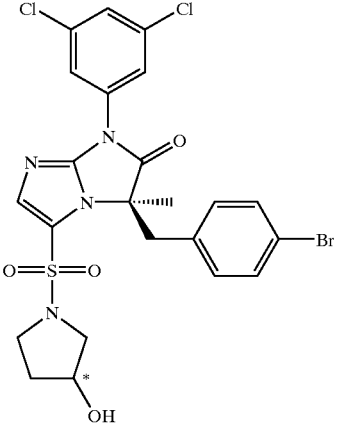 | foam |

-continued
| Example No. | Structure | Melting Point (° C.) |
| --- | --- | --- |
| 232 | 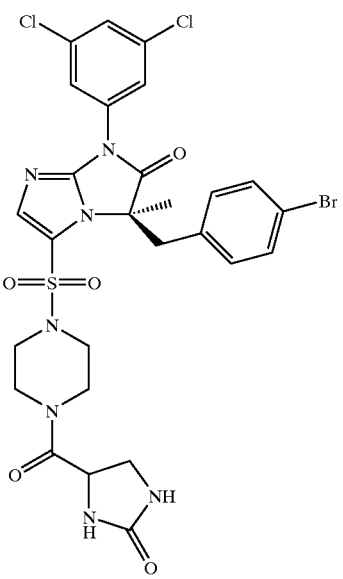 | not determined |
| 233 | 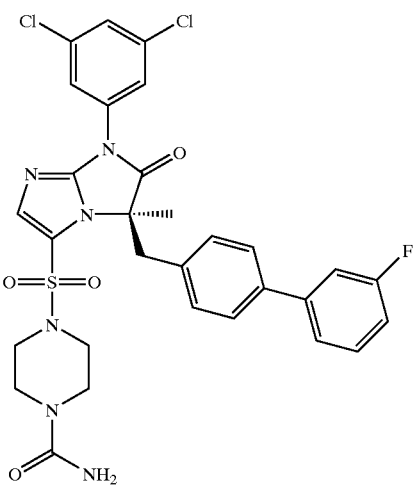 | not determined |
| 234 | 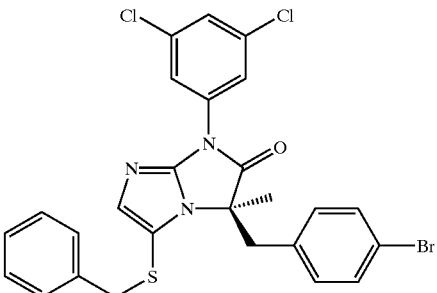 | gummy solid |

-continued
| Example No. | Structure | Melting Point (° C.) |
|---|---|---|
| 235 | 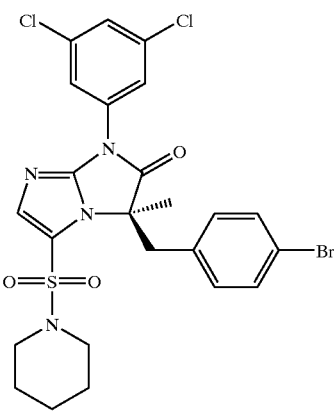 | not determined |
| 236 | 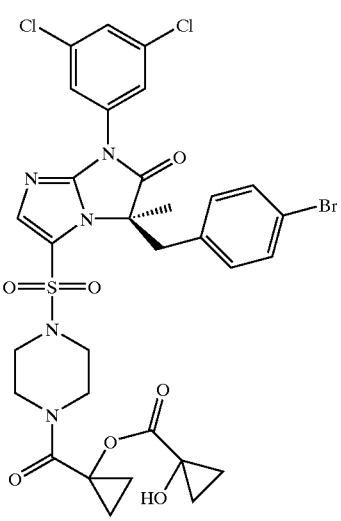 | not determined |
| 237 | 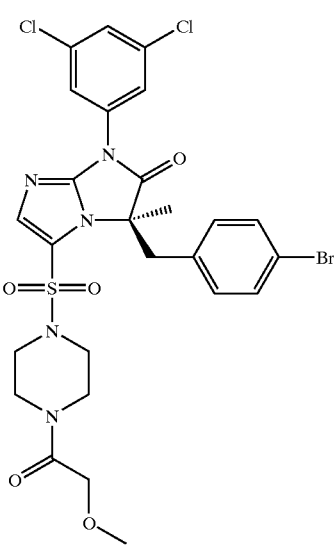 | resin |

-continued
| Example No. | Structure | Melting Point (° C.) |
|---|---|---|
| 238 | 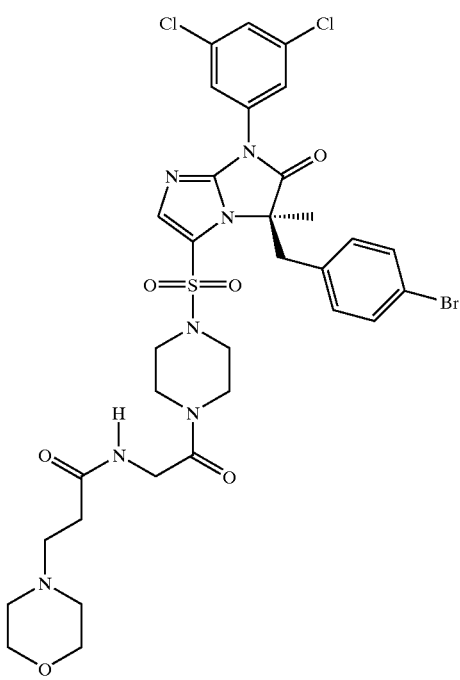 | foam |
| 239 | 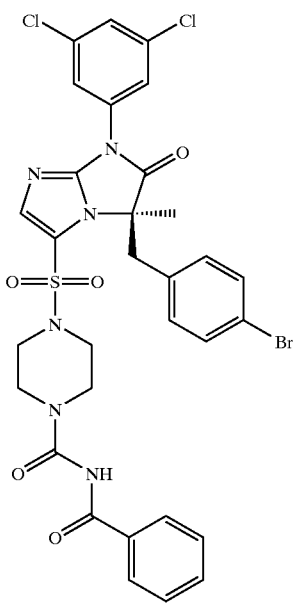 | resin |

| Example No. | Structure | Melting Point (° C.) |
|---|---|---|
| 240 | 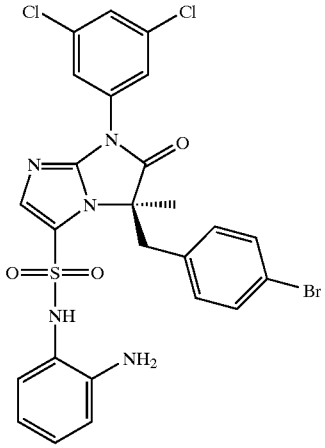 | resin |
| 241 | 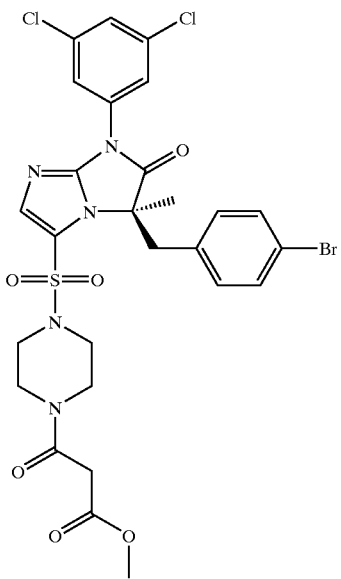 | resin |

-continued
| Example No. | Structure | Melting Point (° C.) |
|---|---|---|
| 242 | 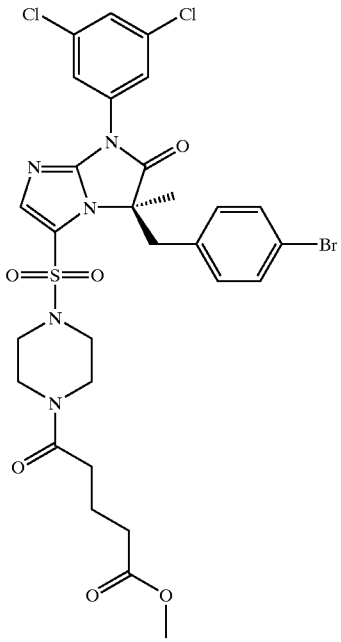 | resin |
| 243 | 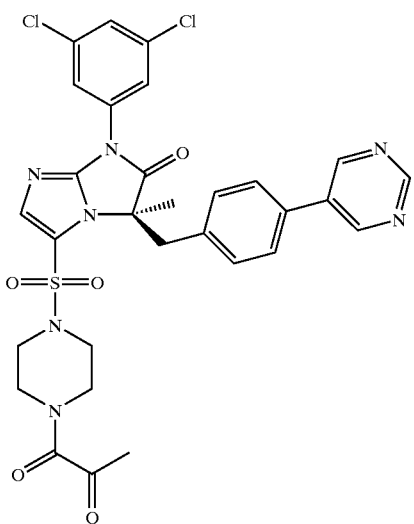 | not determined |

-continued

| Example No. | Structure | Melting Point (° C.) |
|---|---|---|
| 244 | 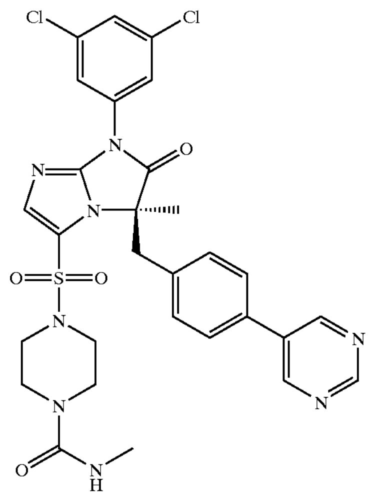 | resin |
| 245 | 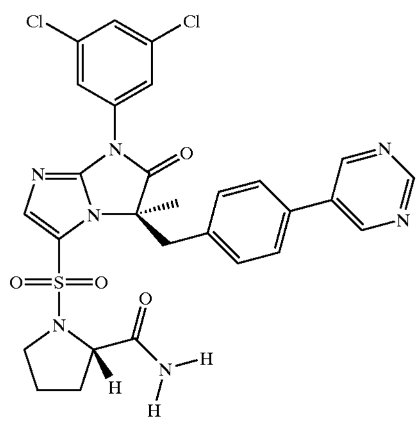 | 100–102 |
| 246 | 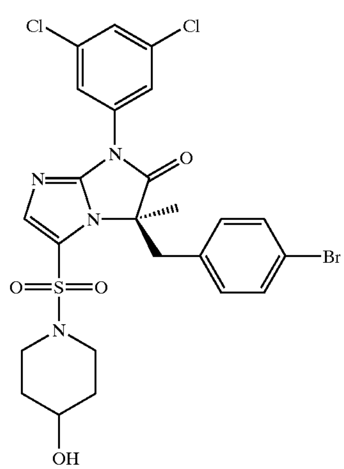 | 67.2–68.5 |

| Example No. | Structure | Melting Point (° C.) |
|---|---|---|
| 247 | 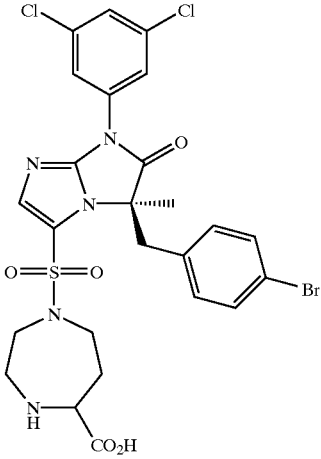 | not determined |
| 248 | 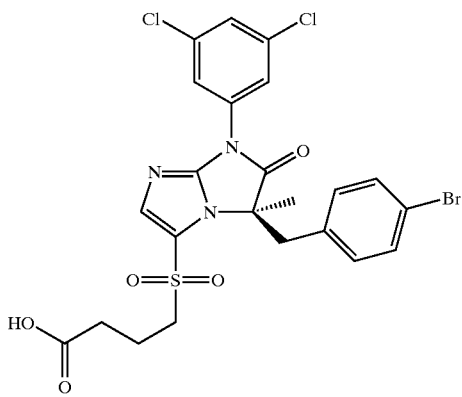 | foam |
| 249 | 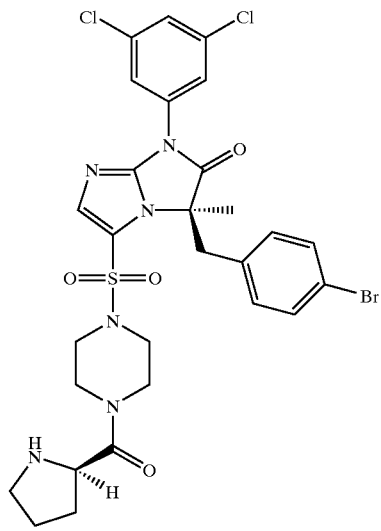 | foam |

-continued
| Example No. | Structure | Melting Point (° C.) |
|---|---|---|
| 250 | 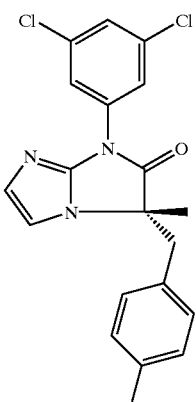 | not determined |
| 251 | 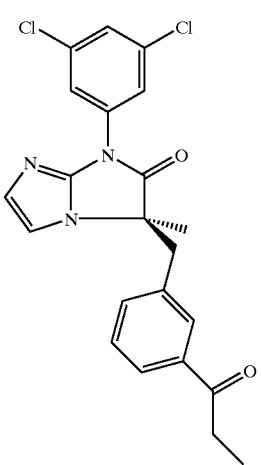 | foam |
| 252 | 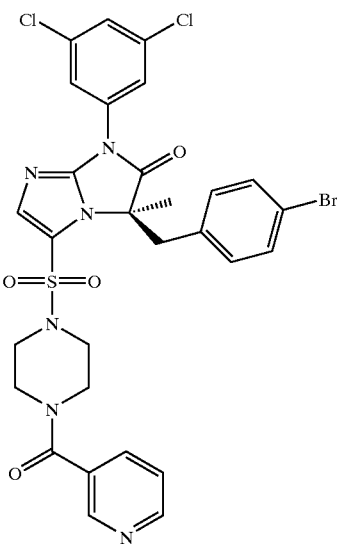 | not determined |

-continued

| Example No. | Structure | Melting Point (° C.) |
|---|---|---|
| 253 | 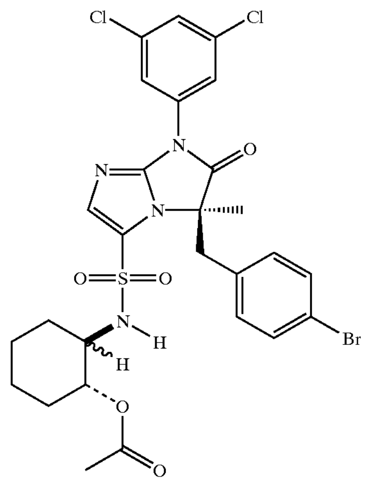 | foam |
| 254 | 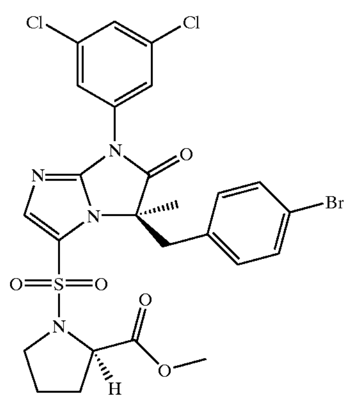 | 92–93.5 |
| 255 | 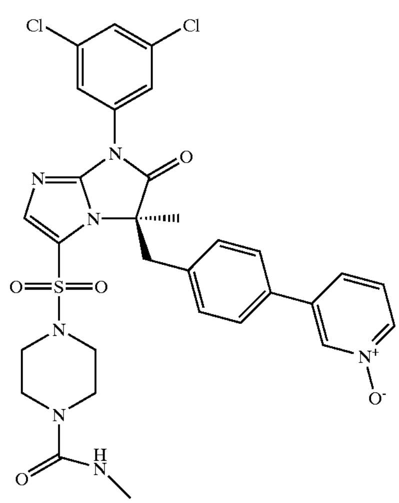 | waxy solid |

-continued
| Example No. | Structure | Melting Point (° C.) |
|---|---|---|
| 256 | 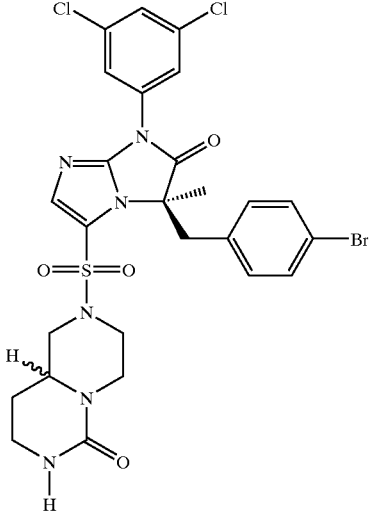 | foam |
| 257 | 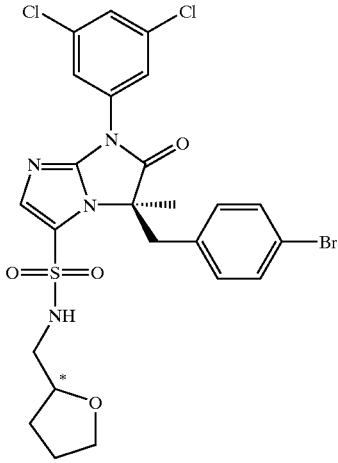 | foam |
| 258 | 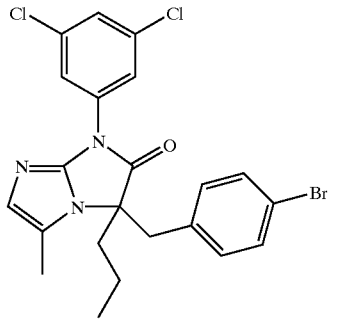 | resin |

-continued

| Example No. | Structure | Melting Point (° C.) |
| --- | --- | --- |
| 259 | 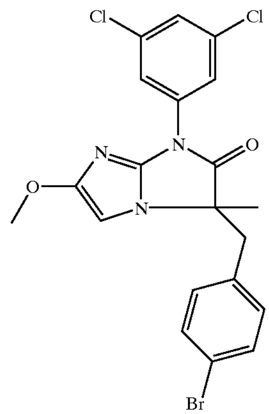 | 170–171 |
| 260 | 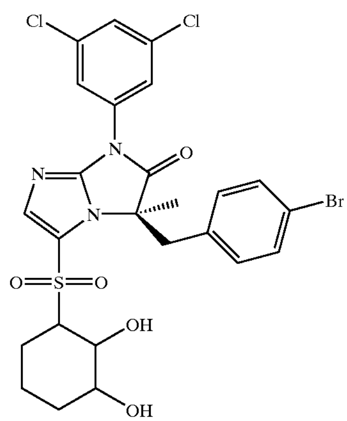 | not determined |
| 261 | 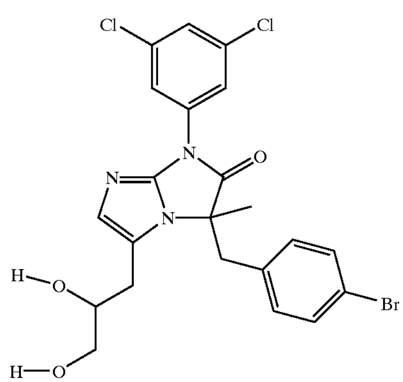 | thick oil |

-continued

| Example No. | Structure | Melting Point (° C.) |
|---|---|---|
| 262 | 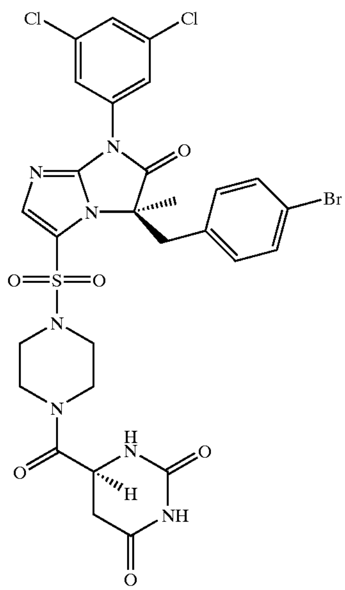 | not determined |
| 263 | 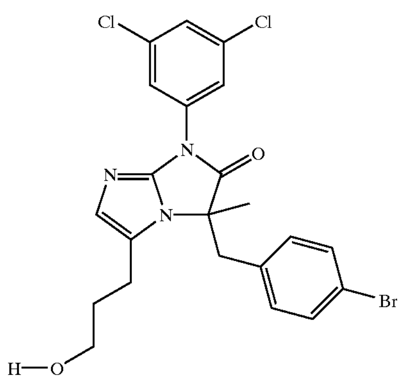 | foam |

| Example No. | Structure | Melting Point (° C.) |
|---|---|---|
| 264 | 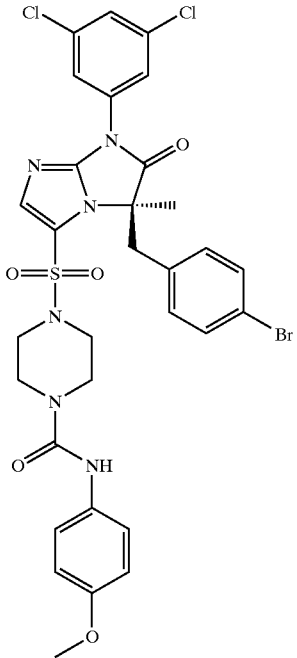 | 111–114 |
| 265 | 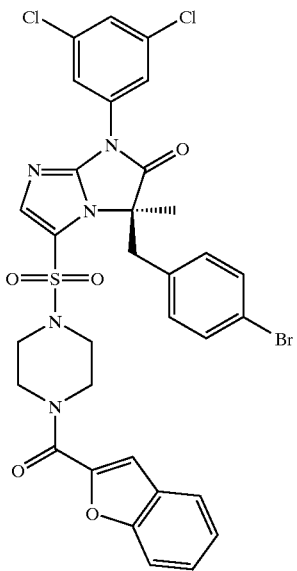 | 176–178 |

-continued
| Example No. | Structure | Melting Point (° C.) |
|---|---|---|
| 266 | 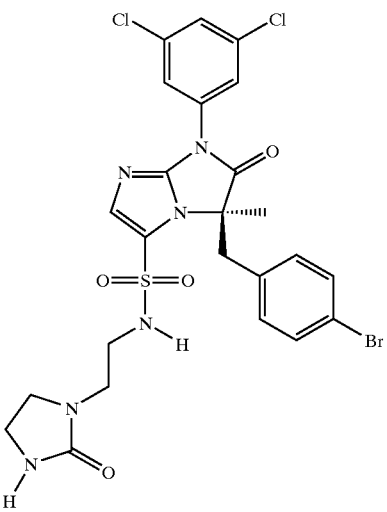 | resin |
| 267 | 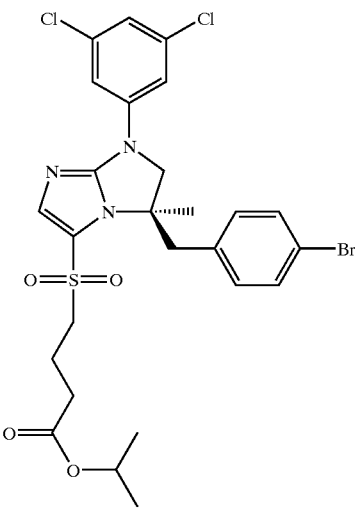 | oil |
| 268 | 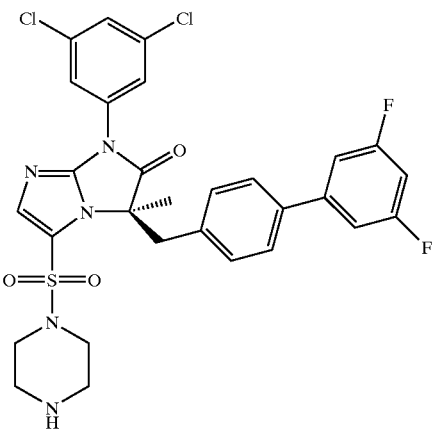 | not determined |

-continued

| Example No. | Structure | Melting Point (° C.) |
|---|---|---|
| 269 | 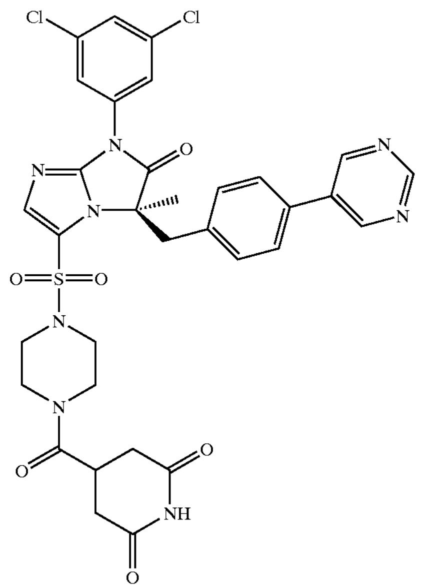 | not determined |
| 270 | 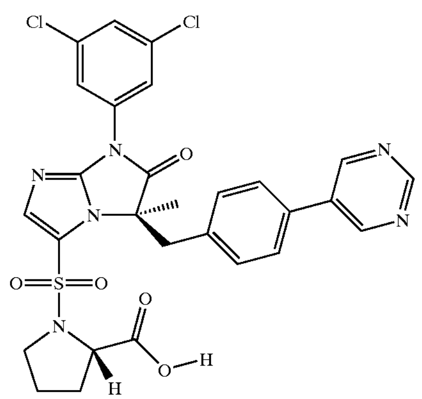 | not determined |
| 271 | 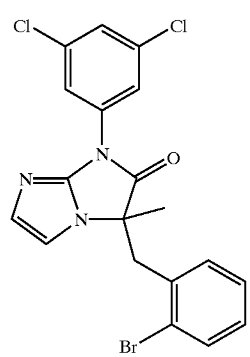 | not determined |

-continued

| Example No. | Structure | Melting Point (° C.) |
|---|---|---|
| 272 | 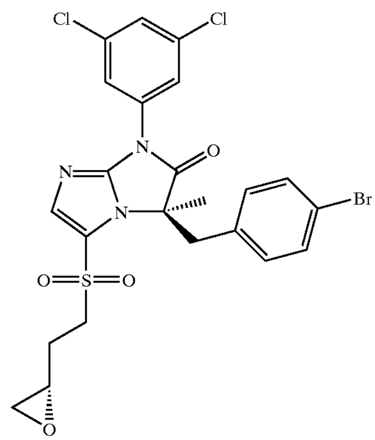 | not determined |
| 273 | 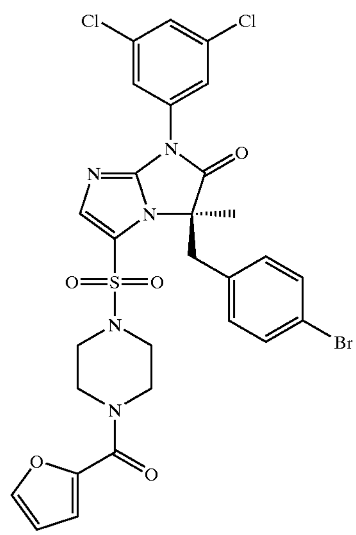 | 95–101 |
| 274 | 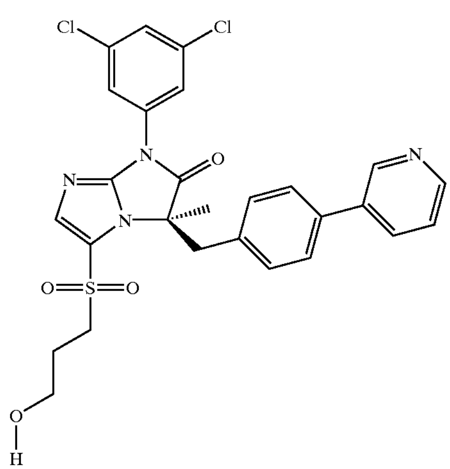 | not determined |

-continued
| Example No. | Structure | Melting Point (° C.) |
|---|---|---|
| 275 | 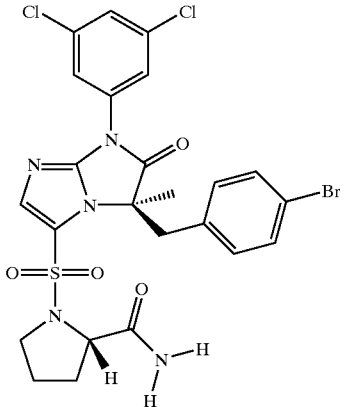 | 99.5–101 |
| 276 | 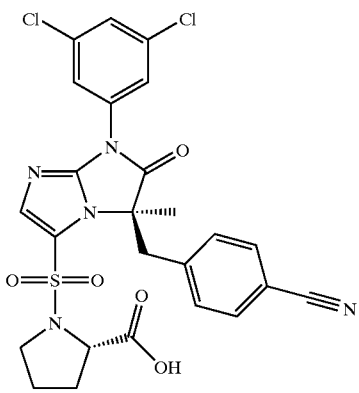 | resin |
| 277 | 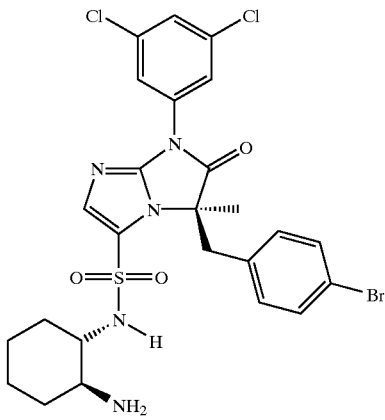 | foam |

-continued
| Example No. | Structure | Melting Point (° C.) |
|---|---|---|
| 278 | 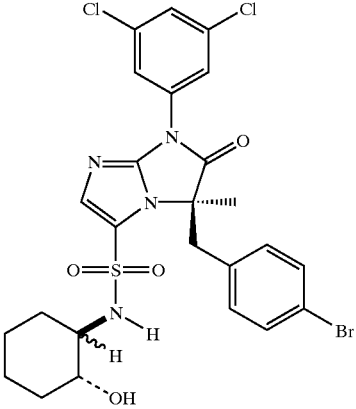 | foam |
| 279 | 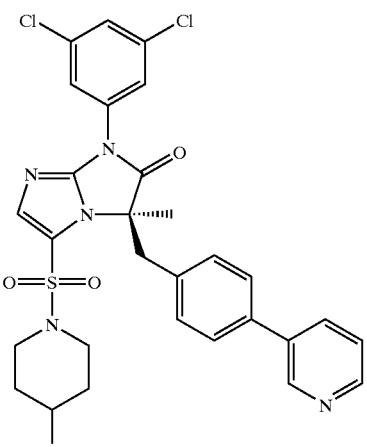 | 110–115 |
| 280 | 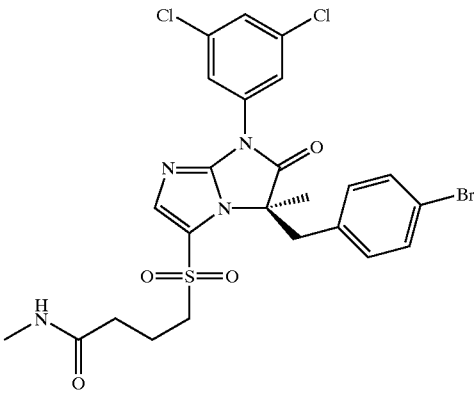 | oil |

-continued

| Example No. | Structure | Melting Point (° C.) |
|---|---|---|
| 281 | 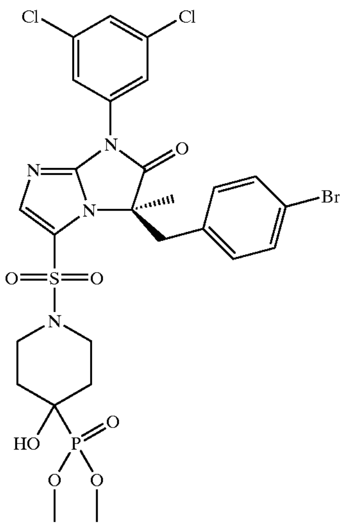 | foam |
| 282 | 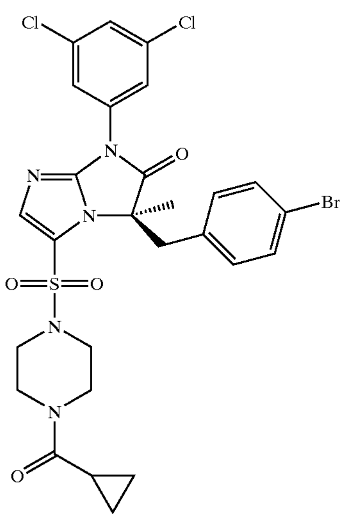 | not determined |
| 283 | 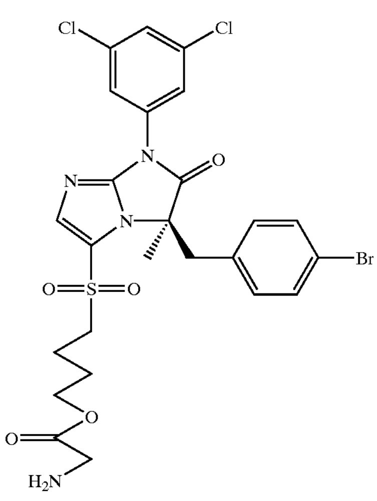 | not determined |

-continued
| Example No. | Structure | Melting Point (° C.) |
|---|---|---|
| 284 | 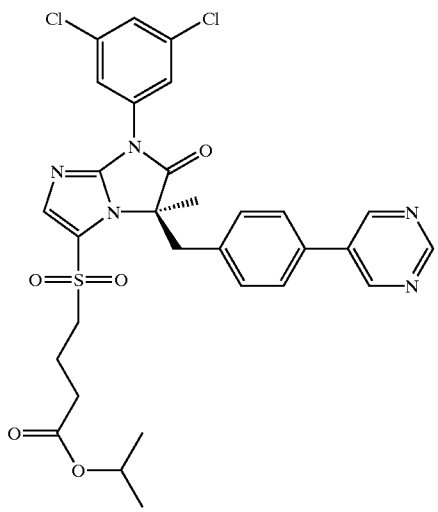 | waxy solid |
| 285 | 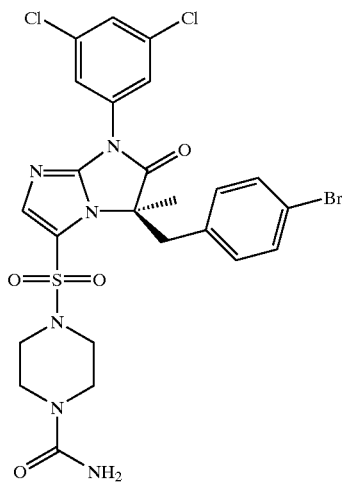 | foam |
| 286 | 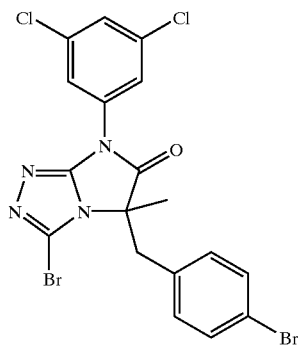 | 192–194 |

-continued
| Example No. | Structure | Melting Point (° C.) |
|---|---|---|
| 287 | 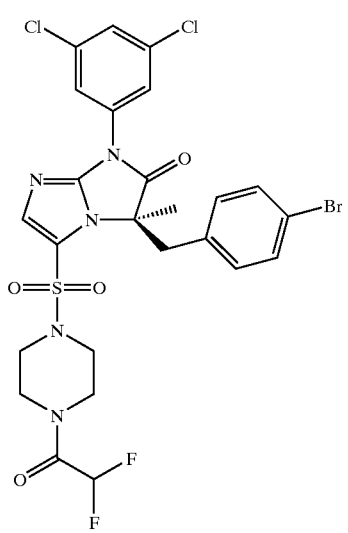 | not determined |
| 288 | 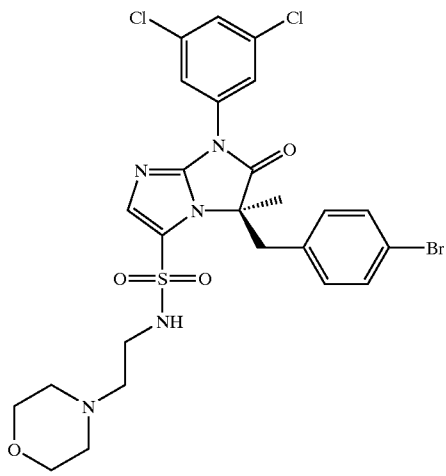 | foam |
| 289 | 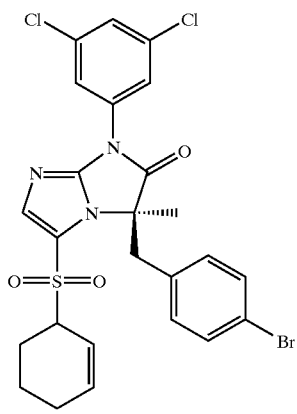 | not determined |

-continued
| Example No. | Structure | Melting Point (° C.) |
|---|---|---|
| 290 | 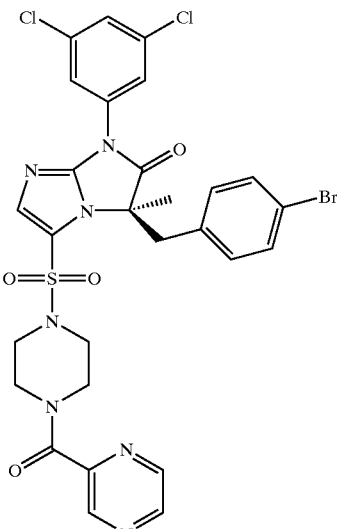 | not determined |
| 291 | 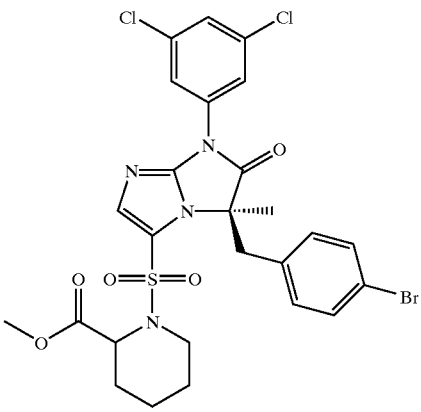 | not determined |
| 292 | 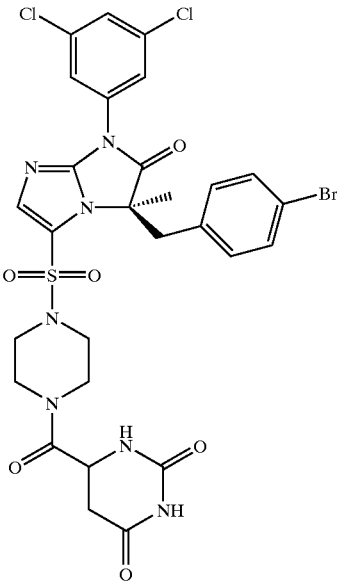 | not determined |

-continued
| Example No. | Structure | Melting Point (° C.) |
|---|---|---|
| 293 | 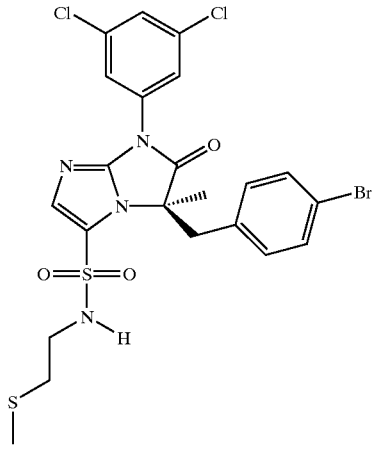 | not determined |
| 294 | 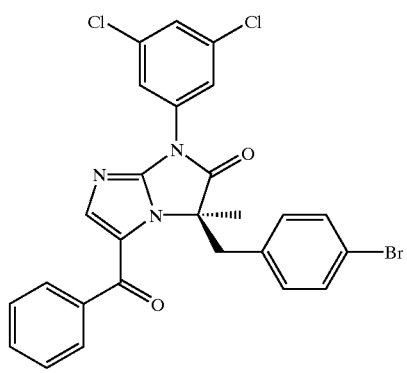 | foam |
| 295 | 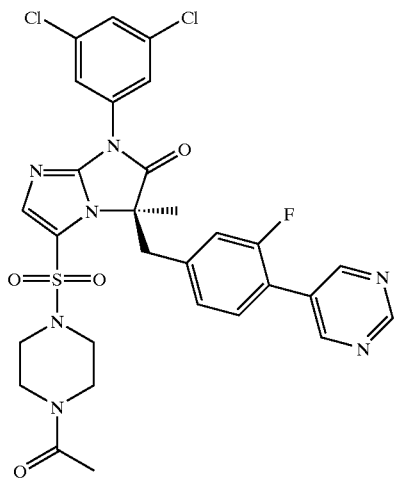 | resin |

-continued
| Example No. | Structure | Melting Point (° C.) |
|---|---|---|
| 296 | 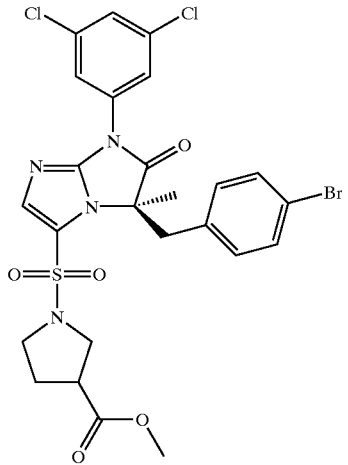 | not determined |
| 297 | 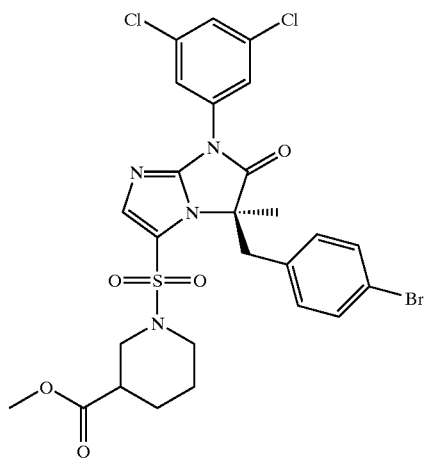 | not determined |
| 298 | 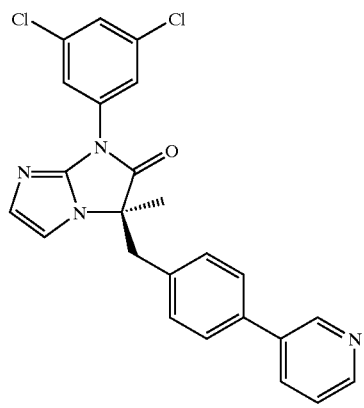 | 71.2–72.3 |

| Example No. | Structure | Melting Point (° C.) |
|---|---|---|
| 299 | 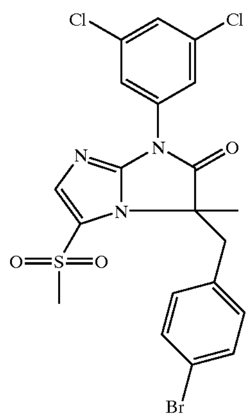 | not determined |
| 300 | 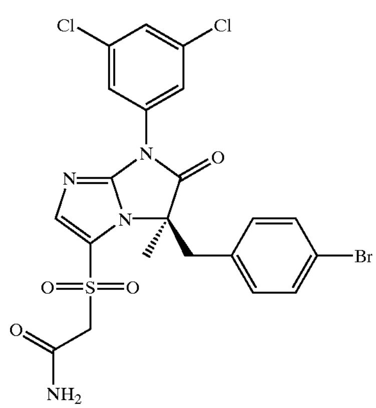 | 96–99 |
| 301 | 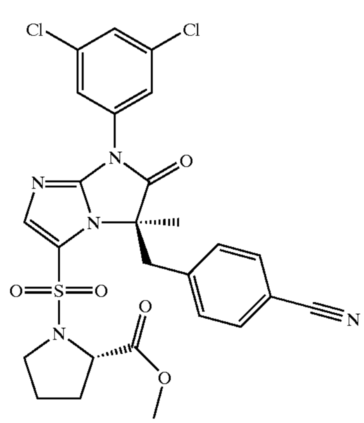 | resin |

-continued

| Example No. | Structure | Melting Point (° C.) |
|---|---|---|
| 302 | 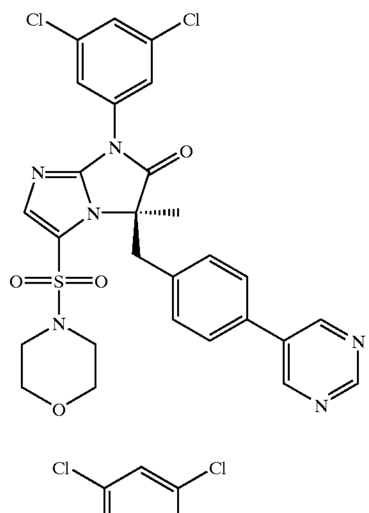 | 201–202 |
| 303 | 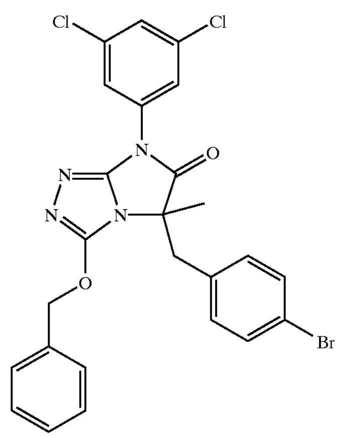 | 142–144 |
| 304 | 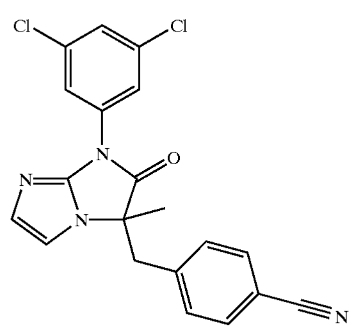 | 47.9–49.4 |
| 305 | 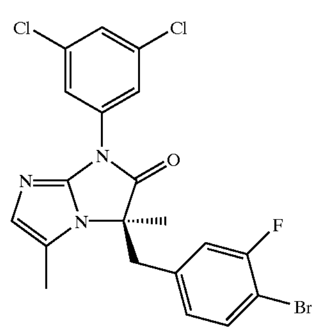 | hard oil |

-continued

| Example No. | Structure | Melting Point (° C.) |
|---|---|---|
| 306 | 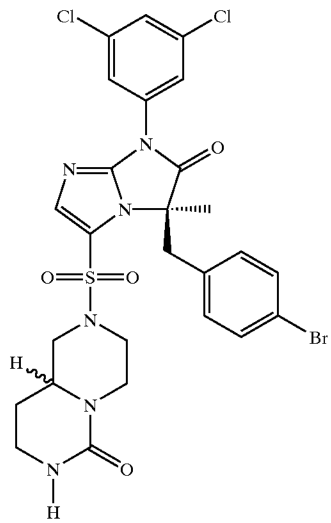 | foam |
| 307 | 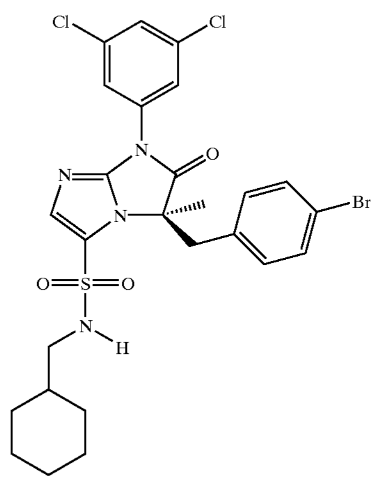 | not determined |
| 308 | 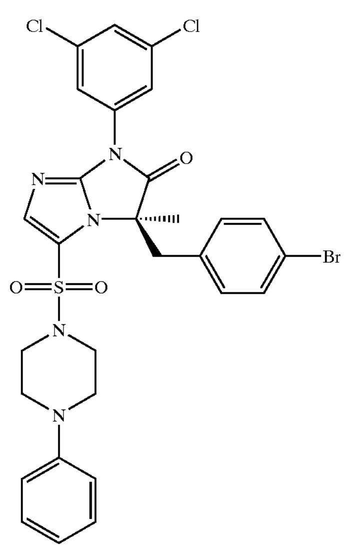 | 58–60 |

-continued

| Example No. | Structure | Melting Point (° C.) |
|---|---|---|
| 309 | 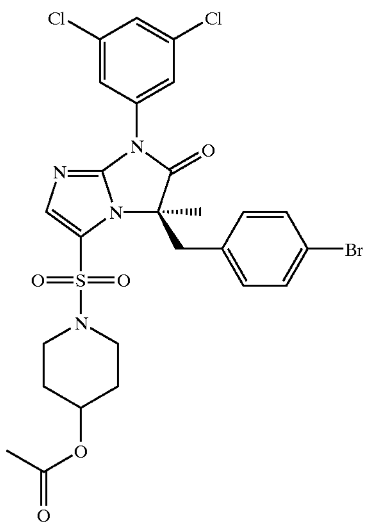 | 77.9–78.9 |
| 310 | 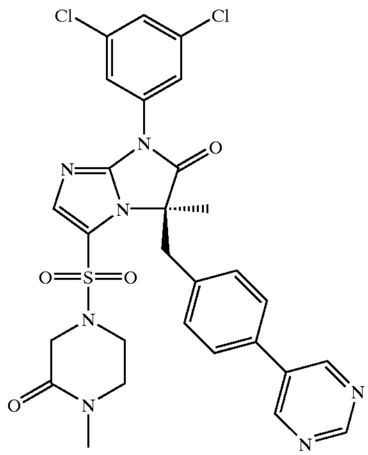 | not determined |
| 311 | 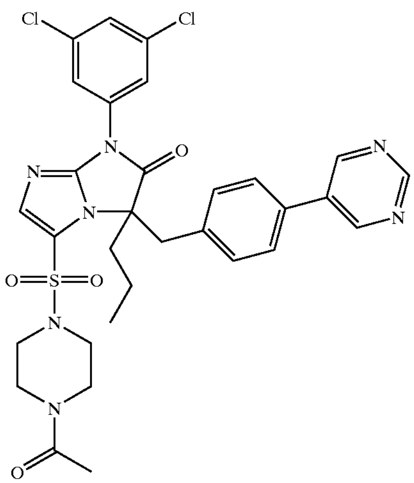 | resin |

-continued

| Example No. | Structure | Melting Point (° C.) |
|---|---|---|
| 312 | 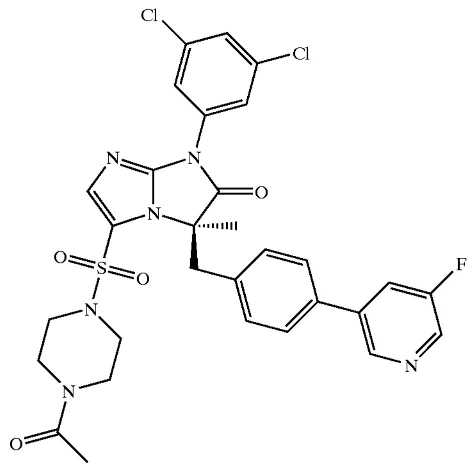 | resin |
| 313 | 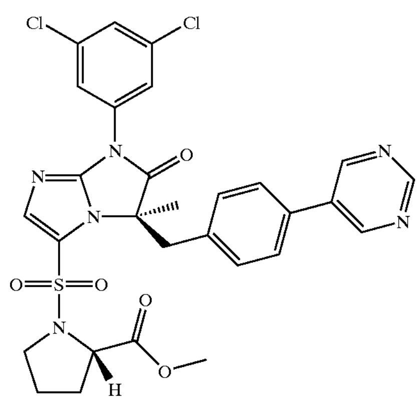 | not determined |
| 314 | 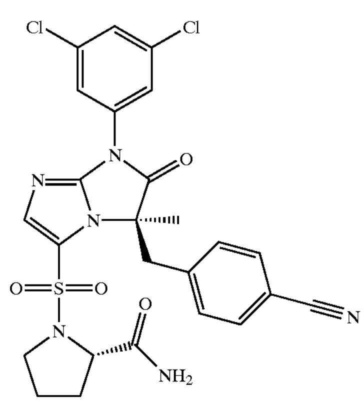 | resin |

-continued

| Example No. | Structure | Melting Point (° C.) |
|---|---|---|
| 315 | 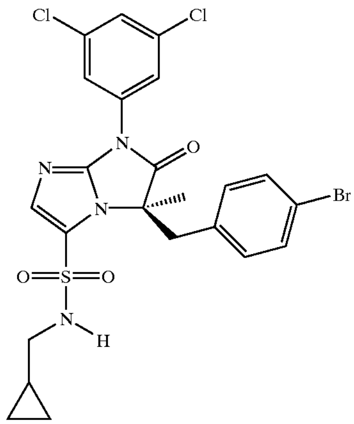 | not determined |
| 316 | 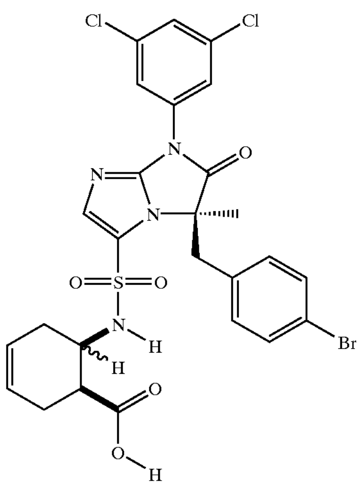 | resin |
| 317 | 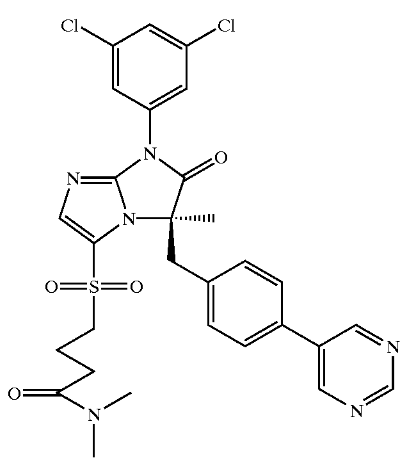 | film |

-continued

| Example No. | Structure | Melting Point (° C.) |
|---|---|---|
| 318 | 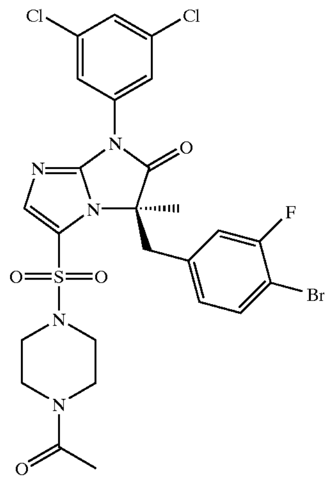 | resin |
| 319 | 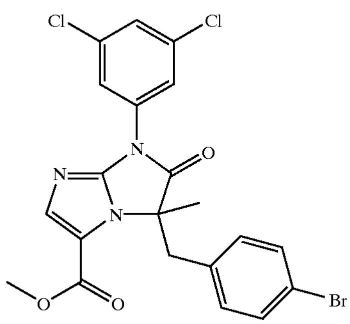 | 74.1–76.0 |
| 320 | 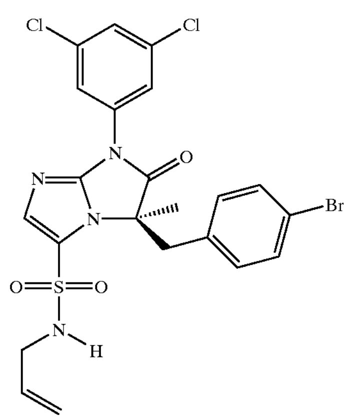 | not determined |

| Example No. | Structure | Melting Point (° C.) |
|---|---|---|
| 321 | 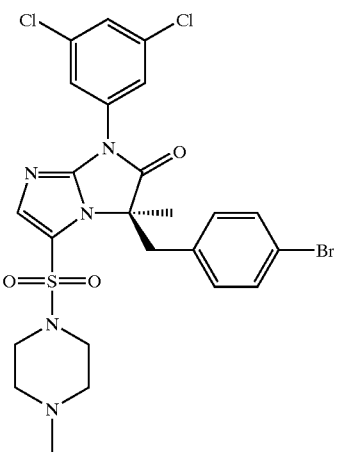 | foam |
| 322 | 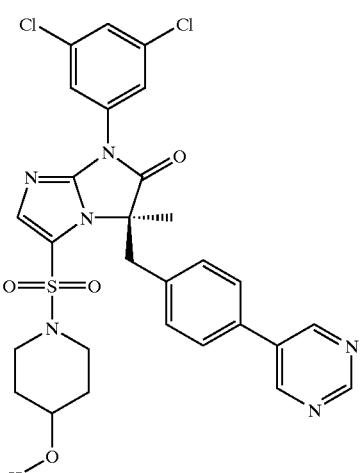 | foam |
| 323 | 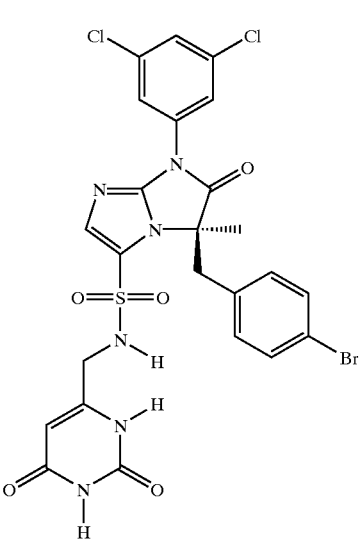 | foam |

-continued
| Example No. | Structure | Melting Point (° C.) |
|---|---|---|
| 324 | 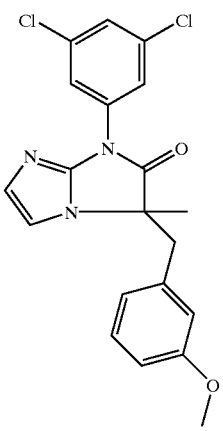 | 101.3–102.1 |
| 325 | 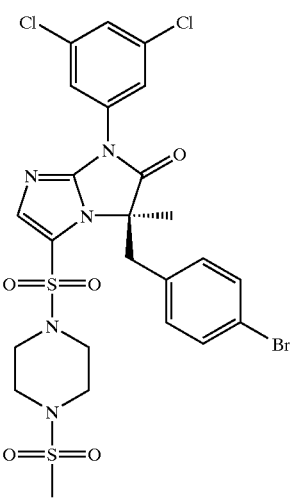 | 196–197 |
| 326 | 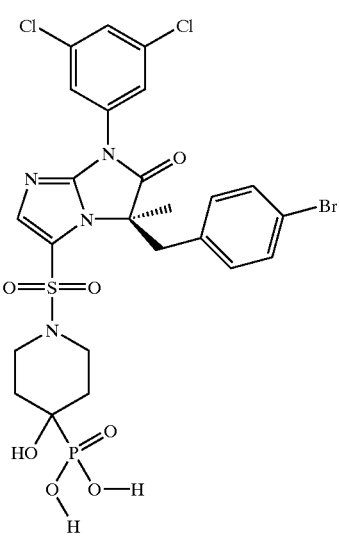 | not determined |

-continued
| Example No. | Structure | Melting Point (° C.) |
|---|---|---|
| 327 | 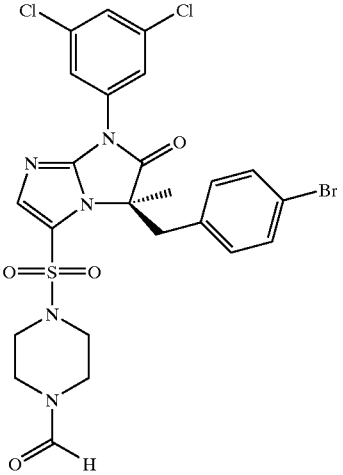 | foam |
| 328 | 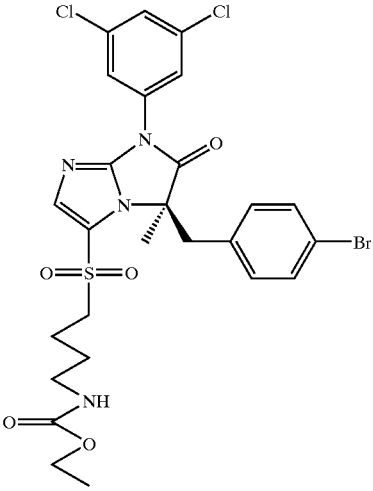 | not determined |
| 329 | 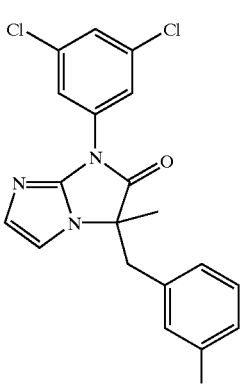 | 132.3–133.7 |

-continued

| Example No. | Structure | Melting Point (° C.) |
|---|---|---|
| 330 | 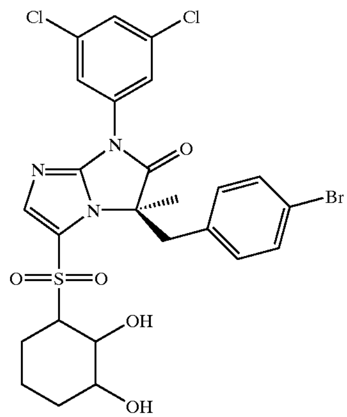 | not determined |
| 331 | 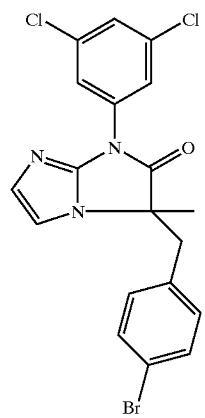 | oil |
| 332 | 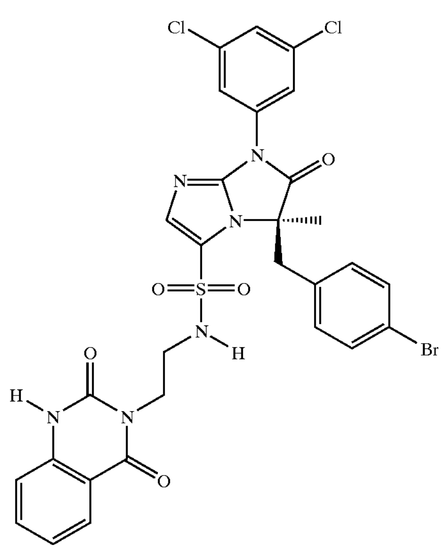 | 82.3–85.4 |

-continued

| Example No. | Structure | Melting Point (° C.) |
|---|---|---|
| 333 | 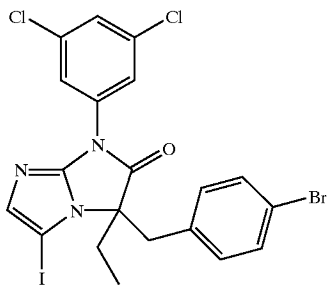 | resin |
| 334 | 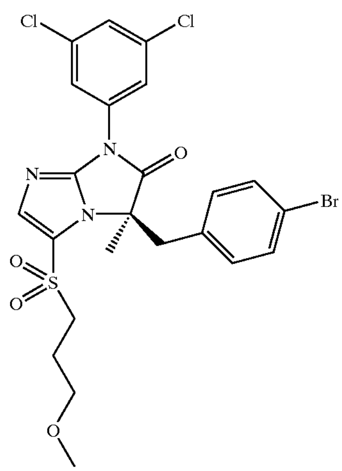 | resin |
| 335 | 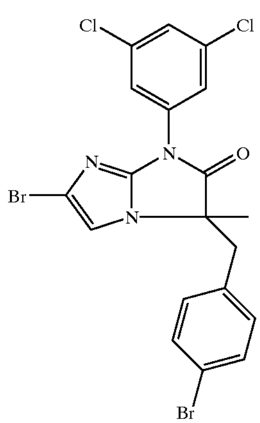 | not determined |

-continued

| Example No. | Structure | Melting Point (° C.) |
|---|---|---|
| 336 | 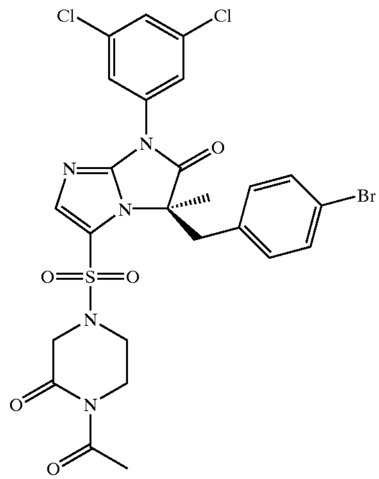 | film |
| 337 | 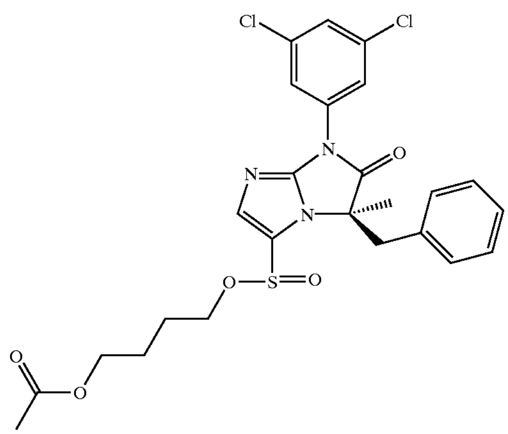 | resin |
| 338 | 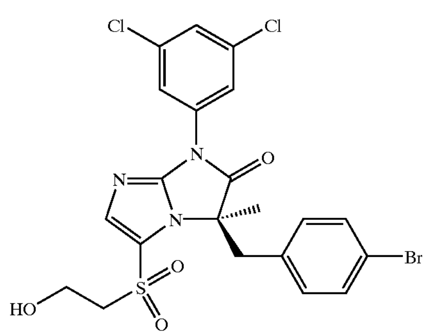 | 139.2–140.0 |

-continued

| Example No. | Structure | Melting Point (° C.) |
|---|---|---|
| 339 | 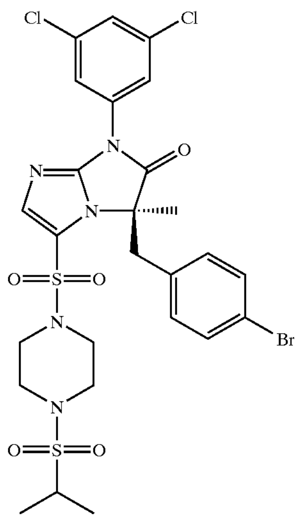 | 126–127 |
| 340 | 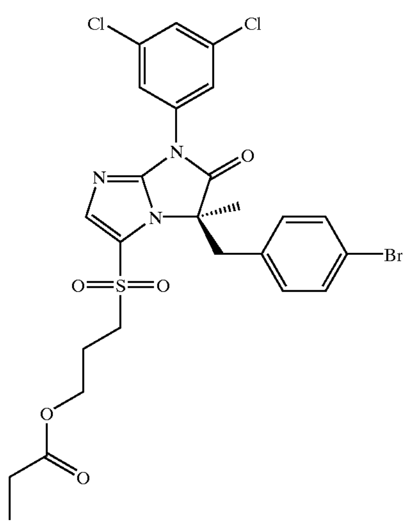 | foam |

-continued
| Example No. | Structure | Melting Point (° C.) |
|---|---|---|
| 341 | 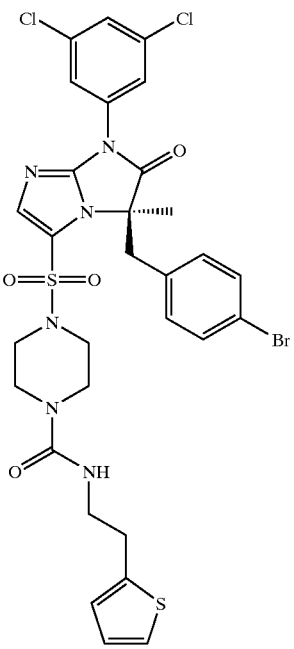 | resin |
| 342 | 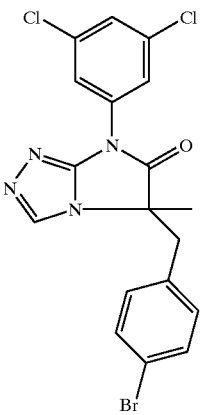 | not determined |
| 343 | 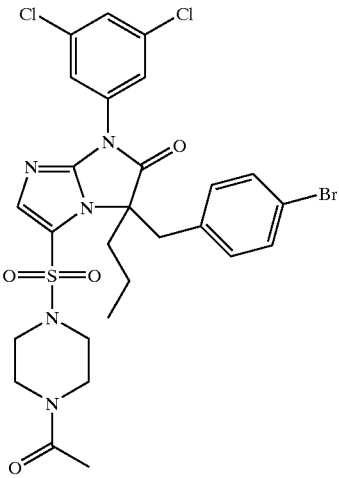 | resin |

-continued

| Example No. | Structure | Melting Point (° C.) |
|---|---|---|
| 344 | 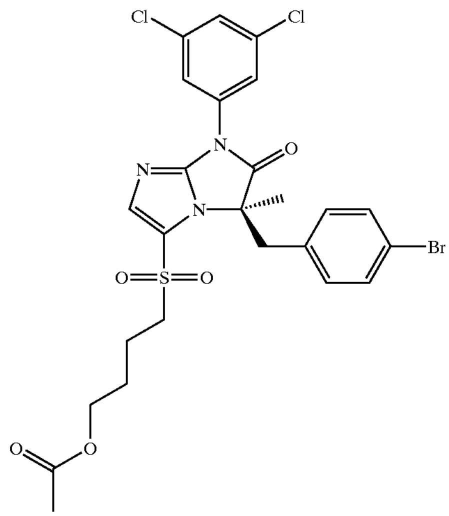 | foam |
| 345 | 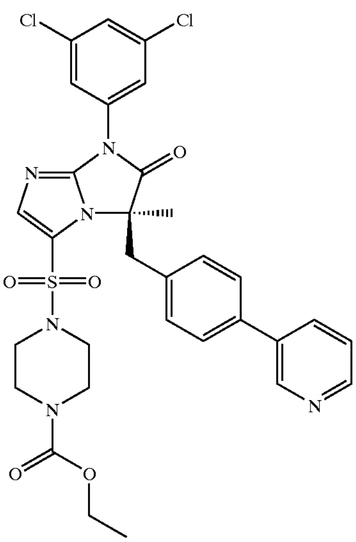 | 88–90 |
| 346 | 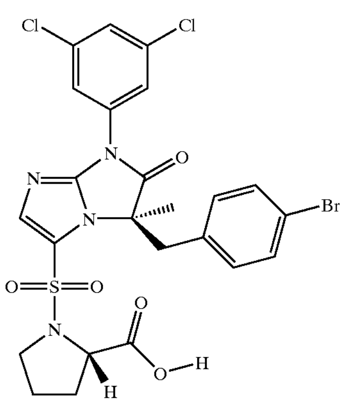 | not determined |

-continued

| Example No. | Structure | Melting Point (° C.) |
|---|---|---|
| 347 | 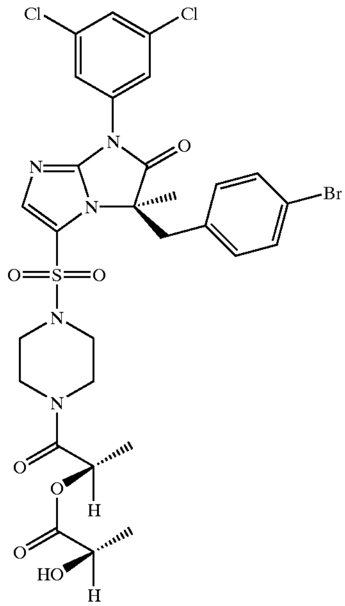 | not determined |
| 348 | 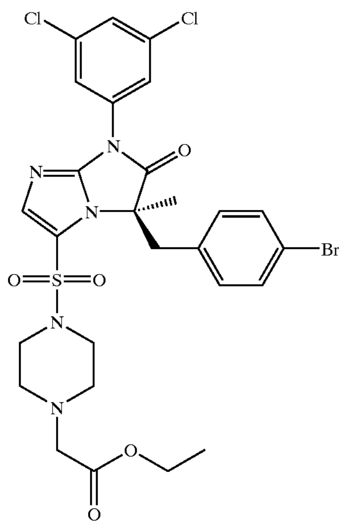 | 72–78 |
| 349 | 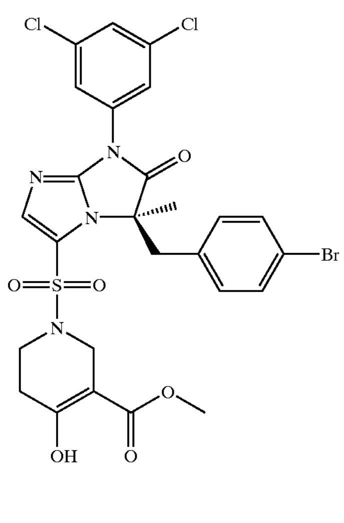 | 90–95 |

-continued
| Example No. | Structure | Melting Point (° C.) |
|---|---|---|
| 350 | 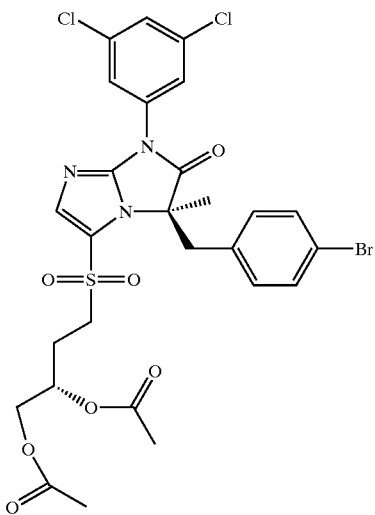 | foam |
| 351 | 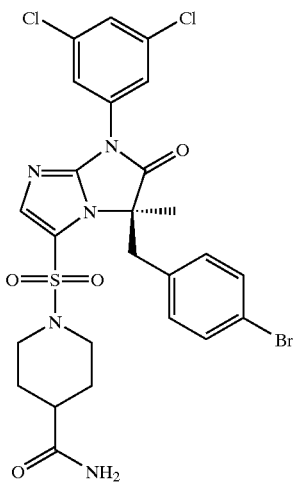 | 115.4–117.1 |
| 352 | 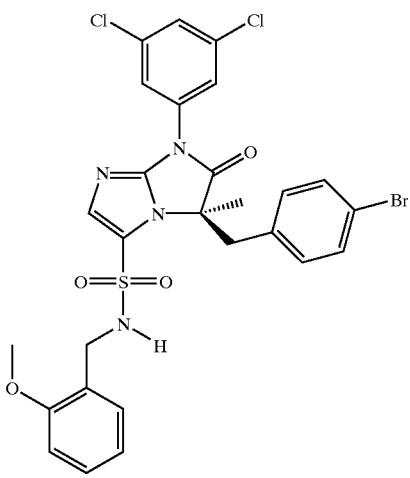 | not determined |

-continued
| Example No. | Structure | Melting Point (° C.) |
|---|---|---|
| 353 | 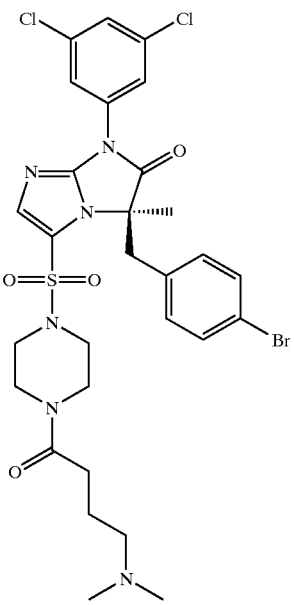 | 90–92.5 |
| 354 | 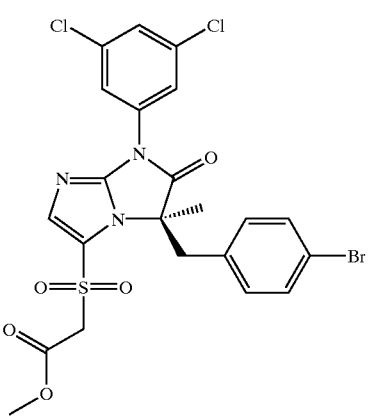 | oil |
| 355 | 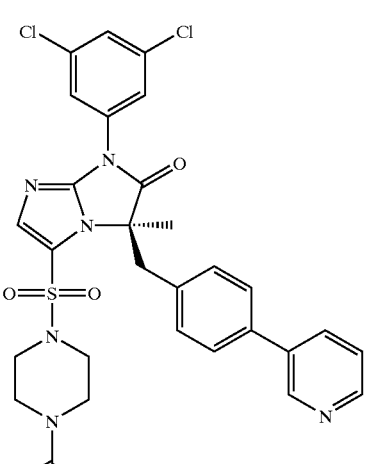 | 92–97 |

-continued
| Example No. | Structure | Melting Point (° C.) |
|---|---|---|
| 356 | 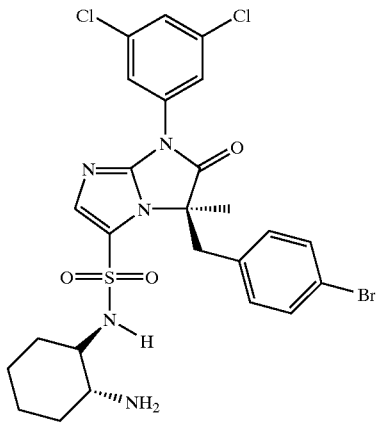 | foam |
| 357 | 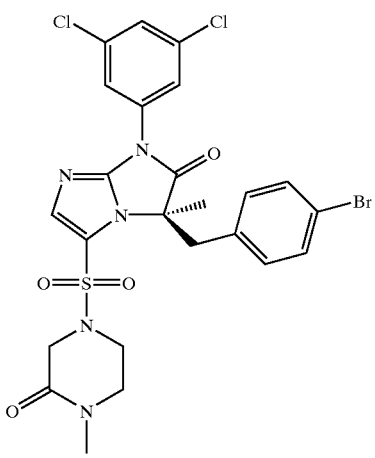 | film |
| 358 | 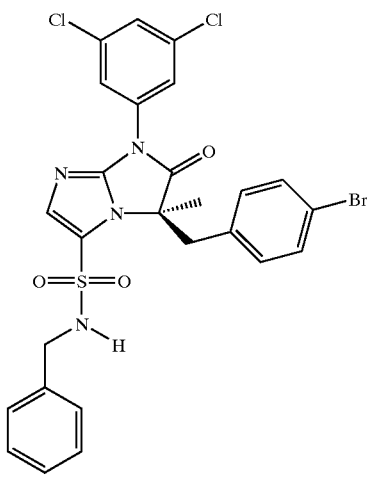 | not determined |

| Example No. | Structure | Melting Point (° C.) |
|---|---|---|
| 359 | 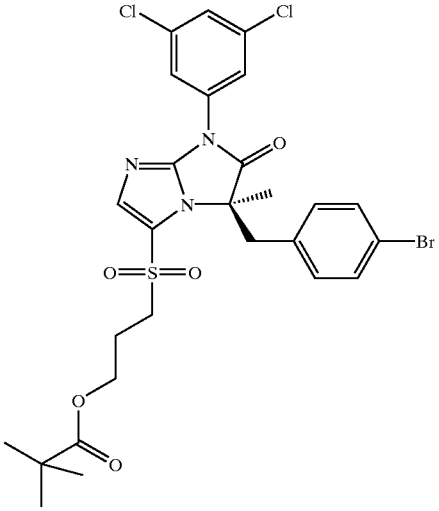 | foam |
| 360 | 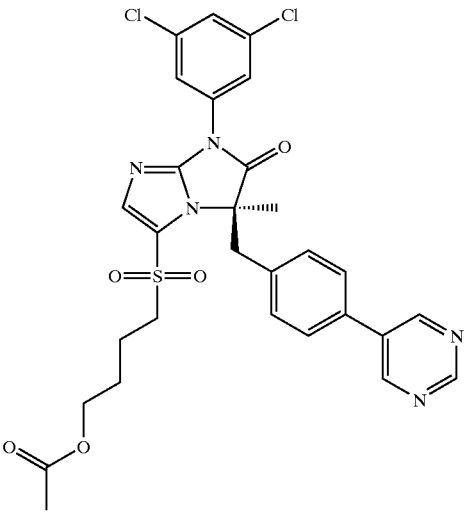 | foam |
| 361 | 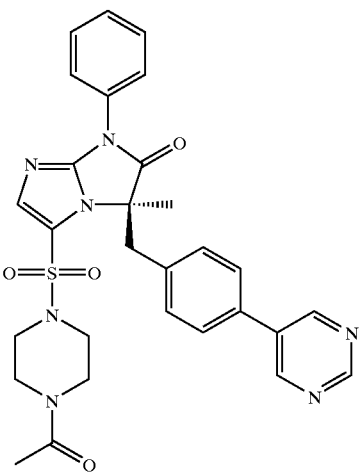 | foam |

-continued

| Example No. | Structure | Melting Point (° C.) |
|---|---|---|
| 362 | 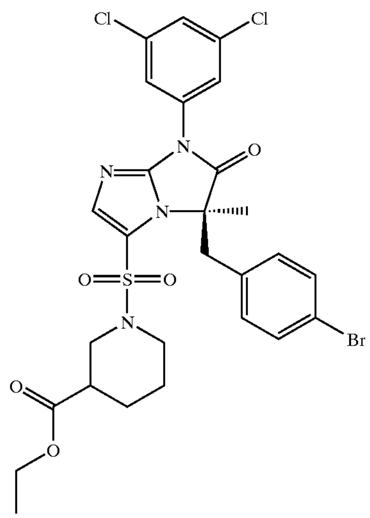 | not determined |
| 363 | 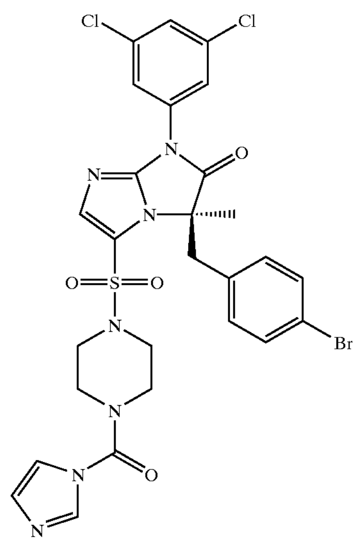 | 101–105 |
| 364 | 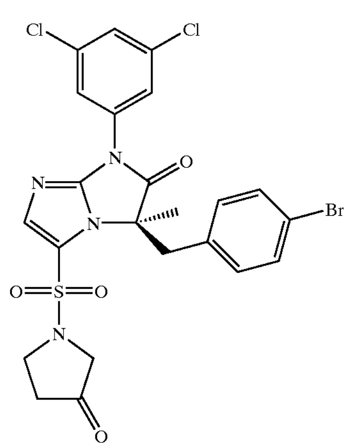 | foam |

-continued

| Example No. | Structure | Melting Point (° C.) |
|---|---|---|
| 365 | 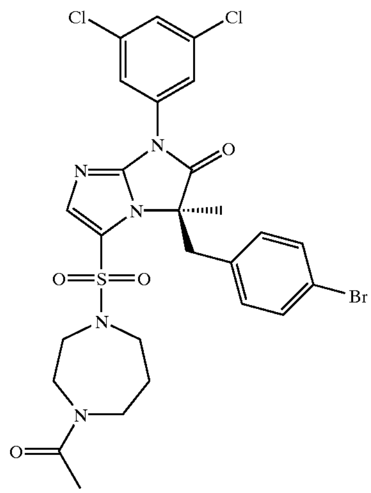 | resin |
| 366 | 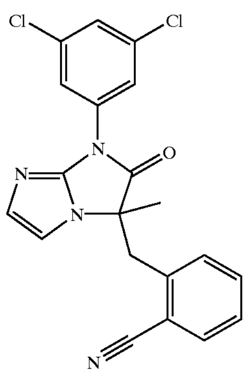 | 114.9–116.3 |
| 367 | 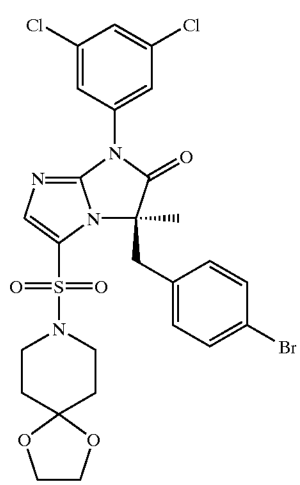 | foam |

| Example No. | Structure | Melting Point (° C.) |
|---|---|---|
| 368 | 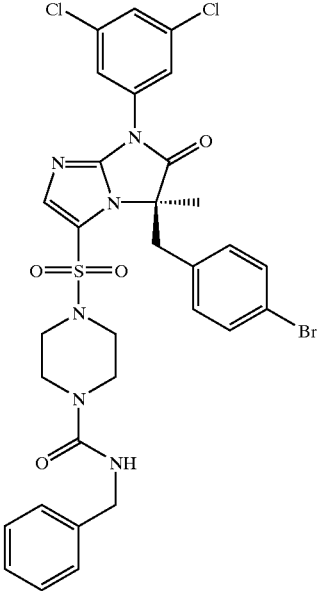 | 88–92 |
| 369 | 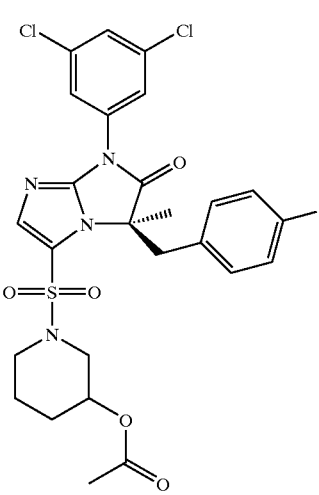 | not determined |
| 370 | 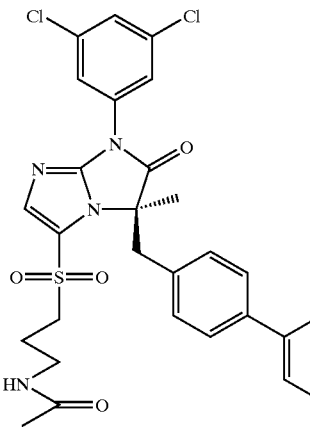 | not determined |

-continued
| Example No. | Structure | Melting Point (° C.) |
|---|---|---|
| 371 | 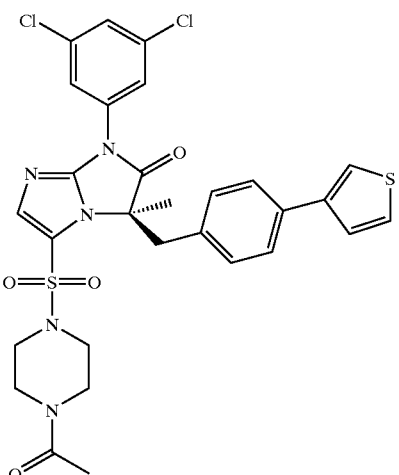 | not determined |
| 372 | 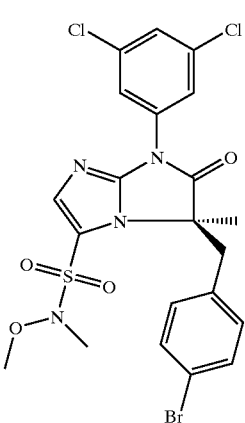 | 125–126 |
| 373 | 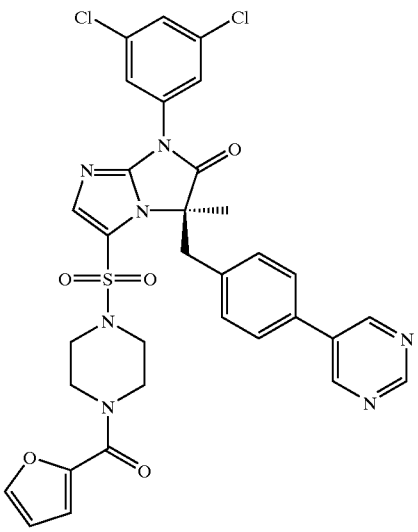 | 109–114 |

Description of Biological Properties

The biological properties of representative compounds of the formula I were investigated by way of the experimental protocol described below.

Assay to Determine Inhibition of LFA-1 Binding to ICAM-1

Purpose of Assay:

This assay protocol is designed to study the direct antagonism, by a test compound, of the interaction of the CAM, ICAM-1 with the Leukointegrin CD18/CD11a (LFA-1).

Description of Assay Protocol:

LFA-1 is immunopurified using the TS2/4 antibody from a 20 g pellet of human JY or SKW3 cells, utilizing a protocol previously described (Dustin, M. J.; et al., *J. Immunol.* 1992, 148, 2654–2660). The LFA-1 is purified from SKW3 lysates by immunoaffinity chromatography on $TS_{2/4}$ LFA-1 mAb Sepharose and eluted at pH 11.5 in the presence of 2 mM $MgCl_2$ and 1% octylglucoside. After collection and neutralization of fractions from the $TS_{2/4}$ column, samples are pooled and precleared with Protein G agarose.

A soluble form of ICAM-1 is constructed, expressed, purified and characterized as previously described (Marlin, S.; et al., *Nature*, 1990, 344, 70–72 and see Arruda, A.; et al., *Antimicrob. Agents Chemother.* 1992, 36, 1186–1192). Briefly, isoleucine 454 which is located at the putative boundary between domain 5 of the ectodomain and the transmembrane domain, is changed to a stop codon using standard oligonucleotide-directed mutagenesis. This construction yields a molecule identical with the first 453 amino acids of membrane bound ICAM-1. An expression vector is created with a hamster dihydrofolate reductase gene, a neomycin-resistance marker, and the coding region of the sICAM-1 construct described above, along with the promoter, splice signals, and polyadenylation signal of the SV40 early region. The recombinant plasmid is transfected into CHO DUX cells using standard calcium phosphate methods. Cells are passaged in selective media (G418) and colonies secreting sICAM-1 are amplified using methotrexate. sICAM-1 is purified from serum-free media using traditional non-affinity chromatographic techniques, including ion exchange and size exclusion chromatography.

LFA-1 binding to ICAM-1 is monitored by first incubating sICAM-1 at 40 μg/mL in Dulbecco's phosphate buffered saline with calcium and magnesium, additional 2 mM $MgCl_2$ and 0.1 mM PMSF (Diluting Buffer) in a 96-well plate for 30 min at room temperature. Plates are then blocked by the addition of 2% (w/v) bovine serum albumin in Diluting Buffer for 37° C. for 1 h. Blocking solution is removed from wells, and test compounds are diluted and then added followed by the addition of approximately 25 ng of immunoaffinity purified LFA-1. The LFA-1 is incubated in the presence of test compound and ICAM-1 at 37° C. for 1 h. Wells are washed 3 times with Diluting Buffer. The bound LFA-1 is detected by the addition of a polyclonal antibody directed against a peptide corresponding to the CD18 cytoplasmic tail in a 1:100 dilution with Diluting Buffer and 1% BSA and allowed to incubate for 45 min at 37° C. Wells are washed 3 times with Diluting Buffer and the bound polyclonal antibody is detected by the addition of a 1:4000 dilution of horse radish peroxidase conjugated to goat immunoglobulin directed against rabbit immunoglobulin. This reagent is allowed to incubate for 20 min at 37° C., wells are washed as above and the substrate for the horse radish peroxidase is added to each well to develop a quantitative colorimetric signal proportional to the amount of LFA-1 bound to sICAM-1. Soluble ICAM-1 (60 μg/mL) is used as a positive control for inhibition of the LFA-1/ICAM-1 interaction. The lack of the addition of LFA-1 to the binding assay is used as a background control for all samples. A dose-response curve is obtained for all test compounds.

All compounds made in the above examples were tested in this assay and each found to have a $K_d < 10$ μM.

Description of Therapeutic Use

The novel small molecules of formula I provided by the invention inhibit the ICAM-1/LFA-1 dependent homotypic aggregation of human lymphocytes and human lymphocyte adherence to ICAM-1. These compounds have therapeutic utility in the modulation of immune cell activation/proliferation, e.g., as competitive inhibitors of intercellular ligand/receptor binding reactions involving CAMs and Leukointegrins. To be more specific, the compounds of the invention may be used to treat certain inflammatory conditions, including conditions resulting from a response of the non-specific immune system in a mammal (e.g., adult respiratory distress syndrome, shock, oxygen toxicity, multiple organ injury syndrome secondary to septicemia, multiple organ injury syndrome secondary to trauma, reperfusion injury of tissue due to cardiopulmonary bypass, myocardial infarction or use with thrombolysis agents, acute glomerulonephritis, vasculitis, reactive arthritis, dermatosis with acute inflammatory components, stroke, thermal injury, hemodialysis, leukapheresis, ulcerative colitis, necrotizing enterocolitis and granulocyte transfusion associated syndrome) and conditions resulting from a response of the specific immune system in a mammal (e.g., psoriasis, organ/tissue transplant rejection, graft vs. host reactions and autoimmune diseases including Raynaud's syndrome, autoimmune thyroiditis, dermatitis, multiple sclerosis, rheumatoid arthritis, insulin-dependent diabetes mellitus, uveitis, inflammatory bowel disease including Crohn's disease and ulcerative colitis, and systemic lupus erythematosus). The compounds of the invention may also be used in treating asthma or as an adjunct to minimize toxicity with cytokine therapy in the treatment of cancers. In general these compounds may be employed in the treatment of those diseases currently treatable through steroid therapy.

Thus, another aspect of the invention is the provision of a method for the treatment or prophylaxis of the above-described conditions through the administration of therapeutic or prophylactic amounts of one or more compounds of the formula I.

In accordance with the method provided by the invention, the novel compounds of formula I may be administered for either a prophylactic or therapeutic purpose either alone or with other immunosuppressive or antiinflammatory agents. When provided prophylactically, the immunosuppressive compound(s) are provided in advance of any inflammatory response or symptom (for example, prior to, at, or shortly after the time of an organ or tissue transplant but in advance of any symptoms of organ rejection). The prophylactic administration of a compound of the formula I serves to prevent or attenuate any subsequent inflammatory response (such as, for example, rejection of a transplanted organ or tissue, etc.). The therapeutic administration of a compound of the formula I serves to attenuate any actual inflammation (such as, for example, the rejection of a transplanted organ or tissue). Thus, in accordance with the invention, a compound of the formula I can be administered either prior to the onset of inflammation (so as to suppress an anticipated inflammation) or after the initiation of inflammation.

The novel compounds of the formula I may, in accordance with the invention, be administered in single or divided doses by the oral, parenteral or topical routes. A suitable oral dosage for a compound of formula I would be in the range of about 0.1 mg to 10 g per day. In parenteral formulations, a suitable dosage unit may contain from 0.1 to 250 mg of said compounds, whereas for topical administration, formulations containing 0.01 to 1% active ingredient are preferred. It should be understood, however, that the dosage administration from patient to patient will vary and the dosage for any particular patient will depend upon the clinician's judgement, who will use as criteria for fixing a proper dosage the size and condition of the patient as well as the patient's response to the drug.

When the compounds of the present invention are to be administered by the oral route, they may be administered as medicaments in the form of pharmaceutical preparations which contain them in association with a compatible pharmaceutical carrier material. Such carrier material can be an inert organic or inorganic carrier material suitable for oral administration. Examples of such carrier materials are water, gelatin, talc, starch, magnesium stearate, gum arabic, vegetable oils, polyalkylene-glycols, petroleum jelly and the like.

The pharmaceutical preparations can be prepared in a conventional manner and finished dosage forms can be solid dosage forms, for example, tablets, dragees, capsules, and the like, or liquid dosage forms, for example solutions, suspensions, emulsions and the like. The pharmaceutical preparations may be subjected to conventional pharmaceutical operations such as sterilization. Further, the pharmaceutical preparations may contain conventional adjuvants such as preservatives, stabilizers, emulsifiers, flavor-improvers, wetting agents, buffers, salts for varying the osmotic pressure and the like. Solid carrier material which can be used include, for example, starch, lactose, mannitol, methyl cellulose, microcrystalline cellulose, talc, silica, dibasic calcium phosphate, and high molecular weight polymers (such as polyethylene glycol).

For parenteral use, a compound of formula I can be administered in an aqueous or non-aqueous solution, suspension or emulsion in a pharmaceutically acceptable oil or a mixture of liquids, which may contain bacteriostatic agents, antioxidants, preservatives, buffers or other solutes to render the solution isotonic with the blood, thickening agents, suspending agents or other pharmaceutically acceptable additives. Additives of this type include, for example, tartrate, citrate and acetate buffers, ethanol, propylene glycol, polyethylene glycol, complex formers (such as EDTA), antioxidants (such as sodium bisulfite, sodium metabisulfite, and ascorbic acid), high molecular weight polymers (such as liquid polyethylene oxides) for viscosity regulation and polyethylene derivatives of sorbitol anhydrides. Preservatives may also be added if necessary, such as benzoic acid, methyl or propyl paraben, benzalkonium chloride and other quaternary ammonium compounds.

The compounds of this invention may also be administered as solutions for nasal application and may contain in addition to the compounds of this invention suitable buffers, tonicity adjusters, microbial preservatives, antioxidants and viscosity-increasing agents in an aqueous vehicle. Examples of agents used to increase viscosity are polyvinyl alcohol, cellulose derivatives, polyvinylpyrrolidone, polysorbates or glycerin. Microbial preservatives added may include benzalkonium chloride, thimerosal, chloro-butanol or phenylethyl alcohol.

Additionally, the compounds provided by the invention can be administered topically or by suppository.

Formulations

Compounds of the formula I can be formulated for therapeutic administration in a number of ways. Descriptions of several exemplary formulations are given below.

Example A

Capsules or Tablets

| Example A-1 | | Example A-2 | |
| --- | --- | --- | --- |
| Ingredients | Quantity | Ingredients | Quantity |
| Compound of formula I | 250 mg | Compound of formula I | 50 mg |
| Starch | 160 mg | Dicalcium Phosphate | 160 mg |
| Microcrys. Cellulose | 90 mg | Microcrys. Cellulose | 90 mg |
| Sodium Starch Glycolate | 10 mg | Stearic acid | 5 mg |
| Magnesium Stearate | 2 mg | Sodium Starch Glycolate | 10 mg |
| Fumed colloidal silica | 1 mg | Fumed colloidal silica | 1 mg |

The compound of formula I is blended into a powder mixture with the premixed excipient materials as identified above with the exception of the lubricant. The lubricant is then blended in and the resulting blend compressed into tablets or filled into hard gelatin capsules.

Example B

Parenteral Solutions

| Ingredients | Quantity |
| --- | --- |
| Compound of formula I | 500 mg |
| PEG 400 | 40% by volume |
| Ethyl Alcohol | 5% by volume |
| Saline | 55% by volume |

The excipient materials are mixed and then added to one of the compounds of formula I in such volume as is necessary for dissolution. Mixing is continued until the solution is clear. The solution then filtered into the appropriate vials or ampoules and sterilized by autoclaving.

Example C

Suspension

| Ingredients | Quantity |
| --- | --- |
| Compound of formula I | 100 mg |
| Citric acid | 1.92 g |
| Benzalkonium chloride | 0.025% by weight |
| EDTA | 0.1% by weight |
| Polyvinylalcohol | 10% by weight |
| Water | q.s. to 100 mL |

The excipient materials are mixed with the water and thereafter one of the compounds of formula I is added and mixing is continued until the suspension is homogeneous. The suspension is then transferred into the appropriate vials or ampoules.

Example D

| Topical Formulation | |
|---|---|
| Ingredients | Quantity |
| Compound of formula I | 5% by weight |
| Tefose 63 | 13% by weight |
| Labrafil M 1944 CS | 3% by weight |
| Paraffin Oil | 8% by weight |
| Methylparaben (MP) | 0.15% by weight |
| Propylparaben (PP) | 0.05% by weight |
| Deionized water | q.s. to 100 |

The proper amounts of Tefose 63, Labrafil M 1944 CS, Paraffin oil and water are mixed and heated at 75° C. until all components have melted. The mixture is then cooled to 50° C. with continuous stirring. Methylparaben and propylparaben are added with mixing and the mixture is cooled to ambient temperature. The compound of formula I is added to the mixture and blended well.

What is claimed is:

1. A compound of the formula I,

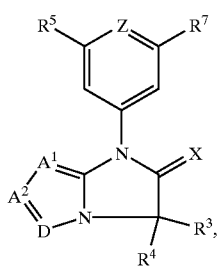

(I)

wherein:
$A^1$ is =N—;
$A^2$ is =C(H)—;
D is =C(SO$_2$R$^1$)—, wherein R$^1$ is selected from the group consisting of:
(A) —R$^{100e}$, which is:
branched or unbranched alkyl of 1 to 6 carbon atoms, alkenyl of 2 to 6 carbon atoms or cycloalkyl or cycloalkenyl of 3 to 6 carbon atoms, in which alkyl, alkenyl, cycloalkyl or cycloalkenyl group one or more hydrogen atoms are optionally and independently replaced with:
  (i) oxo,
  (ii) a group of the formula —COOR$^{18}$, wherein R$^{18}$ is straight or branched alkyl of 1 to 7 carbon atoms or cycloalkyl of 3 to 6 carbon atoms,
  (iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
  (iv) a group of the formula —OR$^{21}$, wherein R$^{21}$ is a hydrogen atom, or a straight or branched alkyl or acyl group of 1 to 7 carbon atoms, wherein one or more hydrogen atoms of said alkyl or acyl group are optionally replaced with a group independently selected from the group consisting of —OH, —Oalkyl (wherein the alkyl moiety contains 1 to 6 carbon atoms), —NH$_2$, —NHMe and —NMe$_2$, or
  (v) a group of the formula —NR$^{23}$R$^{24}$, wherein R$^{23}$ and R$^{24}$ are each, independently,
    (a) a hydrogen atom,
    (b) straight or branched alkyl or acyl of 1 to 7 carbon atoms or cycloalkyl of 3 to 7 carbon atoms, wherein said one or more hydrogen atoms of said alkyl or acyl group are optionally replaced with a group independently selected from the group consisting of —OH, —Oalkyl (wherein the alkyl moiety is 1 to 6 carbon atoms), —NH$_2$, —NHMe and —NMe$_2$,
    (c) a group of the formula —(CH$_2$)$_m$COOH, wherein m is 0, 1 or 2,
    (d) a group of the formula —(CH$_2$)$_n$COOR$^{25}$, wherein n is 0, 1 or 2, and wherein R$^{25}$ is straight or branched alkyl of 1 to 6 carbon atoms, or
    (e) a group of the formula —(CH$_2$)$_n$CONHR$^{25}$, wherein n is 0, 1 or 2, and wherein R$^{25}$ is straight or branched alkyl of 1 to 6 carbon atoms,
(B) groups of the formula —NR$^{46}$R$^{47}$, wherein R$^{46}$ and R$^{47}$ are each independently a hydrogen atom, phenyl which is optionally monosubstituted with halogen, or R$^{100e}$, wherein R$^{100e}$ is as hereinbefore defined, and
(C) saturated or unsaturated heterocyclic groups selected from the group consisting of pyrrolinyl, pyrrolidinyl, piperidinyl, piperazinyl, morpholinyl and thiomorpholinyl, wherein said heterocyclic groups are optionally mono- or poly-substituted with moieties independently selected from the group consisting of:
  (i) oxo,
  (ii) —OR$^{101}$, wherein R$^{101}$ is:
    (a) a hydrogen atom,
    (b) alkyl of 1 to 7 carbons, wherein any hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
    (c) acyl of 1 to 7 carbons, wherein any hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
    (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
    (e) —COOR$^{104}$, wherein R$^{104}$ is alkyl of 1 to 7 atoms ,
  (iii) —CONR$^{105}$R$^{106}$, wherein R$^{105}$ and R$^{106}$ are each independently:
    (a) a hydrogen atom, or
    (b) straight or branched alkyl of 1 to 7 atoms or cycloalkyl of 3 to 7 atoms, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) —COOR$^{107}$, wherein R$^{107}$ is a hydrogen atom, or straight or branched alkyl of 1 to 7 carbon atoms,
(v) straight or branched alkyl of 1 to 7 carbon atoms, alkenyl or alkynyl of 2 to 7 carbon atoms, or cycloalkyl of 3 to 7 carbons, wherein one or more hydrogen atoms of said alkyl, alkenyl, alkynyl or cycloalkyl group is optionally replaced with a moiety independently selected from the group consisting of:
  (a) oxo,
  (b) —OH,
  (c) —OR$^{113}$, wherein R$^{113}$ is alkyl of 1 to 6 carbon atoms,
  (d) —OCOCH$_3$,
  (e) —NH$_2$,
  (f) —NHMe,
  (g) —NMe$_2$,
  (h) —CO$_2$H, and
  (i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which may be straight, branched or cyclic, and wherein one or more hydrogen atoms of said acyl group is optionally replaced with a moiety independently selected from the group consisting of:
  (a) —OH,
  (b) —OR$^{115}$, wherein R$^{115}$ is alkyl of 1 to 6 carbon atoms,
  (c) —NH$_2$,
  (d) —NHMe,
  (e) —NMe$_2$,
  (f) —NHCOMe,
  (g) oxo,
  (h) —CO$_2$R$^{116}$, wherein R$^{116}$ is alkyl of 1 to 3 carbon atoms,
  (i) —CN,
  (j) the halogen atoms,
  (k) heterocycles selected from the group consisting of pyrrolidinyl, piperidinyl, piperazinyl, morpholinyl and thiomorpholinyl, and
  (l) aryl or heteroaryl selected from the group consisting of phenyl, thiophenyl, pyridyl, pyrimidinyl, furyl, pyrrolyl and oxazolyl,
(vii) —SO$_2$R$^{108}$, wherein R$^{108}$ is:
  (a) phenyl, wherein said phenyl moiety is optionally substituted with one or more moieties selected from the group consisting of the halogen atoms, straight or branched alkyl of 1 to 6 carbons, and —OR$^{117}$ (wherein R$^{117}$ is hydrogen or alkyl of 1 to 6 carbon atoms),
  (b) a heterocyclic group selected from the group consisting of pyrrolidinyl, piperidinyl, piperazinyl, morpholinyl and thiomorpholinyl, wherein said heterocyclic group is optionally substituted with one or more moieties selected from the group consisting of the halogen atoms, straight or branched alkyl of 1 to 6 carbons, and —OR$^{118}$ (wherein R$^{118}$ is hydrogen or alkyl of 1 to 6 carbon atoms), or
  (c) straight or branched alkyl of 1 to 7 atoms, wherein said alkyl moiety is optionally substituted with one or more moieties selected from the group consisting of the halogen atoms, straight or branched alkyl of 1 to 6 carbons, and —OR$^{119}$ (wherein R$^{119}$ is hydrogen or alkyl of 1 to 6 carbon atoms),
(viii) —COR$^{109}$, wherein R$^{109}$ is:
  (a) phenyl, wherein said phenyl moiety is optionally substituted with one or more moieties selected from the group consisting of the halogen atoms, straight or branched alkyl of 1 to 6 carbons, and —OR$^{120}$ (wherein R$^{120}$ is hydrogen or alkyl of 1 to 6 carbon atoms),
  (b) a heterocyclic group selected from the group consisting of pyrrolidinyl, piperidinyl, piperazinyl, morpholinyl and thiomorpholinyl, wherein said heterocyclyl is optionally substituted with one or more halogen, straight or branched alkyl of 1 to 6 carbons, or —OR$^{121}$ (wherein R$^{121}$ is hydrogen or alkyl of 1 to 6 carbon atoms), or
  (c) straight or branched alkyl of 1 to 7 atoms, wherein said alkyl moiety is optionally substituted with one or more moieties selected from the group consisting of the halogen atoms, straight or branched alkyl of 1 to 6 carbons, and —OR$^{122}$ (wherein R$^{122}$ is hydrogen or alkyl of 1 to 6 carbon atoms), and
(ix) —CHO;
X is an oxygen atom;
R$^3$ is branched or unbranched alkyl of 1 to 3 carbon atoms;
R$^4$ is a group of the formula —CH$_2$R$^{55}$, wherein,
  R$^{55}$ is:
    phenyl, which is optionally substituted at the 4-position with:
      (A) R$^{59e}$, which is aryl or heteroaryl selected from the group consisting of phenyl, thiophenyl, pyridyl, pyrimidinyl and furyl, wherein one of the hydrogen atoms of said aryl or heteroaryl group is optionally replaced with:
        (i) methyl,
        (ii) —CN,
        (iii) nitro, or
        (iv) halogen,
      (B) methyl,
      (C) —CN,
      (D) nitro, or
      (E) halogen;
R$^5$ is Cl;
Z is =C(H)—; and,
R$^7$ is Cl;
or a pharmaceutically acceptable salt thereof.

2. A compound of the formula I, (I)

wherein:
A$^1$ is =N—;
A$^2$ is =C(H)—;
D is =C(SO$_2$R$^1$)—, wherein R$^1$ is selected from the group consisting of:
  (A) —R$^{100e}$, which is:
    branched or unbranched alkyl of 1 to 6 carbon atoms or cycloalkyl of 3 to 6 carbon atoms, in which alkyl, or cycloalkyl group one to three hydrogen atoms are optionally and independently replaced with:
(i) oxo,
(ii) a group of the formula —COOR$^{18}$, wherein R$^{18}$ is straight or branched alkyl of 1 to 7 carbon atoms or cycloalkyl of 3 to 6 carbon atoms,
(iii) a group of the formula —CONR$^{19}$R$^{20}$, wherein R$^{19}$ and R$^{20}$ are each, independently, a hydrogen atom, alkyl of 1 to 6 carbon atoms or cycloalkyl of 3 to 6 carbon atoms, or wherein R$^{19}$ and R$^{20}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) a group of the formula —OR$^{21}$, wherein R$^{21}$ is a hydrogen atom, or a straight or branched alkyl or acyl group of 1 to 7 carbon atoms, or
(v) a group of the formula —NR$^{23}$R$^{24}$, wherein R$^{23}$ and R$^{24}$ are each, independently,
  (a) a hydrogen atom,
  (b) straight or branched alkyl or acyl of 1 to 7 carbon atoms or cycloalkyl of 3 to 7 carbon atoms,
  (c) a group of the formula —(CH$_2$)$_m$COOH, wherein m is 0, 1 or 2,
  (d) a group of the formula —(CH$_2$)$_n$COOR$^{25}$, wherein n is 0, 1 or 2, and wherein R$^{25}$ is straight or branched alkyl of 1 to 6 carbon atoms, or
  (e) a group of the formula —(CH$_2$)$_n$CONHR$^{25}$, wherein n is 0, 1 or 2, and wherein R$^{25}$ is straight or branched alkyl of 1 to 6 carbon atoms, and (B) saturated heterocyclic groups selected from the group consisting of pyrrolidinyl, piperidinyl, piperazinyl, morpholinyl and thiomorpholinyl, wherein said heterocyclic groups are optionally mono- or di-substituted with moieties independently selected from the group consisting of:
(i) oxo,
(ii) —OR$^{101}$, wherein R$^{101}$ is:
  (a) a hydrogen atom,
  (b) alkyl of 1 to 7 carbons, wherein one hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$,
  (c) acyl of 1 to 7 carbons, wherein one hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$,
  (d) —CONR$^{102}$R$^{103}$, wherein R$^{102}$ and R$^{103}$ are each independently a hydrogen atom or alkyl of 1 to 7 atoms, or wherein R$^{102}$ and R$^{103}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, or
  (e) —COOR$^{104}$, wherein R$^{104}$ is alkyl of 1 to 7 atoms, (iii) —CONR$^{105}$R$^{106}$, wherein R$^{105}$ and R$^{106}$ are each independently:
  (a) a hydrogen atom, or
  (b) straight or branched alkyl of 1 to 7 atoms or cycloalkyl of 3 to 7 atoms, wherein said alkyl or cycloalkyl group is optionally monosubstituted with —OH, —OR$^{123}$ (wherein R$^{123}$ is an alkyl moiety of 1 to 6 carbon atoms), —NH$_2$, —NHMe, —NMe$_2$, pyrrolidinyl, piperidinyl, piperazinyl or morpholinyl, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—,
(iv) —COOR$^{107}$, wherein R$^{107}$ is a hydrogen atom, or straight or branched alkyl of 1 to 7 carbon atoms,
(v) straight or branched alkyl of 1 to 7 carbon atoms or cycloalkyl of 3 to 7 carbons, wherein one to three hydrogen atoms of said alkyl or cycloalkyl group is optionally replaced with a moiety independently selected from the group consisting of:
  (a) oxo,
  (b) —OH,
  (c) —OR$^{113}$, wherein R$^{113}$ is alkyl of 1 to 6 carbon atoms,
  (d) —OCOCH$_3$,
  (e) —NH$_2$,
  (f) —NHMe,
  (g) —NMe$_2$,
  (h) —CO$_2$H, and
  (i) —CO$_2$R$^{114}$ wherein R$^{114}$ is alkyl of 1 to 3 carbon atoms, or cycloalkyl of 3 to 7 carbons,
(vi) acyl of 1 to 7 carbon atoms, which may be straight, branched or cyclic, and wherein one or two hydrogen atoms of said acyl group is optionally replaced with a moiety selected from the group consisting of:
  (a) —OH,
  (b) —OR$^{115}$, wherein R$^{115}$ is alkyl of 1 to 6 carbon atoms,
  (c) —NH$_2$,
  (d) —NHMe,
  (e) —NMe$_2$,
  (f) —NHCOMe,
  (g) oxo,
  (h) —CO$_2$R$^{116}$, wherein R$^{116}$ is alkyl of 1 to 3 carbon atoms,
  (i) —CN,
  (j) the halogen atoms,
  (k) heterocycles selected from the group consisting of pyrrolidinyl, piperidinyl, piperazinyl, morpholinyl and thiomorpholinyl, and
  (l) aryl or heteroaryl selected from the group consisting of phenyl, thiophenyl, pyridyl, pyrimidinyl, furyl, pyrrolyl and oxazolyl,
(vii) —SO$_2$R$^{108}$, wherein R$^{108}$ is:
  (a) phenyl, wherein said phenyl moiety is optionally substituted with one moiety selected from the group consisting of the halogen atoms, straight or branched alkyl of 1 to 6 carbons, and —OR$^{117}$ (wherein R$^{117}$ is hydrogen or alkyl of 1 to 6 carbon atoms),
  (b) a heterocyclic group selected from the group consisting of pyrrolidinyl, piperidinyl, piperazinyl, morpholinyl and thiomorpholinyl, wherein said heterocyclic group is optionally substituted with one moiety selected from the group consisting of the halogen atoms, straight or branched alkyl of 1 to 6 carbons, and —OR$^{118}$ (wherein R$^{118}$ is hydrogen or alkyl of 1 to 6 carbon atoms), or (c) straight or branched alkyl of 1 to 7 atoms, wherein said alkyl moiety is optionally substituted with one moiety selected from the group consisting of the halogen atoms, straight or branched alkyl of 1 to 6 carbons, and —OR$^{119}$ (wherein R$^{119}$ is hydrogen or alkyl of 1 to 6 carbon atoms), (viii) —COR$^{109}$, wherein R$^{109}$ is:

(a) phenyl, wherein said phenyl moiety is optionally substituted with one moiety selected from the group consisting of the halogen atoms, straight or branched alkyl of 1 to 6 carbons, and —OR$^{120}$ (wherein R$^{120}$ is hydrogen or alkyl of 1 to 6 carbon atoms), (b) a heterocyclic group selected from the group consisting of pyrrolidinyl, piperidinyl, piperazinyl, morpholinyl and thiomorpholinyl, wherein said heterocyclyl is optionally substituted with one halogen, straight or branched alkyl of 1 to 6 carbons, or —OR$^{121}$ (wherein R$^{121}$ is hydrogen or alkyl of 1 to 6 carbon atoms), or (c) straight or branched alkyl of 1 to 7 atoms, wherein said alkyl moiety is optionally substituted with one moeity selected from the group consisting of the halogen atoms, straight or branched alkyl of 1 to 6 carbons, and —OR$^{122}$ (wherein R$^{122}$ is hydrogen or alkyl of 1 to 6 carbon atoms), and (ix) —CHO;

X is an oxygen atom;

R$^3$ is branched or unbranched alkyl of 1 to 3 carbon atoms;

R$^4$ is a group of the formula —CH$_2$R$^{55}$, wherein,

R$^{55}$ is:

phenyl, which is optionally substituted at the 4-position with:

(A) R$^{59e}$, which is aryl or heteroaryl selected from the group consisting of phenyl, thiophenyl, pyridyl, pyrimidinyl and furyl, wherein one of the hydrogen atoms of said aryl or heteroaryl group is optionally replaced with:

(i) methyl,
(ii) —CN,
(iii) nitro, or
(iv) halogen, (B) methyl,
(C) —CN,
(D) nitro, or
(E) halogen;

R$^5$ is Cl;

Z is =C(H)—; and,

R$^7$ is Cl;

or a pharmaceutically acceptable salt thereof.

3. A compound of the formula I, as set forth in claim 2, wherein:

A$^1$ is =N—;
A$^2$ is =C(H)—;
D is =C(SO$_2$R$^1$)—, wherein R$^1$ is selected from the group consisting of:

(A) methyl, and
(B) saturated heterocyclic groups selected from the group consisting of pyrrolidinyl, piperidinyl, piperazinyl and morpholinyl wherein said heterocyclic groups are optionally mono- or di-substituted with moieties independently selected from the group consisting of:

(i) oxo,
(ii) —OR$^{101}$, wherein R$^{101}$ is:

(a) a hydrogen atom,
(b) alkyl of 1 to 7 carbons, wherein one hydrogen atom of said alkyl group is optionally replaced with —OH, —OR$^{110}$ (wherein R$^{110}$ is an alkyl moiety of 1 to 6 carbon atoms), —NH$_2$, —NHMe or —NMe$_2$, or
(c) acyl of 1 to 7 carbons, wherein one hydrogen atom of said acyl group is optionally replaced with —OH, —OR$^{111}$ (wherein R$^{111}$ is an alkyl moiety of 1 to 6 carbon atoms), —NH$_2$, —NHMe or —NMe$_2$, (iii) —CONR$^{105}$R$^{106}$, wherein R$^{105}$ and R$^{106}$ are each independently:

(a) a hydrogen atom, or
(b) straight or branched alkyl of 1 to 7 atoms or cycloalkyl of 3 to 7 atoms, wherein said alkyl or cycloalkyl group is optionally monosubstituted with —OH, —OR$^{123}$ (wherein R$^{123}$ is an alkyl moiety of 1 to 6 carbon atoms), —NH$_2$, —NHMe, —NMe$_2$, pyrrolidinyl, piperidinyl, piperazinyl or morpholinyl, or, wherein R$^{105}$ and R$^{106}$ constitute a saturated hydrocarbon bridge of 3 to 5 carbon atoms which together with the nitrogen atom between them form a heterocyclic ring, and wherein one carbon atom in said hydrocarbon bridge is optionally replaced by —O—, —NH—, or —NMe—, (iv) —COOR$^{107}$, wherein R$^{107}$ is a hydrogen atom, or straight or branched alkyl of 1 to 7 carbon atoms, (v) straight or branched alkyl of 1 to 7 carbon atoms wherein one or two hydrogen atoms of said alkyl group are optionally replaced with moieties independently selected from the group consisting of:

(a) oxo,
(b) —OH,
(c) —OR$^{113}$, wherein R$^{113}$ is alkyl of 1 to 6 carbon atoms,
(d) —OCOCH$_3$,
(e) —NH$_2$,
(f) —NHMe,
(g) —NMe$_2$,
(h) —CO$_2$H, and
(i) —CO$_2$R$^{114}$ wherein R$^{114}$ is alkyl of 1 to 3 carbon atoms, or cycloalkyl of 3 to 7 carbons, (vi) acyl of 1 to 7 carbon atoms, which may be straight, branched or cyclic, and wherein one or two hydrogen atoms of said acyl group is optionally replaced with a moiety selected from the group consisting of:

(a) —OH,
(b) —OR$^{115}$, wherein R$^{115}$ is alkyl of 1 to 6 carbon atoms,
(c) —NH$_2$,
(d) —NHMe,
(e) —NMe$_2$,
(f) —NHCOMe,
(g) oxo,
(h) —CO$_2$R$^{116}$, wherein R$^{116}$ is alkyl of 1 to 3 carbon atoms,
(i) —CN,
(j) the halogen atoms,
(k) heterocycles selected from the group consisting of pyrrolidinyl, piperidinyl, piperazinyl, morpholinyl and thiomorpholinyl, and (l) aryl or heteroaryl selected from the group consisting of phenyl, thiophenyl, pyridyl, pyrimidinyl, furyl, pyrrolyl and oxazolyl,
(vii) —SO$_2$R$^{108}$, wherein R$^{108}$ is:
  (a) a heterocyclic group selected from the group consisting of pyrrolidinyl, piperidinyl, piperazinyl and morpholinyl wherein said heterocyclic group is optionally substituted with one moiety selected from the group consisting of straight or branched alkyl of 1 to 6 carbons, and —OR$^{118}$ (wherein R$^{118}$ is hydrogen or alkyl of 1 to 6 carbon atoms),
(viii) —COR$^{109}$, wherein R$^{109}$ is:
  (a) a heterocyclic group selected from the group consisting of pyrrolidinyl, piperidinyl, piperazinyl and morpholinyl wherein said heterocyclyl is optionally substituted with one halogen, straight or branched alkyl of 1 to 6 carbons, or —OR$^{121}$ (wherein R$^{121}$ is hydrogen or alkyl of 1 to 6 carbon atoms), and
(ix) —CHO;
X is an oxygen atom;
R$^3$ is methyl;
R$^4$ is a group of the formula —CH$_2$R$^{55}$, wherein,
  R$^{55}$ is:
  phenyl, which is optionally substituted at the 4-position with:
    (A) R$^{59e}$, which is aryl or heteroaryl selected from the group consisting of phenyl, pyridyl, and pyrimidinyl
    (B) —CN,
    (B) nitro, or
    (C) halogen;
R$^5$ is Cl;
Z is =C(H)—; and,
R$^7$ is Cl;
or a pharmaceutically acceptable salt thereof.

4. A compound of the formula I, in accordance with claim 1, 2 or 3, with the absolute stereochemistry depicted below in formula II (below).

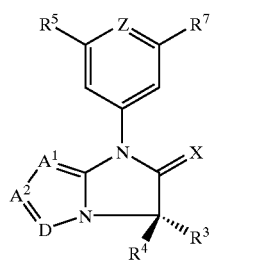
(II)

5. A compound selected from the group consisting of:

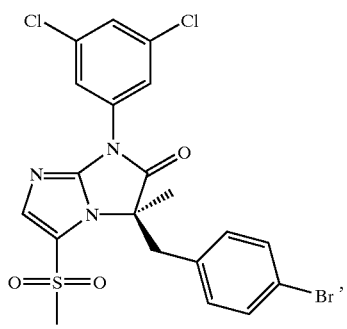

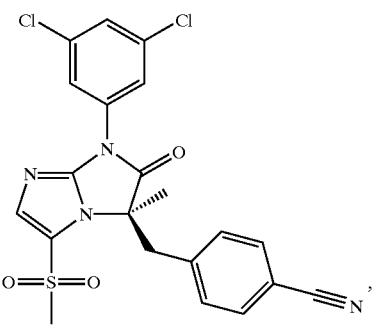

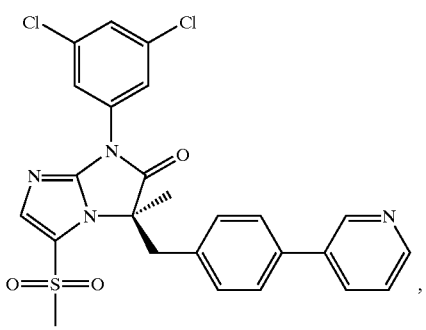

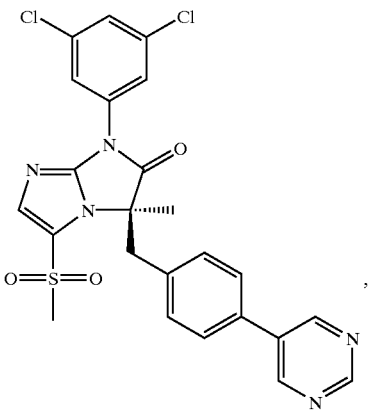

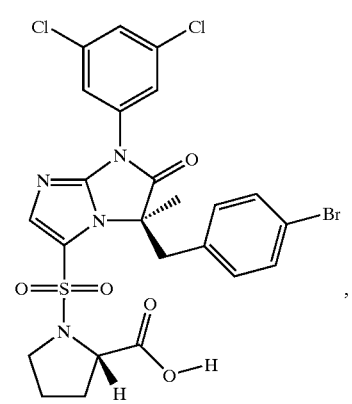

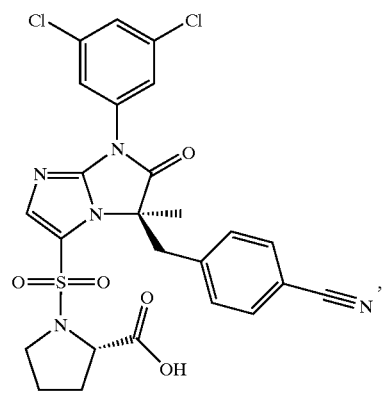
,
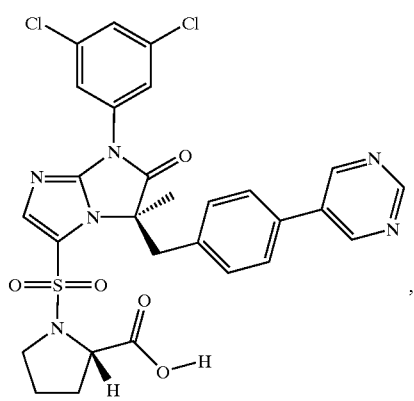
,
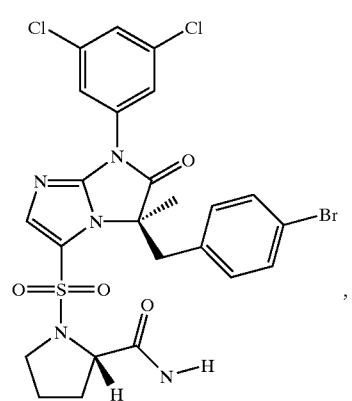
,
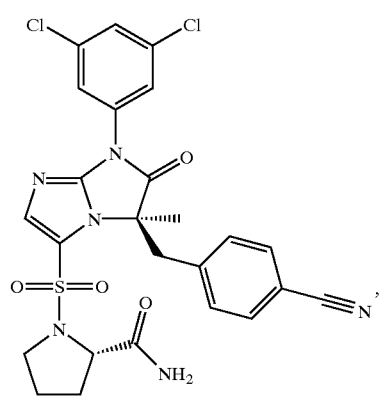
,
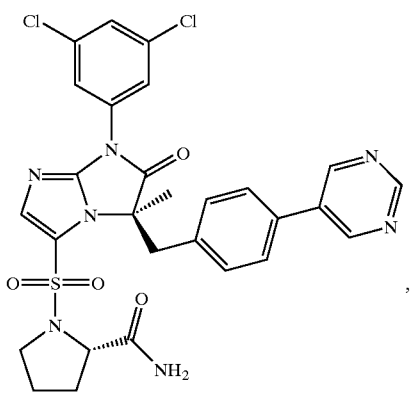
,
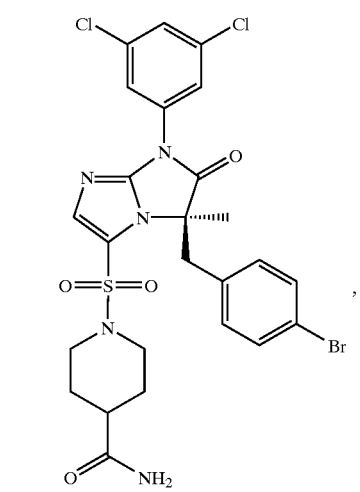
,

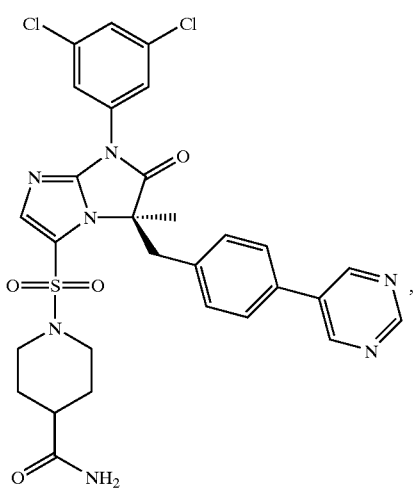
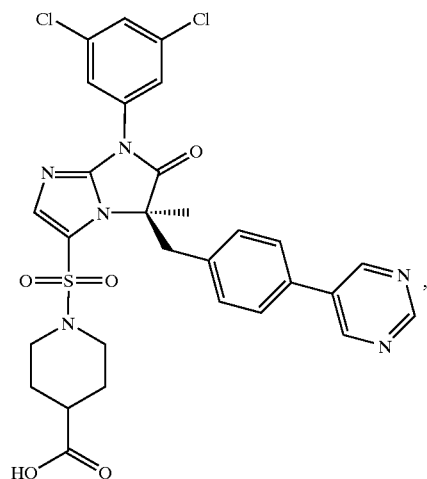
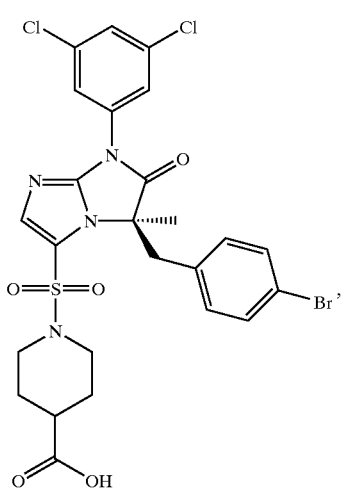
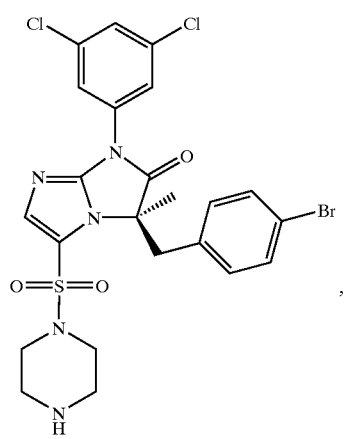
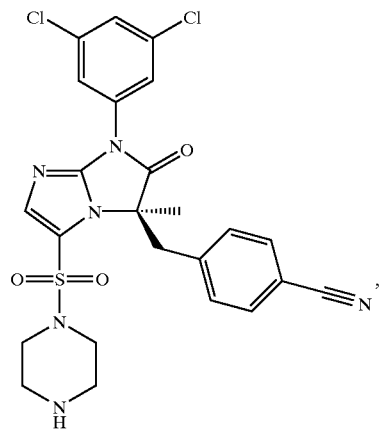

-continued
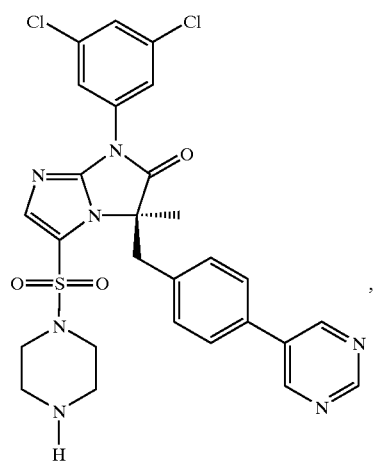
,
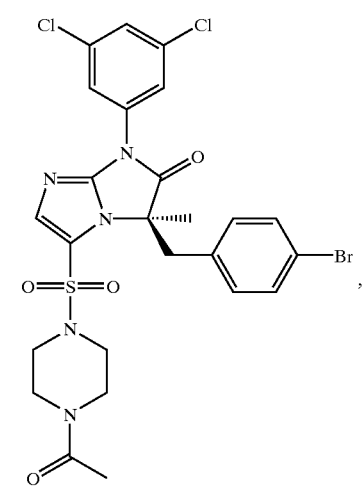
,
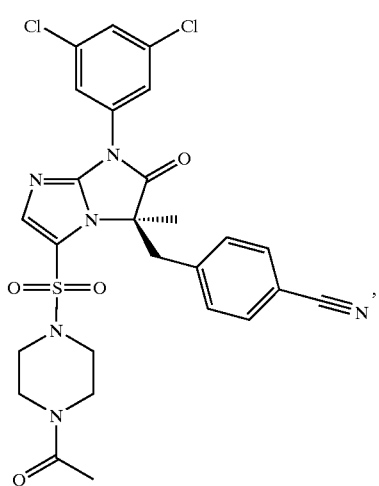
,
-continued
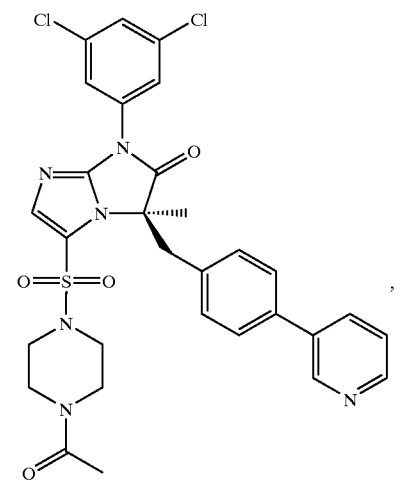
,
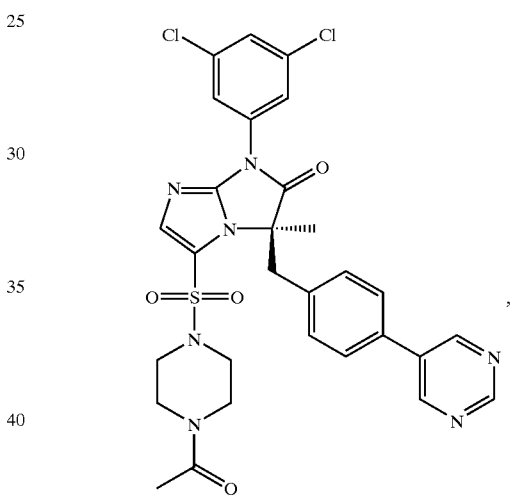
,
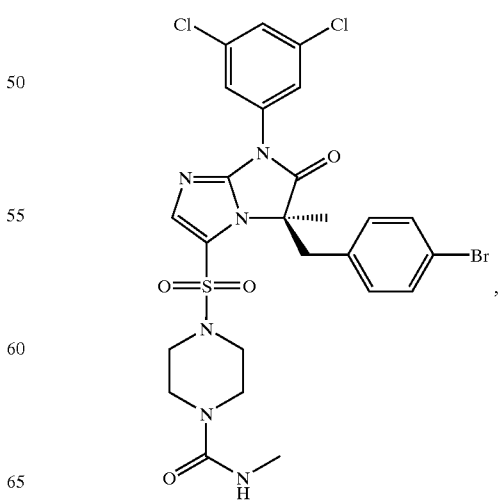
, -continued
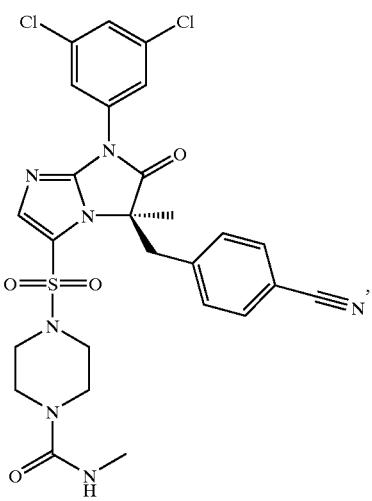
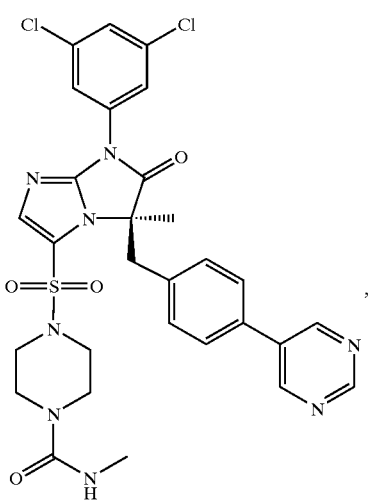
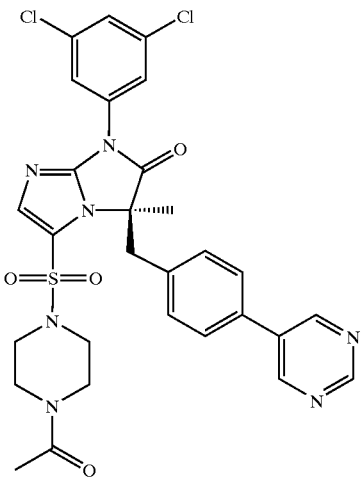
or a pharmaceutically acceptable salt thereof.
6. The compound of the formula
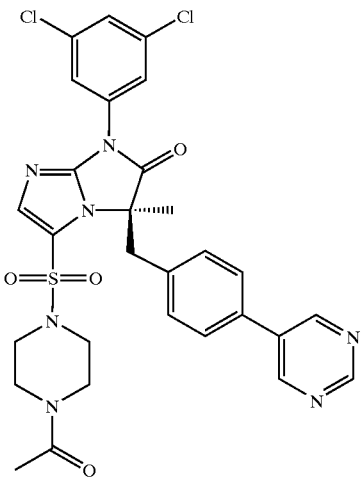
or a pharmaceutically acceptable salt thereof.
7. The compound of the formula
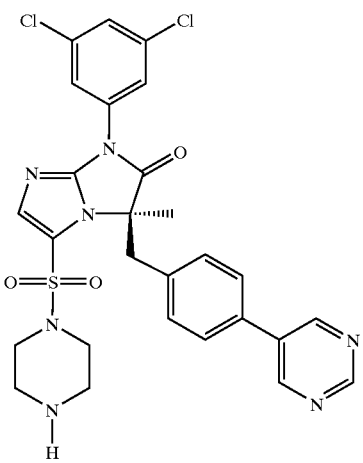
or a pharmaceutically acceptable salt thereof.
8. The compound of the formula
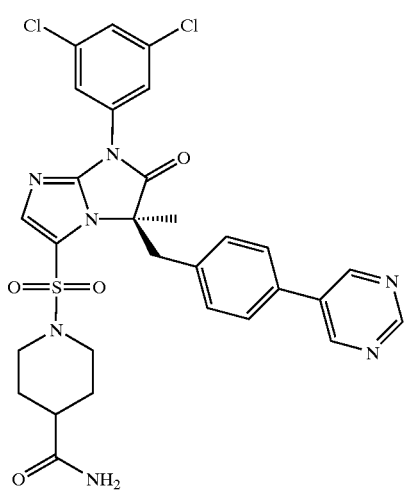
or a pharmaceutically acceptable salt thereof.

9. The compound of the formula
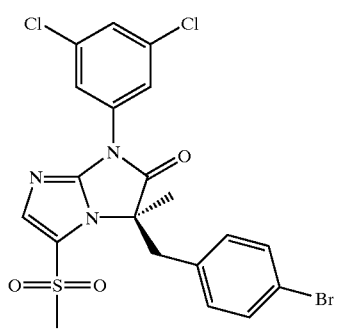
or a pharmaceutically acceptable salt thereof.
10. The compound of the formula
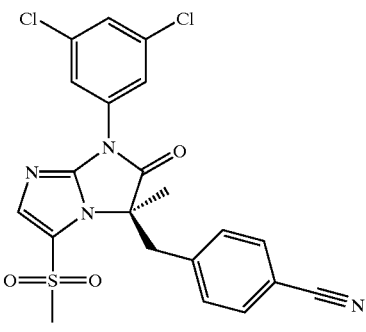
or a pharmaceutically acceptable salt thereof.
11. A pharmaceutical composition comprising a compound in accordance with claim 1, 2, 3, 4, 5, 6, 7, 8, 9, or 10 and a pharmaceutically acceptable carrier or excipient.
* * * * *